US012637466B2

(12) United States Patent
Kim et al.

(10) Patent No.: US 12,637,466 B2
(45) Date of Patent: May 26, 2026

(54) BENZOCARBAZOLE-BASED COMPOUND AND ORGANIC LIGHT-EMITTING DEVICE COMPRISING SAME

(71) Applicant: LG CHEM, LTD., Seoul (KR)

(72) Inventors: Minjun Kim, Daejeon (KR); Hyok Joon Kwon, Daejeon (KR); Ji Young Choi, Daejeon (KR); Young Seok Kim, Daejeon (KR); Kongkyeom Kim, Daejeon (KR); Min Woo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 725 days.

(21) Appl. No.: 16/339,120

(22) PCT Filed: Mar. 27, 2018

(86) PCT No.: PCT/KR2018/003614
§ 371 (c)(1),
(2) Date: Nov. 19, 2019

(87) PCT Pub. No.: WO2018/182297
PCT Pub. Date: Oct. 4, 2018

(65) Prior Publication Data

US 2020/0136058 A1 Apr. 30, 2020

(30) Foreign Application Priority Data

Mar. 27, 2017 (KR) ........................ 10-2017-0038527

(51) Int. Cl.
*C07D 471/04* (2006.01)
*C07D 403/04* (2006.01)
(Continued)

(52) U.S. Cl.
CPC ......... *C07D 487/04* (2013.01); *C07D 403/04* (2013.01); *C07D 403/10* (2013.01);
(Continued)

(58) Field of Classification Search
CPC .. C07D 403/10; C07D 403/14; C07D 405/14; C07D 471/04; C07D 487/04;
(Continued)

(56) References Cited

U.S. PATENT DOCUMENTS

2012/0217485 A1 8/2012 Lee et al.
2014/0191208 A1* 7/2014 Kim .................... H01L 51/5088 546/276.7
(Continued)

FOREIGN PATENT DOCUMENTS

KR 10-2000-0051826 A 8/2000
KR 10-2011-0013220 A 2/2011
(Continued)

OTHER PUBLICATIONS

KR-20170058177-A machine translation (Year: 2017).*
(Continued)

*Primary Examiner* — Elizabeth M. Dahlburg
(74) *Attorney, Agent, or Firm* — Bryan Cave Leighton Paisner LLP

(57) ABSTRACT

The present specification provides a benzocarbazole-based compound of Chemical Formula 1, and an organic light emitting device comprising the same. The benzocarbazole-based compound as a material of an organic material layer of the organic light emitting device provides enhanced efficiency, low driving voltage and increased lifetime.
(Continued)

[Chemical Formula 1]

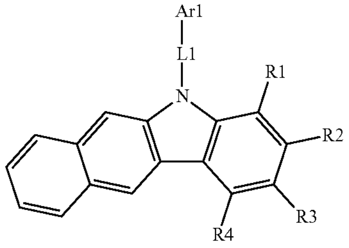

6 Claims, 5 Drawing Sheets

(51) Int. Cl.

| | |
|---|---|
| ***C07D 403/10*** | (2006.01) |
| ***C07D 403/14*** | (2006.01) |
| ***C07D 405/14*** | (2006.01) |
| ***C07D 487/04*** | (2006.01) |
| ***C09K 11/06*** | (2006.01) |
| ***H10K 50/11*** | (2023.01) |
| ***H10K 50/15*** | (2023.01) |
| ***H10K 50/16*** | (2023.01) |
| ***H10K 50/17*** | (2023.01) |
| ***H10K 85/60*** | (2023.01) |

(52) U.S. Cl.
CPC ......... *C07D 403/14* (2013.01); *C07D 405/14* (2013.01); *C07D 471/04* (2013.01); *C09K 11/06* (2013.01); *H10K 85/615* (2023.02); *H10K 85/622* (2023.02); *H10K 85/626* (2023.02); *H10K 85/6572* (2023.02); *H10K 85/6574* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02)

(58) Field of Classification Search
CPC ............ C09K 11/06; C09K 2211/1018; C09K 2211/1022; H01L 51/0052; H01L 51/0054; H01L 51/0058; H01L 51/0072; H01L 51/0073; H01L 51/0074; H01L 51/5012; H01L 51/5016; H01L 51/5056; H01L 51/506; H01L 51/5064; H01L 51/5072; H01L 51/5076; H01L 51/508; H01L 51/5088; H01L 51/5092; H10K 50/11; H10K 50/15; H10K 50/156; H10K 50/16; H10K 50/165; H10K 50/166; H10K 50/17; H10K 85/615; H10K 85/622; H10K 85/626; H10K 85/6572; H10K 85/6574
See application file for complete search history.

(56) References Cited

U.S. PATENT DOCUMENTS

2016/0225992 A1* 8/2016 Ito ............................ C09B 57/02
2019/0131542 A1* 5/2019 Kim .................... H01L 51/0072

FOREIGN PATENT DOCUMENTS

| | | | | | | |
|---|---|---|---|---|---|---|
| KR | 10-2011-0034103 | A | | 4/2011 | | |
| KR | 10-2012-0050557 | A | | 5/2012 | | |
| KR | 10-2014-0083897 | A | | 7/2014 | | |
| KR | 10-2014-0103393 | A | | 8/2014 | | |
| KR | 10-2014-0103395 | A | | 8/2014 | | |
| KR | 10-2014-0103842 | A | | 8/2014 | | |
| KR | 20140103842 | A | * | 8/2014 | ............. | H10K 50/00 |
| KR | 10-2014-0105633 | A | | 9/2014 | | |
| KR | 10-2015-0138105 | A | | 12/2015 | | |
| KR | 10-1595697 | B1 | | 2/2016 | | |
| KR | 102016-0029721 | A | | 3/2016 | | |
| KR | 10-2017-0058177 | A | | 5/2017 | | |
| WO | WO-2017150380 | A1 | * | 9/2017 | ........... | C07D 403/04 |

OTHER PUBLICATIONS

KR_20120050557_A machine translation (Year: 2012).*
WO-2017150380-A1 machine translation (Year: 2017).*
KR-20140103842-A machine translation (Year: 2014).*

* cited by examiner

【FIG. 1】
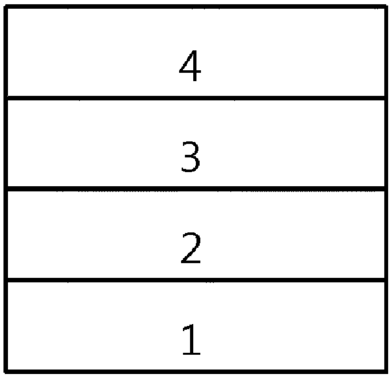

【FIG. 2】
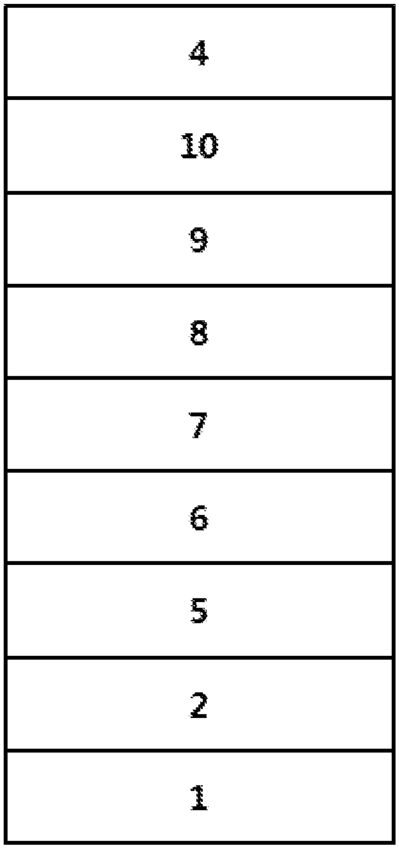

[FIG. 3]
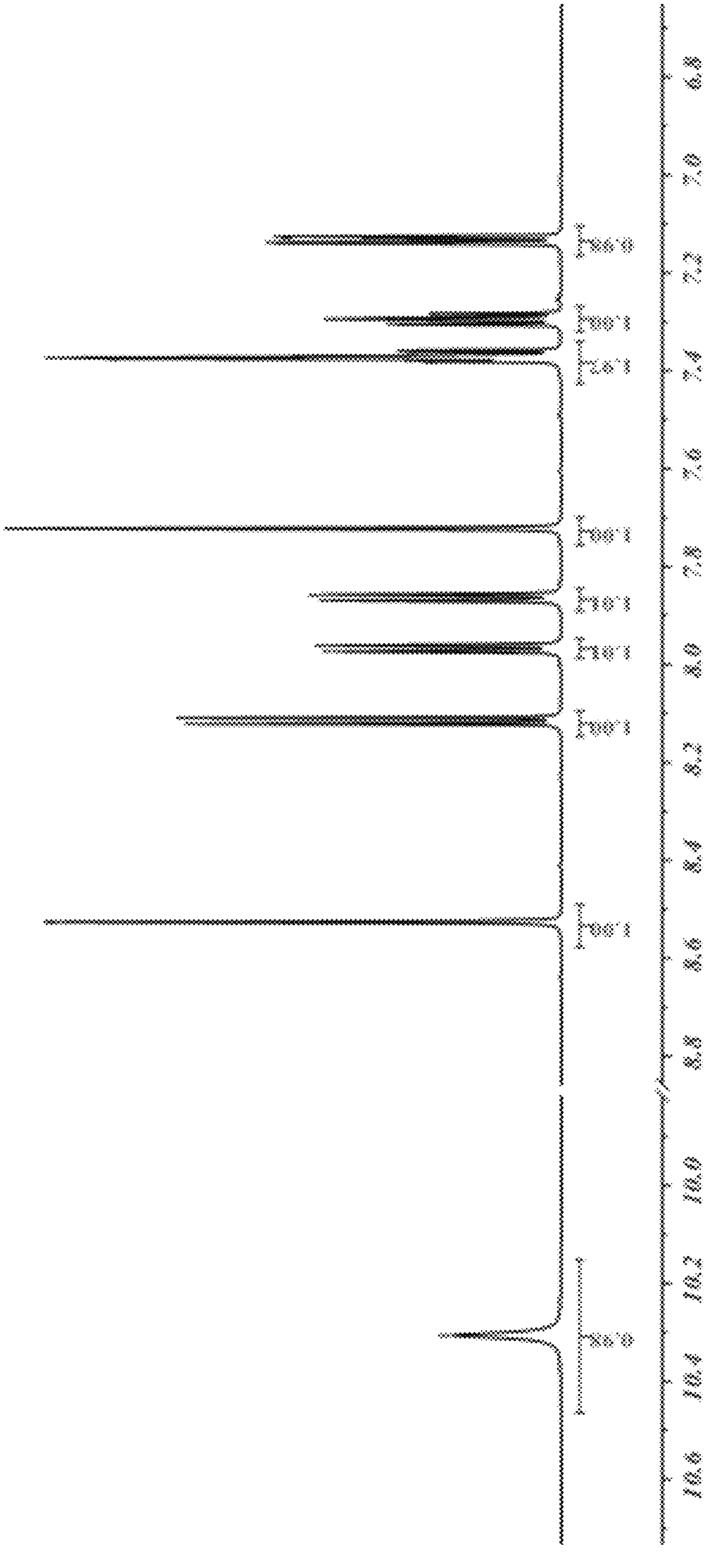

[FIG. 4]
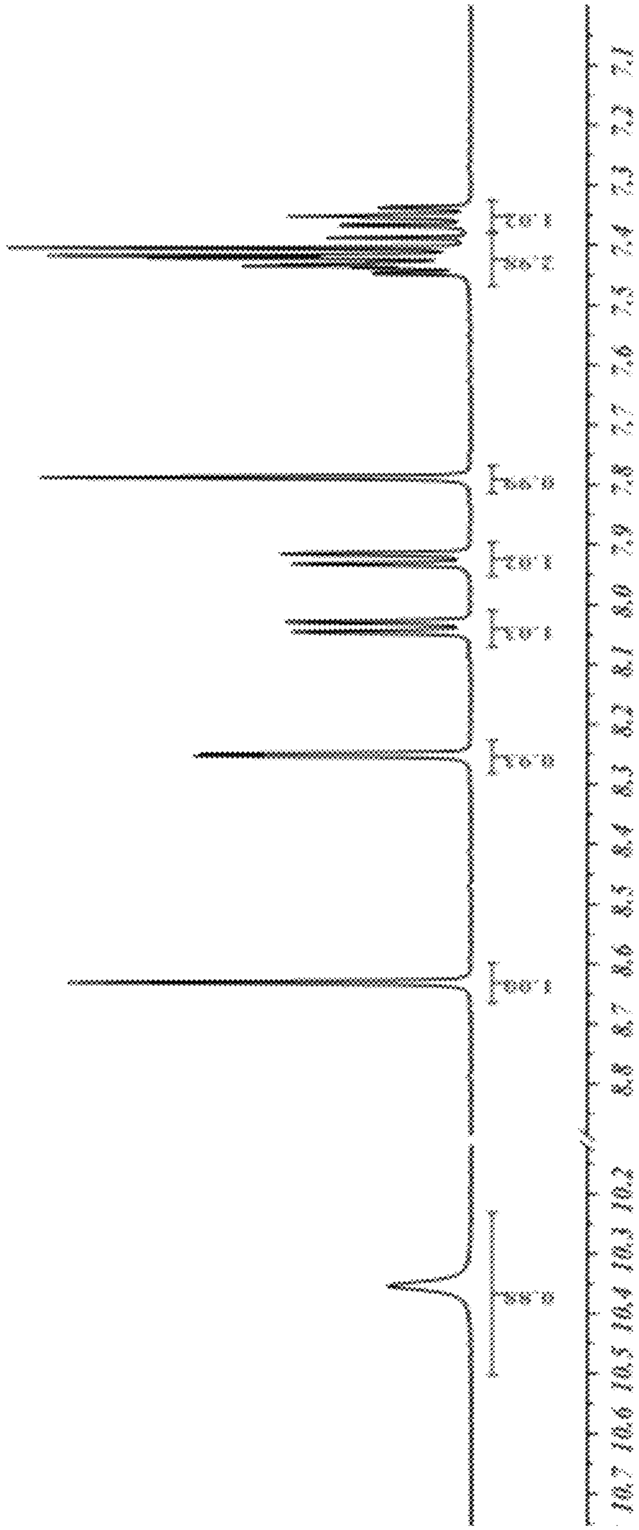

[FIG. 5]
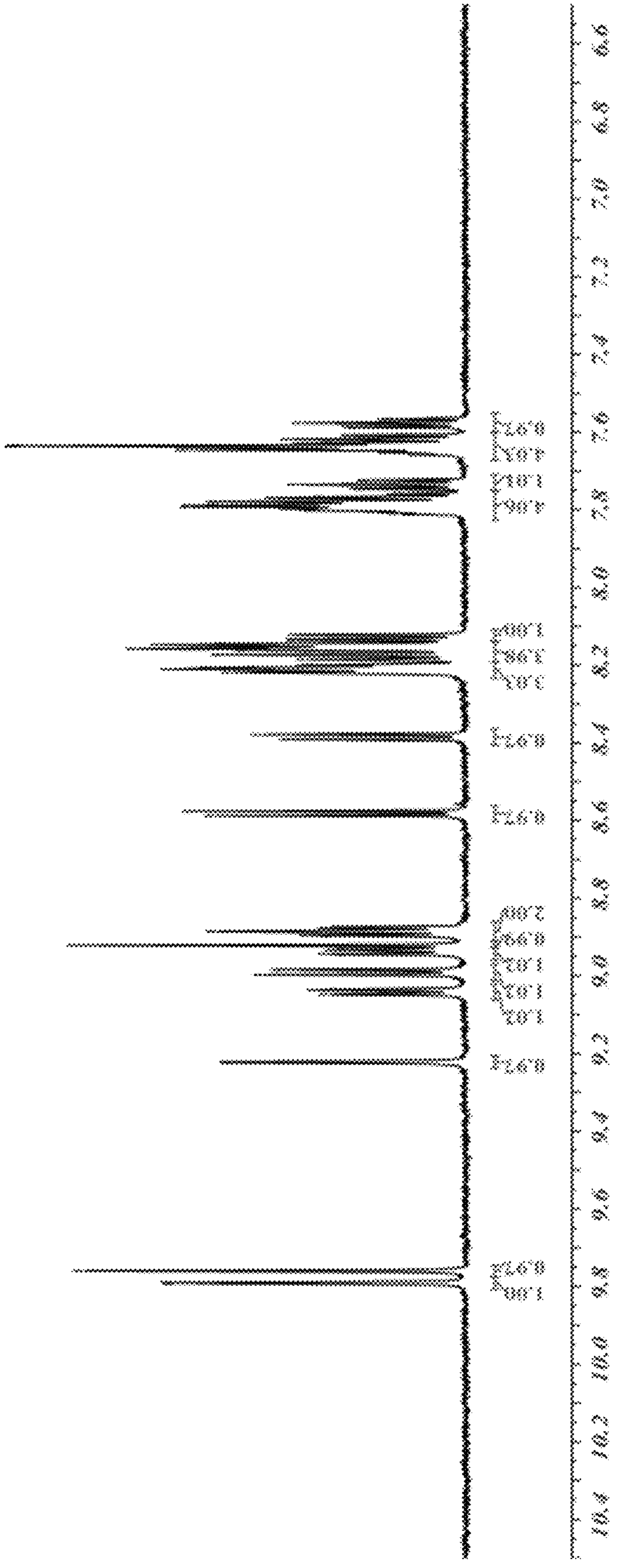

BENZOCARBAZOLE-BASED COMPOUND AND ORGANIC LIGHT-EMITTING DEVICE COMPRISING SAME

TECHNICAL FIELD

The present application claims priority to and the benefits of Korean Patent Application No. 10-20.17-0038527, filed with the Korean Intellectual Property Office on Mar. 27, 2017, the entire contents of which are incorporated herein by reference.

The present specification relates to a benzocarbazole based compound and an organic light emitting device comprising the same.

BACKGROUND ART

An organic light emission phenomenon generally refers to a phenomenon converting electrical energy to light energy using an organic material. An organic light emitting device using an organic light emission phenomenon normally has a structure comprising an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light, emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification describes a benzocarbazole-based compound and an organic light emitting device comprising the same.

Technical Solution

One embodiment of the present specification provides a benzocarbazole-based compound represented by the following Chemical Formula 1.

[Chemical Formula 1]

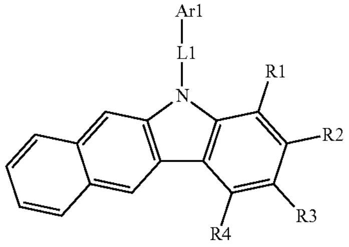

In Chemical Formula 1,

R1 to R4 are the same as or different from each other, and each independently hydrogen; or a substituted or unsubstituted aryl group having 6 to 40 carbon atoms, and at least one of R1 to R4 is a substituted or unsubstituted aryl group having 6 to 40 carbon atoms, L1 is a direct bond; or a substituted or unsubstituted arylene group having 6 to 40 carbon atoms, Ar1 is a fused bicyclic heteroaryl group comprising two or more N atoms and having 2 to 40 carbon atoms.

Another embodiment of the present specification provides an organic light emitting device comprising a first electrode; a second electrode provided opposite to the first electrode; and one or more organic material layers provided between the first, electrode and the second electrode, wherein one or more layers of the organic material layers comprise the benzocarbazole-based compound represented by Chemical Formula 1.

Advantageous Effects

A compound described in the present specification can be used as a material of an organic material layer of an organic light emitting device. A compound according to at least one embodiment is capable of enhancing efficiency, obtaining low driving voltage and/or enhancing lifetime properties in an organic light, emitting device. Particularly, a compound described in the present specification can be used as a material of hole injection, hole transfer, hole injection and hole transfer, electron blocking, light emitting, hole blocking, electron transfer or electron injection.

DESCRIPTION OF. DRAWINGS

FIG. 1 illustrates an example of an organic light emitting device formed with a substrate (1), an anode (2), a light emitting layer (3) and a cathode (4).

FIG. 2 illustrates an example of an organic light emitting device formed with a substrate (1), an anode (2), a hole injection layer (5), a hole transfer layer (6), an electron blocking layer (7), a light emitting layer (8), a hole blocking layer (9), an electron injection and transfer layer (10) and a cathode (4).

FIG. 3 shows a graph measuring 1H-NMR of Chemical Formula a.

FIG. 4 shows a graph measuring 1H-NMR of Chemical Formula b.

FIG. 5 shows a graph measuring 1H-NMR of Compound 122.

FIG. 6 shows a graph measuring LC/MS of Compound 122.

1: Substrate
2: Anode
3: Light Emitting Layer
4: Cathode
5: Hole Injection Layer
6: Hole Transfer Layer
7: Electron Blocking Layer
6: Light Emitting Layer
9: Hole Blocking Layer
10: Electron Injection and Transfer Layer.

MODE FOR DISCLOSURE

Hereinafter, the present specification will be described in more detail.

The present specification provides a benzocarbazole-based compound represented by the following Chemical Formula 1.

[Chemical Formula 1]

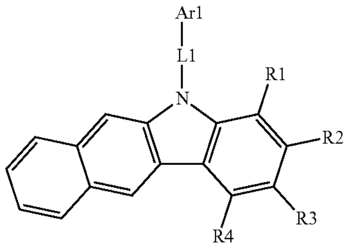

In Chemical Formula 1,

R1 to R4 are the same as or different from each other, and each independently hydrogen; or a substituted or unsubstituted aryl group having 6 to 40 carbon atoms, and at least one of R3 to R4 is a substituted or unsubstituted aryl group having 6 to 40 carbon atoms, L1 is a direct bond; or a substituted or unsubstituted arylene group having 6 to 40 carbon atoms, Ar1 is a fused bicyclic heteroaryl group comprising two or more N atoms and having 2 to 40 carbon atoms.

When using the benzocarbazole-based compound represented by Chemical Formula 1 in an organic material layer of an organic light emitting device, efficiency of the organic light emitting device is enhanced, and a low driving voltage and excellent lifetime properties are obtained as well.

In the Present Specification,

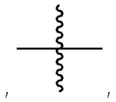

means a site linking to other substituents or Chemical Formula 1.

In the present specification, a description of a certain part "comprising" certain constituents means capable of further comprising other constituents, and does not exclude other constituents unless particularly stated on the contrary.

In the present, specification, a description of one member being placed "on" another member comprises not only a case of the one member adjoining the another member but a case of still another member being present between the two members.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

Examples of the substituents are described below, however, the substituents are not limited thereto.

The term "substituted or unsubstituted" in the present specification means being substituted with one, two or more substituents selected from the group consisting or deuterium; a halogen group; a nitrite group; a hydroxyl group; a carbonyl group; an ester group; a silyl group; a boron group; a substituted or unsubstituted alkyl group; a substituted or unsubstituted cyclo-alkyl group; a substituted or unsubstituted alkoxy group; a substituted or unsubstituted alkenyl group; a substituted or unsubstituted alkylamine group; a substituted or unsubstituted heteroarylamine group; a substituted or unsubstituted arylamine group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may comprise a biphenyl group. In other, words, a biphenyl group may be an aryl group, or interpreted as a substituent linking two phenyl groups.

In the present specification, examples of the halogen group may comprise fluorine (F), chlorine (Cl), bromine (Br) or iodine (I).

In the present specification, the number of carbon atoms of the carbonyl group is not particularly limited, but is preferably from 1 to 40. Specifically, compounds having structures as below may be included, however, the carbonyl group is not limited thereto.

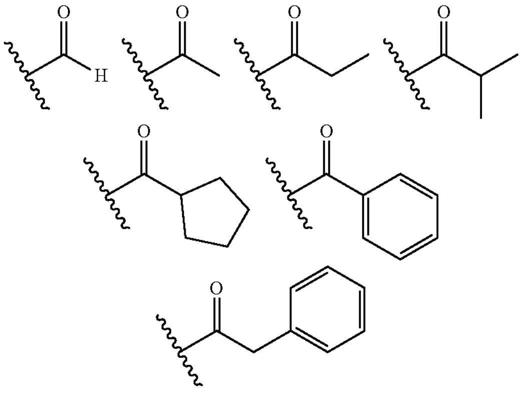

In the present specification, in the ester group, the oxygen of the ester group may be substituted with a linear, branched or cyclic alkyl group having 1 to 40 carbon atoms or an aryl group having 6 to 30 carbon atoms. Specifically, compounds having the following structural formulae may be included, however, the ester group is not limited thereto.

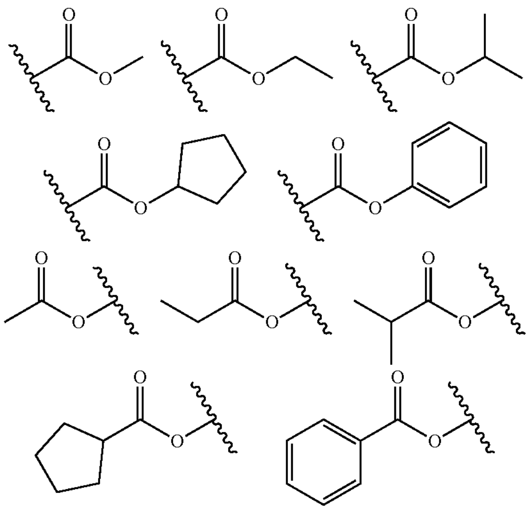

In the present specification, the silyl group may be represented by a chemical formula of —$SiY_aY_bY_c$, and $Y_a$, $Y_b$ and $Y_c$ may each be hydrogen; a substituted or unsubstituted alkyl group; or a substituted or unsubstituted aryl group. Specific examples of the silyl group may comprise a trimethylsilyl group; a triethylsilyl group; a t-butyldimethylsilyl group; a vinyldimethylsilyl group; a propyldimethylsilyl group; a triphenylsilyl group; a diphenylsilyl group; a phenylsilyl group and the like, but are not: limited thereto.

In the present specification, the boron group may be represented by a chemical formula of —$BY_dY_d$, and $Y_d$ and $Y_d$ may each be hydrogen a substituted or unsubstituted alkyl group; or a substituted or unsubstituted aryl group. Specific examples of the boron group may comprise a trimethylboron group, a triethylboron group, a t-butyldimethylboron group, a triphenylboron group, a phenylboron group and the like, but are not limited thereto.

In the present specification, the alkyl group may be linear or branched, and although not particularly limited thereto, the number of carbon atoms is preferably from 1 to 40. According to one embodiment, the number of carbon atoms of the alkyl group is from 1 to 20. According to another embodiment, the number of carbon atoms of the alkyl group is from 1 to 10. According to another embodiment, the number of carbon atoms of the alkyl group is from 1 to 6. Specific examples of the alkyl group may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 4-methylhexyl group, a 5-methylhexyl group and the like, but are not limited thereto.

In the present specification, the alkoxy group may be linear, branched or cyclic. The number of carbon atoms of the alkoxy group is not particularly limited, but is preferably from 1 to 40. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy and the like, but are not limited thereto.

The alkyl group, the alkoxy group and other substituents comprising an alkyl group part: described in the present specification comprise both linear and branched forms.

In the present specification, the alkenyl group way be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to another embodiment, the number of carbon atoms of the alkenyl group is from 2 to 6. Specific examples thereof may comprise vinyl, 1-propenyl, isopropenyl, 1-butenyl, 2-butenyl, 3-butenyl, l-pentenyl, 2-pentenyl, 3-pentenyl, 3-methyl-1-butenyl 1,3-butadienyl and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 40. According to another embodiment, the number of carbon atoms of the cycloalkyl group is from 3 to 20. According to another embodiment, the number of carbon atoms of the cycloalkyl group is from 3 to 6. Specific examples thereof may comprise cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present, specification the alkylamine group preferably has, although not particularly limited thereto, 1 to 40 carbon atoms. Specific examples of the alkylamine group may comprise a methylamine group, a dimethylamine group, an ethylamine group, a diethylamine group and the like, but are not limited thereto.

In the present specification, examples of the arylamine group comprise a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group comprising two or more aryl groups may comprise monocyclic aryl groups, polycyclic aryl groups, or both monocyclic aryl groups and polycyclic aryl groups.

Specific examples of the arylamine group may comprise phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenyl amine group and the like, but are not limited thereto.

In the present specification, examples of the heteroarylamine group may comprise a substituted or unsubstituted monoheteroarylamine group, a substituted or unsubstituted diheteroarylamino group, or a substituted or unsubstituted triheteroarylamine group. The heteroaryl group in the heteroarylamine group may be a monocyclic heterocyclic group or a polycyclic heterocyclic group. The heteroarylamine group comprising two or more heterocyclic groups may comprise monocyclic heterocyclic groups, polycyclic heterocyclic groups, or both monocyclic heterocyclic groups and polycyclic heterocyclic groups.

In the present specification, the aryl group is not particularly limited, but preferably has 6 to 60 carbon atoms, and may be a monocyclic aryl group or a polycyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof may comprise a phenyl group, a biphenyl group, a terphenyl group and the like, but are not limited thereto. Examples of the polycyclic aryl group may comprise a naphthyl group, an anthracenyl group, a pyrenyl group, a perylenyl group, a triphenyl group, a chrysenyl group, a fluorenyl group, a fluoranthene group, a phenanthrene group, a triphenylene group, a spirobifluorenyl group

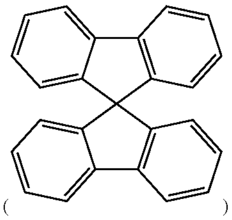 [SMILES: c1ccc2c(c1)-c1ccccc1C21c2ccccc2-c2ccccc21]

and the like, but are not limited thereto.

In the present specification the fluorenyl group may be substituted, and two substituents may bond to each other to form a spiro structure.

When the fluorenyl group is substituted, substituted fluorenyl groups such as

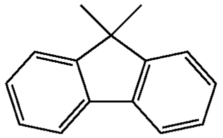

(9,9-dimethylfluorenyl group) and

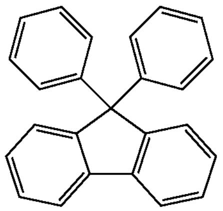 [SMILES: c1ccc(C2(c3ccccc3)c3ccccc3-c3ccccc32)cc1]

(9/9-diphenylfluorenyl group) may be included. However, the structure is not limited thereto.

In the present specification, the heterocyclic group is a heterocyclic group comprising one or more of N, O, P, S, Si and Se as a heteroatom, and although not particularly limited thereto, the number of carbon atoms is preferably from 2 to 60. According to one embodiment, the number of carbon atoms of the heterocyclic group is from 2 to 30. Examples of the heterocyclic group may include a pyridyl group, a pyrrole group, a pyrimidyl group, a pyridazinyl group, a furanyl group, a thiophenyl group, an imidazole group, a pyrazole group, an oxazole group, an isoxazole group, a thiazole group, an isothiazole group, a triazolo group, an oxadiazole group, a thiadiazole group, a dithiazole group, a tetrazole group, a pyranyl group, a thiopyranyl group, a pyrazinyl group, an oxazinyl group, a thiazinyl group, a dioxinyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a benzothiophene group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzimidazoquinazoline group, a benzimidazophenanthridine group or the like, but are not limited thereto.

In the present specification, descriptions on the heterocyclic group provided above may be applied to the heteroaryl group except for being aromatic.

In the present specification, descriptions on the aryl group provided above may be applied to the arylene group except for being divalent.

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the "ring" in the substituted or unsubstituted ring formed by adjacent groups bonding to each other means a substituted or unsubstituted hydrocarbon ring; or a substituted or unsubstituted heteroring.

In the present specification, the hydrocarbon ring may be aromatic, aliphatic or a fused ring of aromatic and aliphatic, and may be selected from among examples of the cycloalkyl group or the aryl group except for those that are divalent.

In the present specification, descriptions on the aryl group may be applied to the aromatic hydrocarbon ring except for being divalent.

In the present specification, the heteroring comprises one or more atoms that are not carbon, that is, heteroatoms, and specifically, the heteroatom may comprise one or more atoms selected from the group consisting of O, N, Se, S and the like. The heteroring may be monocyclic or polycyclic, aromatic, aliphatic or a fused ring of aromatic and aliphatic, and may be selected from among examples of the heteroaryl group except for those that are not monovalent.

In one embodiment of the present specification, Ar1 is a fused bicyclic heteroaryl group comprising two or more N atoms and having 2 to 30 carbon atoms.

In another embodiment, Ar1 is a fused bicyclic heteroaryl group comprising two to four N atoms and having 2 to 30 carbon atoms.

In one embodiment of the present specification, Ar1 is represented by the following Chemical Formula 2.

[Chemical Formula 2]

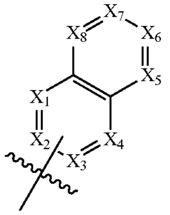

In Chemical Formula 2, $X_1$ to $X_8$ are N, CH or CR, two or more of $X_1$ to $X_8$ are N, and one or more of $X_1$ to $X_8$ are CR, and R is a substituted or unsubstituted aryl group having 6 to 40 carbon atom, or a substituted or unsubstituted heteroaryl group having 2 to 40 carbon atoms.

According to one embodiment of the present specification, $X_1$ to $X_8$ are N, CH or CR, two to four of $X_1$ to $X_8$ are N, one to four of $X_1$ to $X_8$ are CR, and R is a substituted or unsubstituted aryl group having 6 to 40 carbon atom; or a substituted or unsubstituted heteroaryl group having 2 to 40 carbon atoms.

According to another embodiment, R is a substituted or unsubstituted aryl group having 6 to 30 carbon atoms; or a substituted or unsubstituted heteroaryl group having 2 to 30 carbon atoms.

According to one embodiment of the present specification, Ar1 is represented by any one of the following Chemical Formula 3 to Chemical Formula 18.

[Chemical Formula 3]

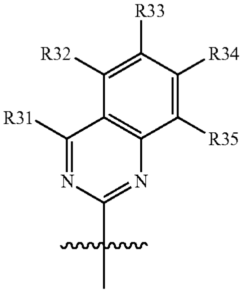

[Chemical Formula 4]

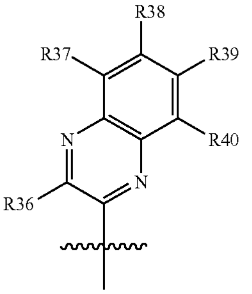

[Chemical Formula 5]

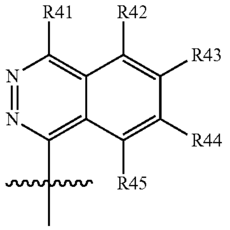

[Chemical Formula 6]

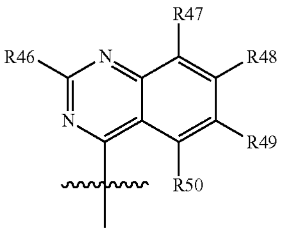

-continued

[Chemical Formula 7]

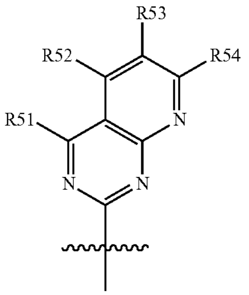

[Chemical Formula 8]

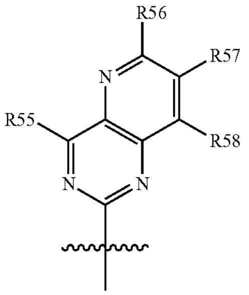

[Chemical Formula 9]

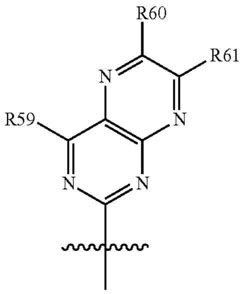

[Chemical Formula 10]

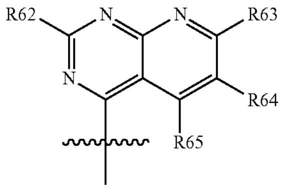

[Chemical Formula 11]

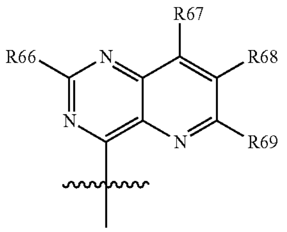

[Chemical Formula 12]

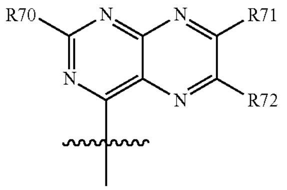

-continued

[Chemical Formula 13]

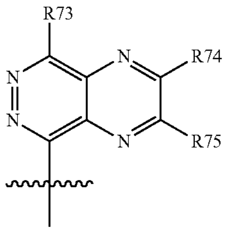

[Chemical Formula 14]

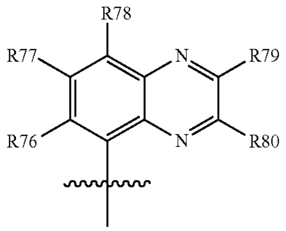

[Chemical Formula 15]

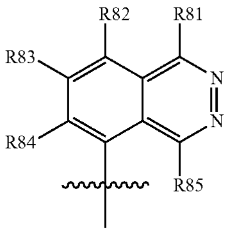

[Chemical Formula 16]

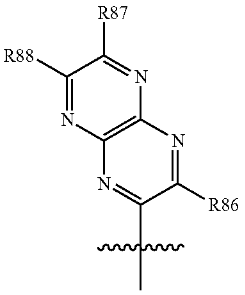

[Chemical Formula 17]

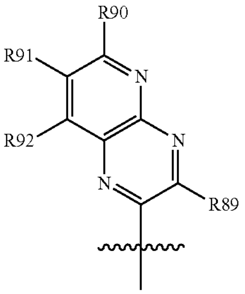

[Chemical Formula 18]

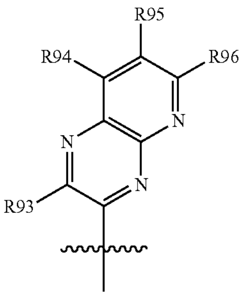

In Chemical Formulae 3 to 13,

R31 to R96 are the same as or different front each other, and each independently hydrogen; a substituted or unsubstituted aryl group having 6 to 40 carbon atoms; or a substituted or unsubstituted heteroaryl group having 2 to 40 carbon atoms, however, at least one of R31 to R35; at least one of R36 to R40; at least one of R41 to R45; at least one of R46 to R50; at least one of R51 to R54 at least: one of R55 to R58; at least one of R59 to R61; at least one of R62 to R65; at least one of R66 to R69; at least one of R70 to R72; at least one of R73 to R75; at least one of R76 to R80; at least one of R81 to R85; at least one of R86 to R88; at least one of R89 to R92; and at least one of R93 to R96 are a substituted or unsubstituted aryl group having 6 to 40 carbon atoms; or a substituted or unsubstituted heteroaryl group having 2 to 40 carbon atoms.

According to one embodiment of the present disclosure, R31 to R96 are the same as or different from each other, and each independently hydrogen; a substituted or unsubstituted aryl group having 6 to 30 carbon atoms; or a substituted or unsubstituted heteroaryl group having 2 to 30 carbon atoms, however, at least one of R31 to R35; at least one of R36 to R40; at least one of R41 to R45; at least one of R46 to R50; at least one of R51 to R54; at least one of R55 to R58; at least one of R59 to R61; at least one of R62 to R65; at least one of R66 to R69; at least one of R70 to R72; at least one of R73 to R75; at least one of R76 to R80; at least one of R81 to R85; at least one of R86 to R88; at least one of R89 to R92; and at least one of R93 to R96 are a substituted or unsubstituted aryl group having 6 to 30 carbon atoms; or a substituted or unsubstituted heteroaryl group having 2 to 30.

In one embodiment of the present disclosure, R31 to R96 are the same as or different from each other, and each independently hydrogen; an aryl group having 3 to 40 carbon atoms unsubstituted or substituted with deuterium, a nitrile group, an alkyl group having 1 to 20 carbon atoms, an aryl group having 6 to 30 carbon atoms unsubstituted or substituted with deuterium, and a heteroaryl group having 2 to 30 carbon atoms; or a heteroaryl group having 2 to 40 carbon atoms unsubstituted or substituted with deuterium, a nitrile group, an alkyl group having 1 to 20 carbon atoms, an aryl group having 6 to 30 carbon atoms unsubstituted or substituted with deuterium, and a heteroaryl group having 2 to 30 carbon atoms, and at least one of R31 to R35; at least one of R36 to R40; at least one of R41 to R45; at least one of R46 to R50; at least one of R51 to R54; at least one of R55 to R58; at least one of R59 to R61; at least one of R62 to R65; at least one of R66 to R69; at least one of R70 to R72; at least one of R73 to R75; at least one of R76 to R80; at least one of R81 to R85; at least one of R86 to R88; at least one of R89 to R92; and at least one of R93 to R96 are an aryl group having 6 to 40 carbon atoms unsubstituted or substituted with deuterium, a nitrile group, an alkyl group having 1 to 20 carbon atoms, an aryl group having 6 to 30 carbon atoms unsubstituted or substituted with deuterium, and a heteroaryl group having 2 to 30 carbon atoms; or a heteroaryl group having 2 to 40 carbon atoms unsubstituted or substituted with deuterium, a nitrile group, an alkyl group having 1 to 20 carbon atoms, an aryl group having 6 to 30 carbon atoms unsubstituted or substituted with deuterium, and a heteroaryl group having 2 to 30 carbon atoms.

In one embodiment of the present specification, R31 to R35 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R31 to R35 is a substituted or unsubstituted aryl group having 6 to 40 carbon atoms; or a substituted or unsubstituted heteroaryl group having 2 to 40 carbon atoms.

In another embodiment, R31 to R35 are the same as or different from each other, and each independently hydrogen; an aryl group having 6 to 40 carbon atoms unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms; or a heteroaryl group having 2 to 40 carbon atoms unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms, and at least one of R31 to R35 is an aryl group having 6 to 40 carbon atoms unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms; or a heteroaryl group having 2 to 40 carbon atoms unsubstituted or substituted with deuterium, a nitrile group, or an aryl group having 6 to 60 carbon atoms unsubstituted or substituted with deuterium, a heteroaryl group having 2 to 60 carton atoms, or an alkyl group having 1 to 30 carbon atoms.

In another embodiment, R31 to R35 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R31 to R35 is a substituted or unsubstituted aryl group having 6 to 30 carbon atoms, or a substituted or unsubstituted heteroaryl group having 2 to 30 carbon atoms.

According to another embodiment, at least one of R31 to R35 is a substituted or unsubstituted phenyl group; a substituted or unsubstituted naphthyl group; a substituted or unsubstituted biphenyl group; a substituted or unsubstituted phenanthrenyl group; a substituted or unsubstituted triphenylene group; a substituted or unsubstituted fluorenyl group; a substituted or unsubstituted benzofluorenyl group; & substituted or unsubstituted carbazole group; a substituted or unsubstituted dibenzofuranyl group; a substituted or unsubstituted dibenzothiophenyl group; a substituted or unsubstituted benzocarbazole group; a substituted or unsubstituted pyridyl group; a substituted or unsubstituted naphthobenzofuranyl group; or a substituted or unsubstituted naphthobenzothiophenyl group.

In another embodiment, at least one of R31 to R35 is a phenyl group unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms; a naphthyl group unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms; a biphenyl group unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms; a phenanthrenyl group unsubstituted or substituted with deuterium, a nitrile group, an aryl group having 6 to 60 carbon atoms unsubstituted or substituted with deuterium, heteroaryl group having 2 to 60 carbon atoms, or an alkyl group having 1 to 30 carbon atoms; a triphenylene group unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms; a fluorenyl group unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms; a benzofluorenyl group unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms; a carbazole group unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms; a dibenzofuranyl group unsubstituted or substituted with deuterium, a nitrite group, an aryl group having 6 to 60 carbon atoms unsubstituted or substituted with deuterium, a heteroaryl group having 2 to 60 carbon atoms, or an alkyl group having 1 to 30 carbon atoms; a dibenzothiophenyl group unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms; a benzocarbazole group unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms; a pyridyl group unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms; a naphthobenzofuranyl group unsubstituted or substituted with deuterium, a nitrile group, an aryl group having 6 to 60 carbon atoms unsubstituted or substituted with deuterium, a heteroaryl group having 2 to 60 carbon atom, or an alkyl group having 1 to 30 carbon atoms; or a naphthobenzothiophenyl group unsubstituted or substituted with deuterium, a nitrile group, an aryl group having 6 to 60 carbon atoms unsubstituted or substituted with deuterium, a heteroaryl group having 2 to 60 carbon atoms, or an alkyl group having 1 to 30 carbon atoms.

According to another embodiment, at least one of R31 to R35 in a phenyl group unsubstituted or substituted with deuterium, a nitrile group, a naphthyl group, a pyridyl group or a quinoline group; a naphthyl group unsubstituted or substituted with deuterium; a biphenyl group unsubstituted or substituted with a nitrile group; a phenanthrenyl group; a triphenylene group; a fluorenyl group substituted with a methyl group; a benzofluorenyl group substituted with a methyl group; a carbazole group substituted with a phenyl group unsubstituted or substituted with deuterium, a biphenyl group unsubstituted or substituted with deuterium, or a naphthyl group unsubstituted or substituted with deuterium; a dibenzofuranyl group; a dibenzothiophenyl group; a benzocarbazole group substituted with a phenyl group unsubstituted or substituted with deuterium; a pyridyl group unsubstituted or substituted with a naphthyl group or a quinoline group; a naphthobenzofuranyl group; or a naphthobenzothiophenyl group.

In one embodiment of the present specification, R36 to R40 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R36 to R40 is a substituted or unsubstituted aryl group having 6 to 40 carbon atoms; or a substituted or unsubstituted heteroaryl group having 2 to 40 carbon atoms.

In one embodiment of the present specification, R36 to R40 are the same as or different from each other, and each independently hydrogen; an aryl group having 6 to 40 carbon atoms unsubstituted or substituted with deuterium, a nitrile group, an alkyl group having 1 to 30 carbon atoms, an aryl group having 6 to 60 carbon atoms or a heteroaryl group having 2 to 60 carbon atoms; or a heteroaryl group having 2 to 40 carbon atoms unsubstituted or substituted with deuterium, a nitrile group, an alkyl group having 1 to 30 carbon atoms, an aryl group having 6 to 60 carbon atoms or a heteroaryl group having 2 to 30 carbon atoms, and at least one of R36 to R40 is an aryl group having 6 to 40 carbon atoms unsubstituted or substituted with deuterium, a nitrile group, an alkyl group having 1 to 30 carbon atoms, an aryl group having 6 to 60 carbon atoms or a heteroaryl group having 2 to 60 carbon atoms; or a heteroaryl group having 2 to 40 carbon atoms unsubstituted or substituted with deuterium, a nitrile group, an alkyl group having 1 to 30 carbon atoms, an aryl group having 6 to 60 carbon atoms or a heteroaryl group having 2 to 60 carbon atoms.

In one embodiment of the present specification, R36 to R40 are the same as or different, from each other, and each independently hydrogen; a substituted or unsubstituted aryl group having 6 to 30 carbon atoms; or a substituted or unsubstituted heteroaryl group having 2 to 30 carbon atoms, and at least one of R36 to R40 is a substituted or unsubstituted aryl group having 6 to 30 carbon atoms; or a substituted or unsubstituted heteroaryl group having 2 to 30 carbon atoms.

According to another embodiment, at least one of R36 to R40 is a substituted or unsubstituted phenyl group; a substituted or unsubstituted biphenyl group; a substituted or unsubstituted naphthyl group; a substituted or unsubstituted phenanthrenyl group; a substituted or unsubstituted triphenylene group; a substituted or unsubstituted pyridyl group; a substituted or unsubstituted fluorenyl group; a substituted or unsubstituted dibenzofuranyl group; a substituted or unsubstituted dibenzothiophenyl group; a substituted or unsubstituted carbazole group; or a substituted or unsubstituted benzocarbazole group.

According to another embodiment, at least one of R36 to R40 is a phenyl group unsubstituted or substituted with deuterium, a nitrile group, an alkyl group having 1 to 30 carbon atoms, an aryl group having 6 to GO carbon atoms or a heteroaryl group having 2 to 60 carbon atoms; a biphenyl group unsubstituted or substituted with deuterium, a nitrile group, an alkyl group having 1 to 30 carbon atoms, an aryl group having 6 to 60 carbon atoms or a heteroaryl group having 2 to 60 carbon atoms; a naphthyl group unsubstituted or substituted with deuterium, a nit rile group, an alkyl group having 1 to 30 carbon atoms, an aryl group having 6 to 60 carbon atoms or a heteroaryl group having 2 to 60 carbon atoms; a phenanthrenyl group unsubstituted or substituted with deuterium, a nitrile group, an alkyl group having 1 to 30 carbon atoms, an aryl group having 6 to 60 carbon atoms or a heteroaryl group having 2 to 60 carbon atoms; a triphenylene group unsubstituted or substituted with deuterium, a nitrile group, an alkyl, group having 1 to 30 carbon atoms, an aryl group having 6 to 60 carbon atoms or a heteroaryl group having 2 to 60 carbon atoms; a pyridyl group unsubstituted or substituted with deuterium, a nitrile group, an alkyl group having 1 to 30 carbon atoms, an aryl group having 6 to 60 carbon atoms or a heteroaryl group having 2 to 60 carbon atoms; a fluorenyl group unsubstituted or substituted with deuterium, a nitrile group, an alkyl group having 1 to 30 carbon atoms, an aryl group having 6 to 60 carbon atoms or a heteroaryl group having 2 to 60 carbon atoms; a dibenzofuranyl group unsubstituted or substituted with deuterium, a nitrile group, an alkyl group having 1 to 30 carbon atoms, an aryl group having 6 to 60 carbon atoms or a heteroaryl group having 2 to 60 carbon atoms; a dibenzothiophenyl group unsubstituted or substituted with deuterium, a nitrile group, an alkyl group having 1 to 30 carbon atoms, an aryl group having 6 to 60 carbon atoms or a heteroaryl group having 2 to 60 carbon atoms; a carbazole group unsubstituted or substituted with deuterium, a nitrile group, an alkyl group having 1 to 30 carbon atoms, an aryl group having 6 to 60 carbon atoms or a heteroaryl group having 2 to 60 carbon atoms; or a benzocarbazole group unsubstituted or substituted with deuterium, a nitrile group, an alkyl group having 1 to 30 carbon atoms, an aryl group having 6 to 60 carbon atoms or a heteroaryl group having 2 to 60 carbon atoms.

In another embodiment, at least one of R36 to R40 is a phenyl group unsubstituted or substituted with deuterium, a nitrile group or a naphthyl group; a biphenyl group; a naphthyl group unsubstituted or substituted with a nitrile group or a phenyl group; a phenanthrenyl group; a triphenylene group; a pyridyl group; a fluorenyl group substituted with a methyl, group; a dibenzofuranyl group; a dibenzothiophene group; a carbazole group substituted with a phenyl group unsubstituted or substituted with deuterium; or a benzocarbazole group substituted with a phenyl group.

In one embodiment of the present specification, R41 to R45 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R41 to R45 is a substituted or unsubstituted aryl group having 6 to 40 carbon atoms; or a substituted or unsubstituted heteroaryl group having 2 to 40 carbon atoms.

In another embodiment, R41 to R45 are the same as or different from each other, and each independently hydrogen; an aryl group having 6 to 40 carbon atoms unsubstituted or substituted with an alkyl group having 1 to 30 carbon atoms or an aryl group having 6 to 30 carbon atoms; or a heteroaryl group having 2 to 40 carbon atoms unsubstituted or substituted with an alkyl group having 1 to 30 carbon atoms or an aryl group having 6 to 30 carbon atoms, and at least one of R41 to R45 is an aryl group having 6 to 40 carbon atoms unsubstituted or substituted with an alkyl group having 1 to 30 carbon atoms or an aryl group having 6 to 30 carbon atoms; or a heteroaryl group having 2 to 40 carbon atoms unsubstituted or substituted with an alkyl group having 1 to 30 carbon atoms or an aryl group having 6 to 30 carbon atoms.

In one embodiment of the present specification, R41 to R45 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R41 to R45 is a substituted or unsubstituted aryl group having 6 to 30 carbon atoms or a substituted or unsubstituted heteroaryl group having 2 to 30 carbon atoms.

According to another embodiment, at least one of R41 to R45 is a substituted or unsubstituted phenyl group; a substituted or unsubstituted biphenyl group; a substituted or unsubstituted naphthyl group; a substituted or unsubstituted phenanthrenyl group; a substituted or unsubstituted terphenyl group; a substituted or unsubstituted fluorenyl group; a substituted or unsubstituted dibenzofuranyl group; or a substituted or unsubstituted dibenzothiophenyl group.

According to another embodiment, at least one of R41 to R45 is a phenyl group substituted with a naphthyl group a biphenyl group; a naphthyl group unsubstituted or substituted with a phenyl group; a phenanthrenyl group; a terphenyl group; a fluorenyl group substituted with a methyl group; a dibenzofuranyl group; or a dibenzothiophenyl group.

In one embodiment of the present specification, R46 to R50 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R46 to R50 is a substituted or unsubstituted aryl group having 6 to 40 carbon atoms; or a substituted or unsubstituted heteroaryl group having 2 to 40 carbon atoms.

In one embodiment of the present specification. R46 to R50 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R46 to R50 is a substituted or unsubstituted aryl group having 6 to 30 carbon atoms; or a substituted or unsubstituted heteroaryl group having 2 to 30 carbon atoms.

According to another embodiment, at least one of R46 to R50 is a substituted or unsubstituted phenyl group; a substituted or unsubstituted biphenyl group; a substituted or unsubstituted terphenyl group; a substituted or unsubstituted naphthyl group; a substituted or unsubstituted phenanthrenyl group; a substituted or unsubstituted triphenylene group; a substituted or unsubstituted fluorenyl group; a substituted or unsubstituted pyridyl group; a substituted or unsubstituted quinoline group; a substituted or unsubstituted dibenzofuranyl group; a substituted or unsubstituted dibenzothiophenyl group; a substituted or unsubstituted carbazole group; or a substituted or unsubstituted benzocarbazole group.

In another embodiment, at least one of R46 to R50 is a phenyl group unsubstituted or substituted with deuterium, a nitrile group, a naphthyl group, a quinoline group, deuterium and a quinoline group, or a pyridyl group; a biphenyl group; a terphenyl group; a naphthyl group unsubstituted or substituted with deuterium; a phenanthrenyl group; a triphenylene group; a fluorenyl group substituted with a methyl group; a pyridyl group unsubstituted or substituted with a quinoline group; a quinoline group; a dibenzofuranyl group; a dibenzothiophenyl group; a carbazole group substituted with a phenyl group, a biphenyl group or a naphthyl group; or a benzocarbazole group unsubstituted or substituted with a phenyl group unsubstituted or substituted with deuterium.

In one embodiment of the present specification, R51 to R54 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R51 to R54 is a substituted or unsubstituted aryl group having 6 to 40 carbon atoms; or a substituted or unsubstituted heteroaryl group having 2 to 40 carbon atoms.

In one embodiment of the present specification, R51 to R54 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R51 to R54 is a substituted or unsubstituted aryl group having 6 to 30 carbon atoms; or a substituted or unsubstituted heteroaryl group having 2 to 30 carbon atoms.

According to another embodiment, at least: one of R51 to R54 is a substituted or unsubstituted phenyl group; a substituted or unsubstituted biphenyl group; a substituted or unsubstituted naphthyl group; or a substituted or unsubstituted carbazole group.

According to another embodiment, at least one of R51 to R54 is a phenyl group; a biphenyl group unsubstituted or substituted with a nitrile group; a naphthyl group; or a carbazole group substituted with a phenyl group.

In one embodiment of the present specification, R55 to R58 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R55 to R58 is a substituted or unsubstituted aryl group having 6 to 40 carbon atoms; or a substituted or unsubstituted heteroaryl group having 2 to 40 carbon atoms.

In one embodiment of the present specification, R55 to R58 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R55 to R58 is a substituted or unsubstituted aryl group having 6 to 30 carbon atoms; or a substituted or unsubstituted heteroaryl group having 2 to 30 carbon atoms.

In another embodiment, at least one of R55 to R58 is a substituted or unsubstituted phenyl group; a substituted or unsubstituted naphthyl group; or a substituted or unsubstituted carbazole group.

In another embodiment, at least one of R55 to R58 is a phenyl group unsubstituted or substituted with deuterium; a naphthyl group; or a carbazole group substituted with a phenyl group.

In one embodiment of the present specification, R59 to R61 are the same as or different from each other, and each independently hydrogen; a substituted or unsubstituted aryl group having 6 to 40 carbon atoms; or a substituted or unsubstituted heteroaryl group having 2 to 40 carbon atoms, and au least one of R59 to R61 is a substituted or unsubstituted aryl group having 6 to 40 carbon atoms; or a substituted or unsubstituted heteroaryl group having 2 to 40 carbon atoms.

In one embodiment of the present specification, R59 to R61 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R59 to R61 is a substituted or unsubstituted aryl group having 6 to 30 carbon atoms; or a substituted or unsubstituted heteroaryl group having 2 to 30 carbon atoms.

In another embodiment, at least one of R59 to R61 is a substituted or unsubstituted phenyl group; a substituted or unsubstituted naphthyl group; or a substituted or unsubstituted carbazole group.

In another embodiment, at least one of R59 to R61 is a phenyl group unsubstituted or substituted with a nitrite group; a naphthyl group; or a carbazole group substituted with a phenyl group.

In one embodiment of the present spec if-cat ion, R62 to R65 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R62 to R65 is a substituted or unsubstituted aryl group having 6 to 40 carbon atoms; or a substituted or unsubstituted heteroaryl group having 2 to 40 carbon atoms.

In one embodiment of the present specification, R62 to R65 are the same as or different from each other, and each independently hydrogen; a substituted or unsubstituted aryl group having 6 to 30 carbon atoms; or a substituted or unsubstituted heteroaryl group having 2 to 30 carbon atoms, and at least one on R62 to R65 is a substituted or unsubstituted aryl group having 6 to 30 carbon atoms; or a substituted or unsubstituted heteroaryl group having 2 to 30 carbon atoms.

In another embodiment, at least one of R62 to R65 is a substituted or unsubstituted phenyl group; a substituted or unsubstituted biphenyl group; a substituted or unsubstituted naphthyl group; a substituted or unsubstituted fluorenyl group; a substituted or unsubstituted dibenzofuranyl group; a substituted or unsubstituted dibenzothiophenyl group; or a substituted or unsubstituted carbazole group.

In another embodiment, at least one of R62 to R65 is a phenyl group; a biphenyl group substituted with deuterium; a naphthyl group; fluorenyl group substituted with a methyl group; a dibenzofuranyl group; a dibenzothiophenyl group; or a carbazole group substituted with a phenyl group.

In one embodiment of the present specification, R66 to R69 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R66 to R69 is a substituted or unsubstituted aryl group having 6 to 40 carbon atoms; or a substituted or unsubstituted heteroaryl group having 2 to 40 carbon atoms.

In one embodiment of the present specification, R66 to R69 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R66 to R69 is a substituted or unsubstituted aryl group having 6 to 30 carbon atoms; or a substituted or unsubstituted heteroaryl group having 2 to 30 carbon atoms.

In another embodiment, at least one of R66 to R69 is a substituted or unsubstituted phenyl group; a substituted or unsubstituted naphtyl group; a substituted or unsubstituted dibenzofuranyl group; or a substituted or unsubstituted carbazole group.

In another embodiment, at least: one of R66 to R69 as a phenyl group substituted with a nitrile group; a naphthyl group; a dibenzofuranyl group; or a carbazole group substituted with a phenyl group.

In one embodiment of the present specification, R70 to R72 are the same as or different from each other and each independently hydrogen; a substituted or unsubstituted aryl group having 6 to 40 carbon atoms; or a substituted or unsubstituted heteroaryl group having 2 to 40 carbon atoms, and at least one of R70 to R72 is a substituted or unsubstituted aryl group having 6 to 40 carbon atoms; or a substituted or unsubstituted heteroaryl group having 2 to 40 carbon atoms.

In one embodiment of the present specification R70 to R72 are the same as or different from each other and each independently hydrogen; a substituted or unsubstituted aryl group having 6 to 30 carbon atom; or a substituted or unsubstituted heteroaryl group having 2 to 30 carbon atoms, and at least one of R70 to R72 is a substituted or unsubstituted aryl group having 6 to 30 carbon atoms; or a substituted or unsubstituted heteroaryl group having 2 to 30 carbon atoms.

In another embodiment, at least one of R70 to R72 is a substituted or unsubstituted fluorenyl group; or a substituted or unsubstituted carbazole group.

In another embodiment, at least: one of R70 to R72 is a fluorenyl group substituted with a methyl group; or a carbazole group substituted with a phenyl group unsubstituted or substituted with deuterium.

In one embodiment of the present specification, R73 to R75 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R73 to R75 is a substituted or unsubstituted aryl group having 6 to 40 carbon atoms; or a substituted or unsubstituted heteroaryl group having 2 to 40 carbon atoms.

In one embodiment of the present specification, R73 to R75 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R73 to R75 is a substituted or unsubstituted aryl group having 6 to 30 carbon atoms; or a substituted or unsubstituted heteroaryl group having 2 to 30 carbon atoms.

In another embodiment, at least one of R73 to R75 is a substituted or unsubstituted fluorenyl group; a substituted or unsubstituted dibenzofuranyl group; a substituted or unsubstituted dibenzothiophenyl group; or a substituted or unsubstituted carbazole group.

In another embodiment, at least one of R73 to R75 is a fluorenyl group substituted with a methyl group; a dibenzofuranyl group; a dibenzothiophenyl group; or a carbazole group substituted with a phenyl group.

In one embodiment of the present specification, R76 to R80 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R76 to R80 is a substituted or unsubstituted aryl group having 6 to 40 carbon atoms; or a substituted or unsubstituted heteroaryl group having 2 to 40 carbon atoms.

In one embodiment of the present specification, R76 to R80 are the same as or different front each other, and each independently hydrogen; a substituted or unsubstituted aryl group having 6 to 30 carbon atoms; or a substituted or unsubstituted heteroaryl group having 2 to 30 carbon atoms, and at least one of R76 to R80 is a substituted or unsubstituted aryl group having 6 to 30 carbon atoms; or a substituted or unsubstituted heteroaryl group having 2 to 30 carbon atoms.

In another embodiment, at least one of R76 to R80 is a substituted or unsubstituted phenyl group; a substituted or unsubstituted naphthyl group; a substituted or unsubstituted fluorenyl group; a substituted or unsubstituted dibenzofuranyl group; a substituted or unsubstituted dibenzothiophenyl group; or a substituted or unsubstituted carbazole group.

In another embodiment, at least one of R76 to R80 is a phenyl group unsubstituted or substituted with a nitrile group or a naphthyl group; a naphthyl group unsubstituted or substituted with a phenyl group; a fluorenyl group substituted with a methyl group; a dibenzofuranyl group; a dibenzothiophenyl group; or a carbazole group substituted with a phenyl group.

In one embodiment of the present specification, R81 to R85 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R81 to R85 is a substituted or unsubstituted aryl group having 6 to 40 carbon atoms; or a substituted or unsubstituted heteroaryl group having 2 to 40 carbon atoms.

In one embodiment of the present specification, R81 to R85 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R81 to R85 is a substituted or unsubstituted aryl group having 6 to 30 carbon atoms; or a substituted or unsubstituted heteroaryl group having 2 to 30 carbon atoms.

According to another embodiment, at least one of R81 to R85 is a substituted or unsubstituted phenyl group; a substituted or unsubstituted biphenyl group; a substituted or unsubstituted naphthyl group; a substituted or unsubstituted phenanthrenyl group; a substituted or unsubstituted triphenylene group; a substituted or unsubstituted fluorenyl group; a substituted or unsubstituted dibenzofuranyl group; a substituted or unsubstituted dibenzothiophenyl group; or a substituted or unsubstituted carbazole group.

According to another embodiment, at least one of R81 to R85 is a phenyl group unsubstituted or substituted with deuterium; a biphenyl group; a naphthyl group; a phenanthrenyl group; a triphenylene group; a fluorenyl group substituted with a methyl group; a dibenzofuranyl group; a dibenzothiophenyl group; or a carbazole group substituted with a phenyl group.

In one embodiment of the present specification, R86 to R88 are the same as or different from each other, and each independently hydrogen; a substituted or unsubstituted aryl group having 6 to 40 carbon atoms or a substituted or unsubstituted heteroaryl group having 2 to 40 carbon atoms, and at least one of R86 to R88 is a substituted or unsubstituted aryl group having 6 to 40 carbon atoms; or a substituted or unsubstituted heteroaryl group having 2 to 40 carbon atoms.

In one embodiment of the present specification, R86 to R88 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R86 to R88 is a substituted or unsubstituted aryl group having 6 to 30 carbon atoms; or a substituted or unsubstituted heteroaryl group having 2 to 30 carbon atoms.

In another embodiment, at least one of R86 to R88 is a substituted or unsubstituted phenyl group; a substituted or unsubstituted naphthyl group; a substituted or unsubstituted dibenzofuranyl group; or a substituted or unsubstituted benzocarbazole group.

In another embodiment, at least one of R86 to R88 is a phenyl group unsubstituted or substituted with a nitrile group; a naphthyl group; a dibenzofuranyl group; or a benzocarbazole group substituted with a phenyl group.

In one embodiment of the present specification, R89 to R92 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R89 to R92 is a substituted or unsubstituted aryl group having 6 to 40 cartoon atoms; or a substituted or unsubstituted heteroaryl group having 2 to 40 carbon atoms.

In one embodiment, of the present specification, R89 to R92 are the same as or different from each other, and each independently hydrogen; a substituted or unsubstituted aryl group having 6 to 30 carbon atoms; or a substituted or unsubstituted heteroaryl group having 2 to 30 cartoon atoms, and at least one of R89 to R92 is a substituted or unsubstituted aryl group having 6 to 30 carbon atoms; or a substituted or unsubstituted heteroaryl group having 2 to 30 carbon atoms.

In another embodiment, at least one of R89 to R92 is a substituted or unsubstituted phenyl group; a substituted or unsubstituted biphenyl group; a substituted or unsubstituted phenanthrenyl group; a substituted or unsubstituted fluorenyl group; or a substituted or unsubstituted dibenzothiophenyl group.

In another embodiment, at least one of R89 to R92 is a phenyl group substituted with a quinoline group; a biphenyl group; a phenanthrenyl group; a fluorenyl group substituted with a methyl group; or a dibenzothiophenyl group.

In one embodiment of the present specification, R93 to R96 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R93 to R96 is a substituted or unsubstituted aryl group having 6 to 40 carbon atoms; or a substituted or unsubstituted heteroaryl group having 2 to 40 carbon atoms.

In one embodiment of the present specification, R93 to R96 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R93 to R96 is a substituted or unsubstituted aryl group having 6 to 30 carbon atoms; or a substituted or unsubstituted heteroaryl group having 2 to 30 carbon atoms.

In another embodiment, at least one of R93 to R96 is a substituted or unsubstituted phenyl group; a substituted or unsubstituted phenanthrenyl group; a substituted or unsubstituted pyridyl group; or a substituted or unsubstituted dibenzofuranyl group.

In another embodiment, at least one of: R93 to R96 is a phenyl group substituted with a naphthyl group or a quinoline group; a phenanthrenyl group; a pyridyl group; or a dibenzofuranyl group.

In one embodiment of the present specification, L1 is n direct bond; or a substituted or unsubstituted arylene group having 6 to 40 carbon atoms.

In another embodiment, L1 is a direct bond; or a substituted or unsubstituted arylene group having 6 to 30 carbon atoms.

According to another embodiment, L1 is a direct bond; or an arylene group having 6 to 30 carbon atoms unsubstituted or substituted with deuterium or a nitrile group.

In another embodiment, L1 is a direct bond; or a substituted or unsubstituted arylene group having 6 to 20 carbon atoms.

According to another embodiment, L1 is a direct bond; a substituted or unsubstituted phenylene group; or a substituted or unsubstituted naphthylene group.

According to another embodiment, L1 is a direct, bond; a phenylene group unsubstituted or substituted with deuterium or a nitrile group; or a naphthylene group unsubstituted or substituted with deuterium or a nitrile group.

In one embodiment of the present specification, R1 to R4 are the same as or different from each other, and each independently hydrogen; or a substituted or unsubstituted aryl group having 6 to 40 carbon atoms, and at least one of R1 to R4 is a substituted or unsubstituted aryl group having 6 to 40 carbon atoms.

According to another embodiment, one of R1 to R4 is A substituted or unsubstituted aryl group having 6 to 40 carbon atoms, and the rest are hydrogen.

In another embodiment R1 to R4 are the same as or different from each other, and each independently hydrogen; or an aryl group having 6 to 40 carbon atoms unsubstituted or substituted with deuterium, an alkyl group or an aryl group, and at least one of R1 to R4 is an aryl group having 6 to 40 carbon atoms unsubstituted or substituted with deuterium, an alkyl group or an aryl group.

According to another embodiment, R1 to R4 are the same as or different from each other, and each independently hydrogen; or an aryl group having 6 to 40 carbon atoms unsubstituted or substituted with deuterium, an alkyl group having 1 to 20 carbon atoms or an aryl group having 6 to 30 carbon atoms, and at least one of R1 to R4 is an aryl group having 6 to 40 carbon atoms unsubstituted or substituted with deuterium, an alkyl group having 1 to 20 carbon atoms or an aryl group having 6 to 30 carbon atoms.

In another embodiment, R1 to R4 are the same as or different from each other, and each independently hydrogen; or an aryl group having 6 to 40 carbon atoms unsubstituted or substituted with deuterium, a methyl group or a phenyl group, and at least one of R1 to R4 is an aryl group having 6 to 40 carbon atoms unsubstituted or substituted with deuterium, a methyl group or a phenyl group.

In another embodiment, R1 to R4 are the same as or different from each other, and each independently hydrogen; or a substituted or unsubstituted aryl group having 6 to 30 carbon atoms, and at least one of R1 to R4 is a substituted or unsubstituted aryl group having 6 to 30 carbon atoms.

In another embodiment, R1 to R4 are the same as or different from each other, and each independently hydrogen; or a substituted or unsubstituted aryl group having 6 to 20 carbon atoms, and at least one of R1 to R4 is a substituted or unsubstituted aryl, group having 6 to 20 carbon atoms.

According to another embodiment, R1 to R4 are the same as or different from each other, and each independently hydrogen; a substituted or unsubstituted phenyl group; a substituted or unsubstituted biphenyl group; a substituted or unsubstituted naphthyl group; a substituted or unsubstituted fluorenyl group; a substituted or unsubstituted fluoranthene group; a substituted or unsubstituted phenanthrene group; a substituted or unsubstituted triphenylene group; or a substituted or unsubstituted spirobifluorenyl group, and at least one of R1 to R4 is a substituted or unsubstituted phenyl group; a substituted or unsubstituted biphenyl group; a substituted or unsubstituted naphthyl group; a substituted or unsubstituted fluorenyl group; a substituted or unsubstituted fluoranthene group; a substituted or unsubstituted phenanthrene group; a substituted or unsubstituted triphenylene group; or a substituted or unsubstituted spirobifluorenyl group.

In another embodiment, R1 to R4 are the same as or different from each other, and each independently hydrogen; a phenyl group unsubstituted or substituted with deuterium, an alkyl group or an aryl group; a biphenyl group unsubstituted or substituted with deuterium, an alkyl group or an aryl group; a naphthyl group unsubstituted or substituted with deuterium, an alkyl group or an aryl group; a fluorenyl group unsubstituted or substituted with deuterium, an alkyl group or an aryl group; a fluoranthene group unsubstituted or substituted with deuterium, an alkyl group or an aryl group; a phenanthrene group unsubstituted or substituted with deuterium, an alkyl group or an aryl group; a triphenylene group unsubstituted or substituted with deuterium, an alkyl group or an aryl group; or a spirobifluorenyl group unsubstituted or substituted with deuterium, an alkyl group or an aryl group, and at least one of R1 to R4 is a phenyl group unsubstituted or substituted with deuterium, an alkyl group or an aryl group; a biphenyl group unsubstituted or substituted with deuterium, an alkyl group or an aryl group; a naphthyl group unsubstituted or substituted with deuterium, an alkyl group or an aryl group; a fluorenyl group unsubstituted or substituted with deuterium, an alkyl group or an aryl group; a fluoranthene group unsubstituted or substituted with deuterium, an alkyl group or an aryl group; a phenanthrene group unsubstituted or substituted with deuterium, an alkyl group or an aryl group; a triphenylene group unsubstituted or substituted with deuterium, an alkyl group or an aryl group; or a spirobifluorenyl group unsubstituted or substituted with deuterium, an alkyl group or an aryl group.

According to another embodiment, R1 to R4 are the same as or different from each other, and each independently hydrogen; a phenyl group unsubstituted or substituted with deuterium, a methyl group or a phenyl group; a biphenyl group unsubstituted or substituted with deuterium, a methyl group or a phenyl group; a naphthyl group unsubstituted or substituted with deuterium, a methyl group or a phenyl, group; a fluorenyl group unsubstituted or substituted with deuterium, a methyl group or a phenyl group; a fluoranthene group unsubstituted or substituted with deuterium, a methyl group or a phenyl group; a phenanthrene group unsubstituted or substituted with deuterium, a methyl group or a phenyl group; a triphenylene group unsubstituted or substituted with deuterium, a methyl group or a phenyl group; or a spirobifluorenyl group unsubstituted or substituted with deuterium, a methyl group or a phenyl group, and at least one of R1 to R4 is a phenyl group unsubstituted or substituted with deuterium, a methyl group or a phenyl group; a biphenyl group unsubstituted or substituted with deuterium, a methyl group or a phenyl group; a naphthyl group unsubstituted or substituted with deuterium, a methyl group or a phenyl group; a fluorenyl group unsubstituted or substituted with deuterium, a methyl group or a phenyl group; a fluoranthene group unsubstituted or substituted with deuterium, a methyl group or a phenyl group; a phenanthrene group unsubstituted or substituted with deuterium, a methyl group or a phenyl group a triphenylene group unsubstituted or substituted with deuterium, a methyl group or a phenyl group; or a spirobifluorenyl group unsubstituted or substituted with deuterium, a methyl group or a phenyl group.

In another embodiment, R1 to R4 are the same as or different from each other, and each independently hydrogen;

a phenyl group unsubstituted or substituted with deuterium; a fluorenyl group substituted with a phenyl group or a methyl group; a spirobifluorenyl group; a naphthyl group; a fluoranthene group a phenanthrene group; a triphenylene group; or a biphenyl group, and at least one of R1 to R4 is a phenyl group unsubstituted or substituted with deuterium; a fluorenyl group substituted with a phenyl group or a methyl group; a spirobifluorenyl group; a naphthyl group; a fluoranthene group; a phenanthrene group; a triphenylene group; or a biphenyl group.

According to another embodiment, any one of R1 to R4 is a phenyl group unsubstituted or substituted with deuterium; a fluorenyl group substituted with a phenyl, group or a methyl group; a spirobifluorenyl group; a naphthyl group; a fluoranthene group; a phenanthrene group; a triphenylene group; or a biphenyl group, and the rest, are hydrogen.

In one embodiment of the present specification, Chemical Formula 1 may be any one selected from among the following compounds

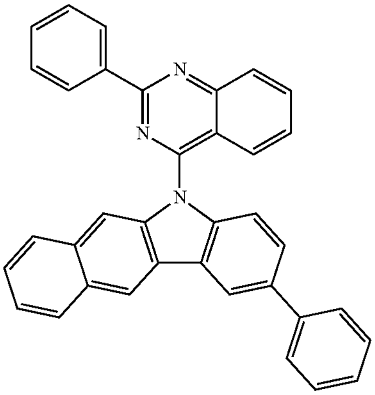

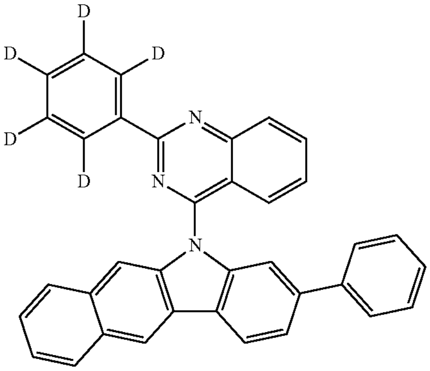

-continued

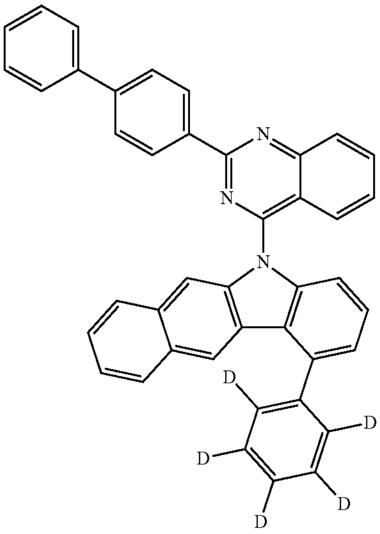

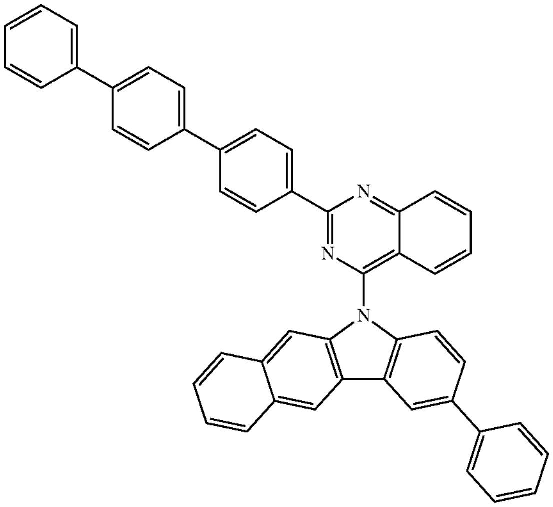

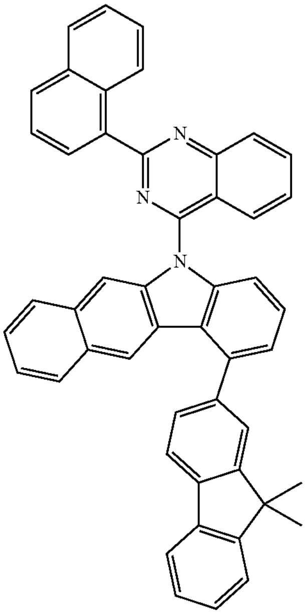

-continued
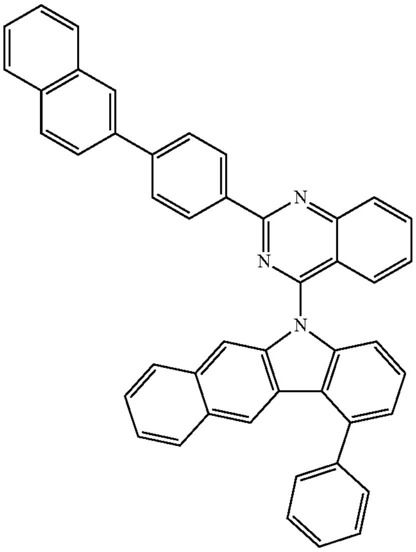
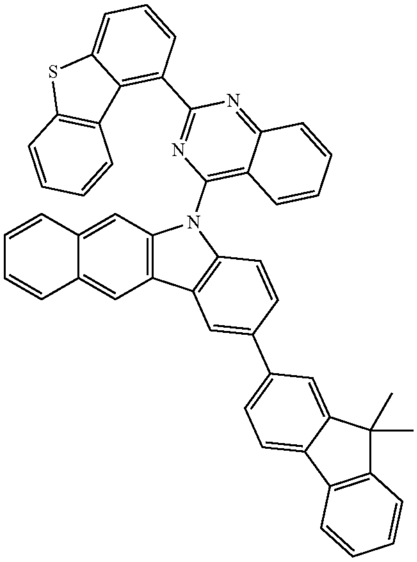
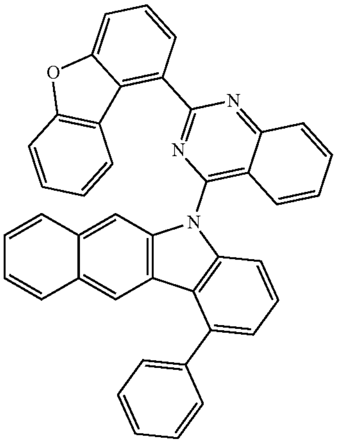
-continued
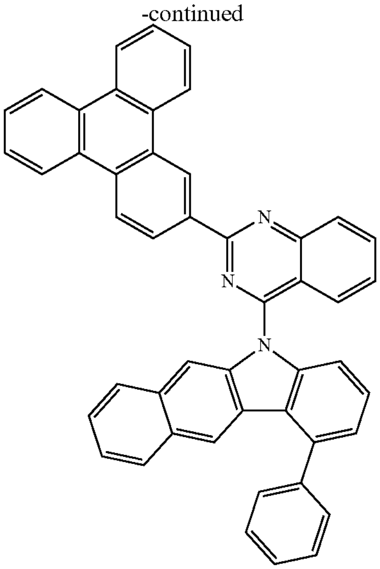
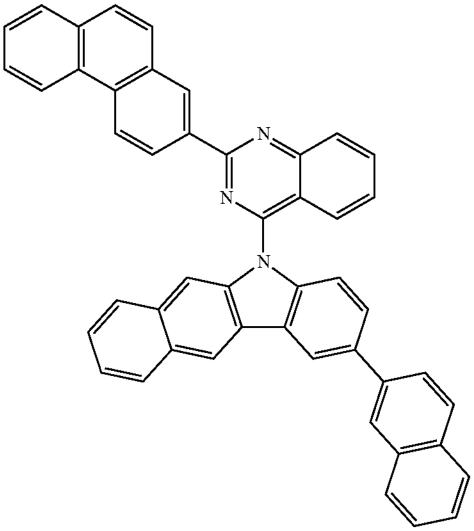
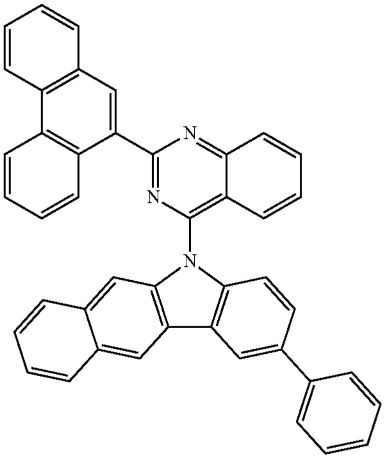

-continued
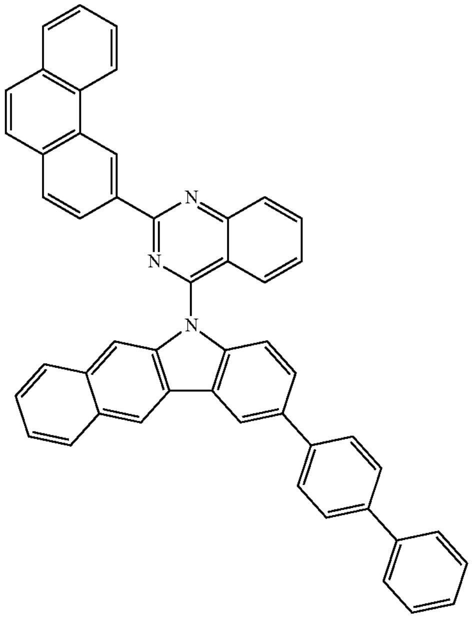
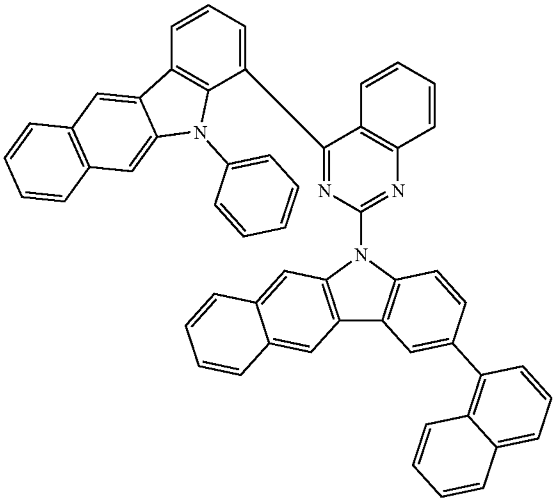
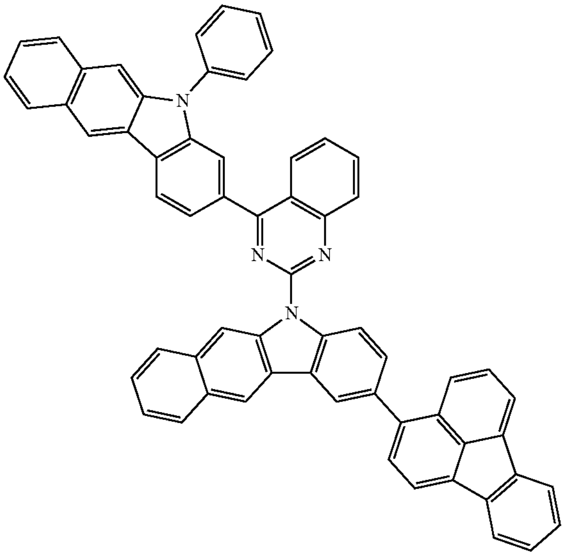
-continued
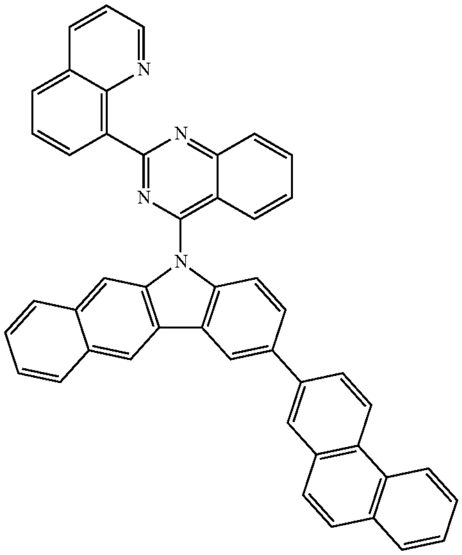
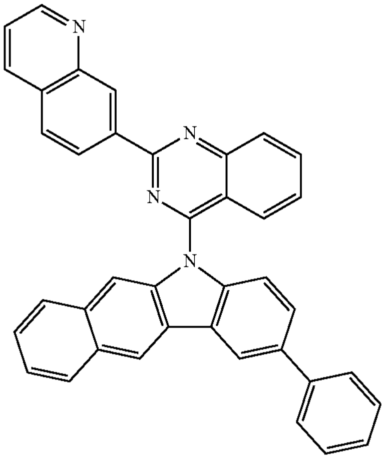
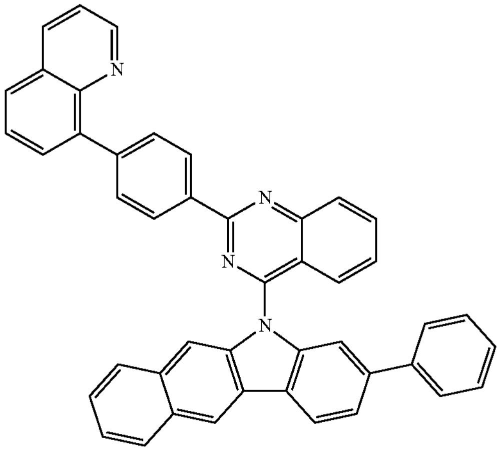

-continued
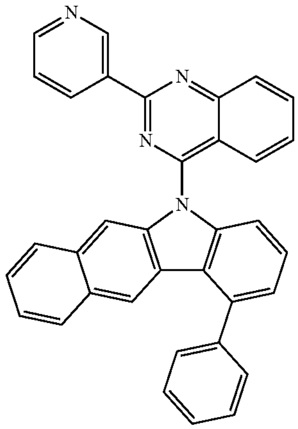
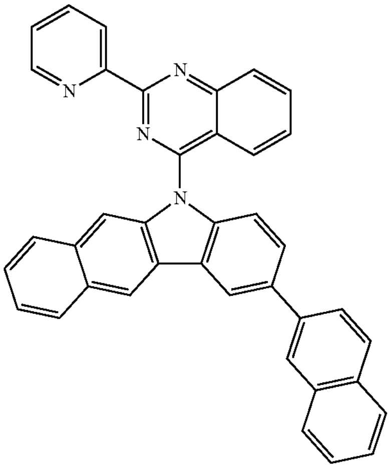
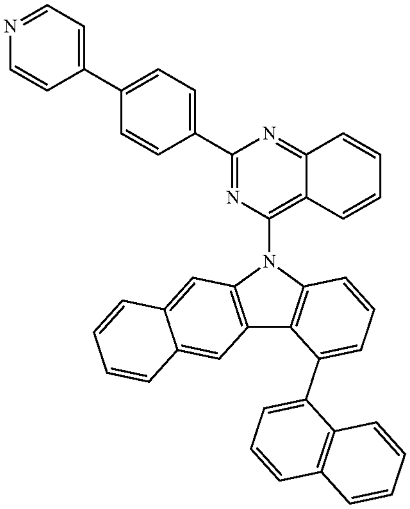
-continued
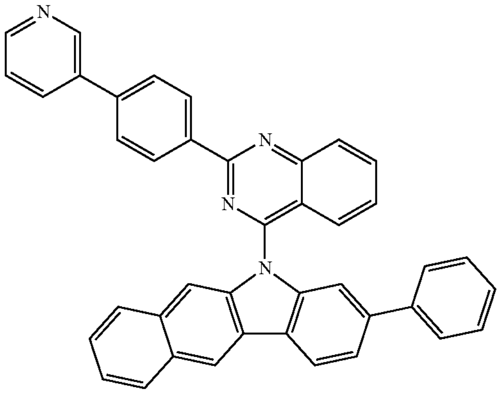
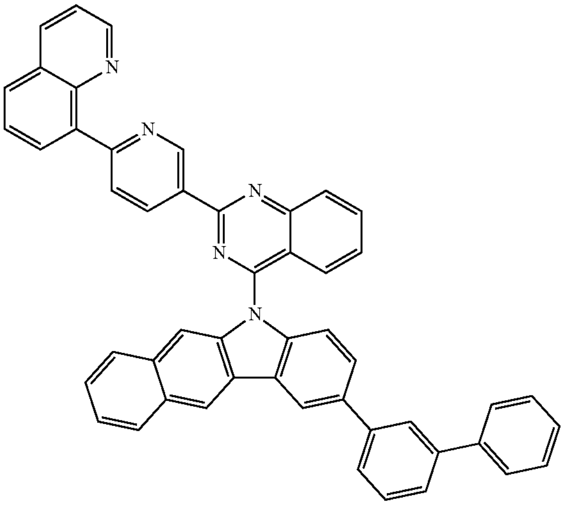
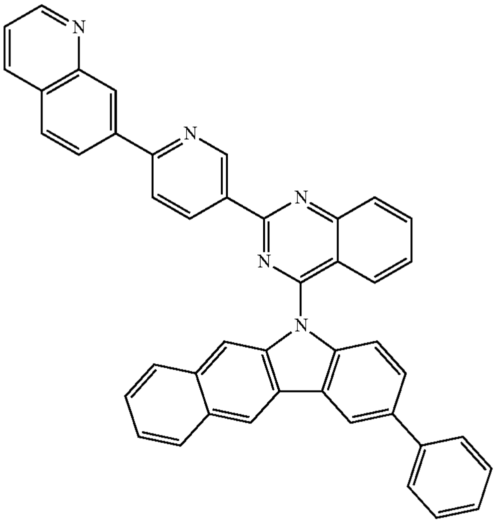

-continued
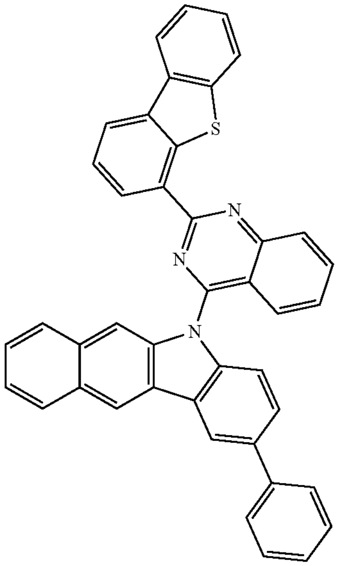
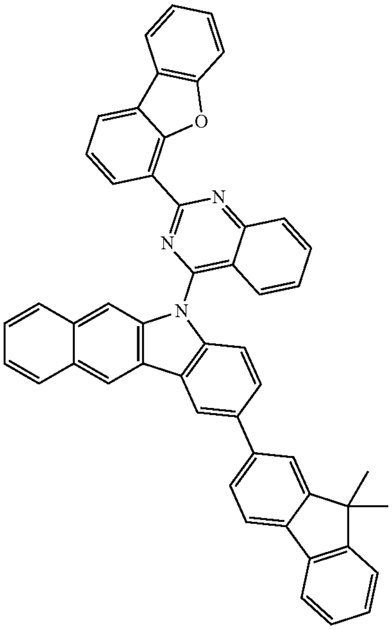
-continued
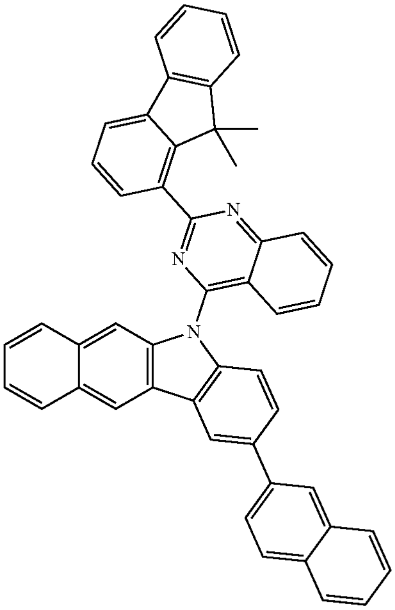
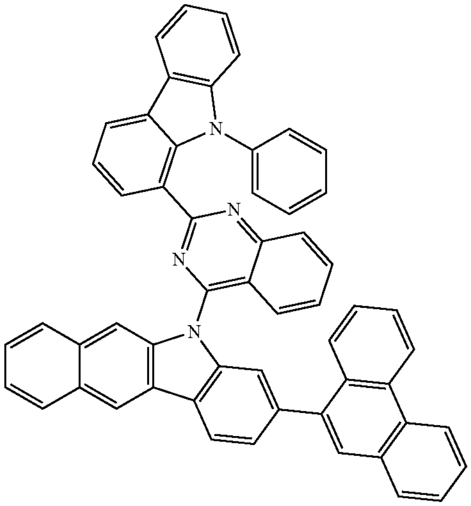
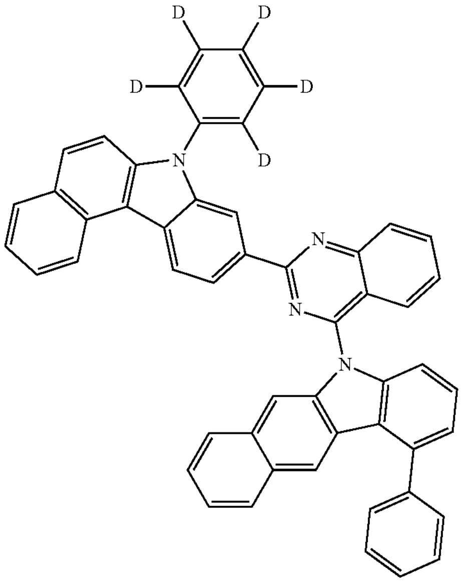

-continued
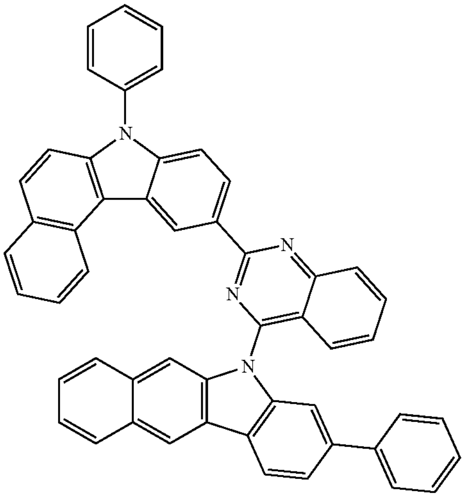
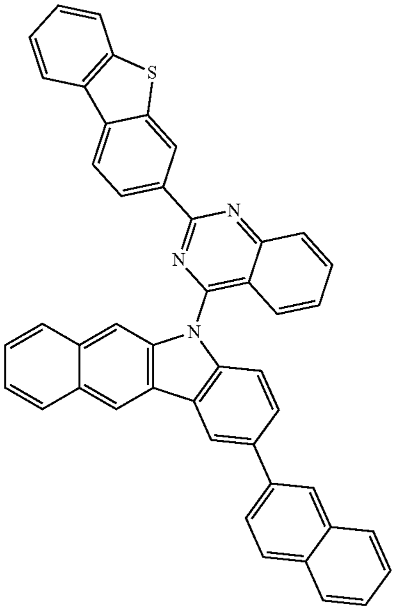
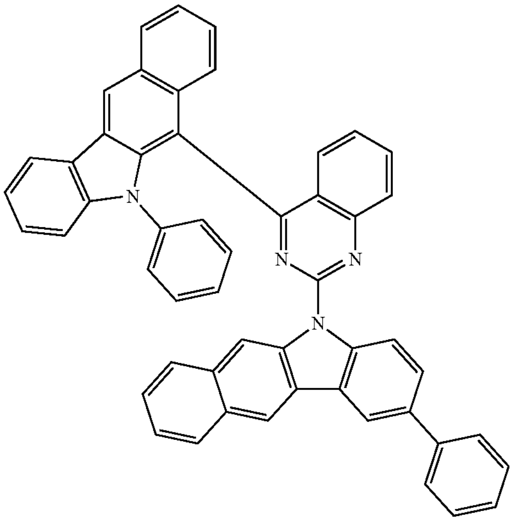
-continued
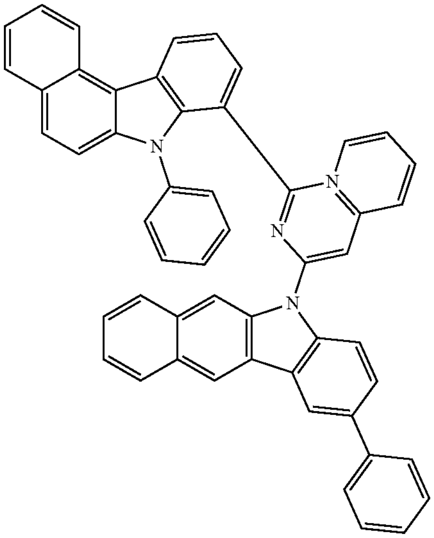
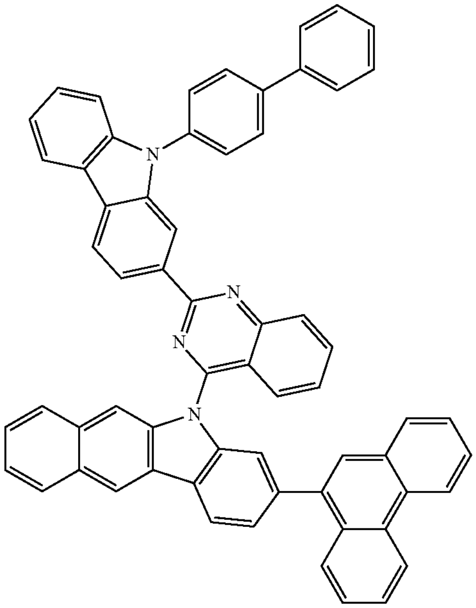
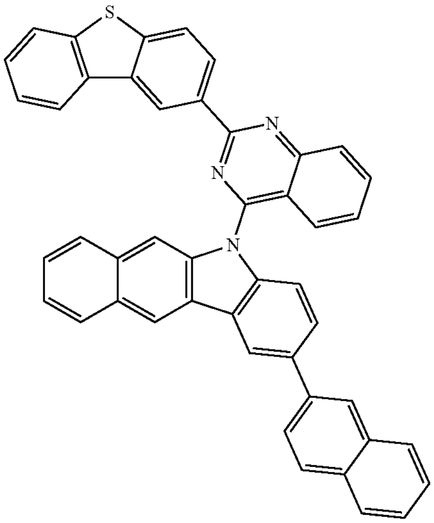

-continued
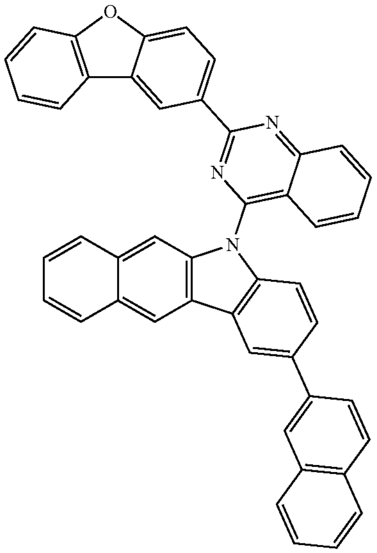
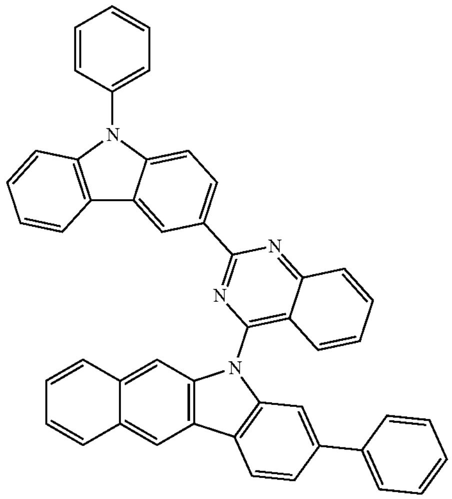
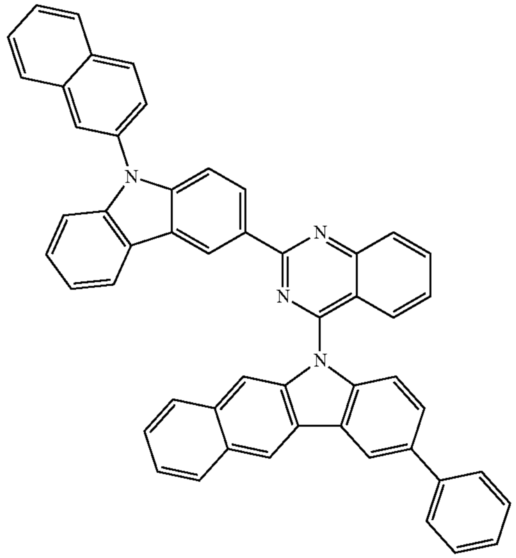
-continued
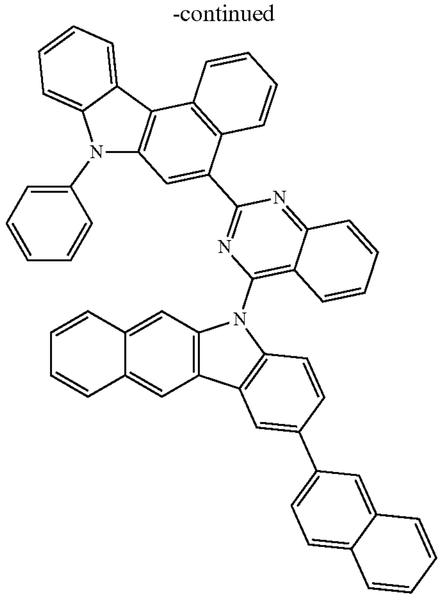
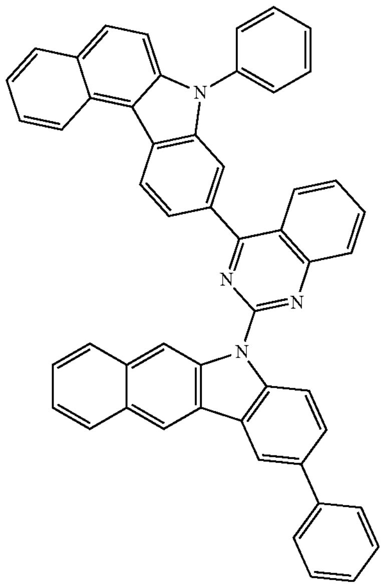

-continued
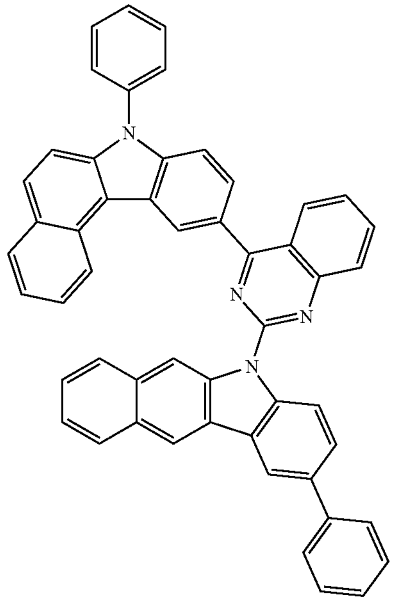
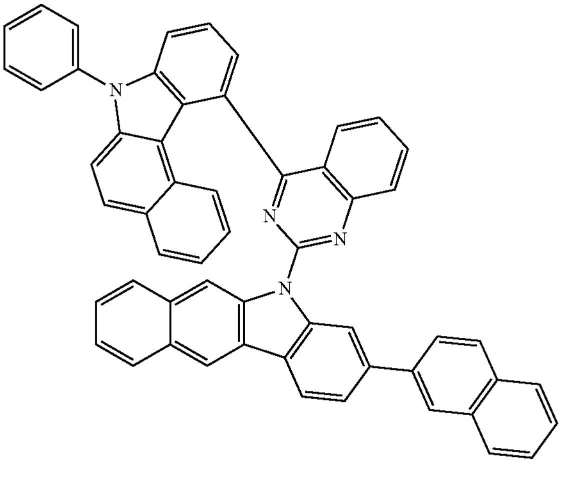
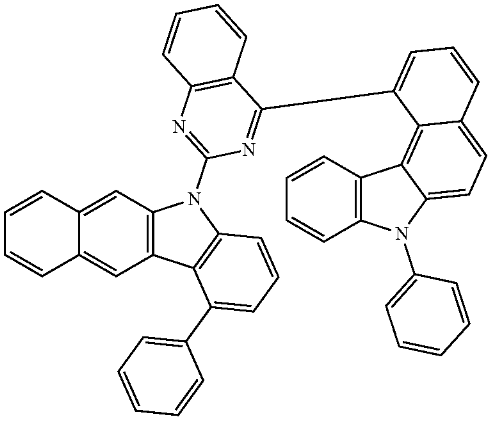
-continued
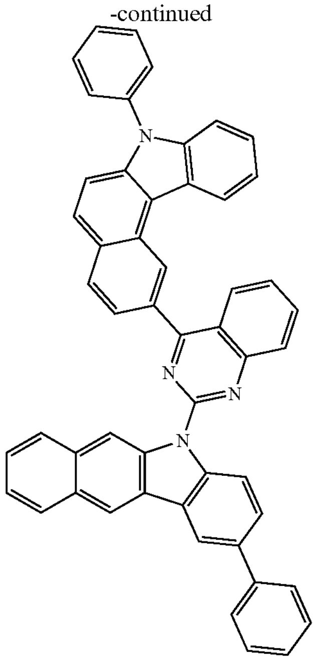
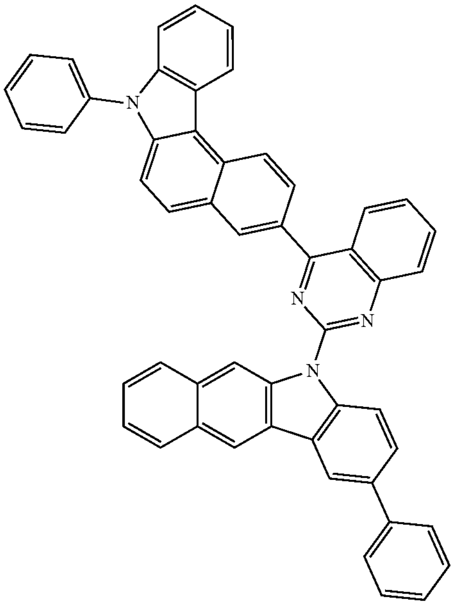
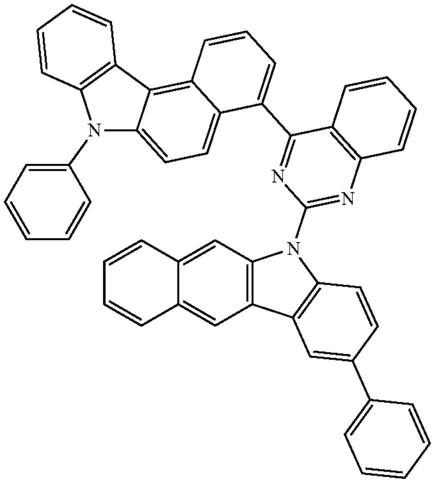

-continued
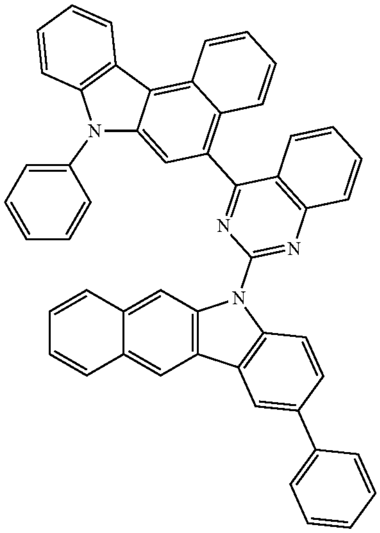
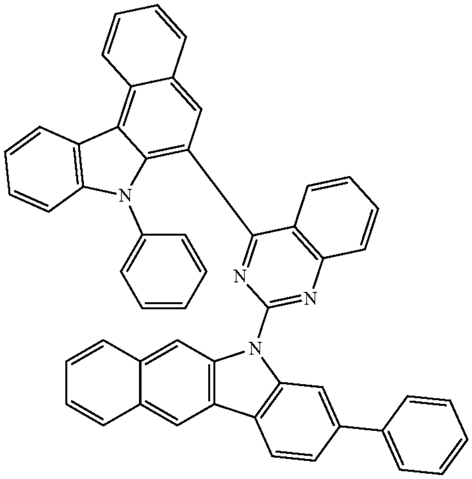
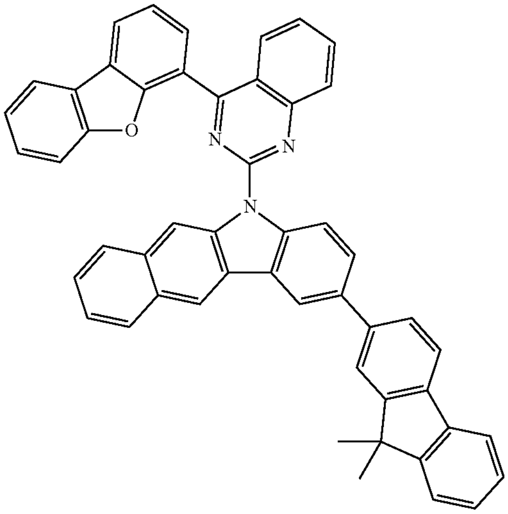
-continued
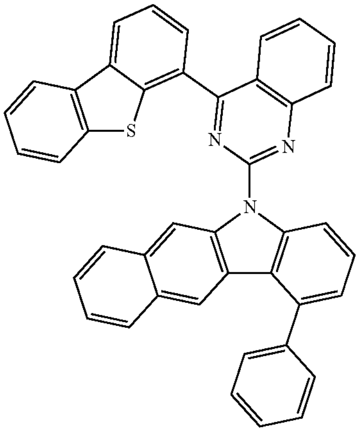
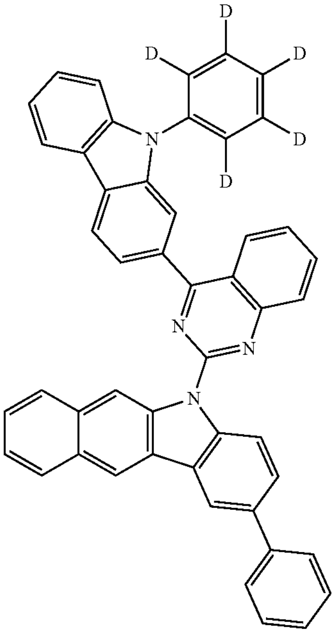
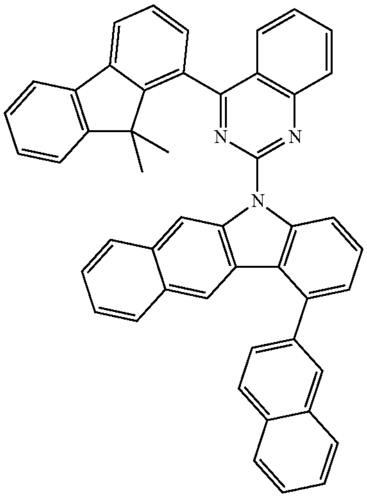

-continued
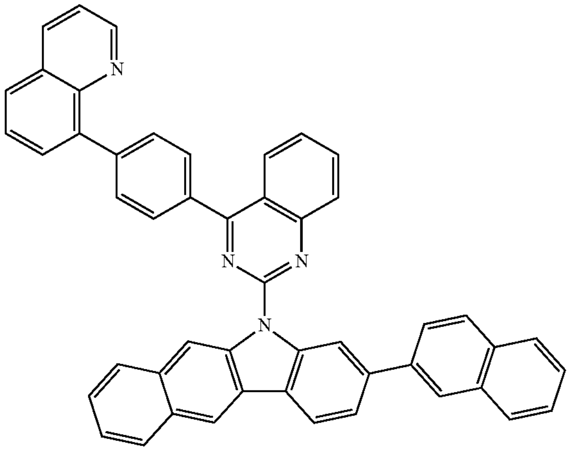
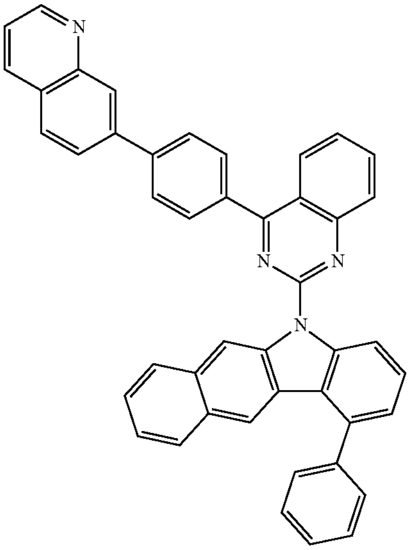
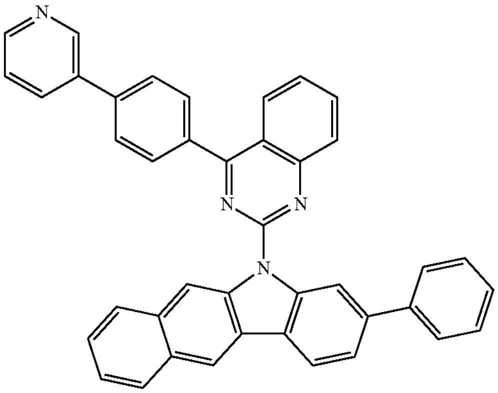
-continued
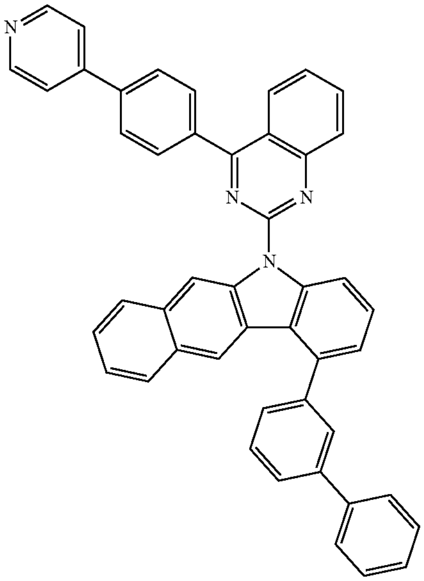
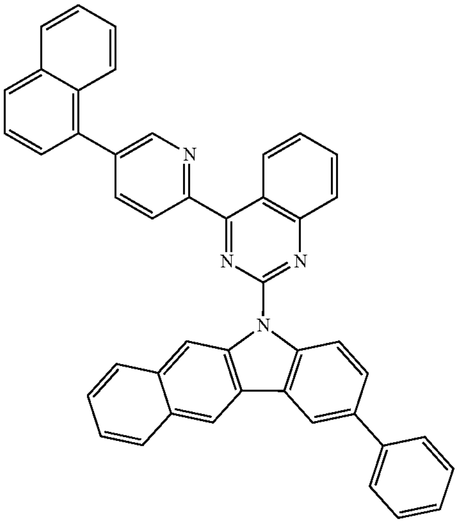

-continued
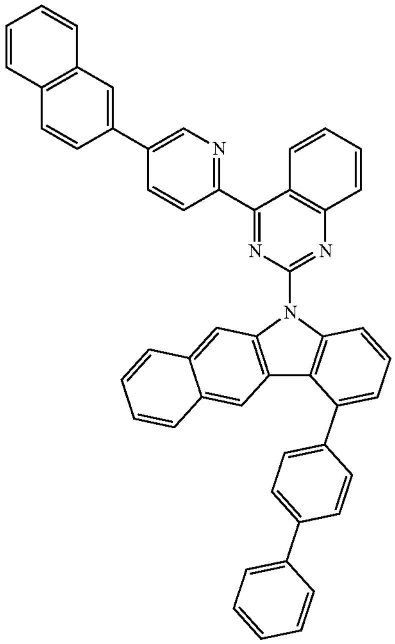
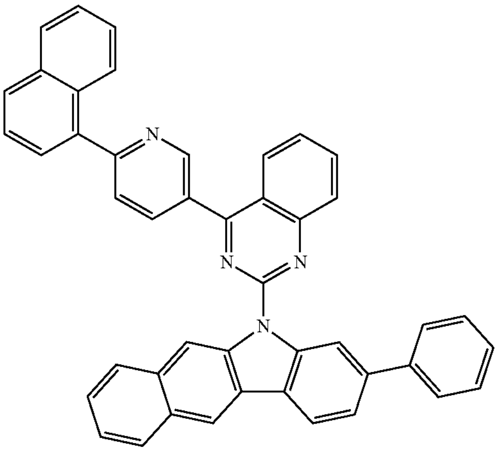
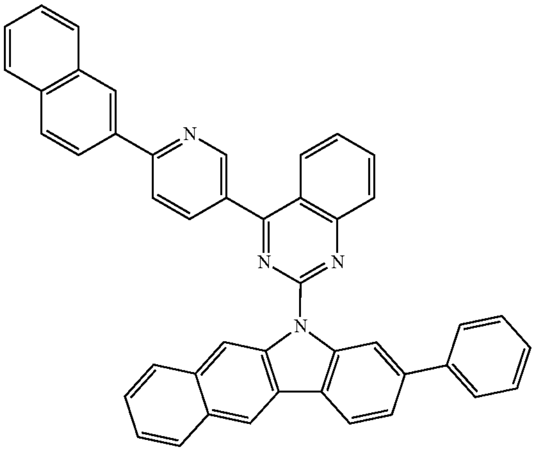
-continued
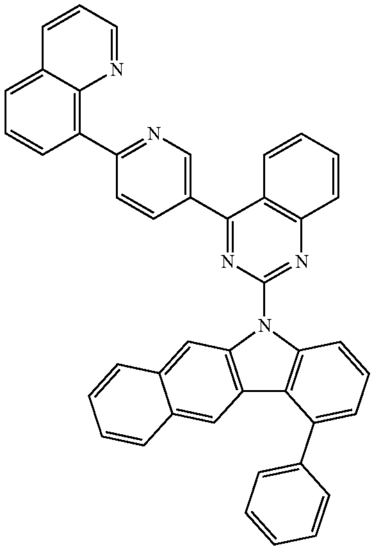
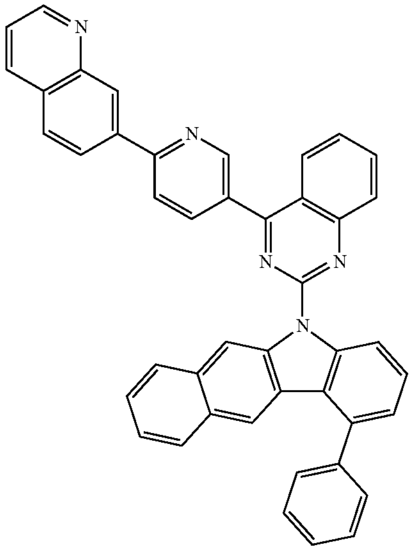
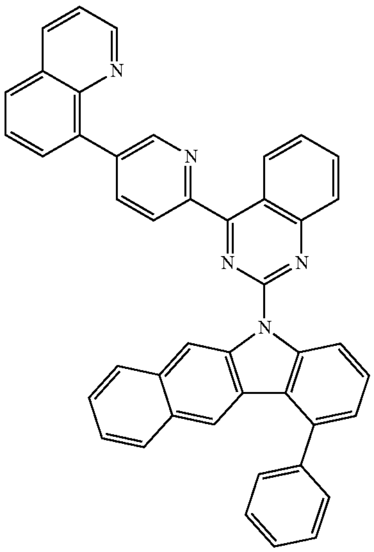

-continued
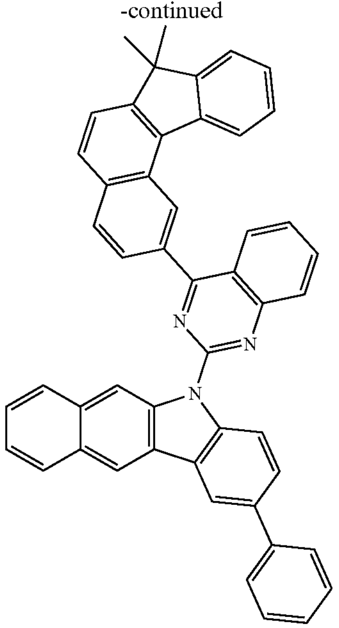
-continued
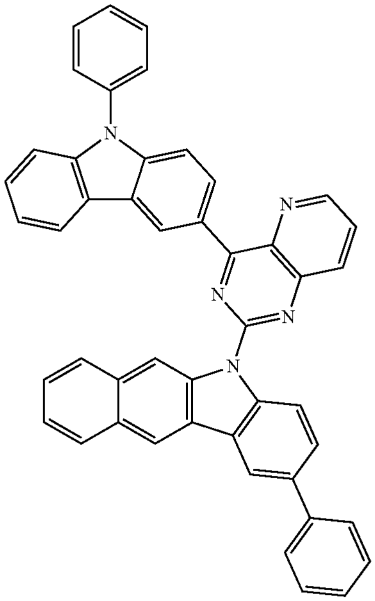
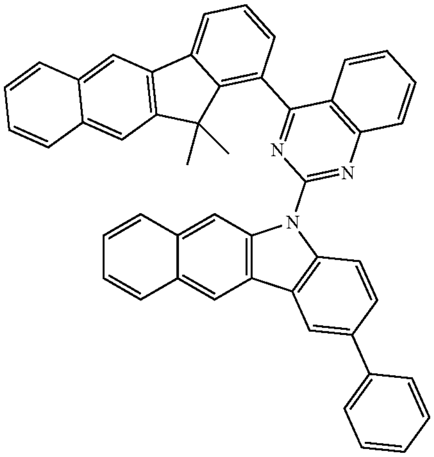
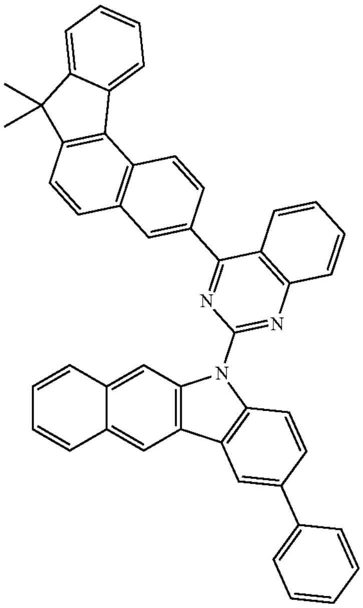
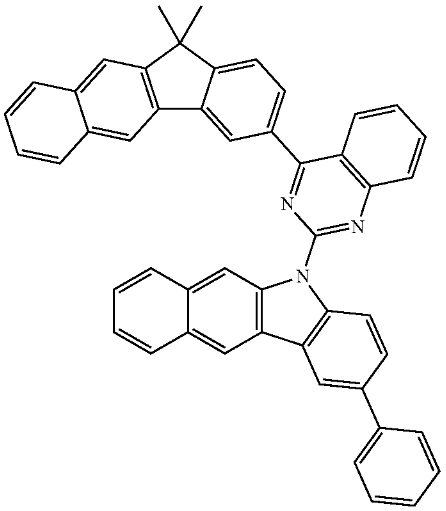

-continued
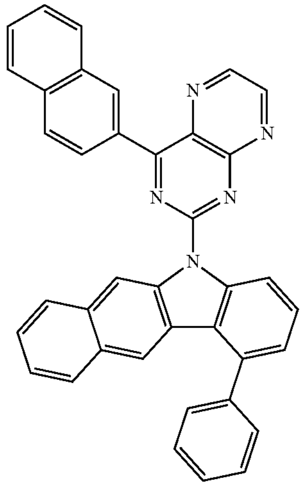
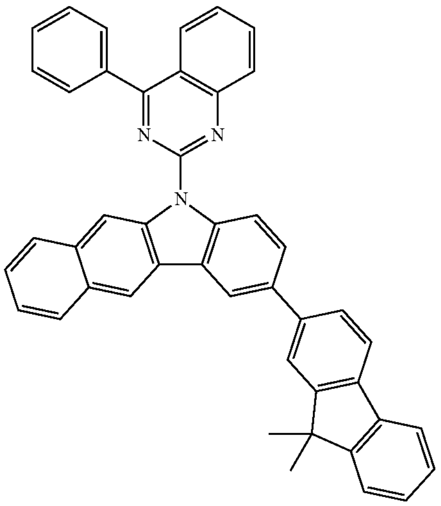
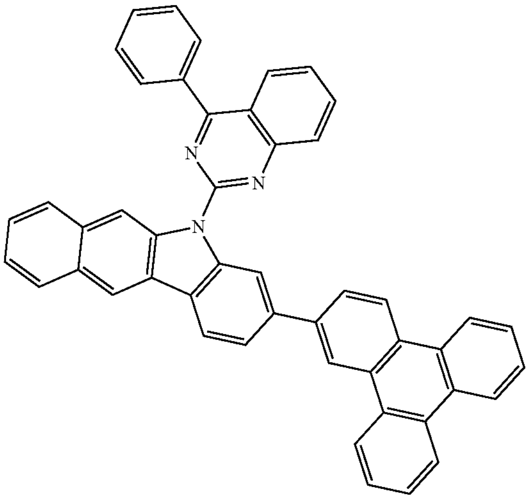
-continued
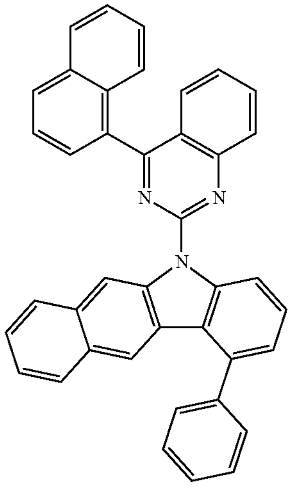
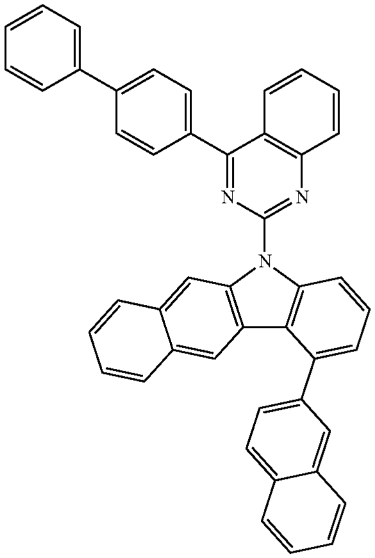
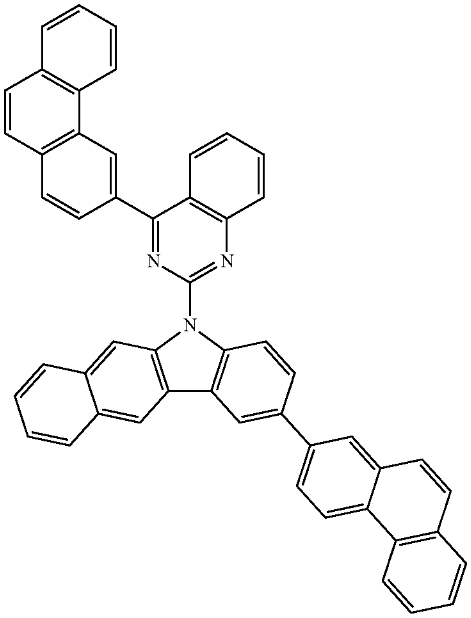

-continued
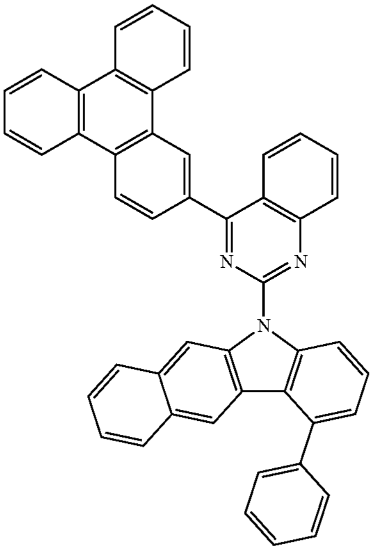
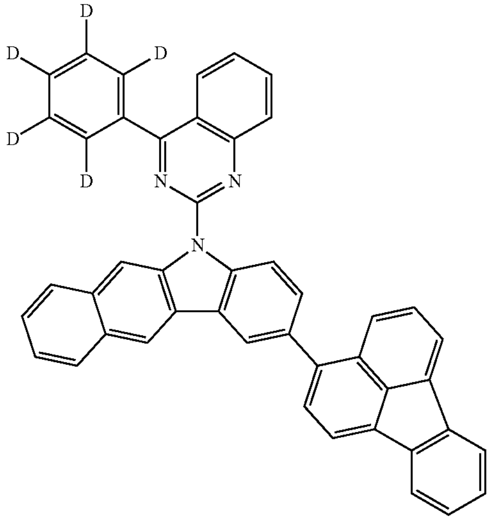
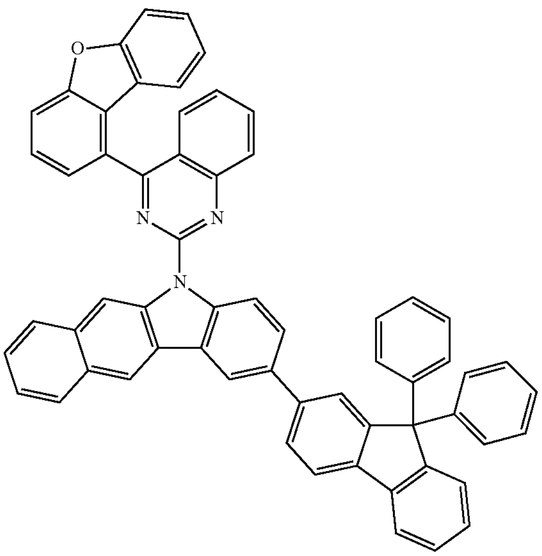
-continued
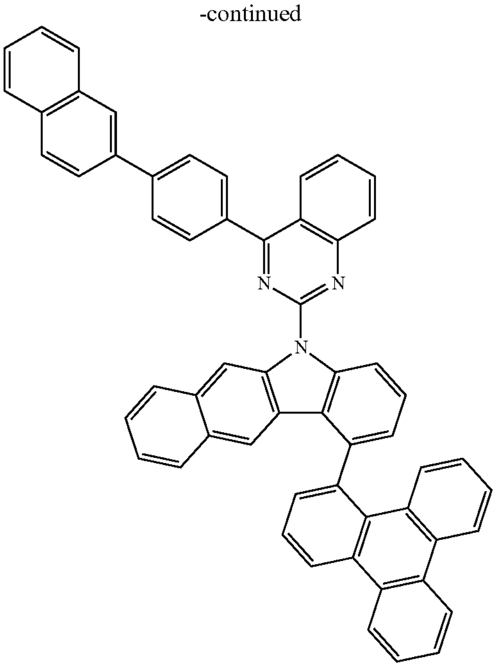
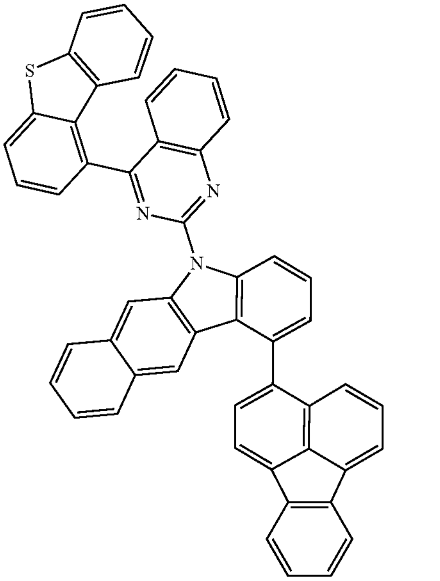
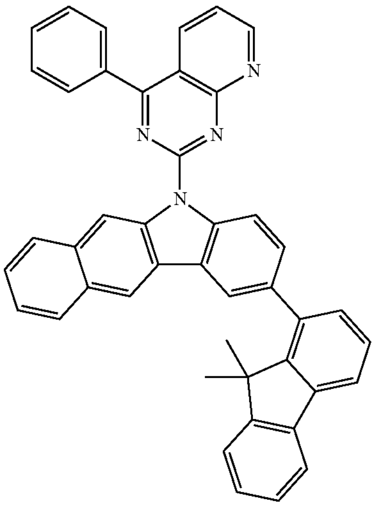

-continued
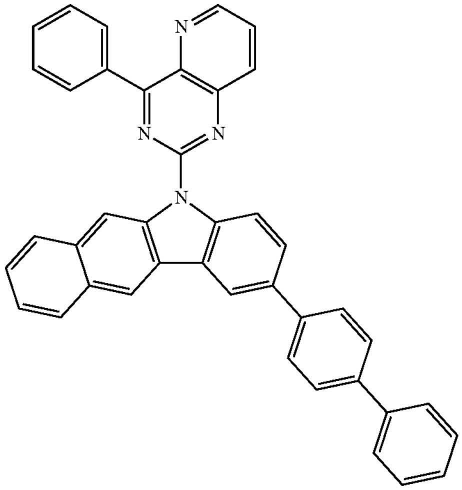
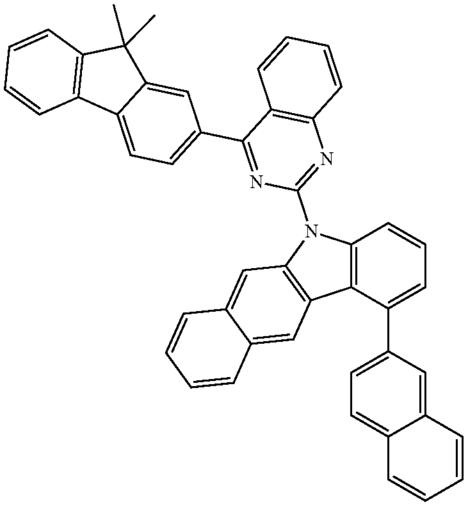
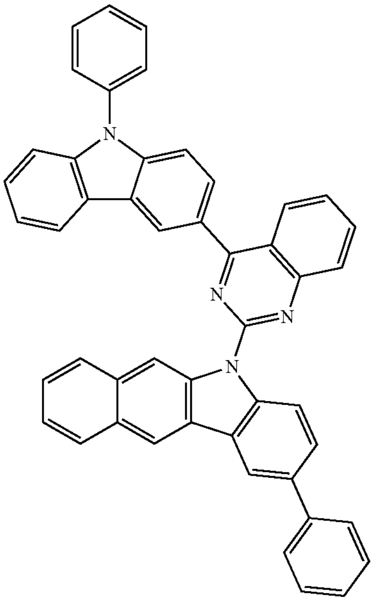
-continued
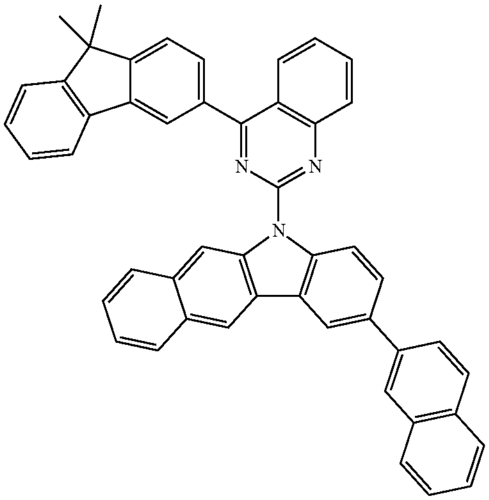
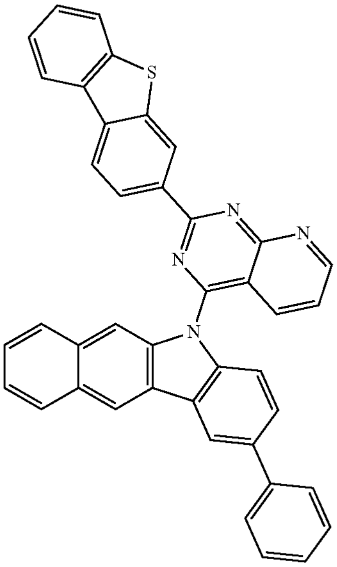
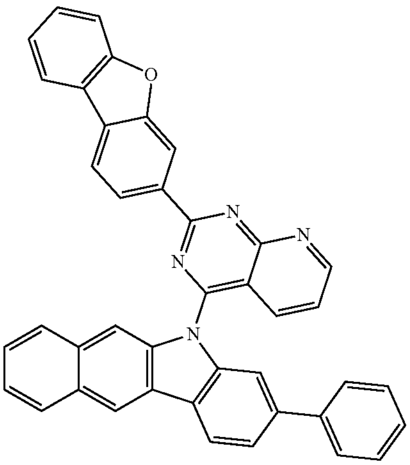

-continued
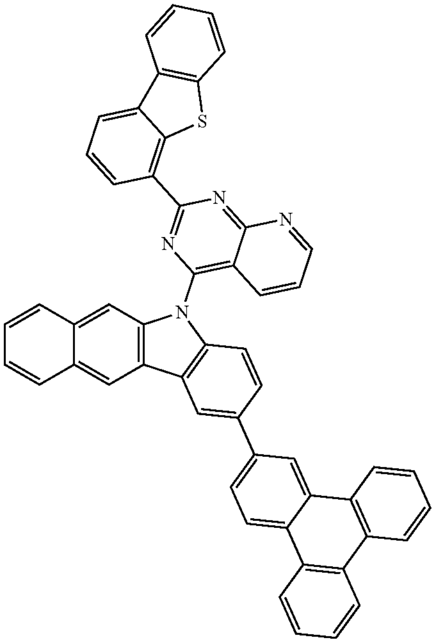
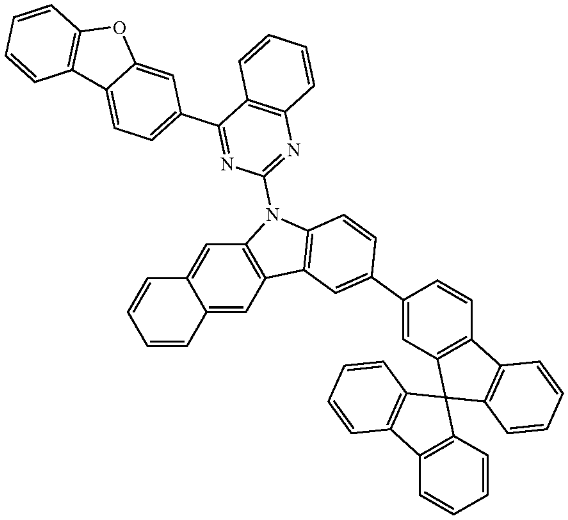
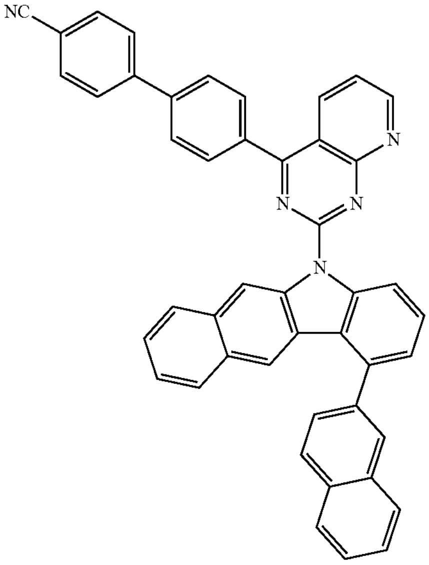
-continued
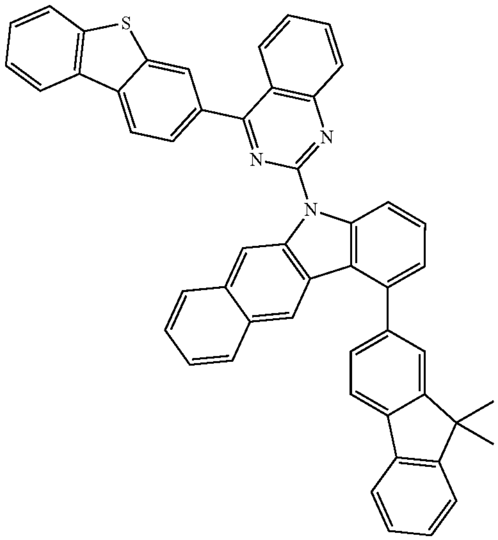
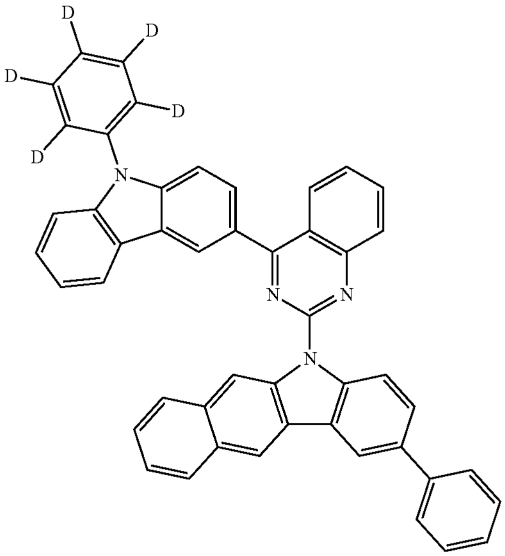
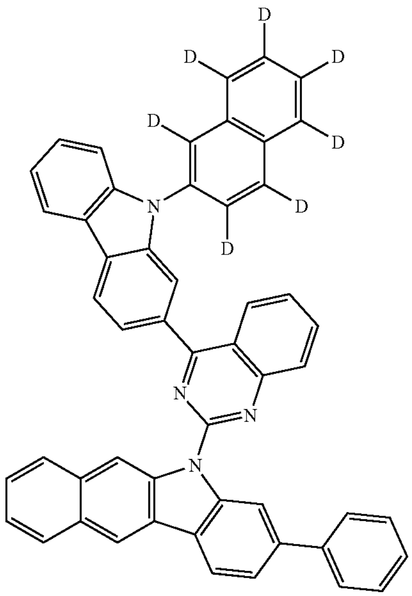

-continued
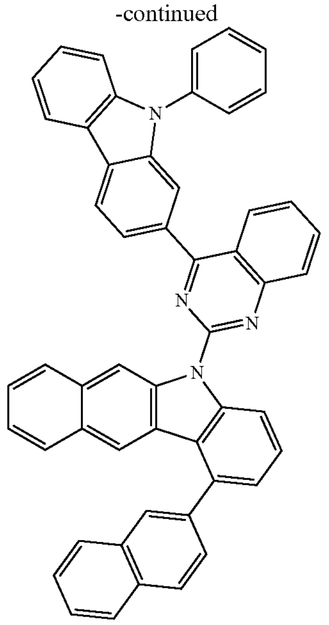
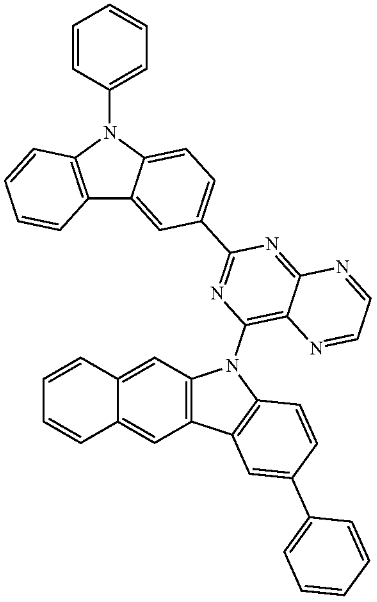
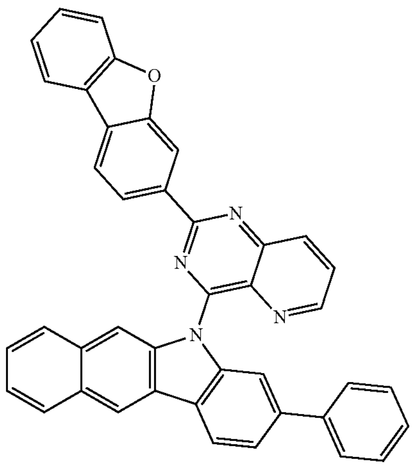
-continued
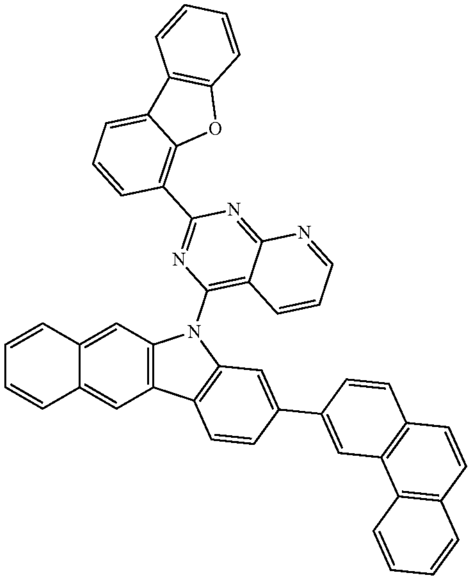
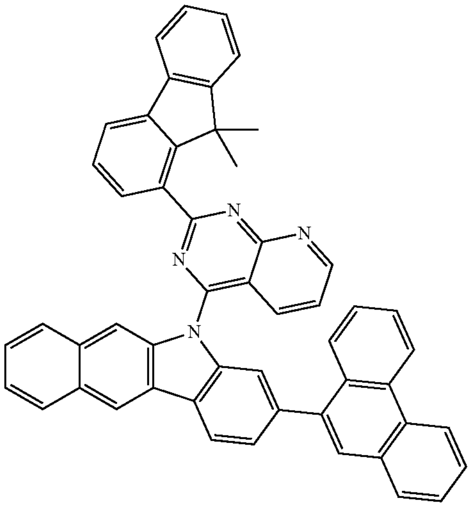
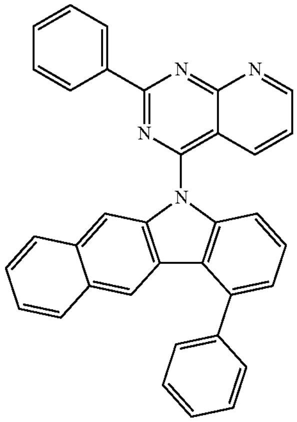

-continued
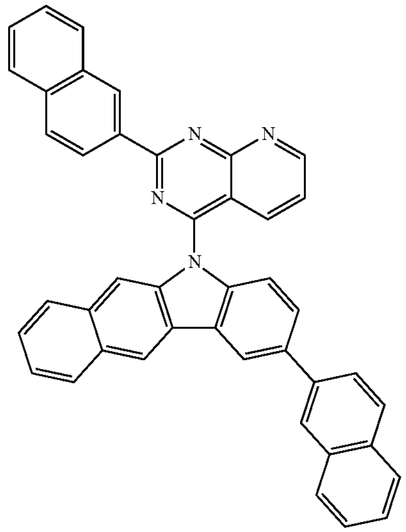
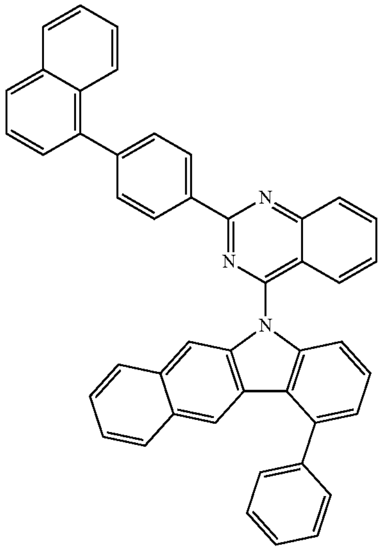
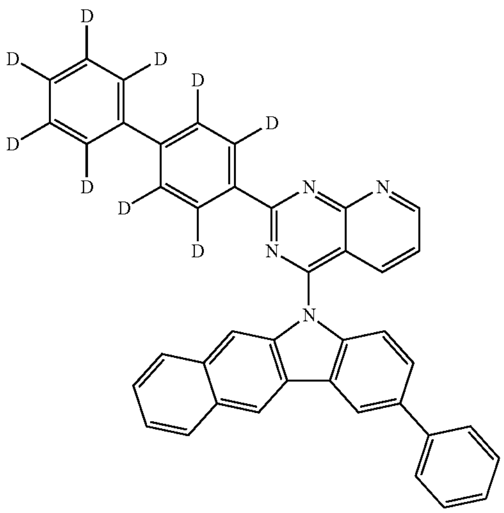
-continued
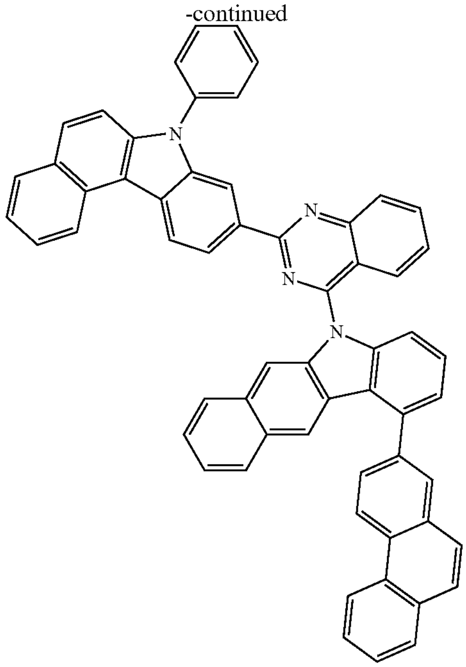
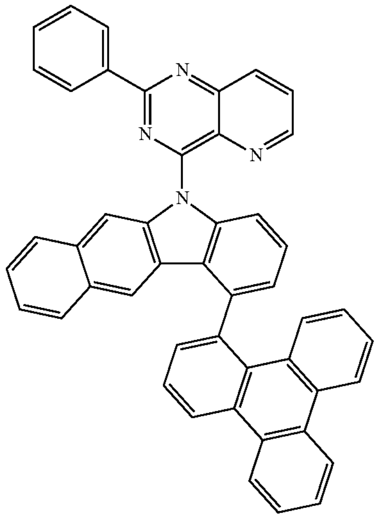

-continued
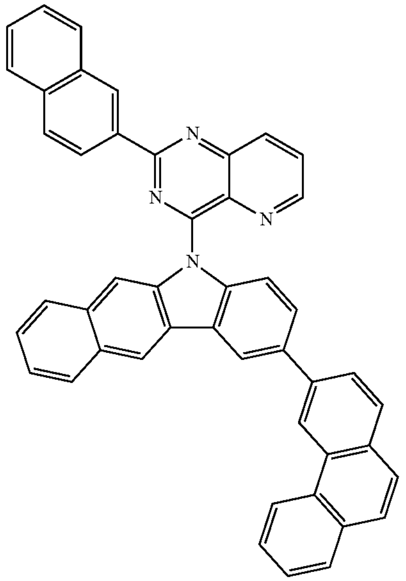
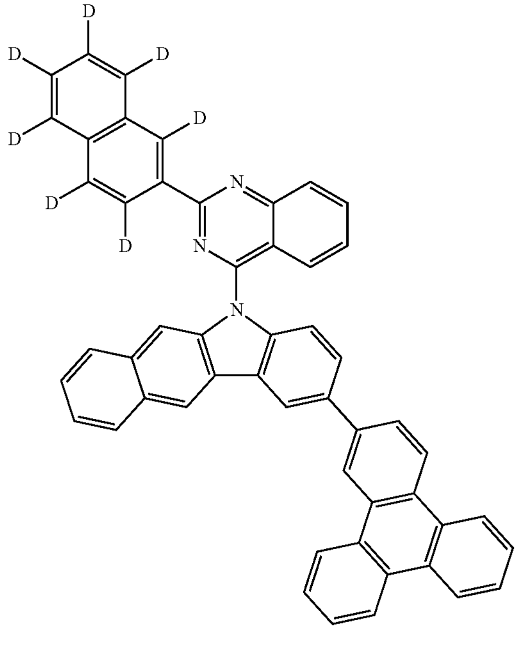
-continued
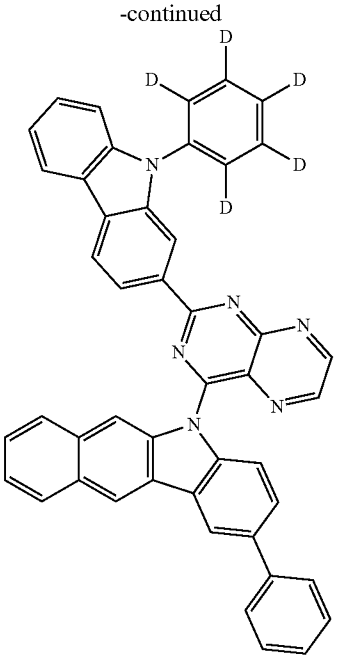
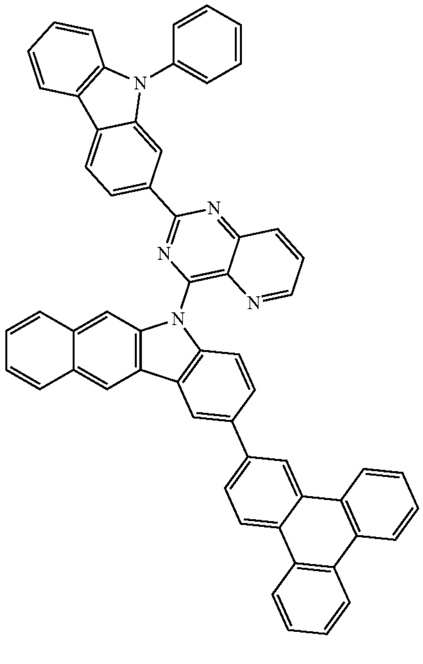

-continued
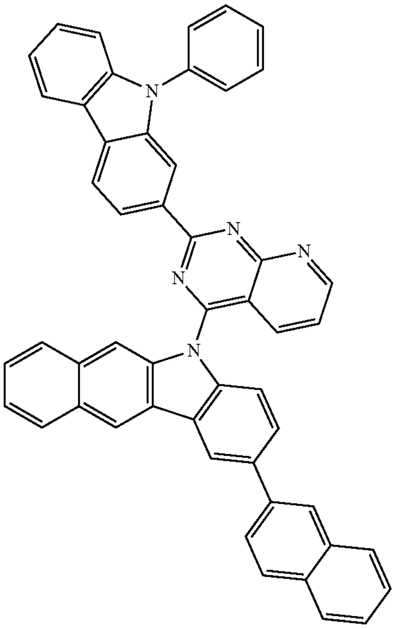
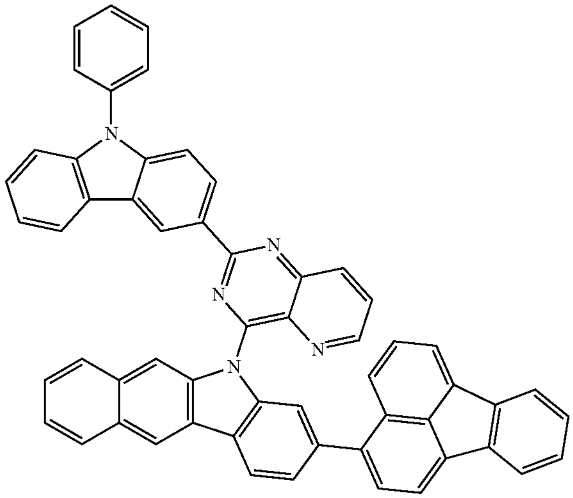
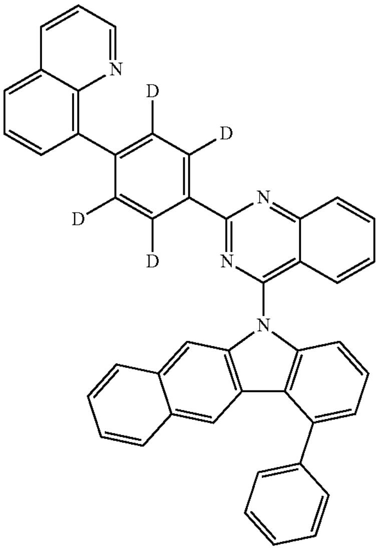
-continued
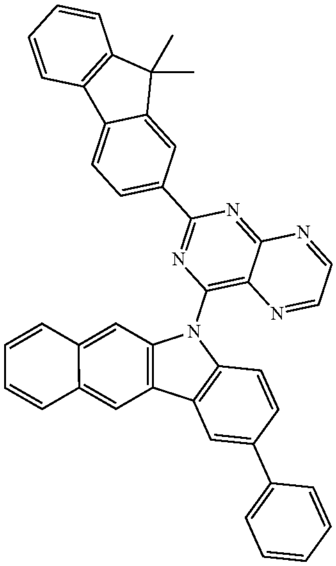
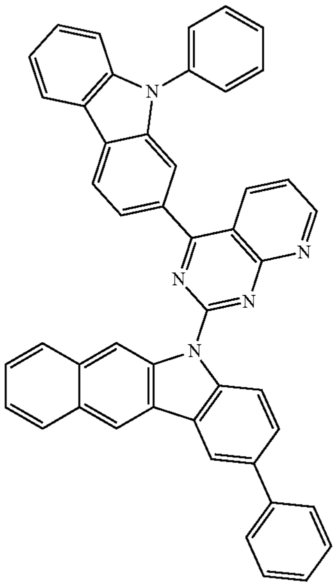
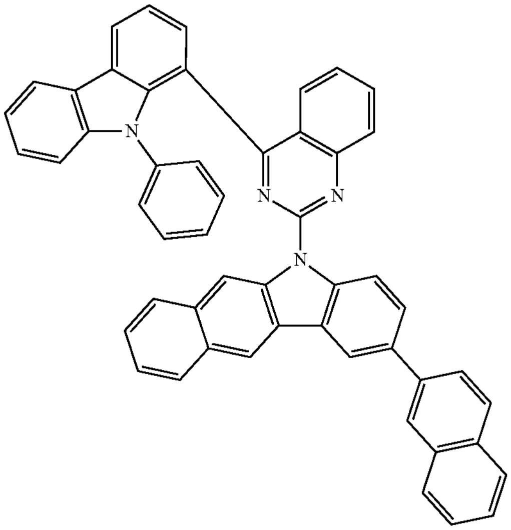

-continued
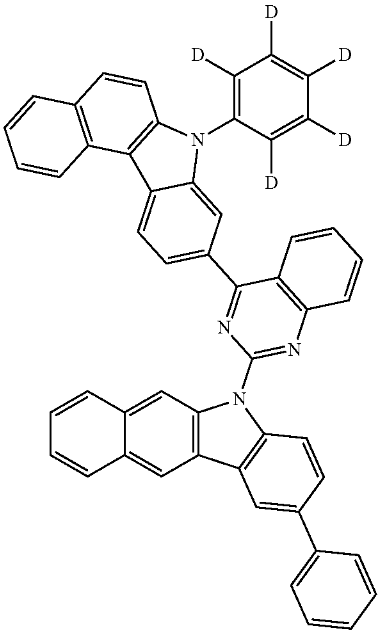
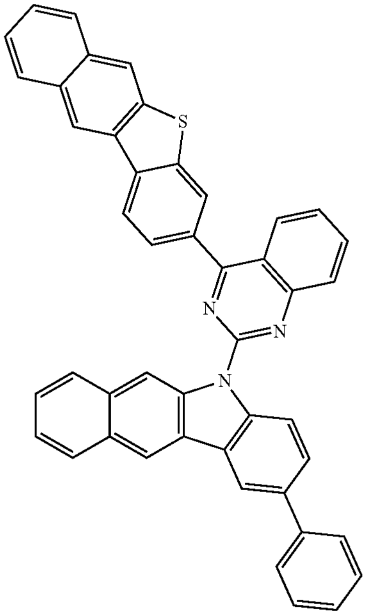
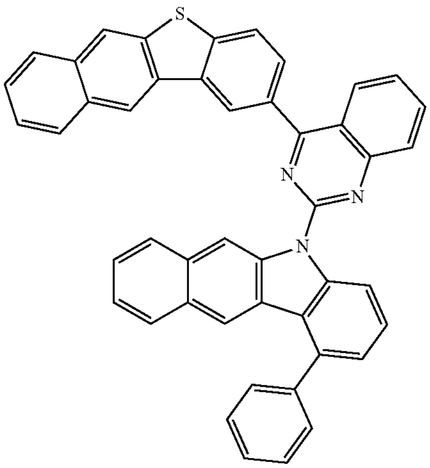
-continued
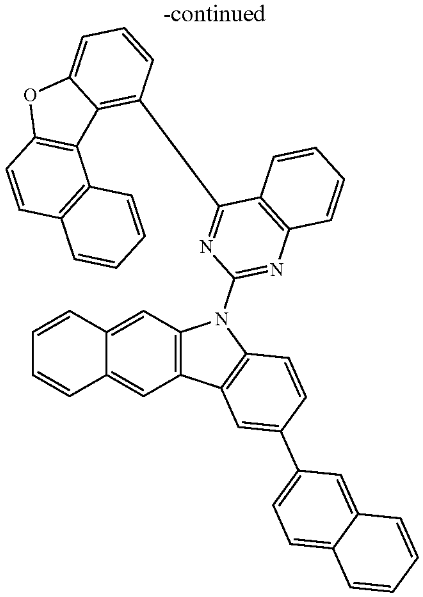
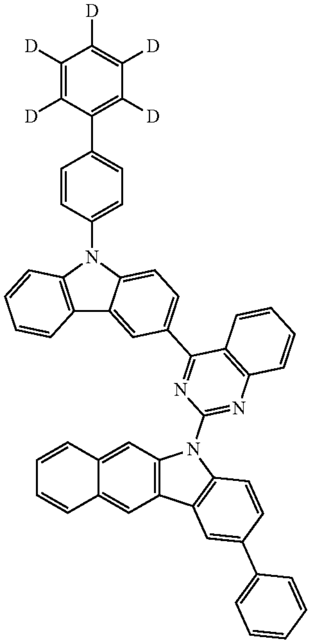

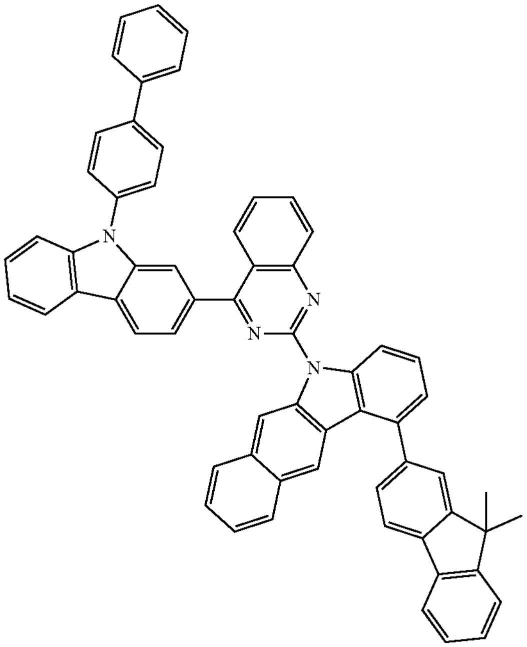
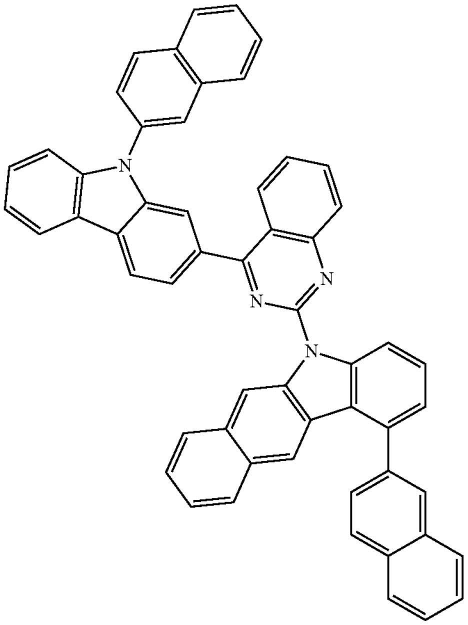
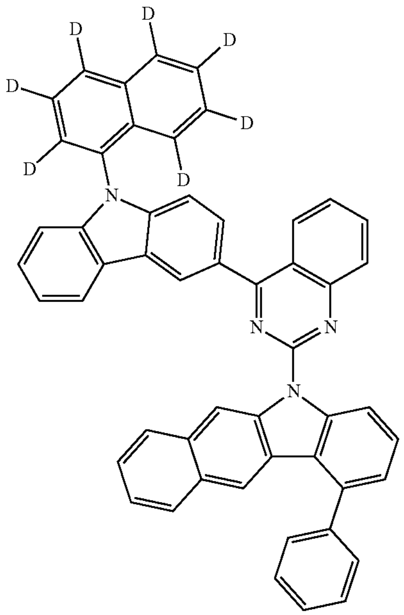
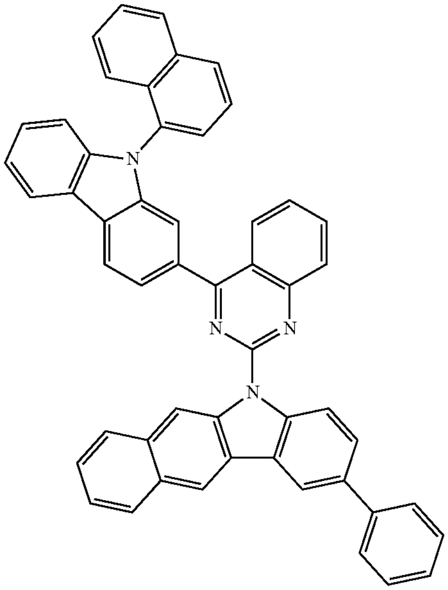
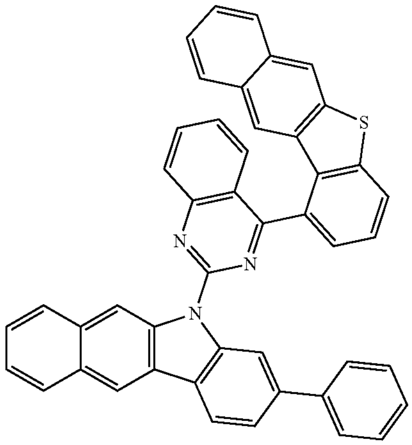

-continued
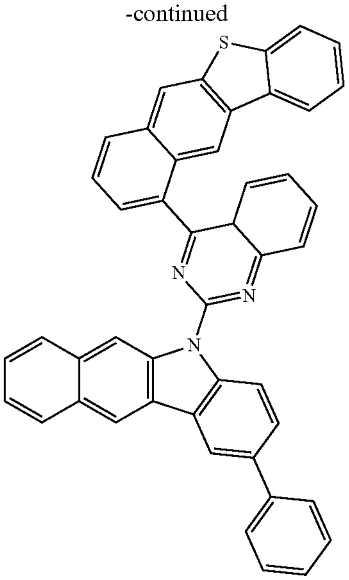
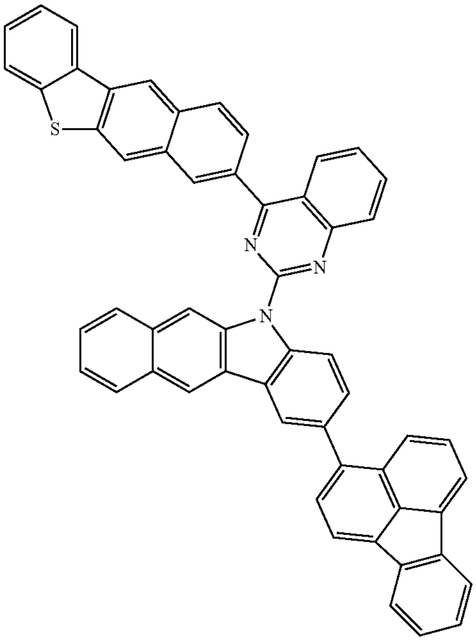
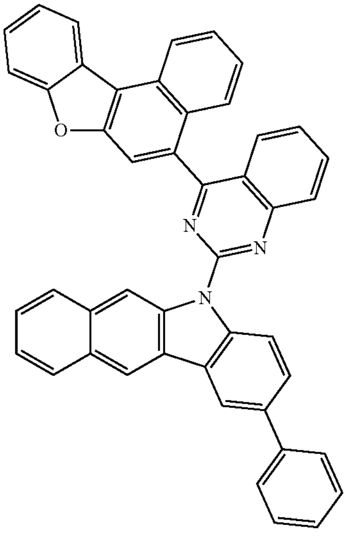
-continued
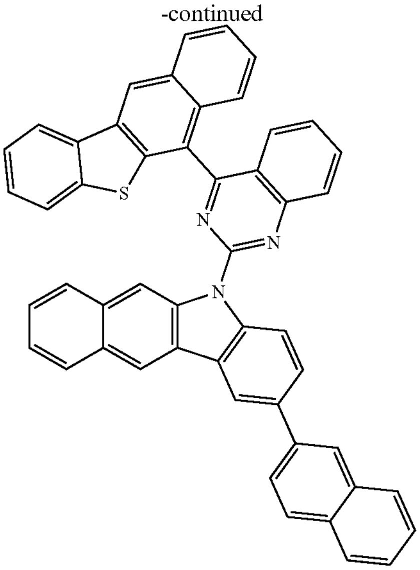
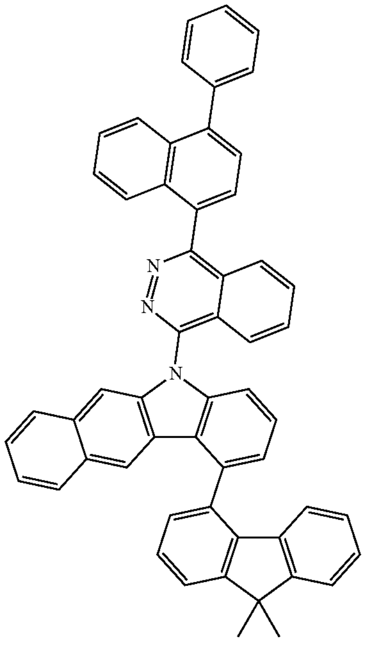

-continued
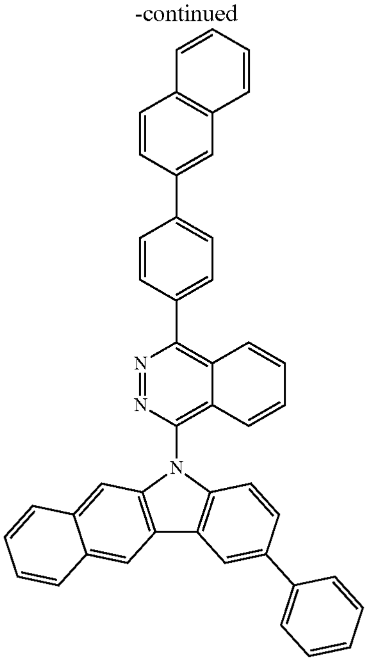
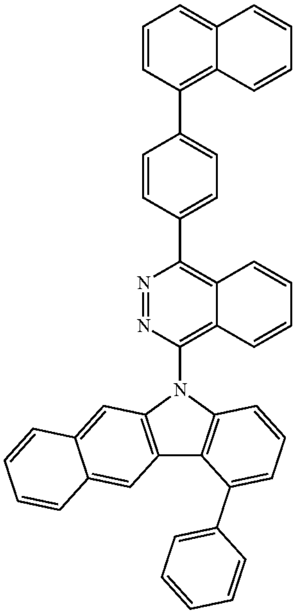
-continued
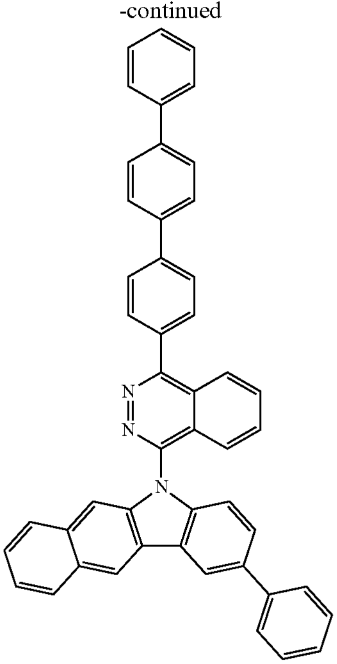
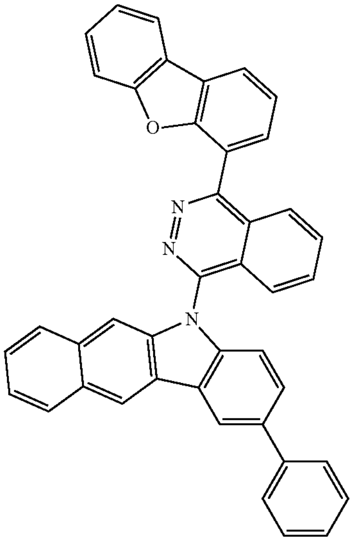

-continued
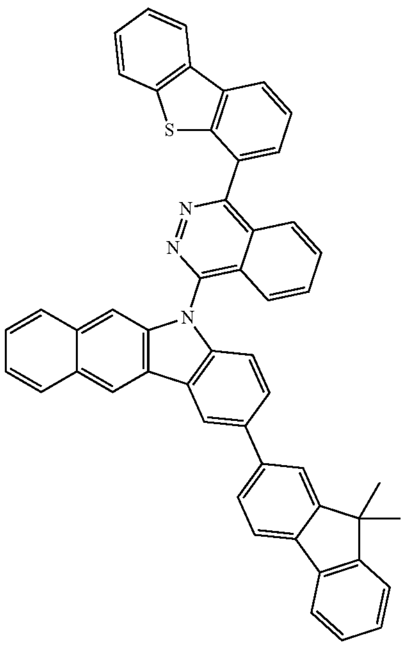
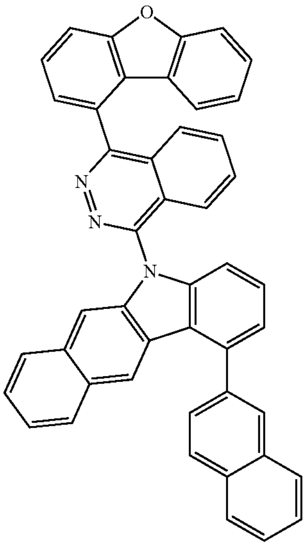
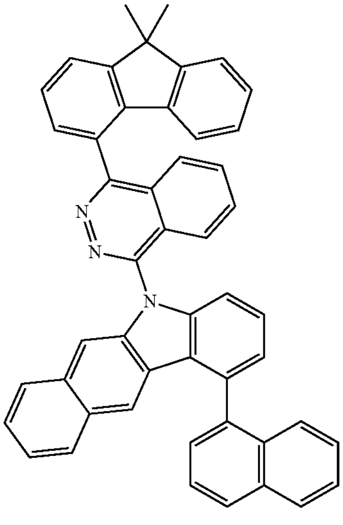
-continued
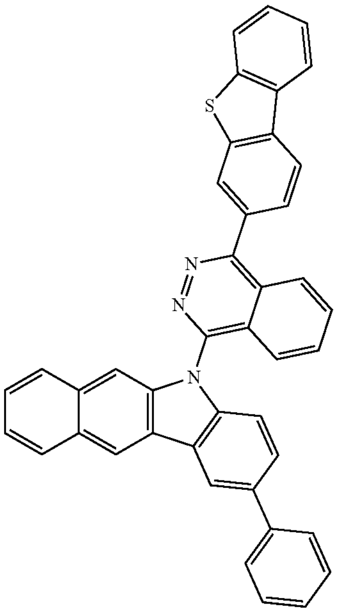
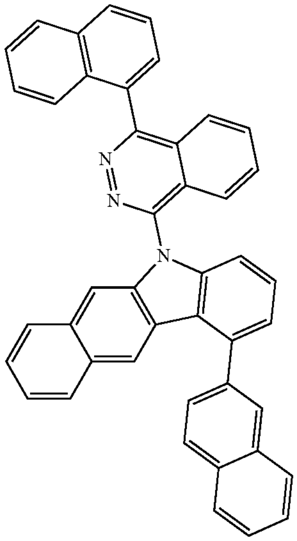
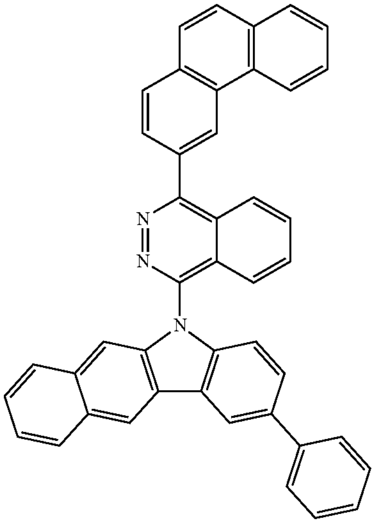

-continued
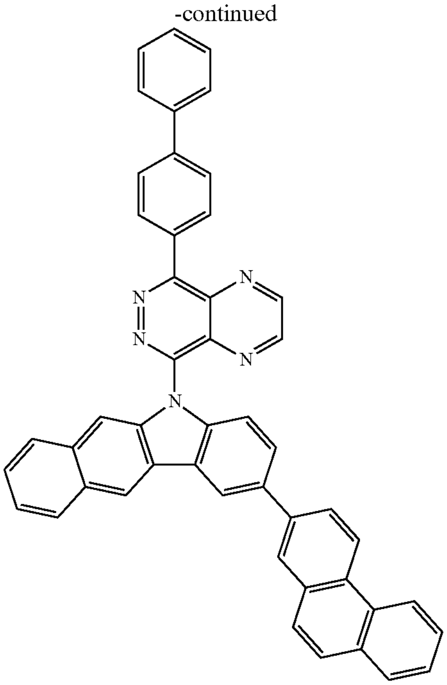
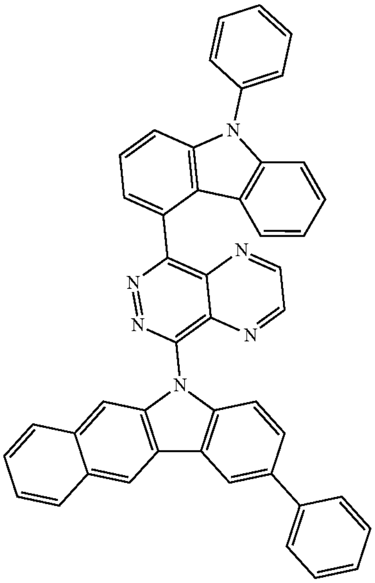
-continued
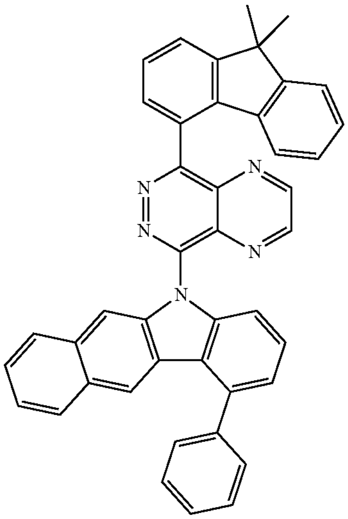
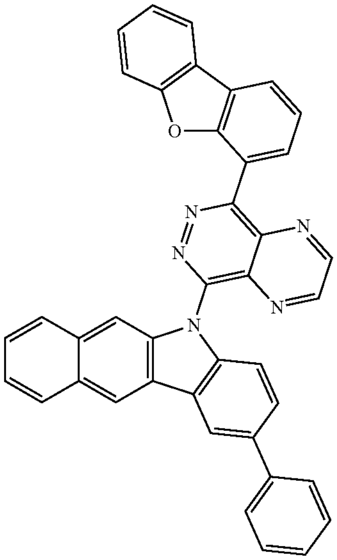
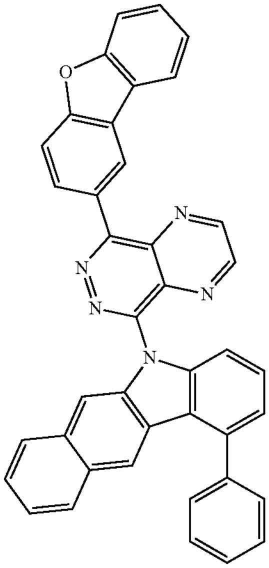

-continued
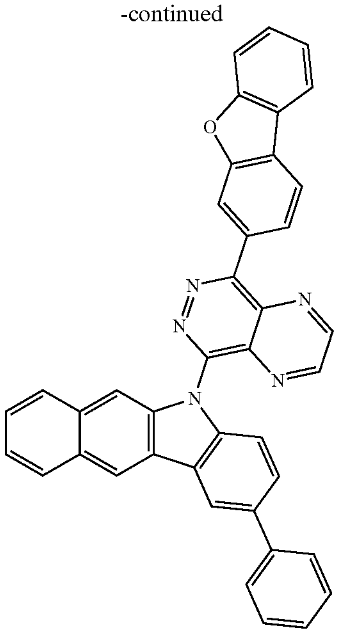
-continued
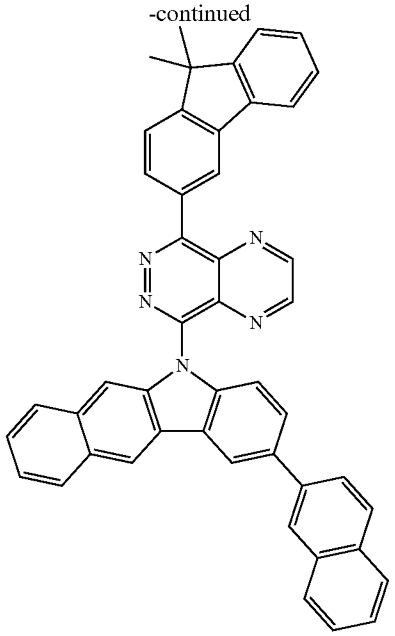
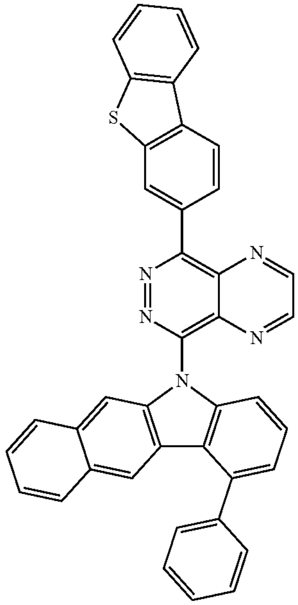
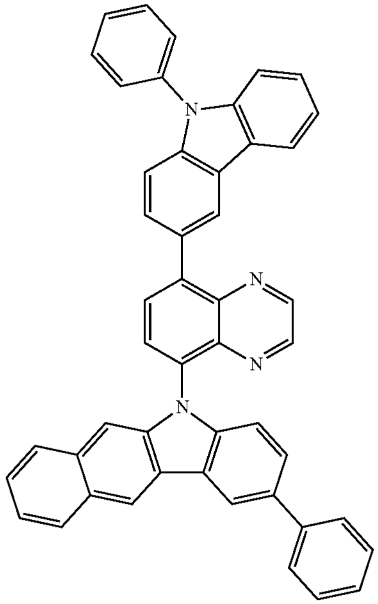

-continued
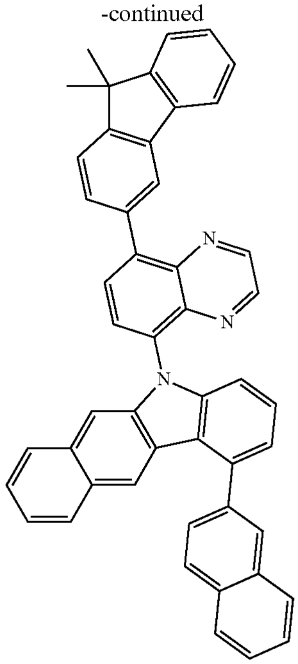
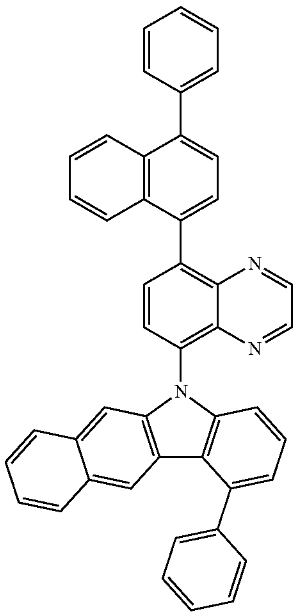
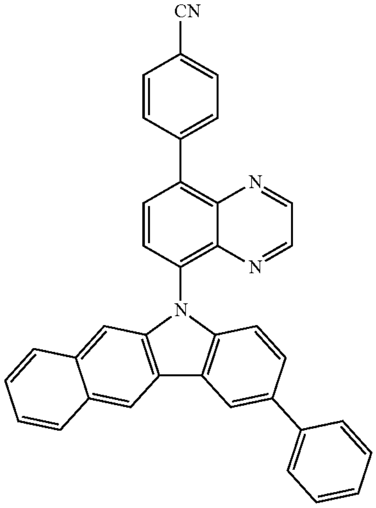
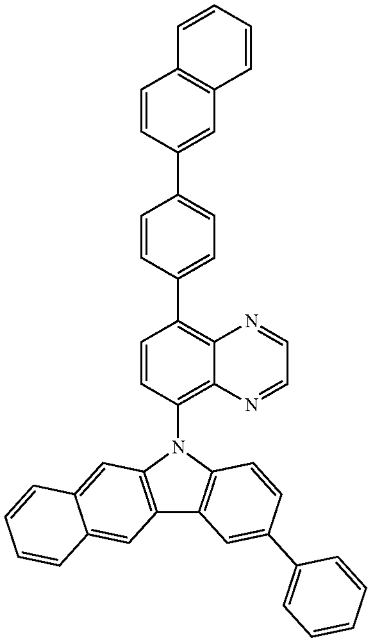

-continued
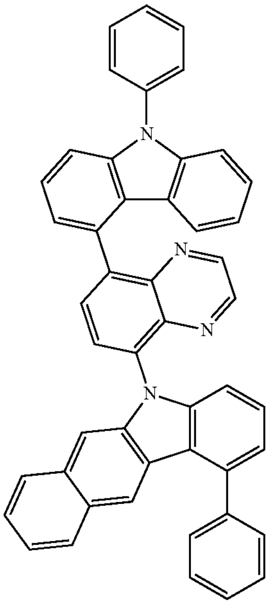
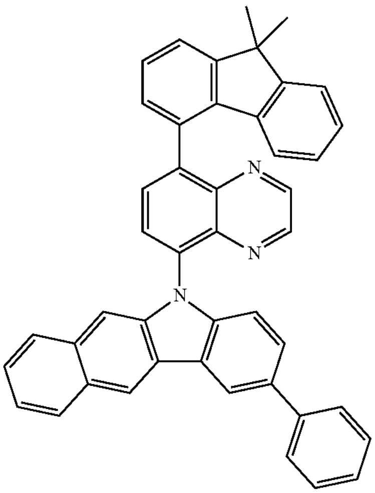
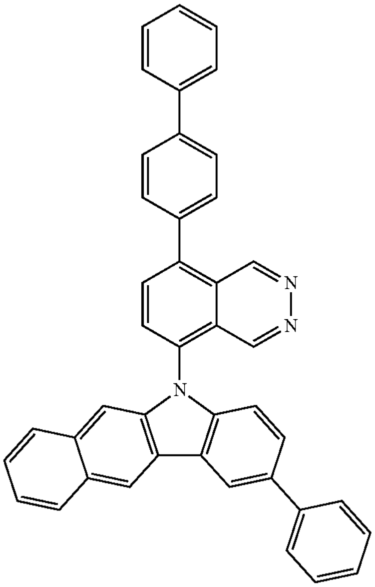
-continued
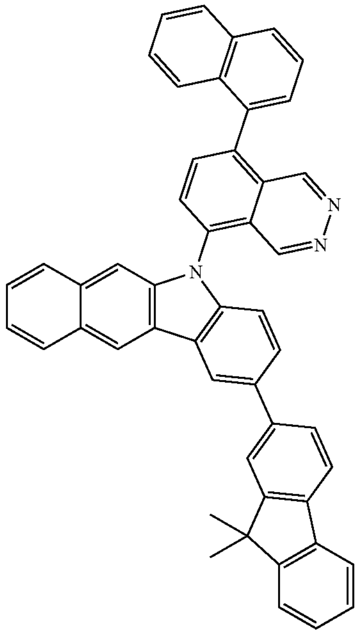
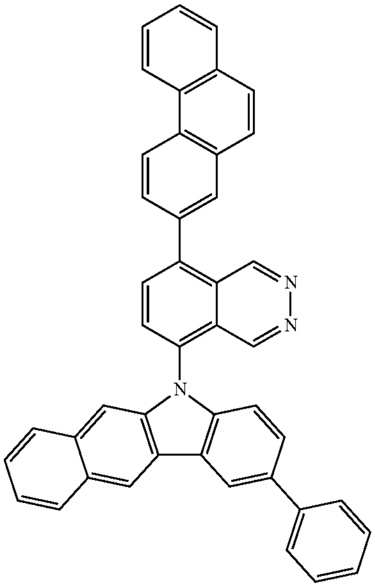
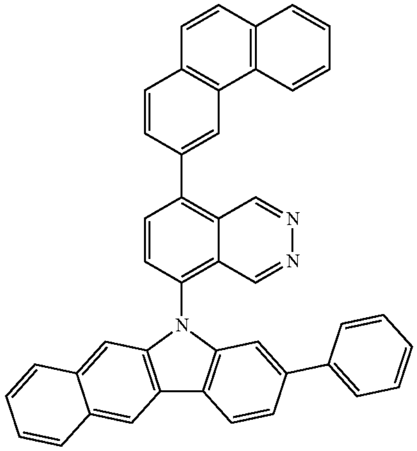

-continued
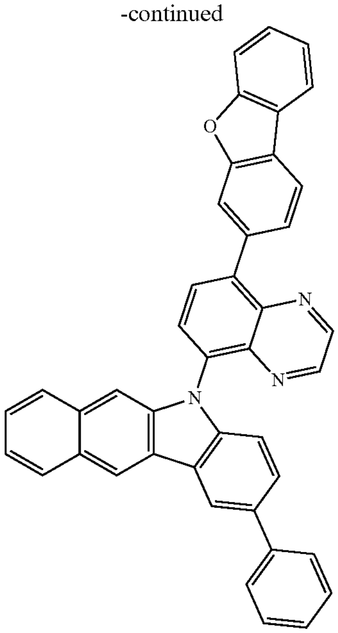
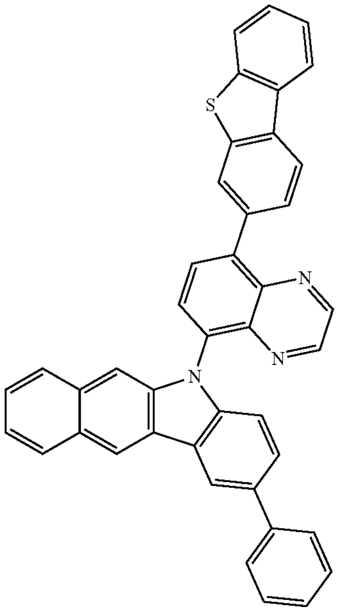
-continued
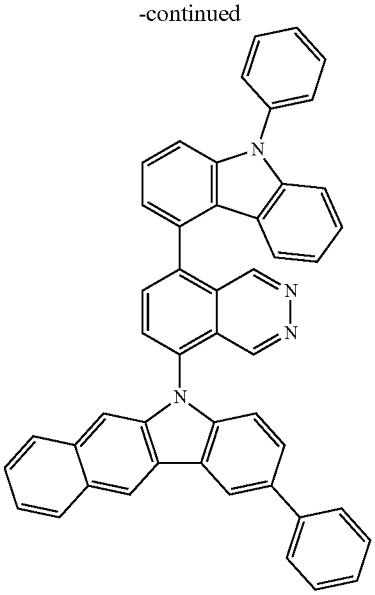
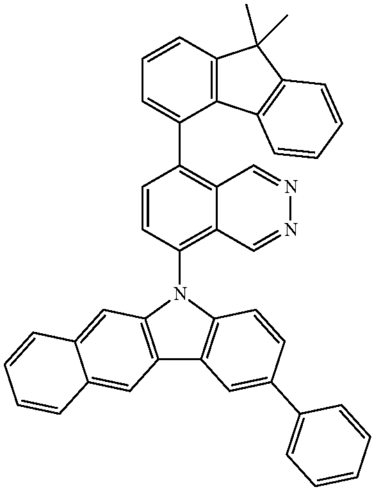
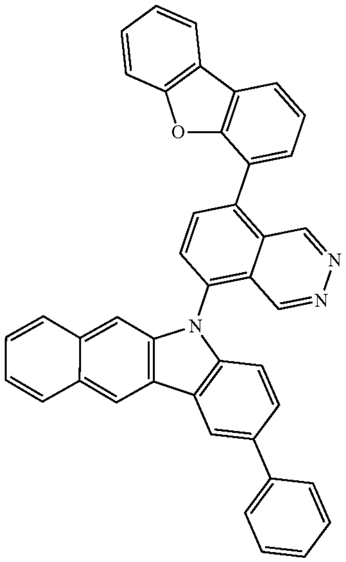

-continued
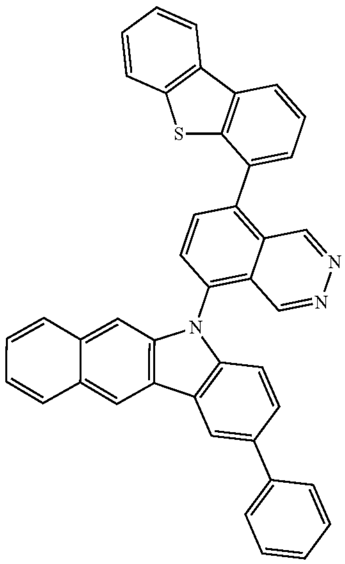
-continued
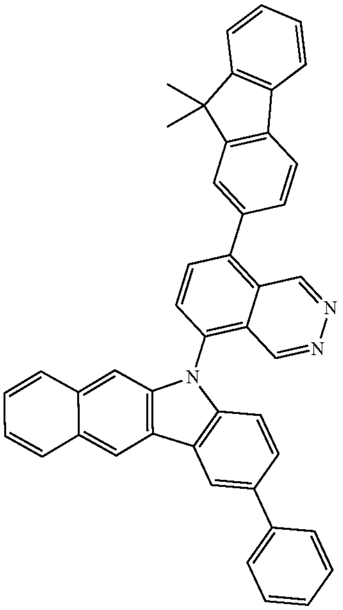
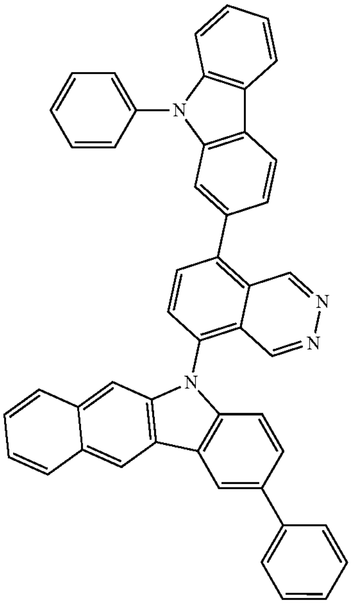
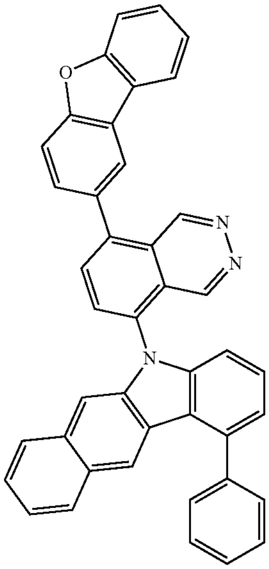

-continued
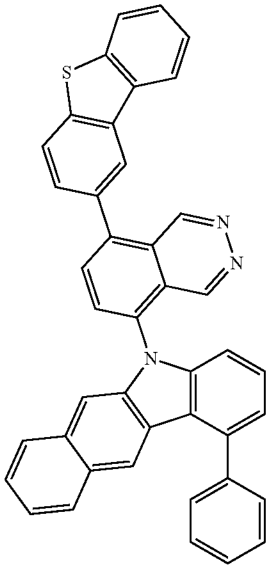
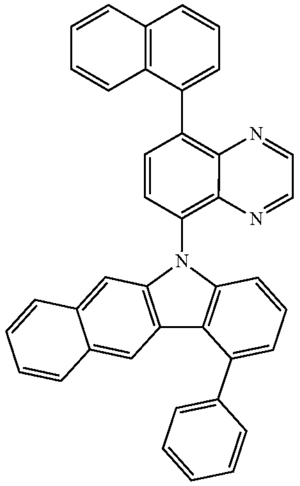
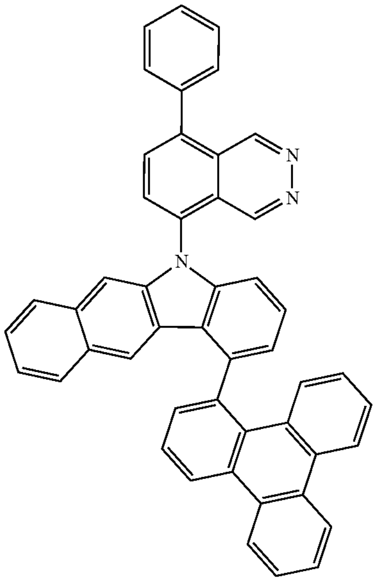
-continued
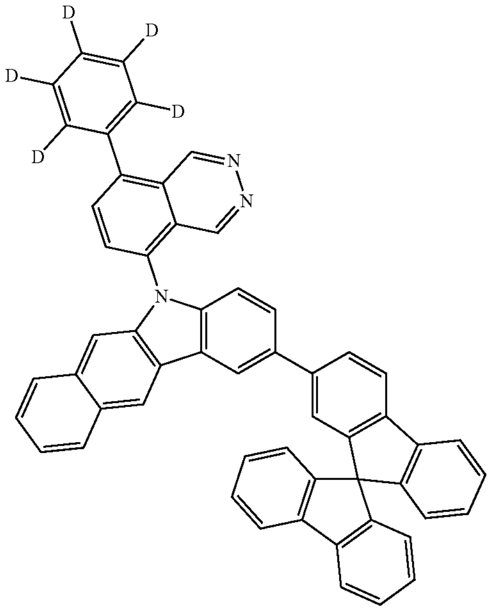
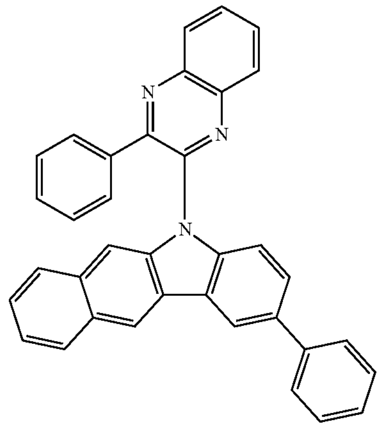
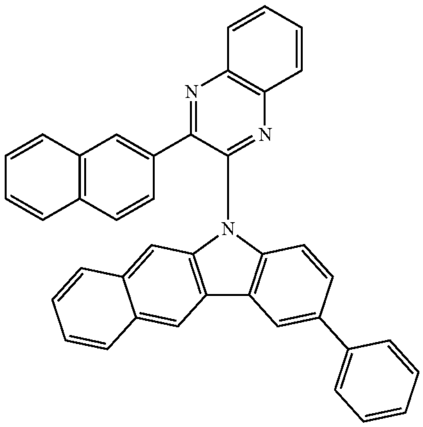

-continued
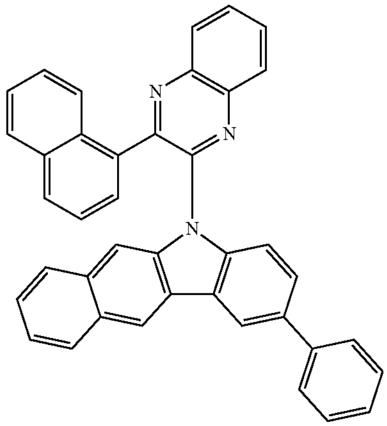
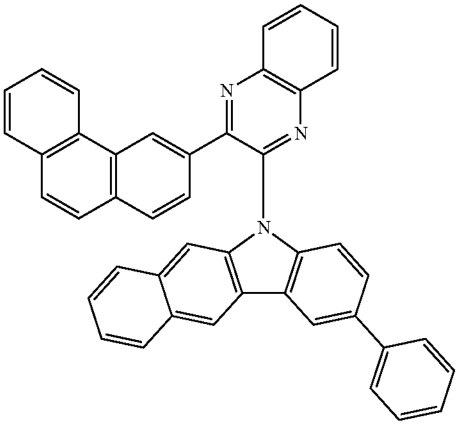
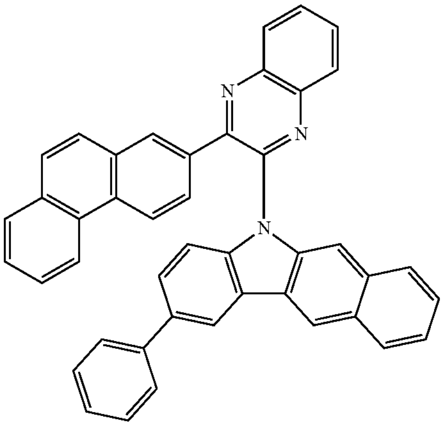
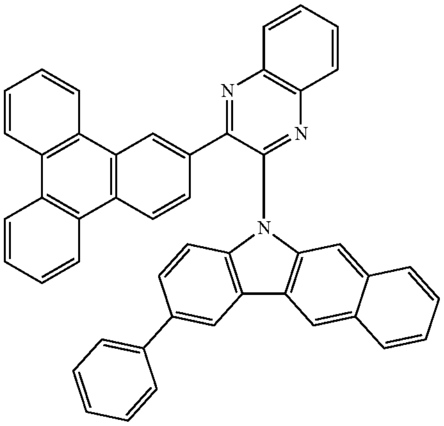
-continued
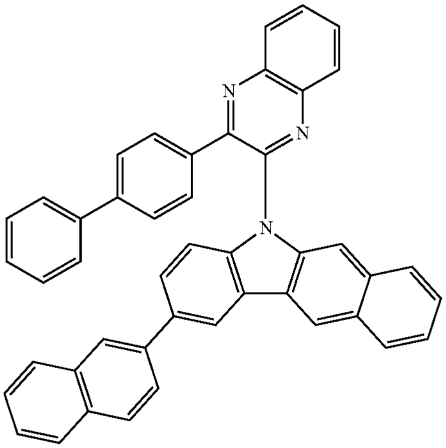
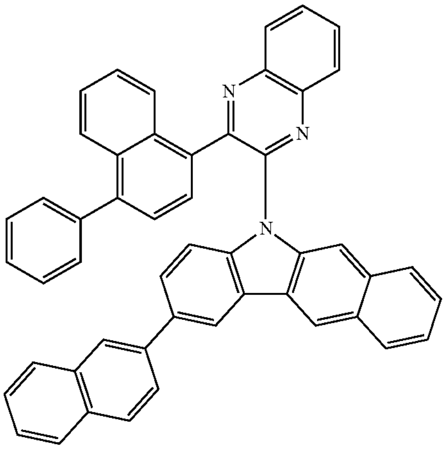
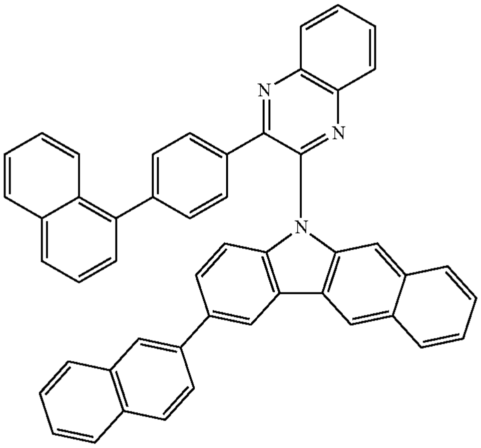

-continued
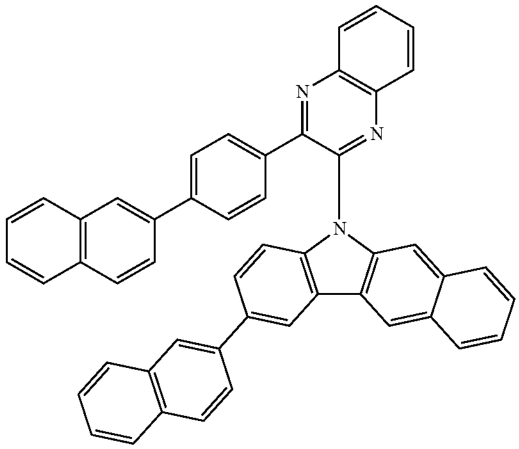
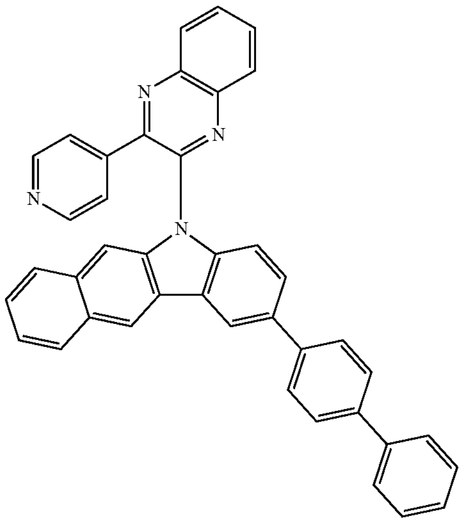
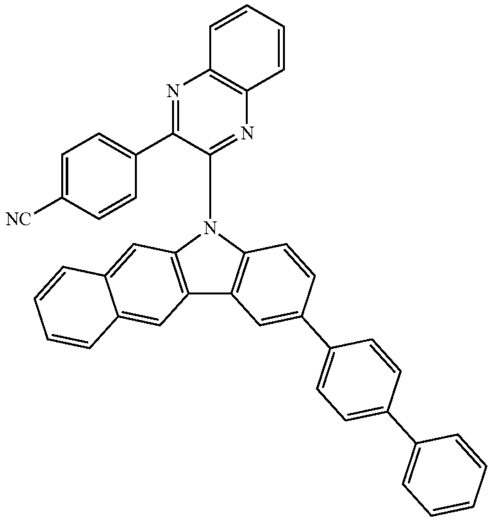
-continued
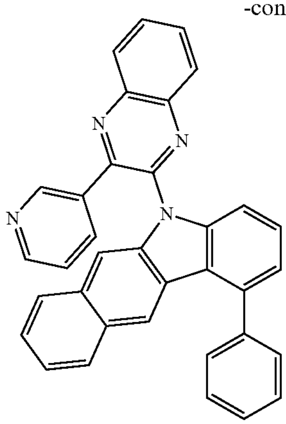
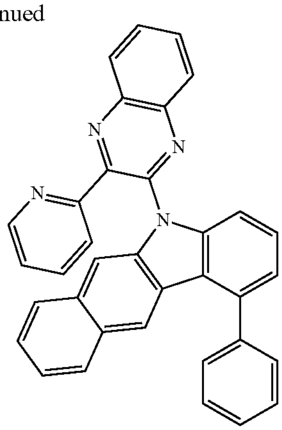
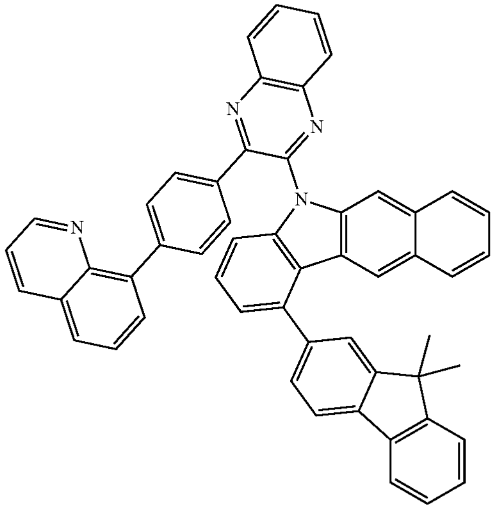
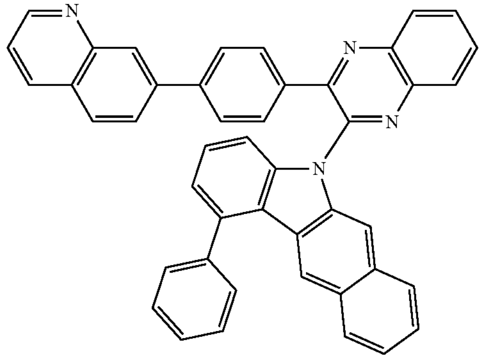
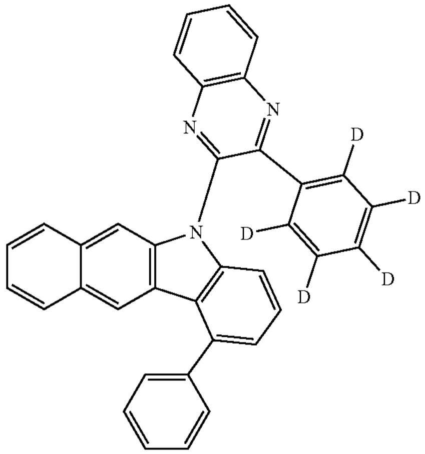

-continued
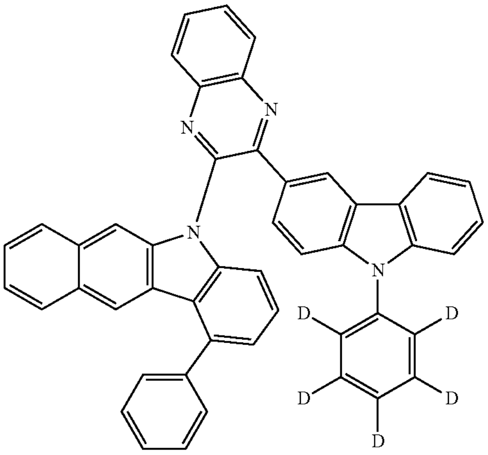
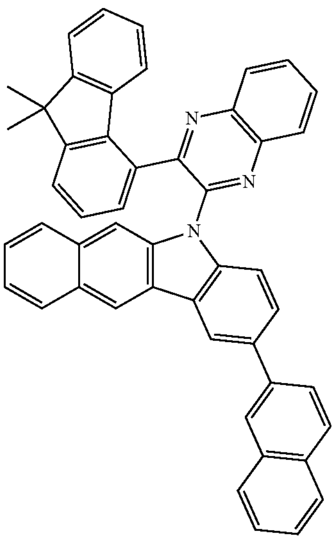
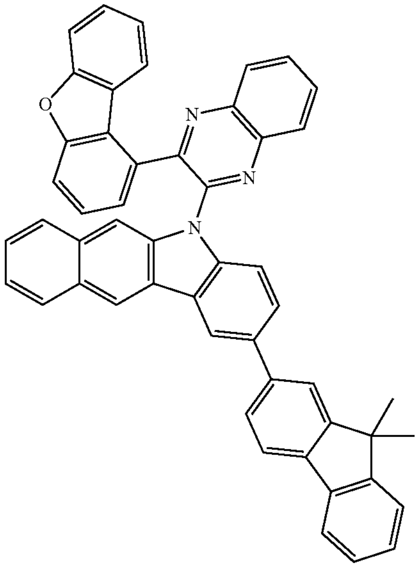
-continued
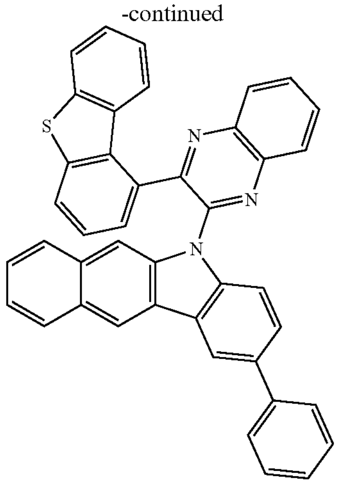
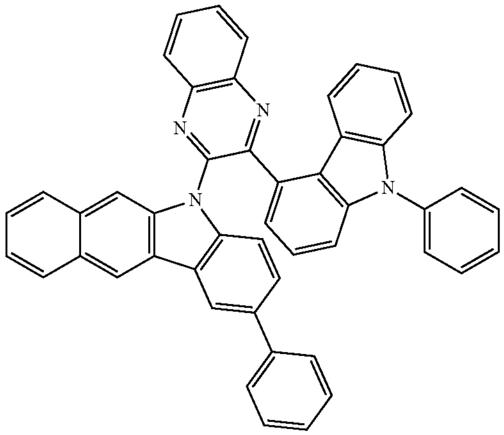
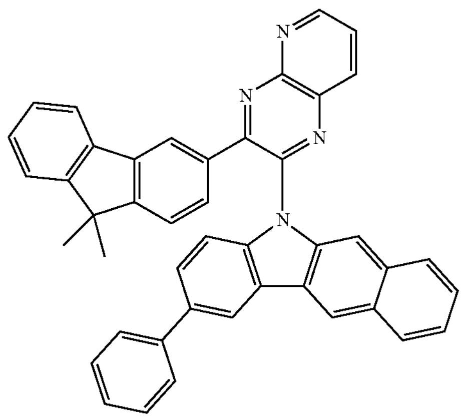

-continued
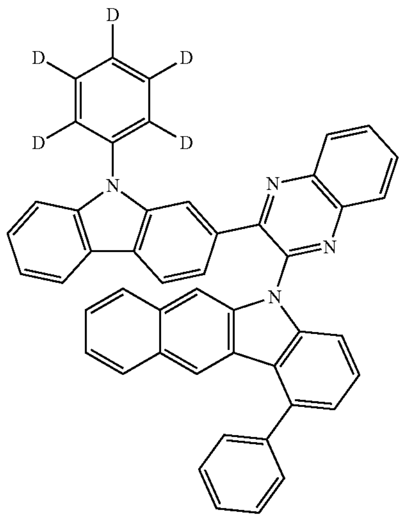
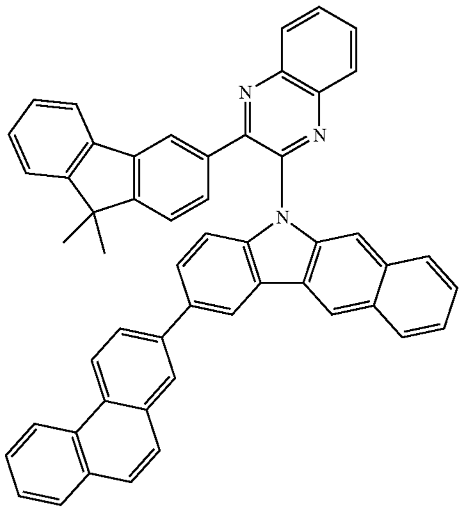
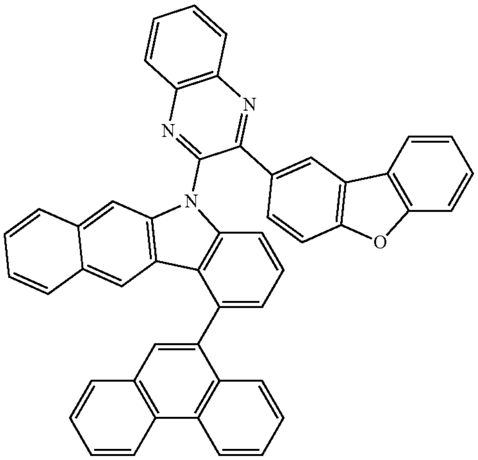
-continued
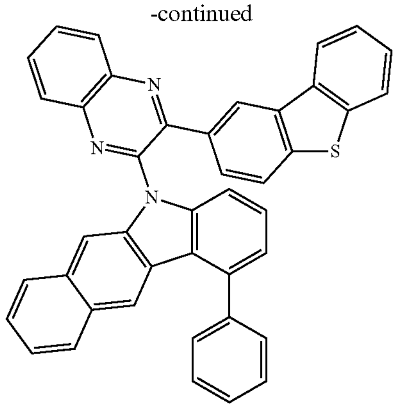
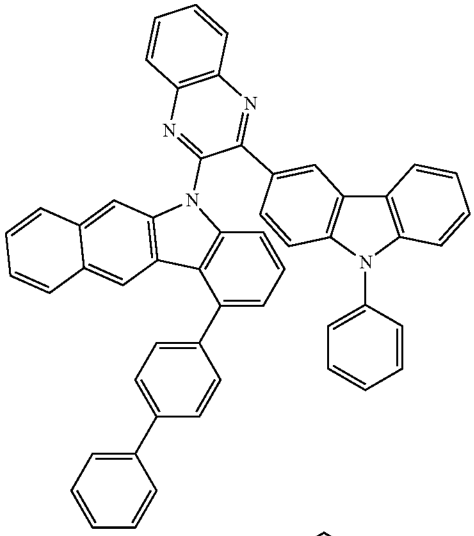
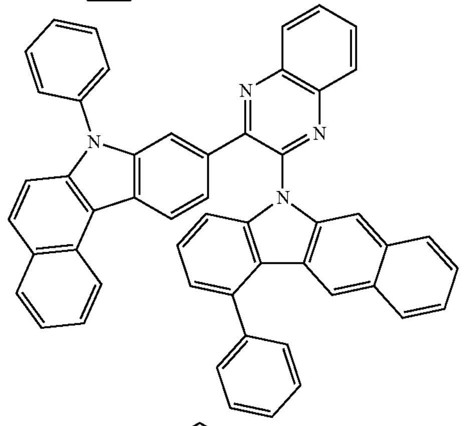
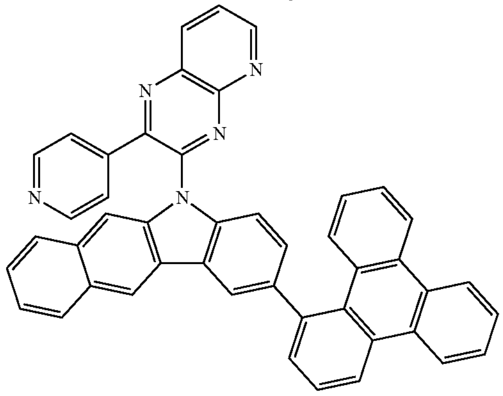

-continued
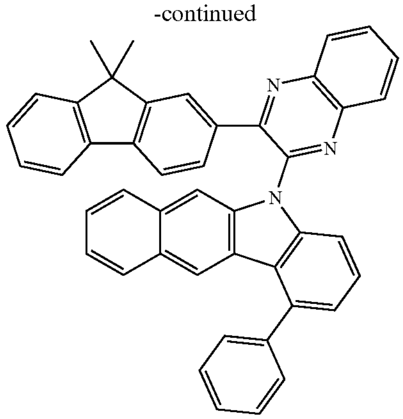
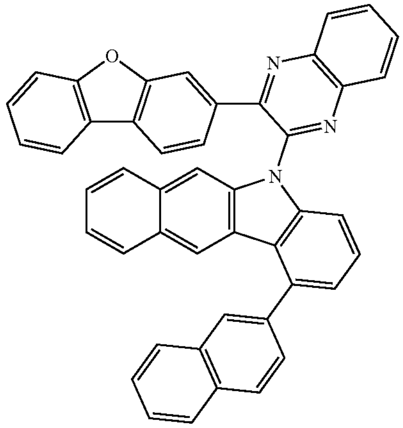
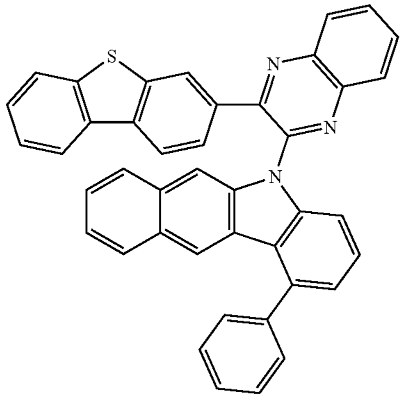
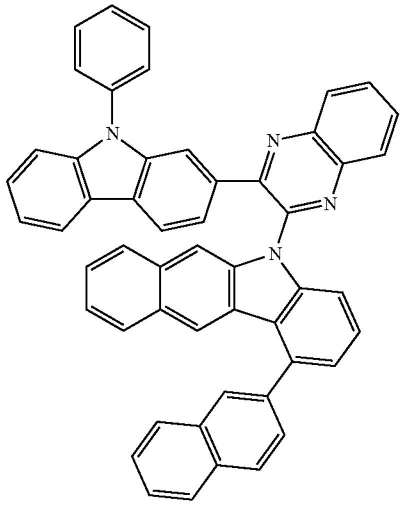
-continued
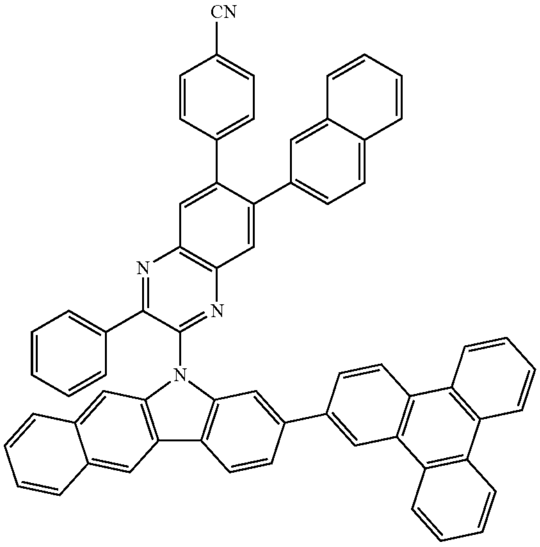
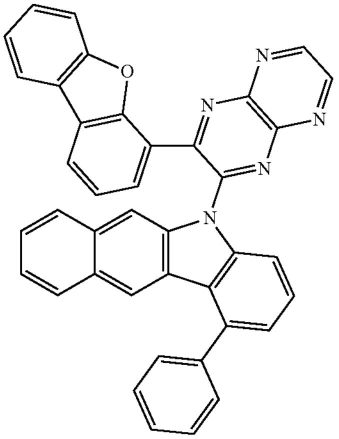
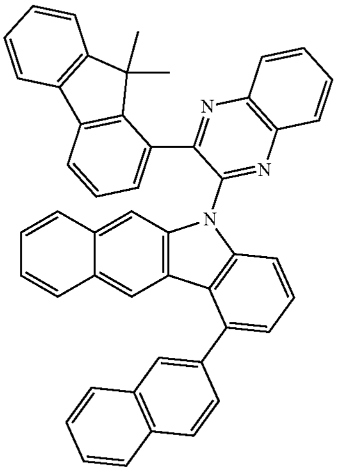

-continued
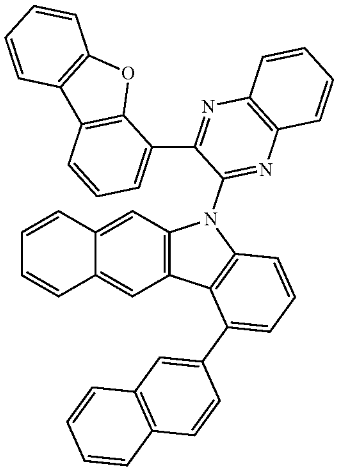
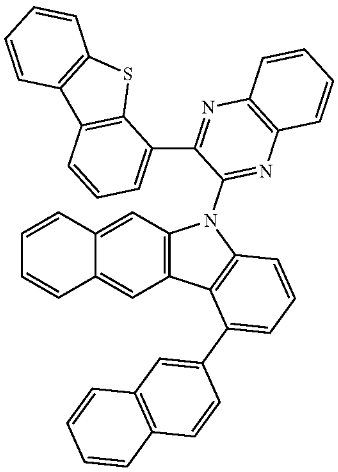
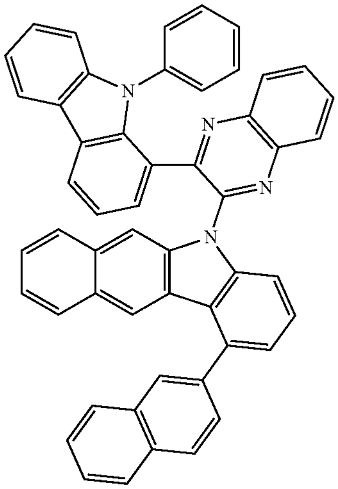
-continued
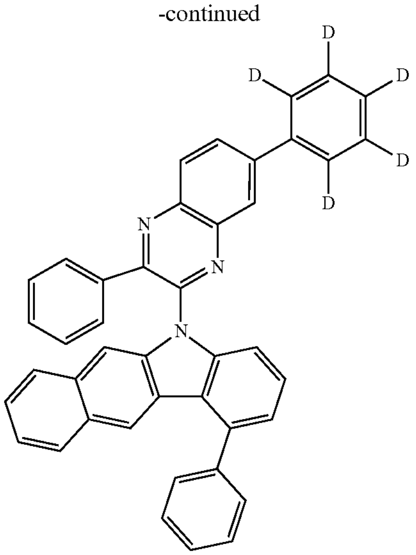
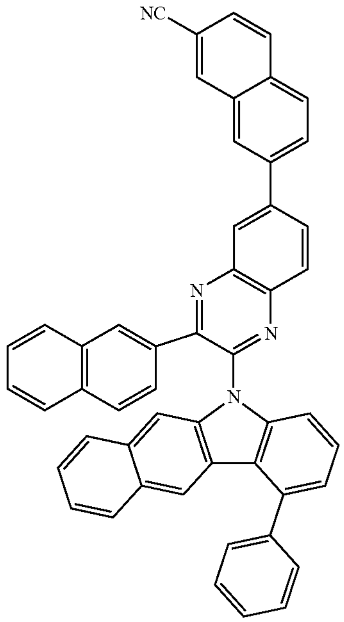
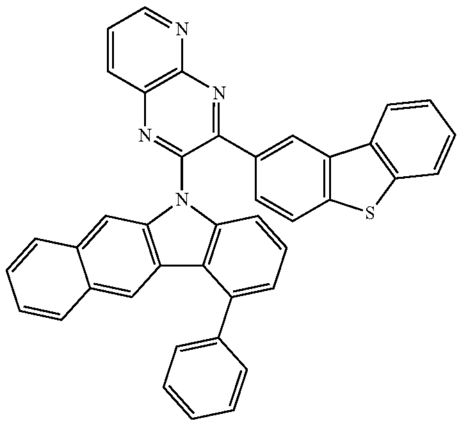

-continued
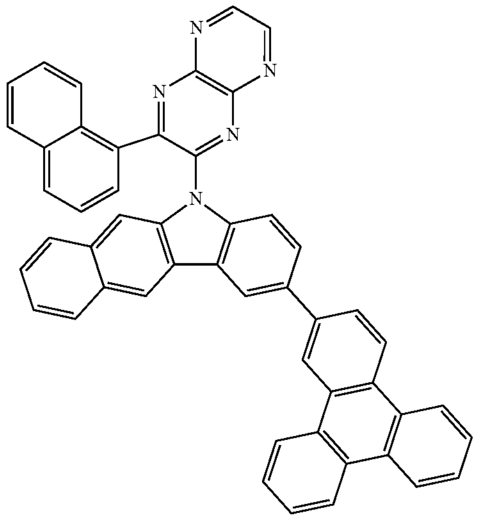
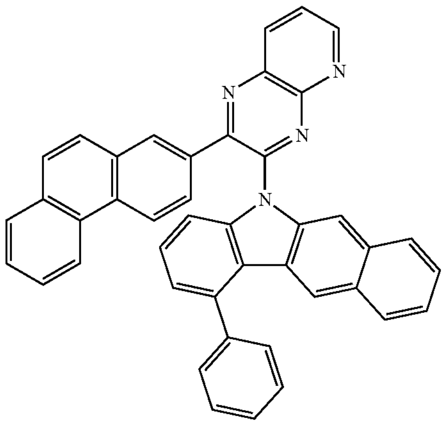
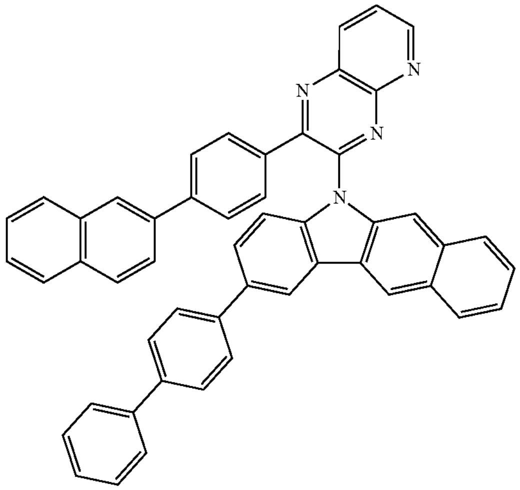
-continued
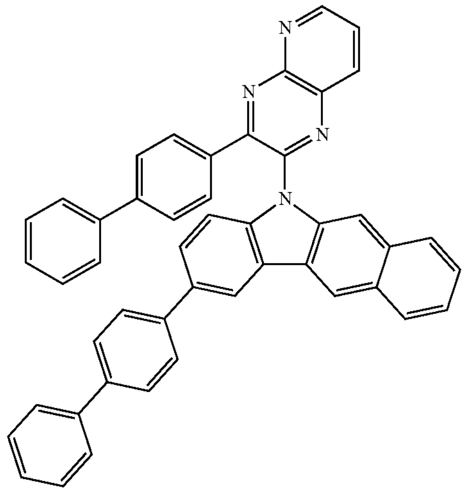
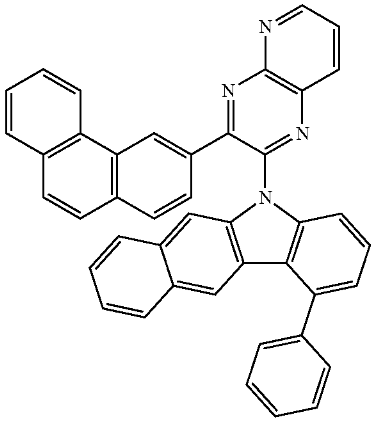
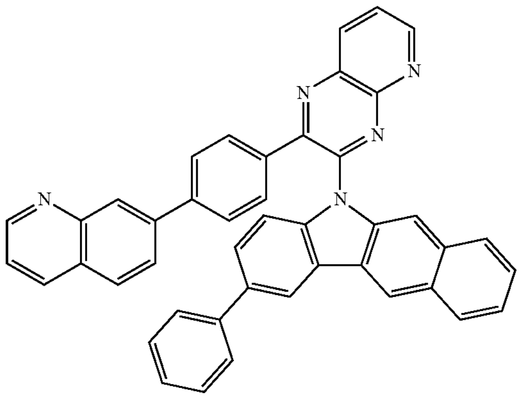

-continued
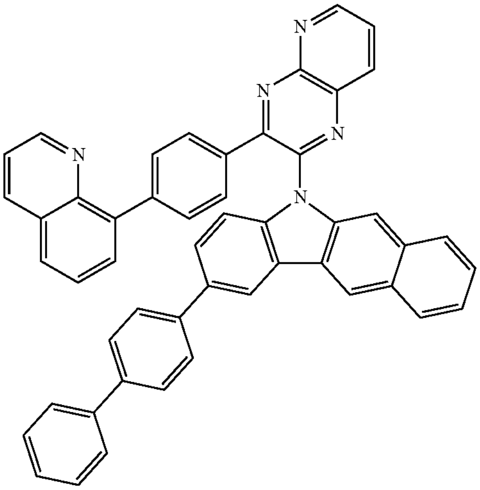
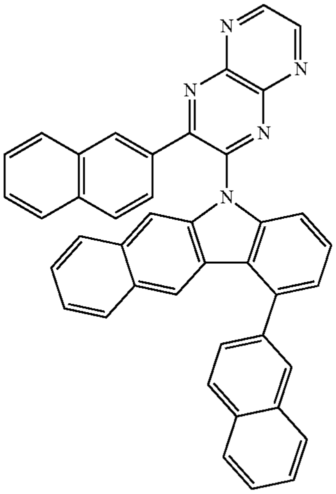
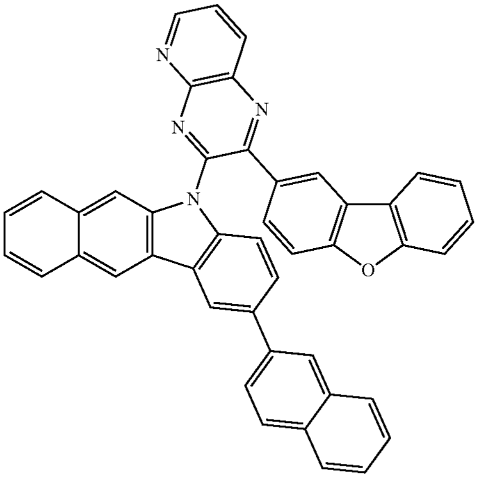
-continued
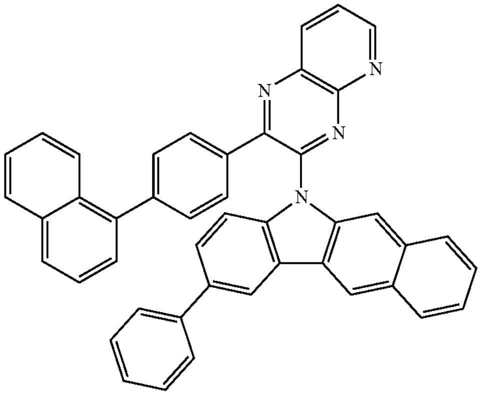
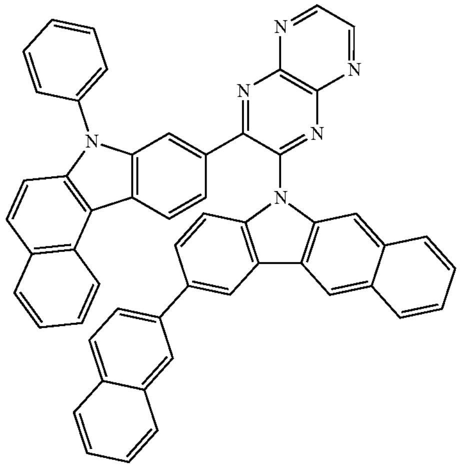
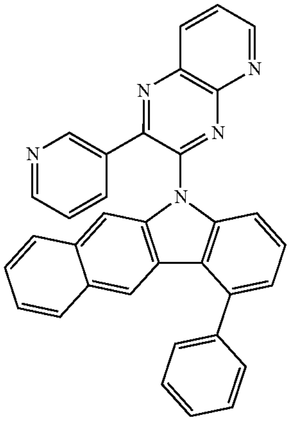

-continued
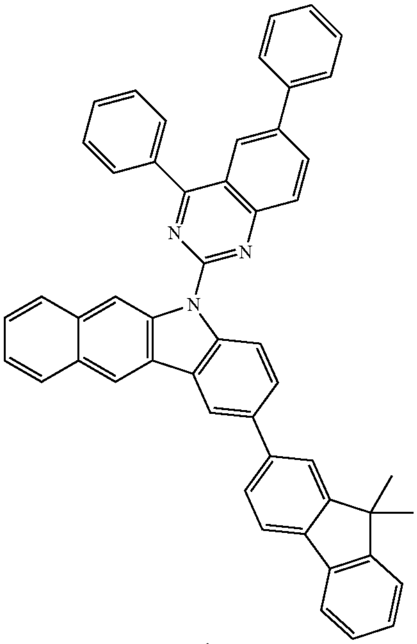
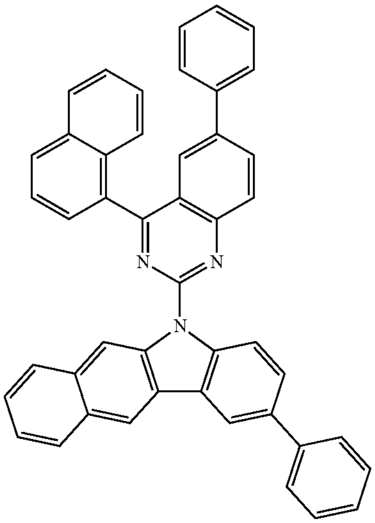
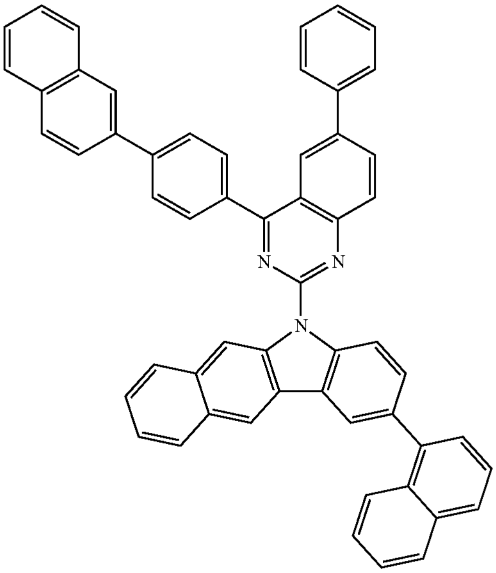
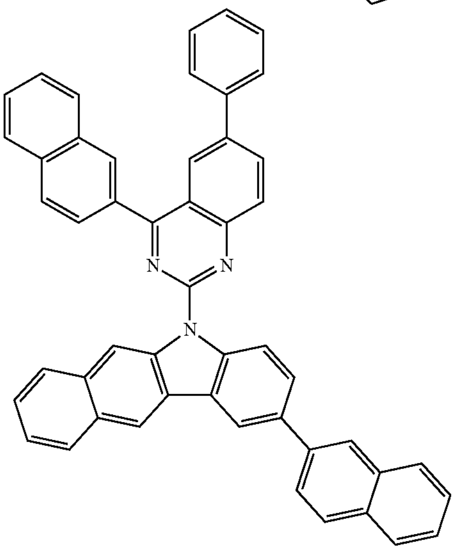
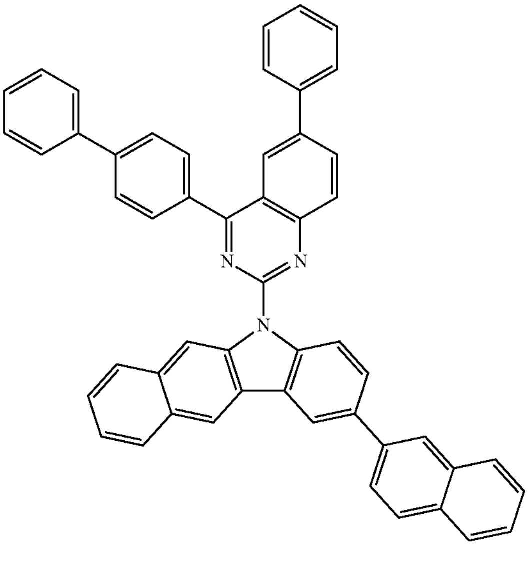
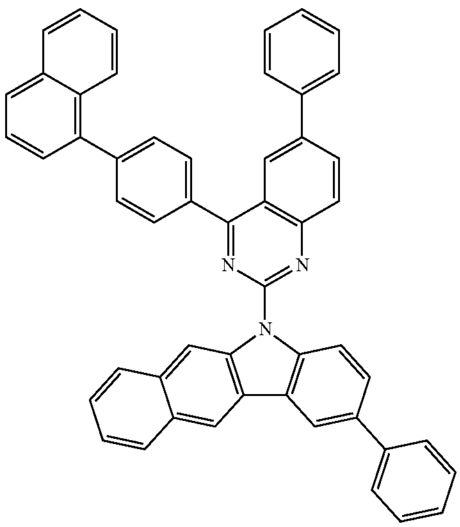

-continued
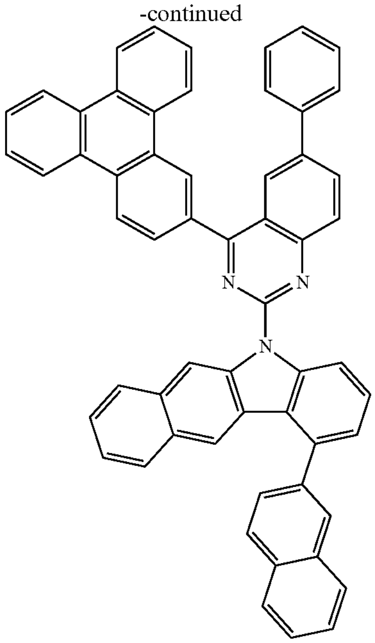
-continued
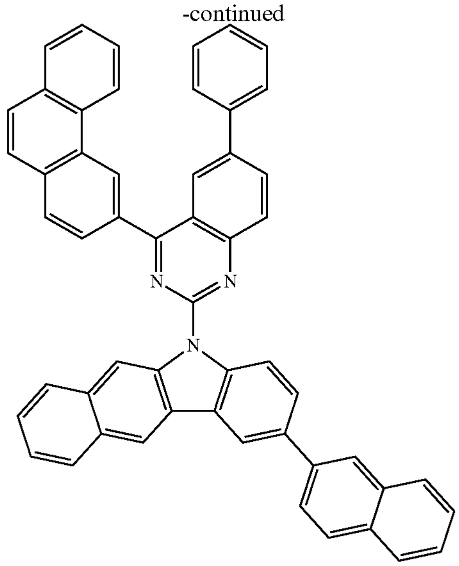
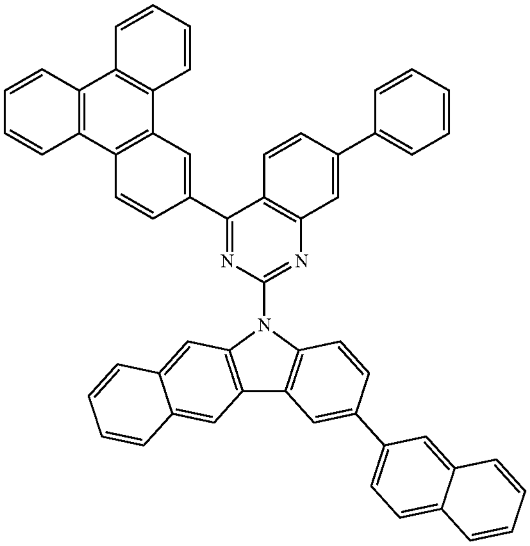
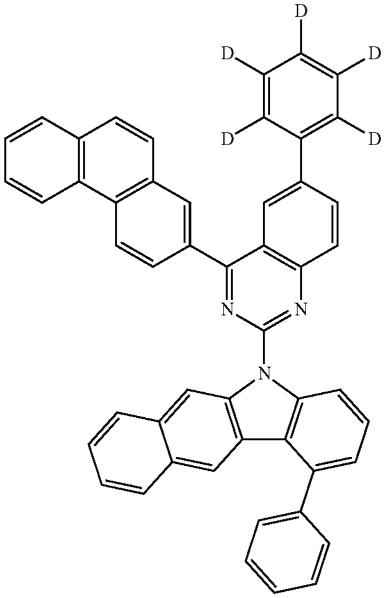
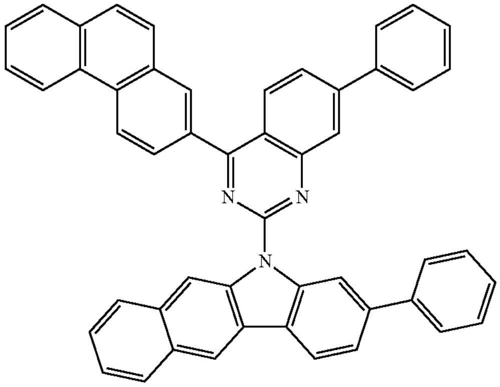

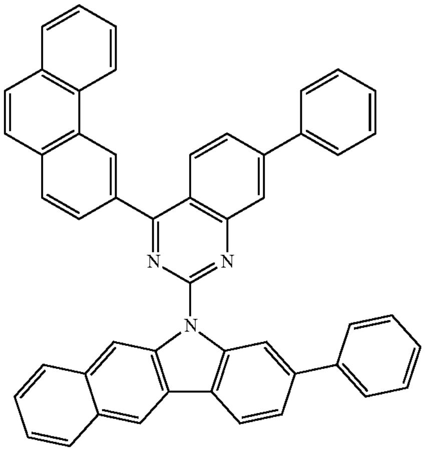
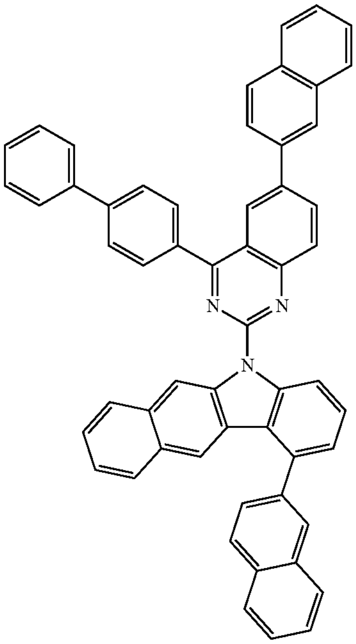
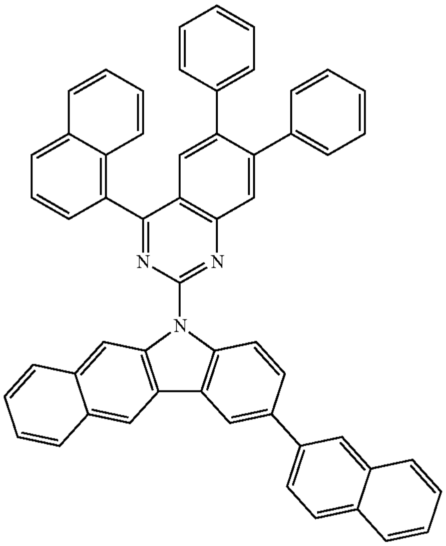
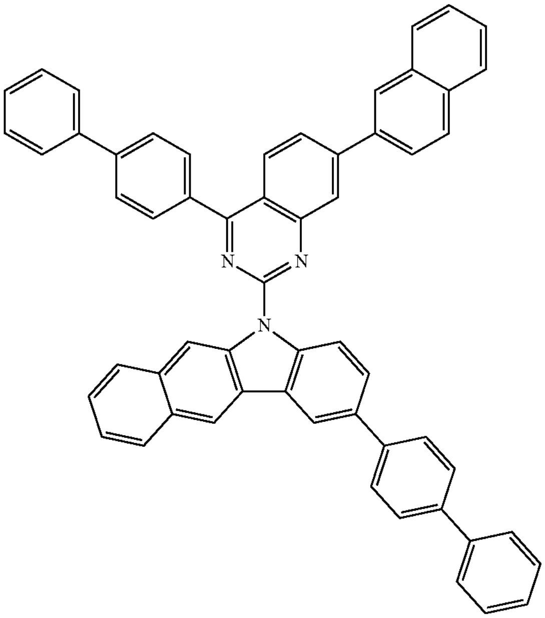
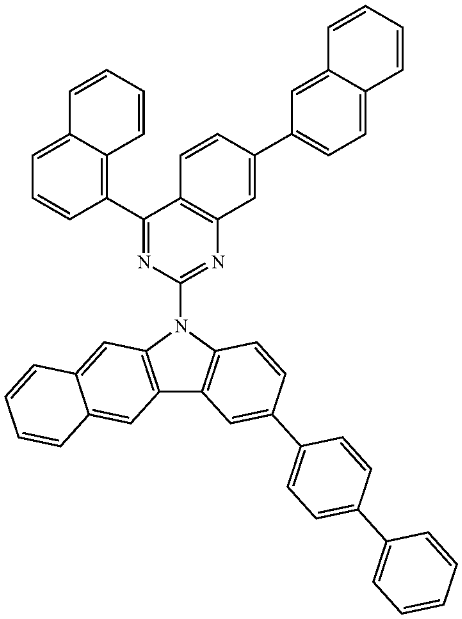

-continued
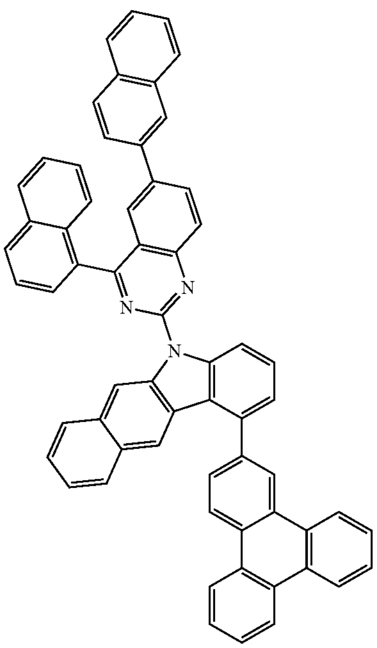
-continued
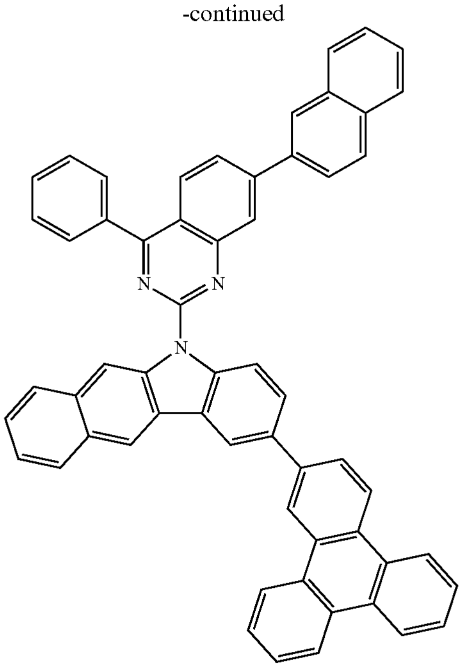
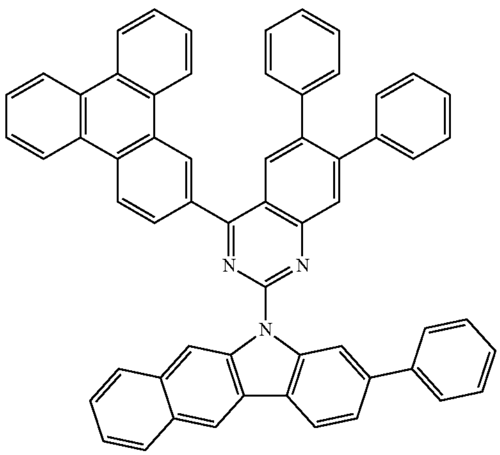
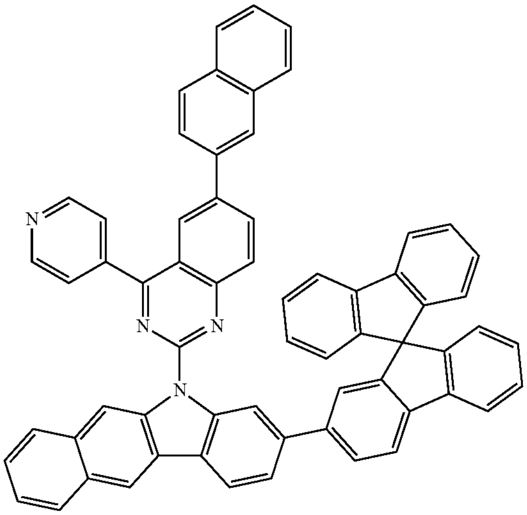

-continued
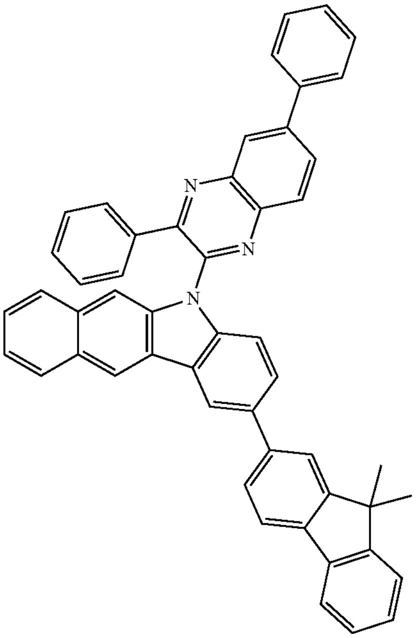
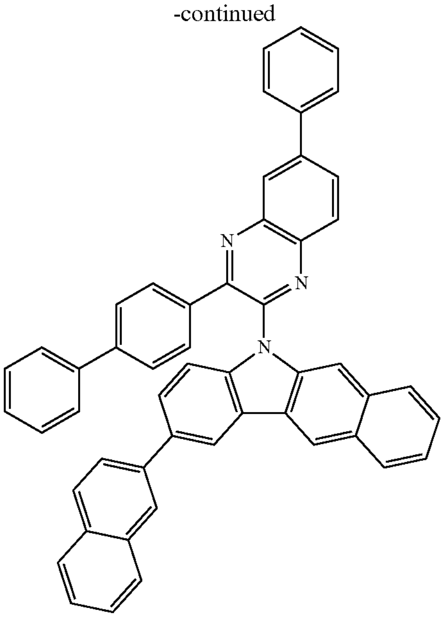
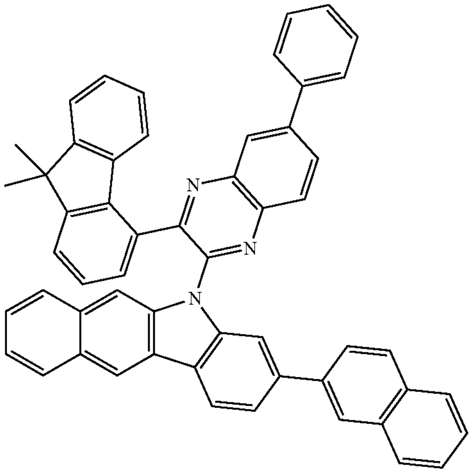
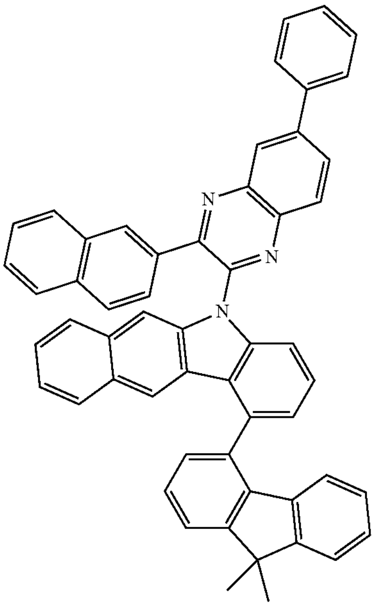
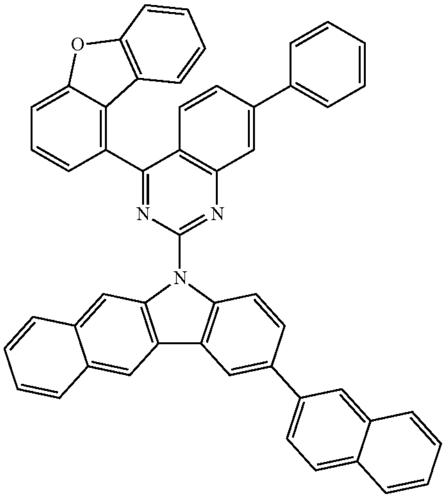

-continued
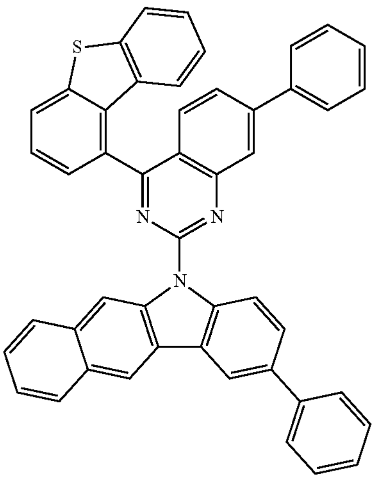
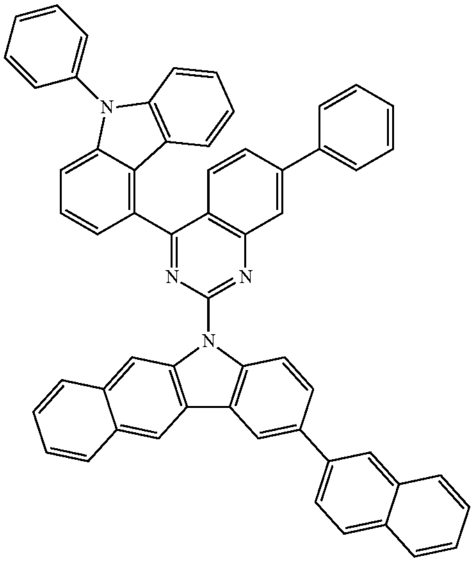
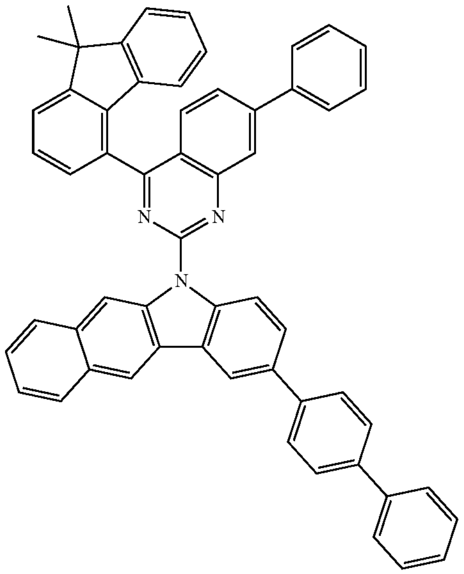
-continued
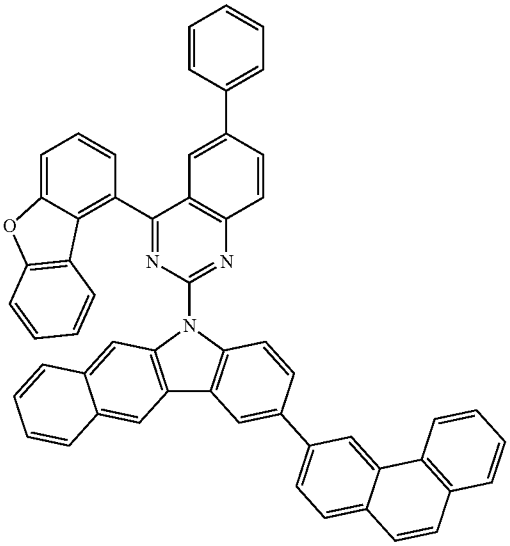
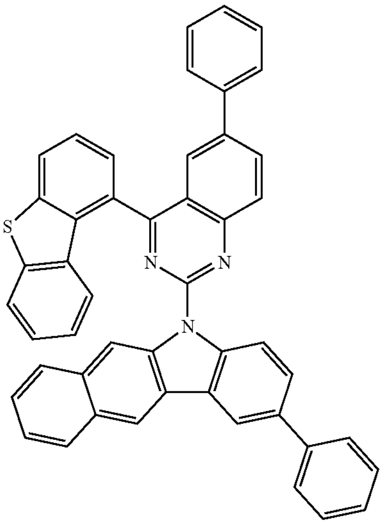
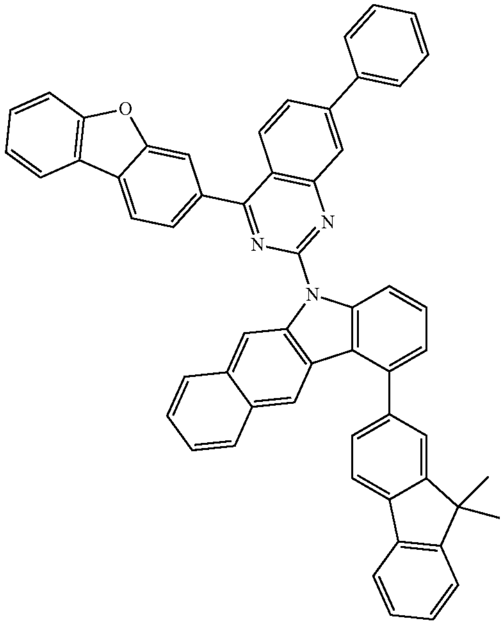

-continued
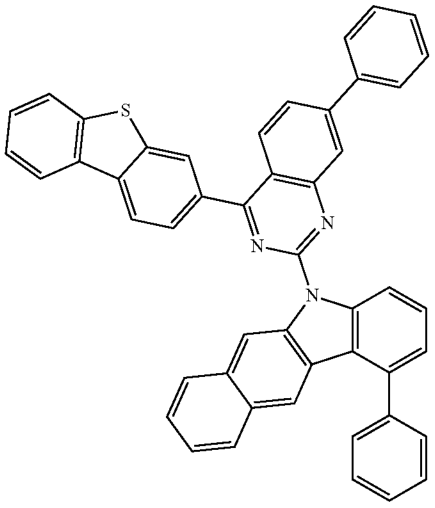
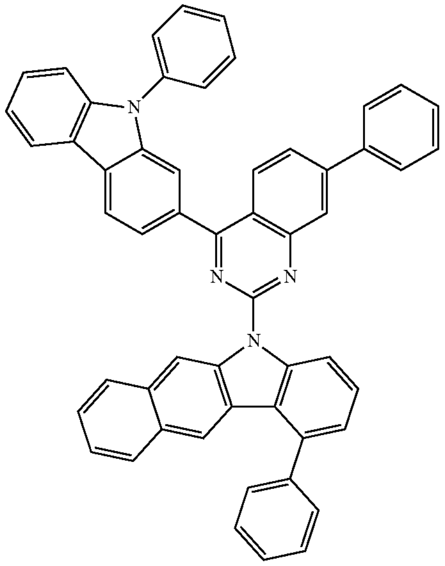
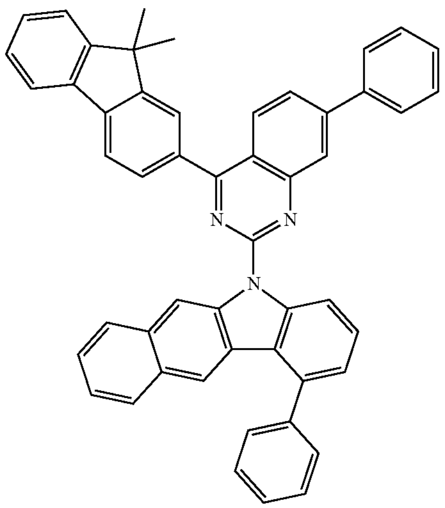
-continued
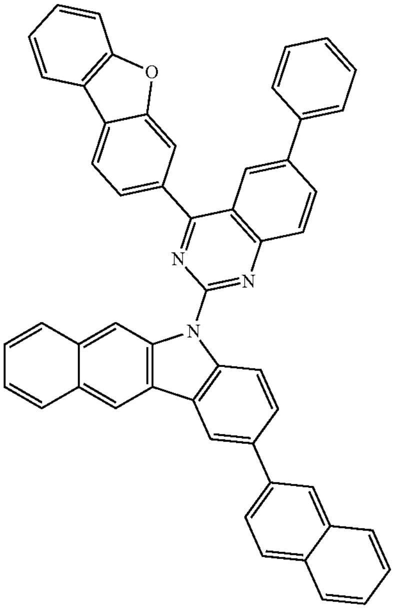
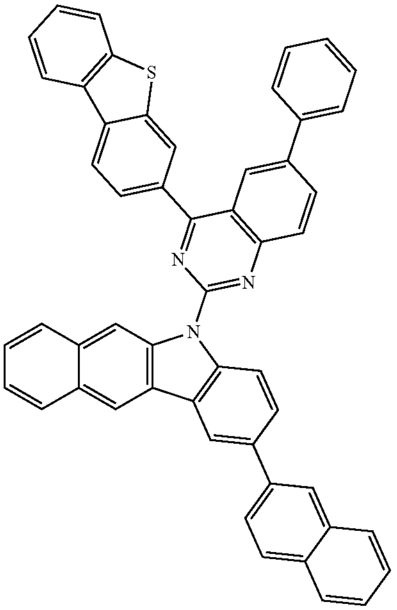

-continued
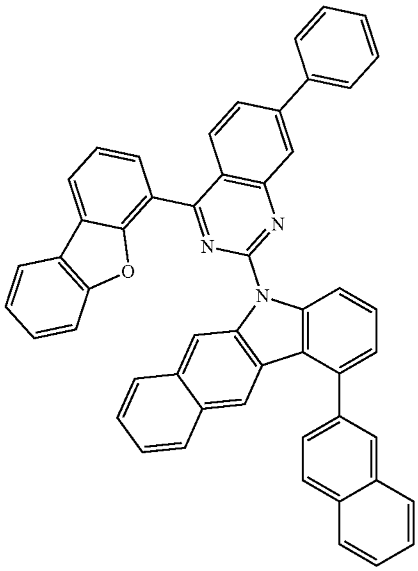
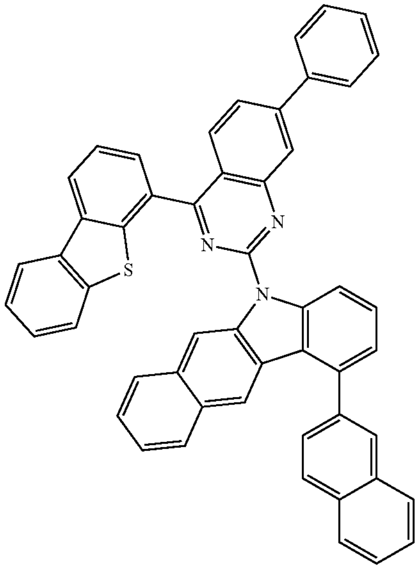
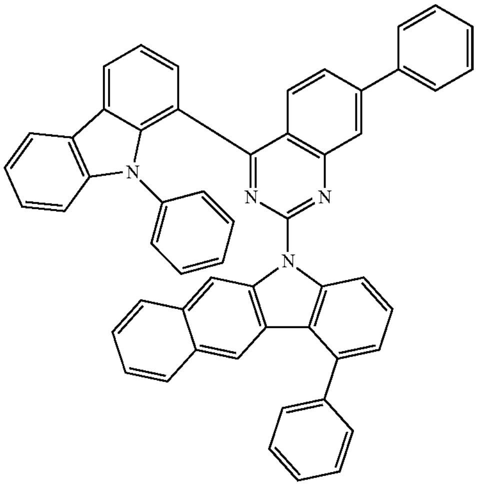
-continued
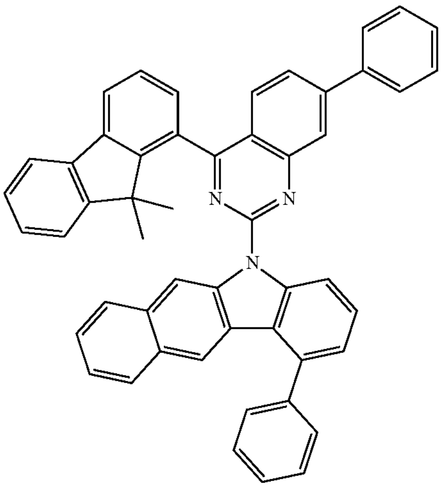
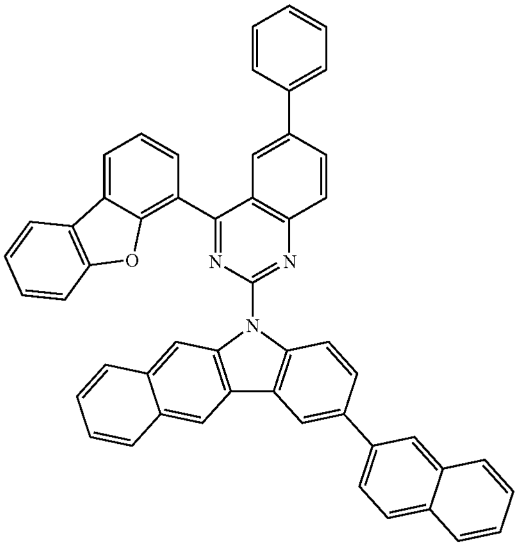
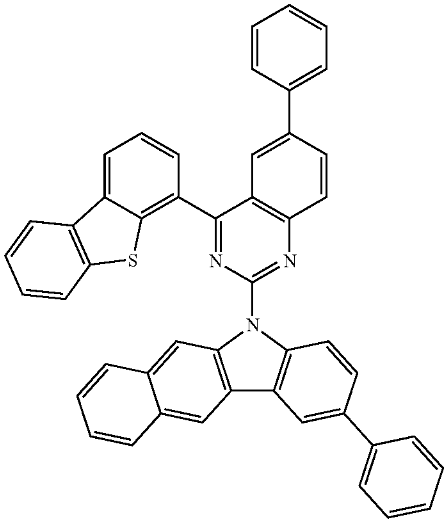

-continued
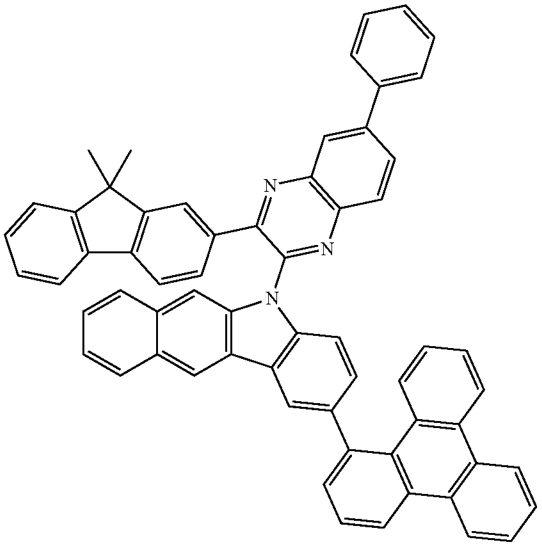
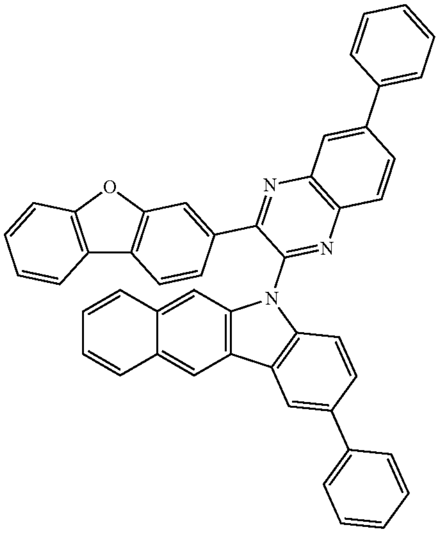
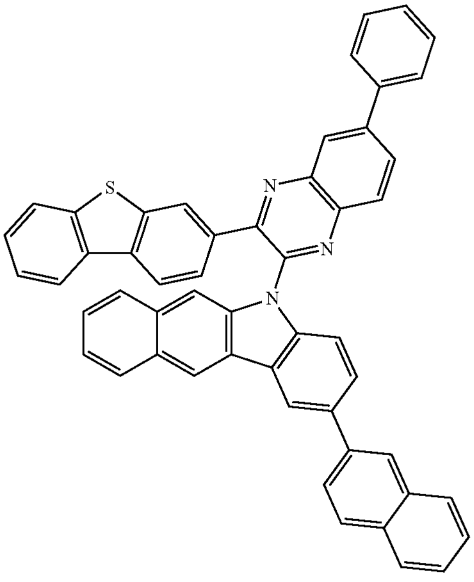
-continued
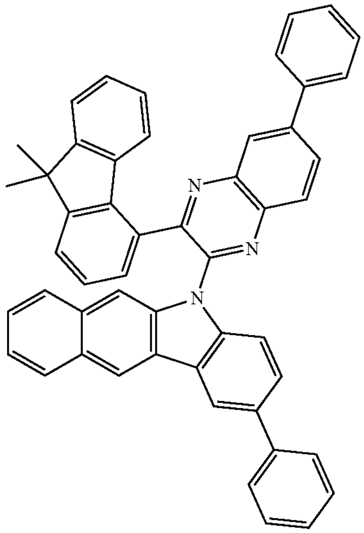
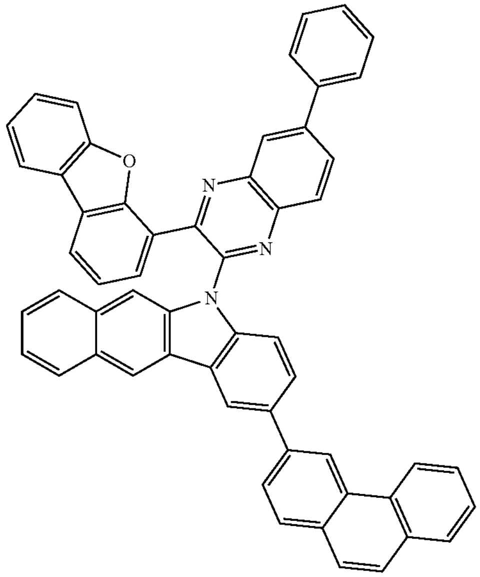
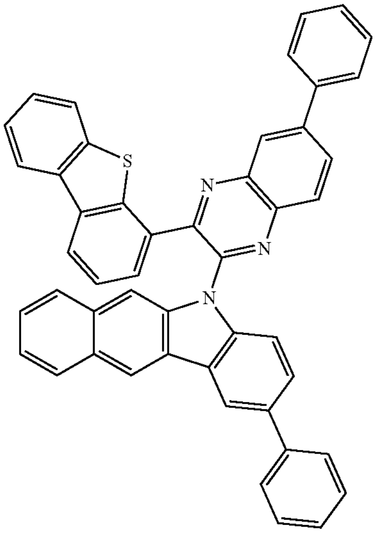

-continued
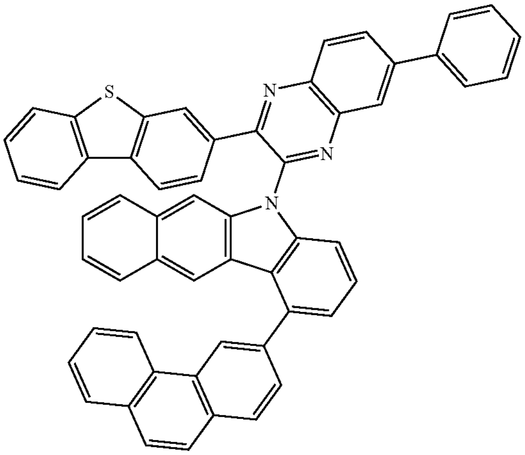
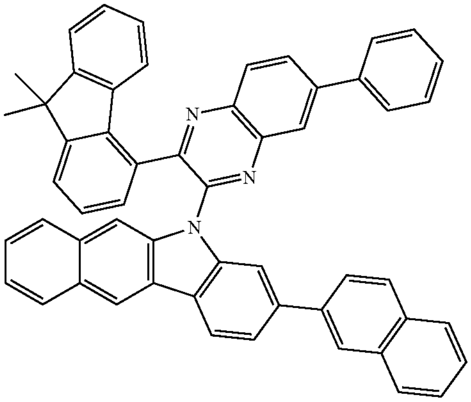
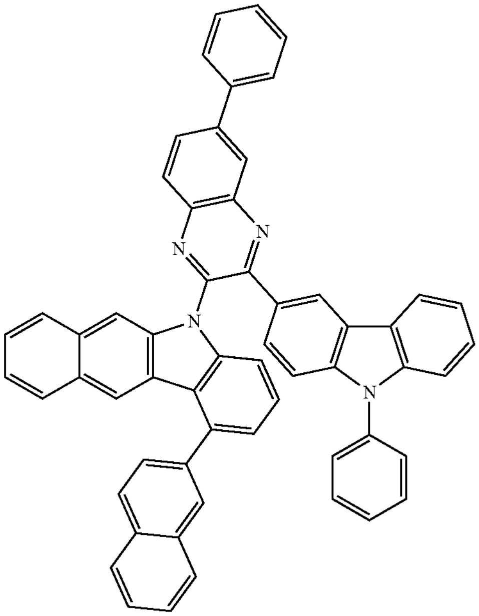
-continued
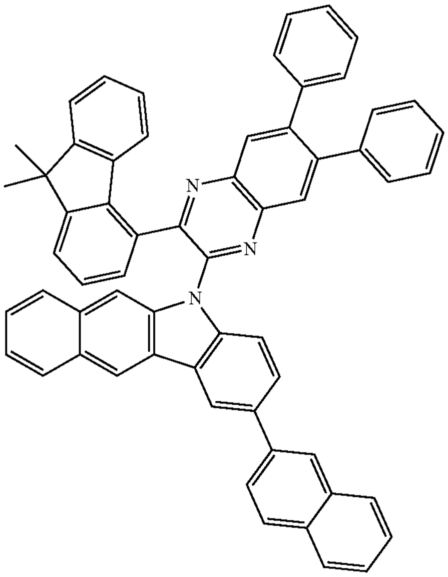
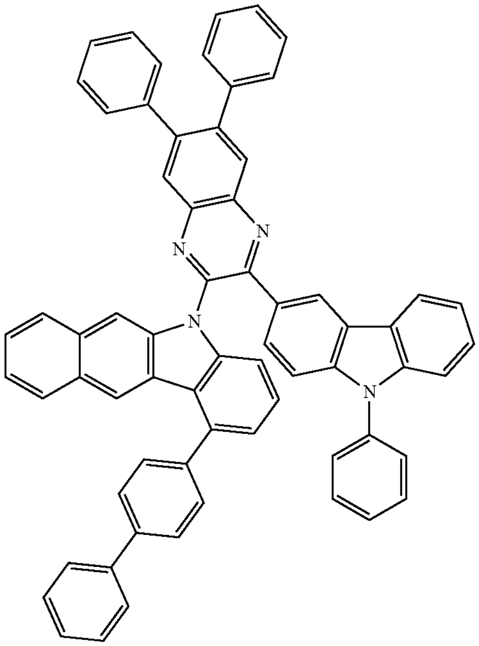

-continued
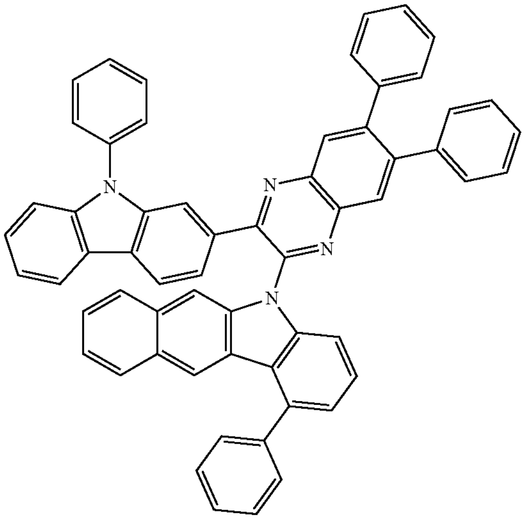
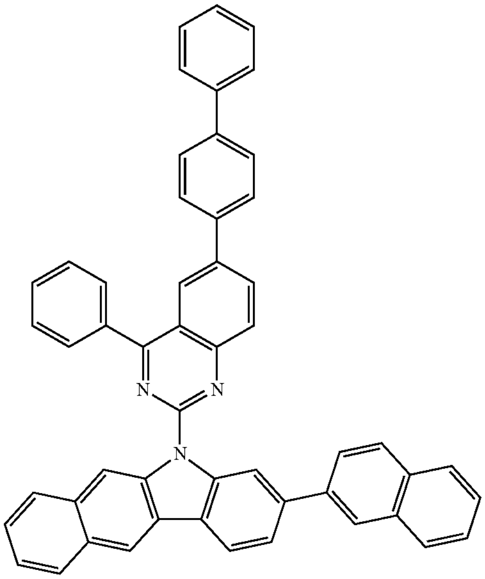
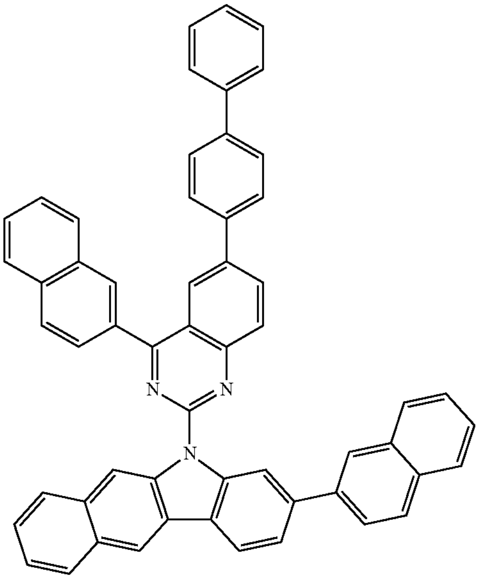
-continued
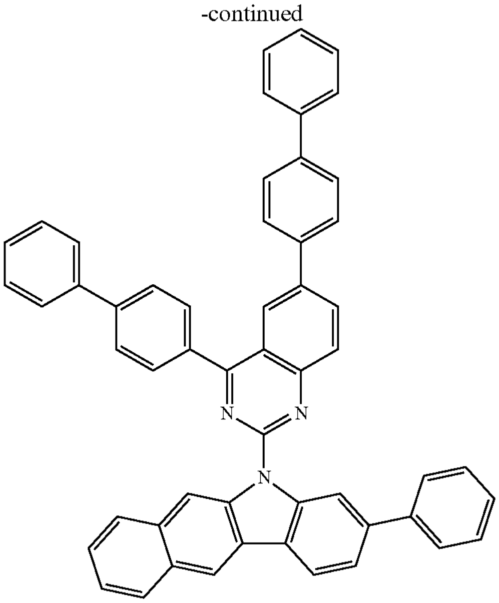
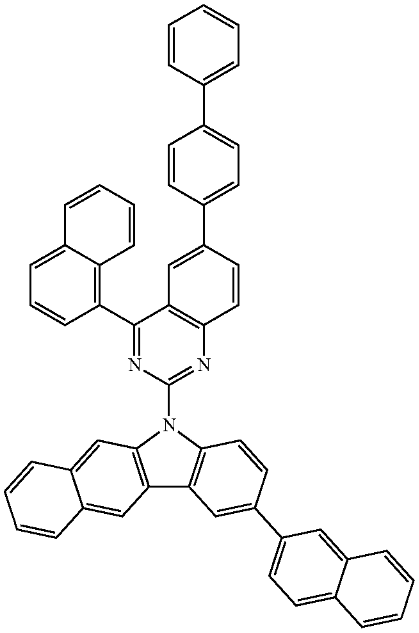

-continued
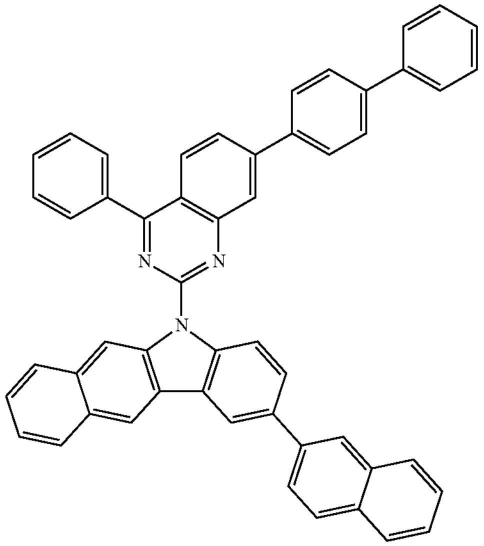
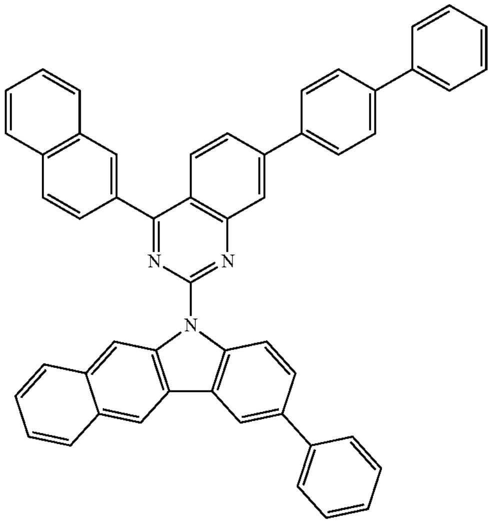
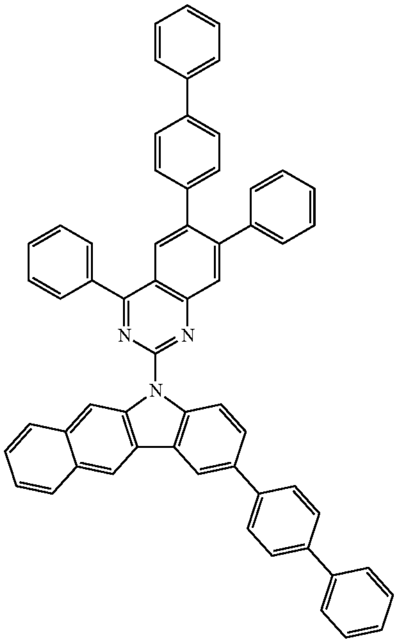
-continued
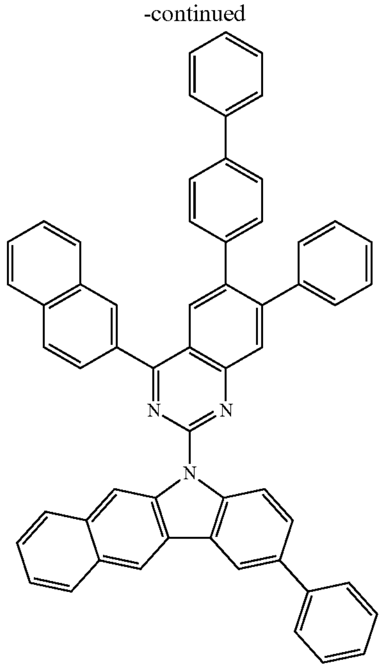
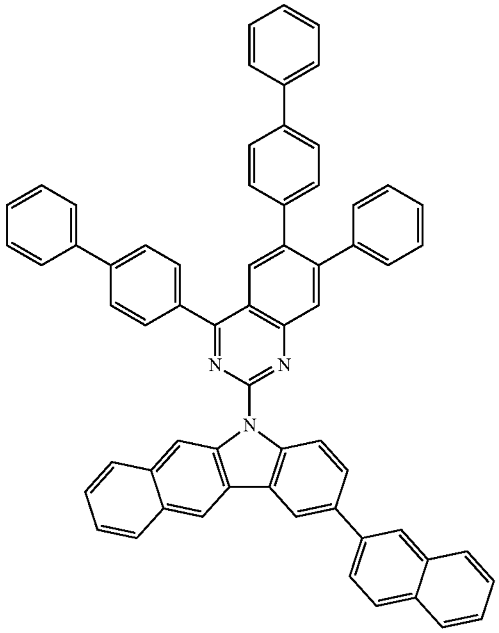

-continued
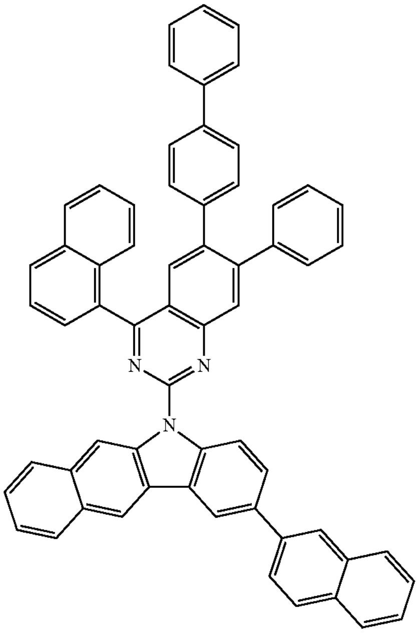
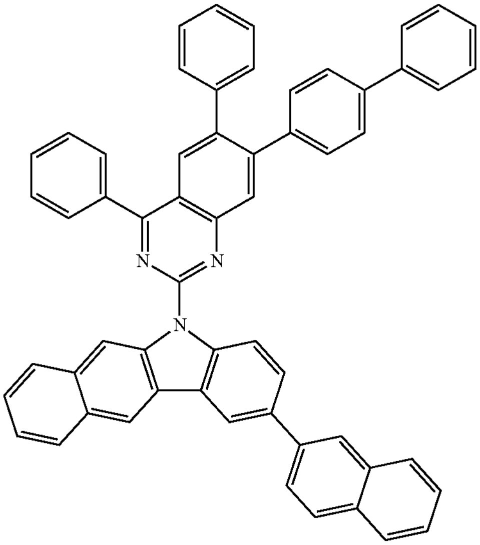
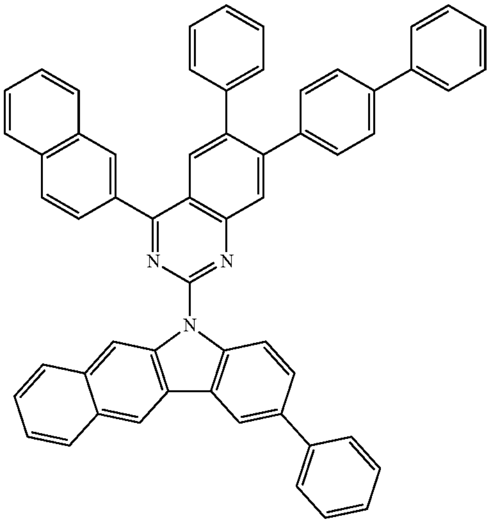
-continued
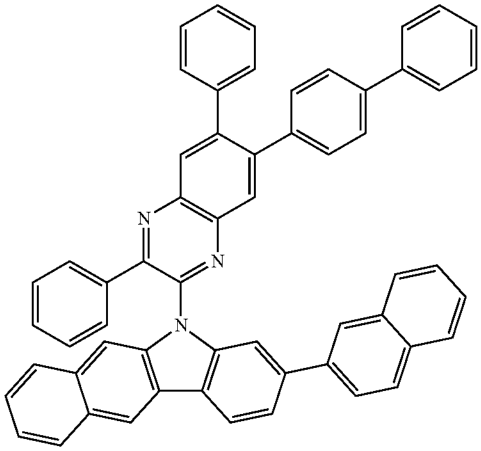
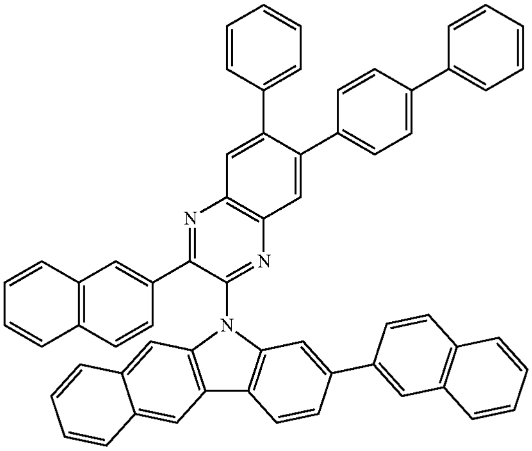
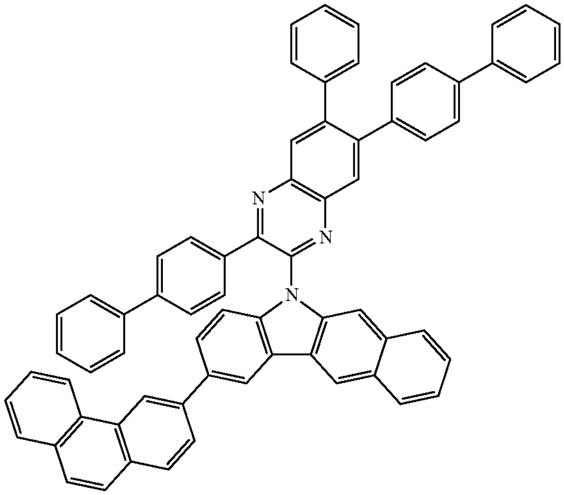

-continued
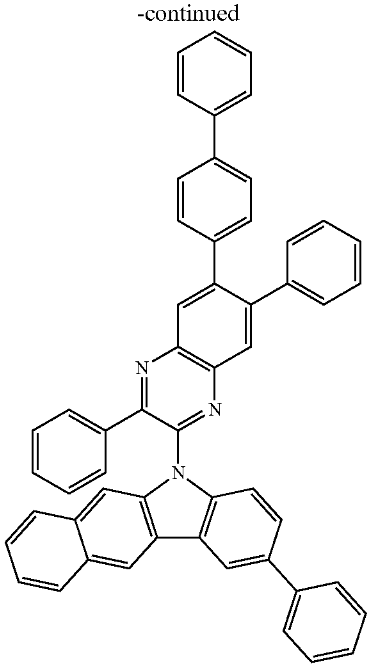
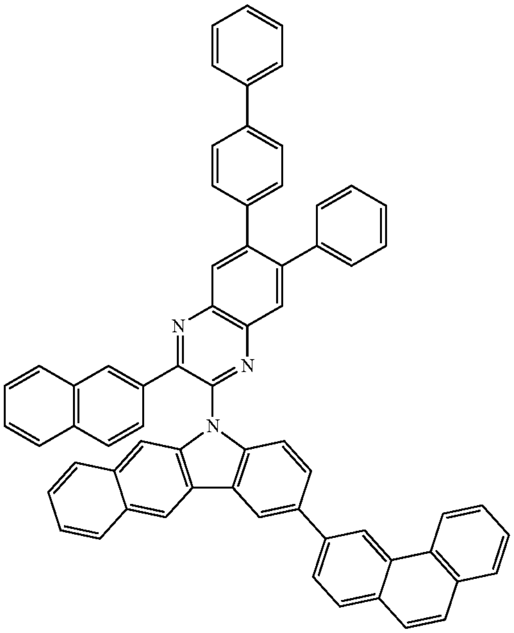
-continued
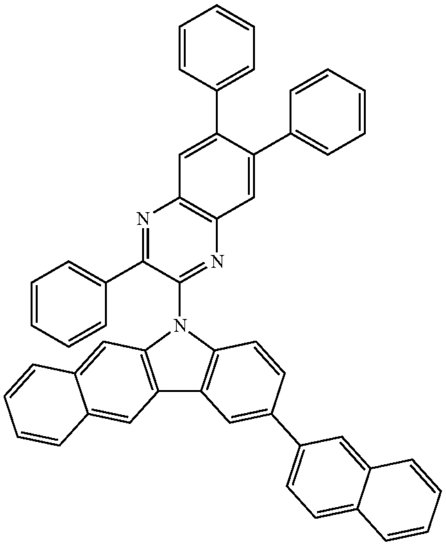
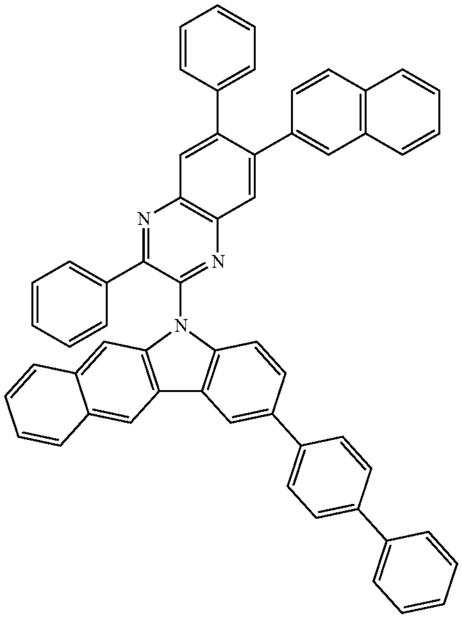

-continued
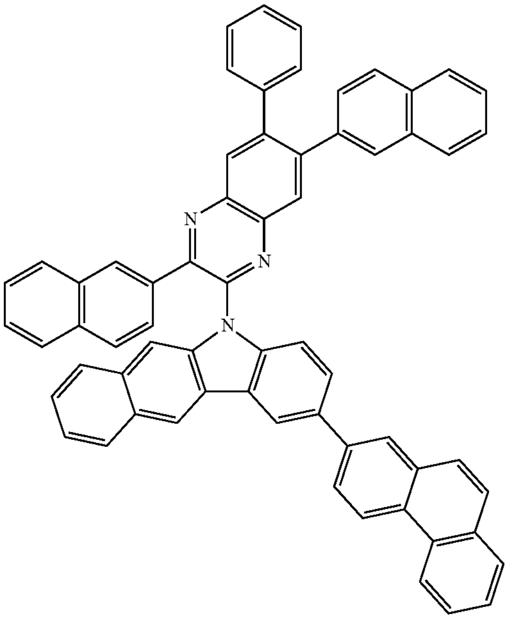
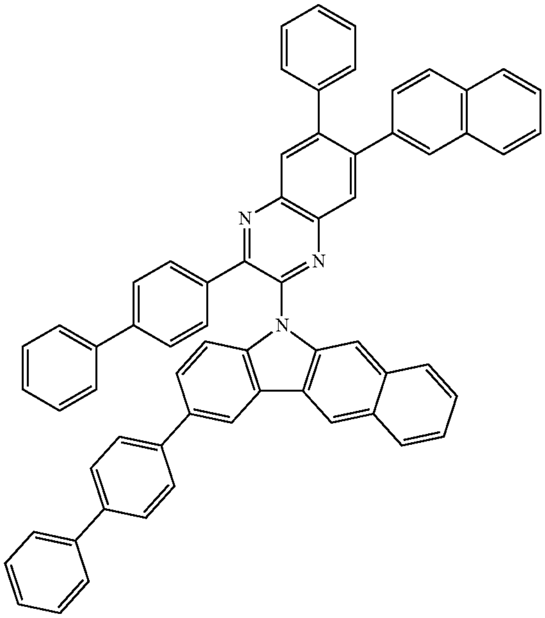
-continued
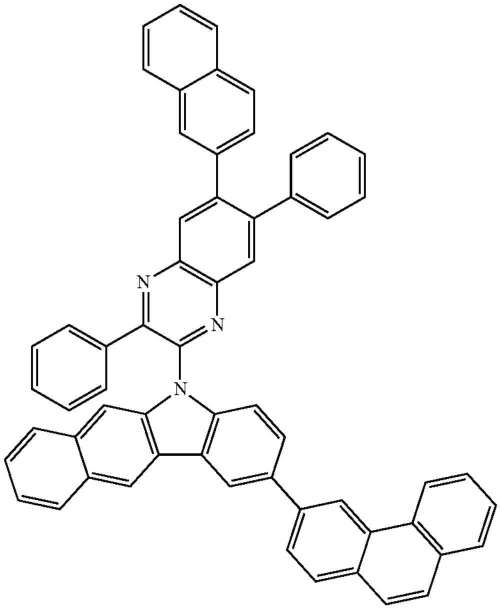
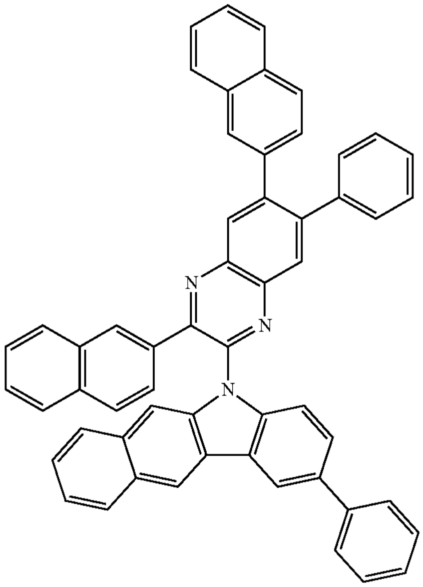

-continued
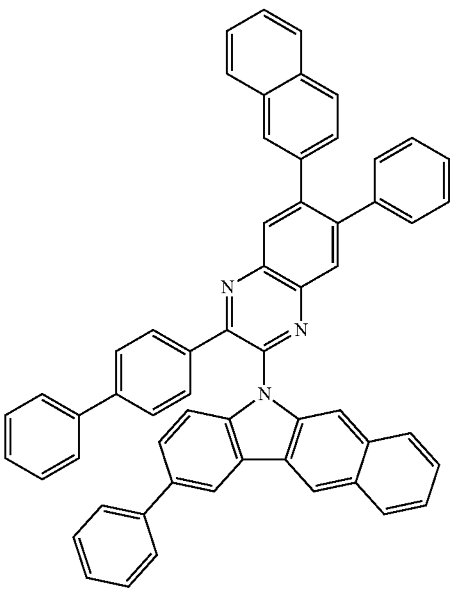
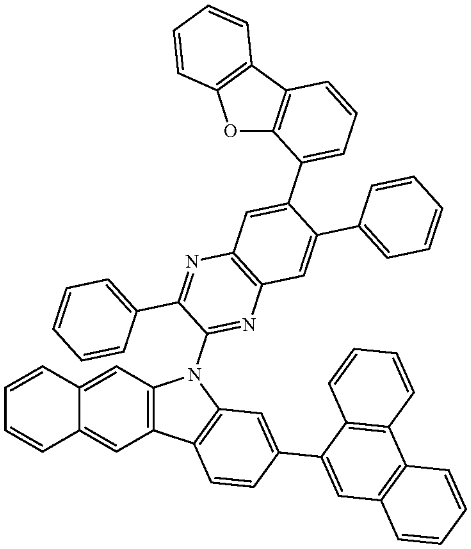
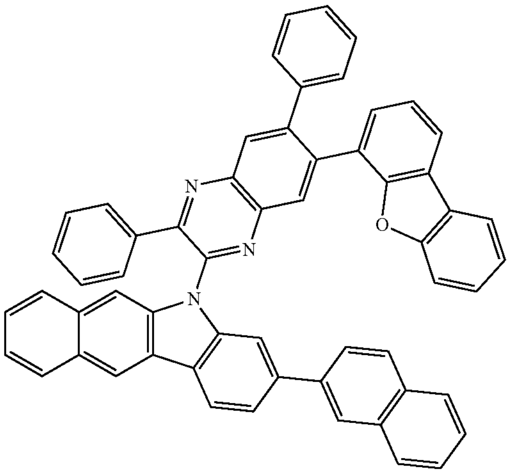
-continued
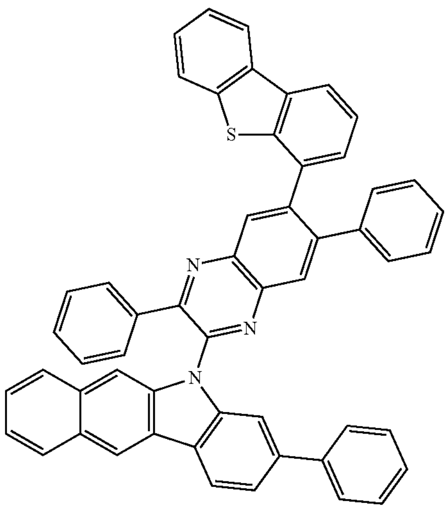
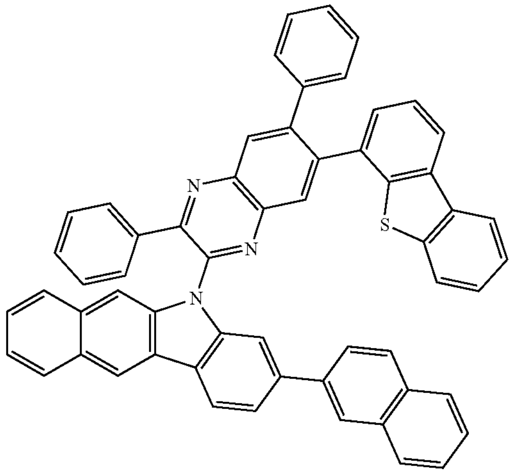
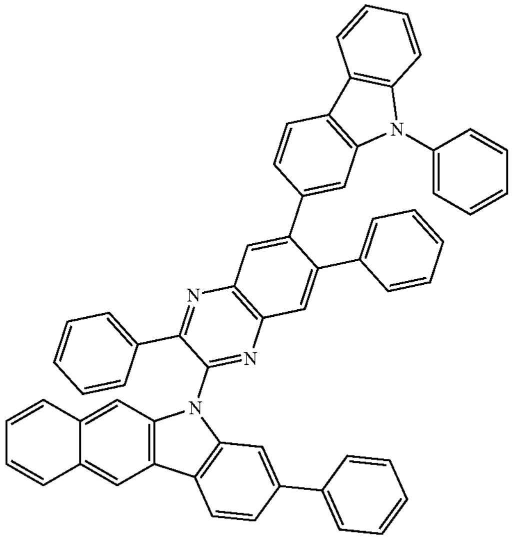

-continued
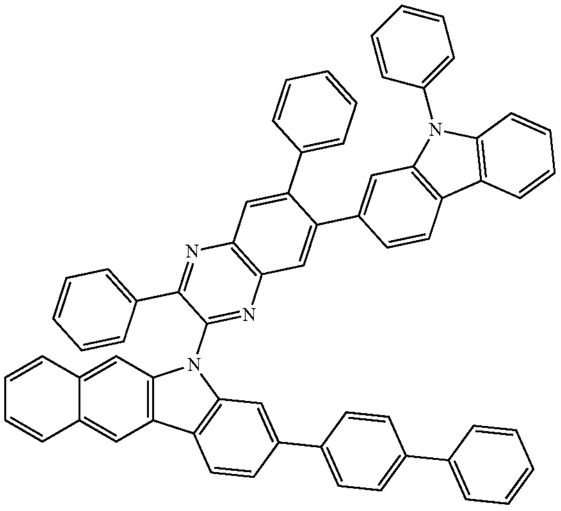
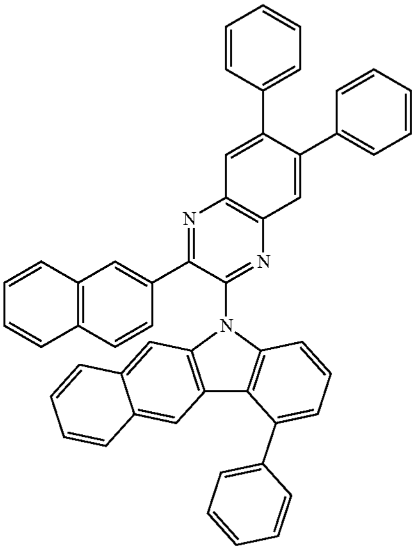 [SMILES: c1ccc(-c2cc3nc(-c4ccc5ccccc5c4)c(-n4c5cc6ccccc6cc5c5c(-c6ccccc6)cccc54)nc3cc2-c2ccccc2)cc1]
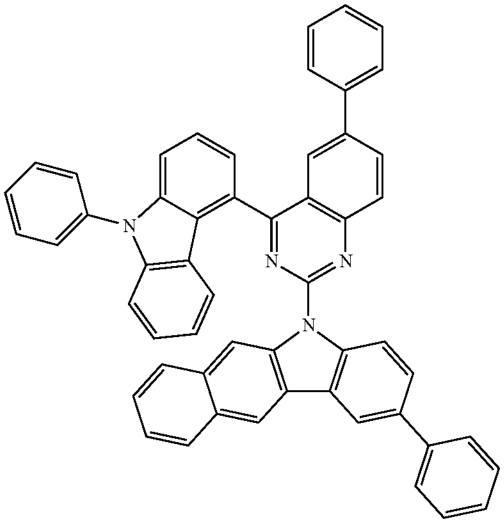
-continued
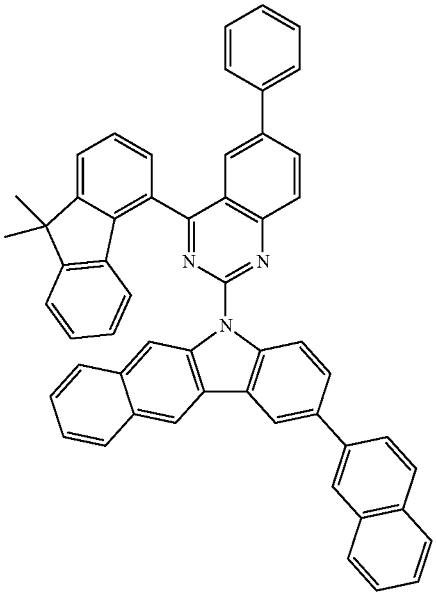
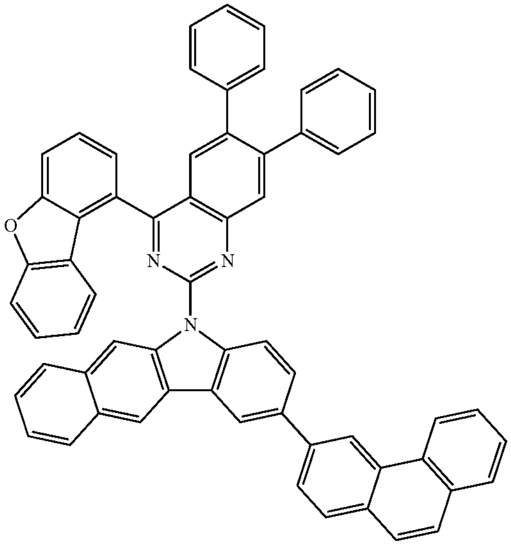
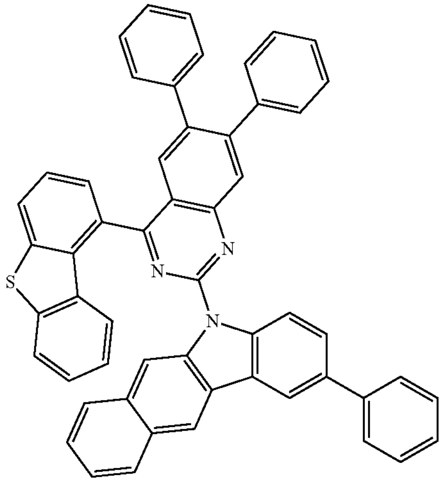

-continued
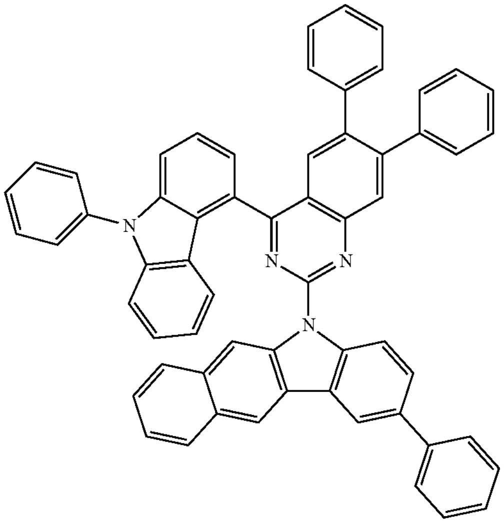
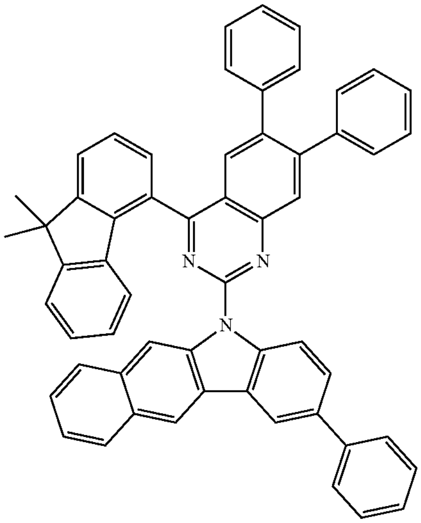
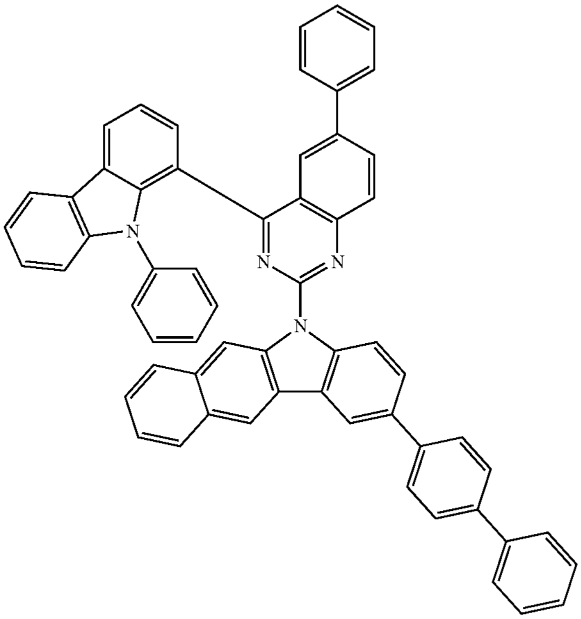
-continued
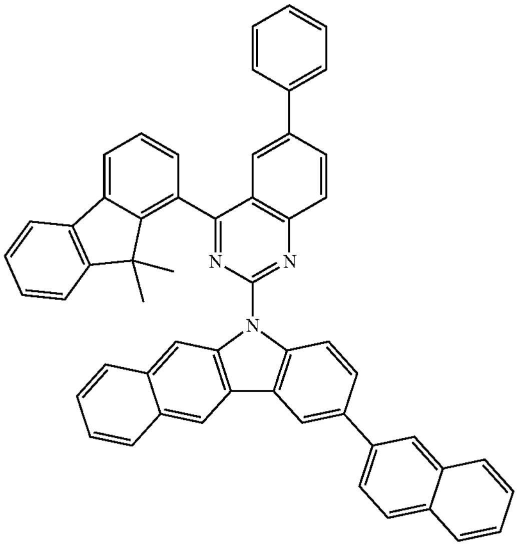
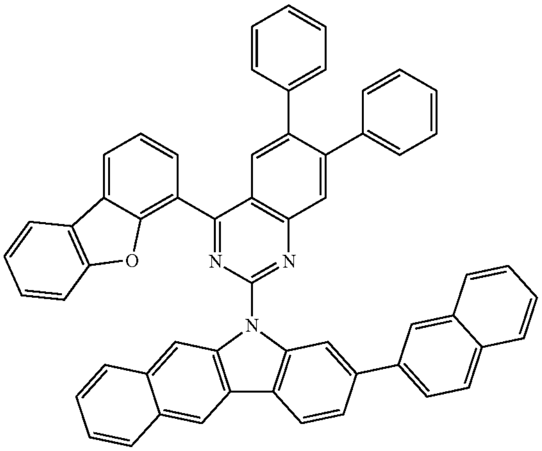
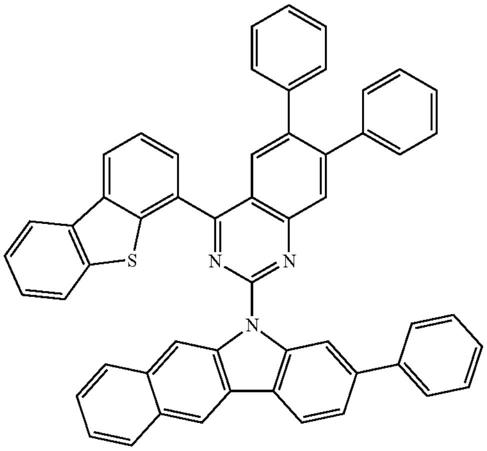

-continued
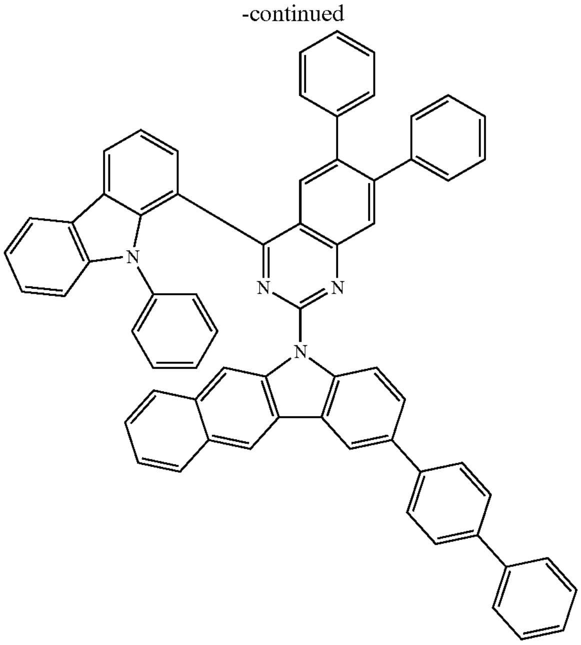
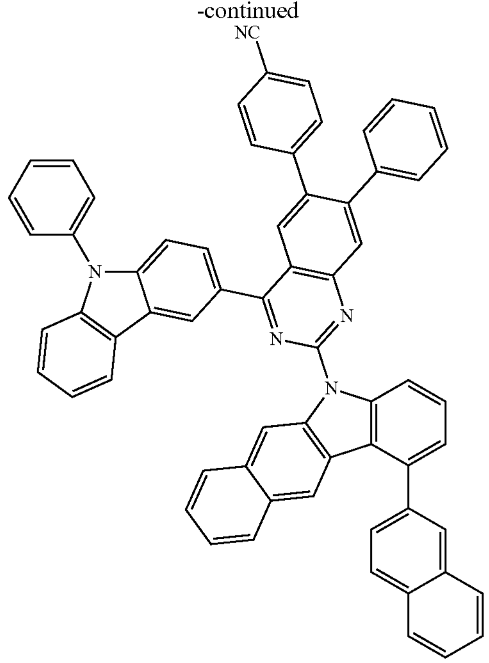
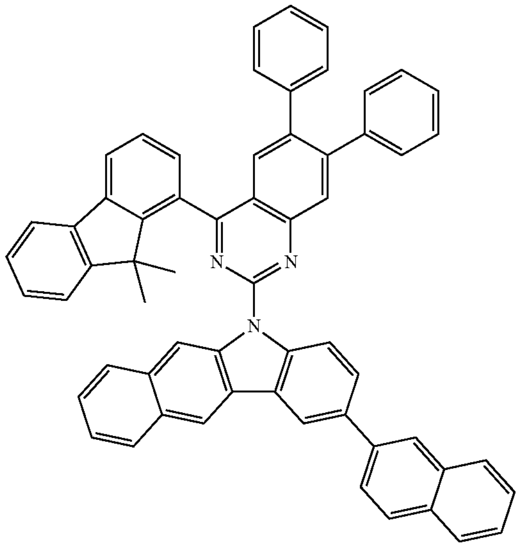
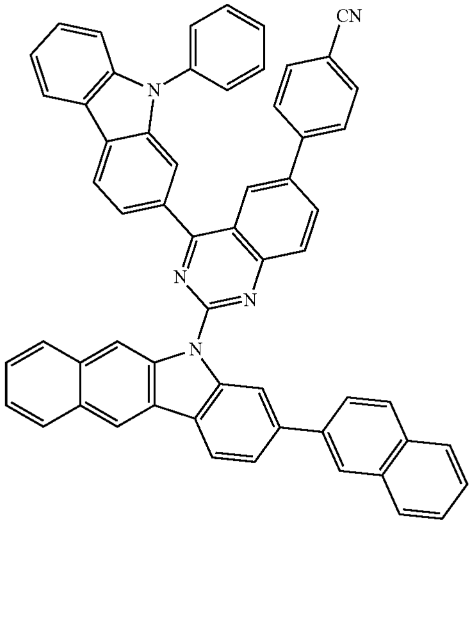
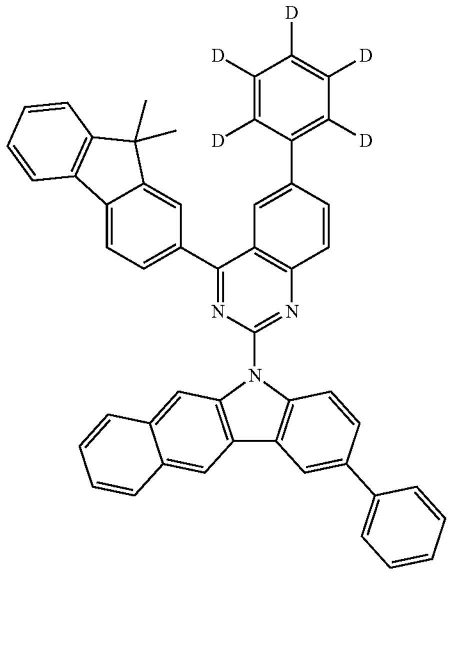

-continued
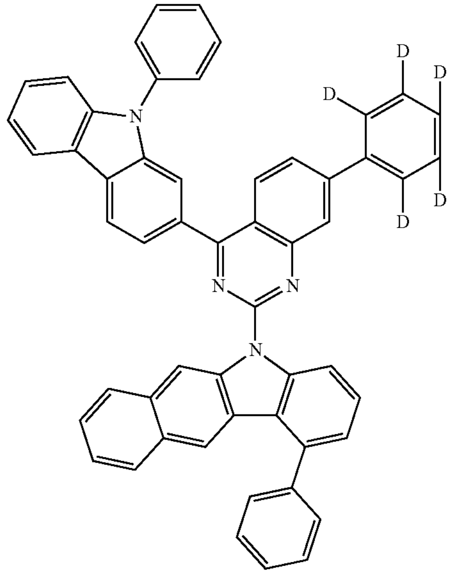
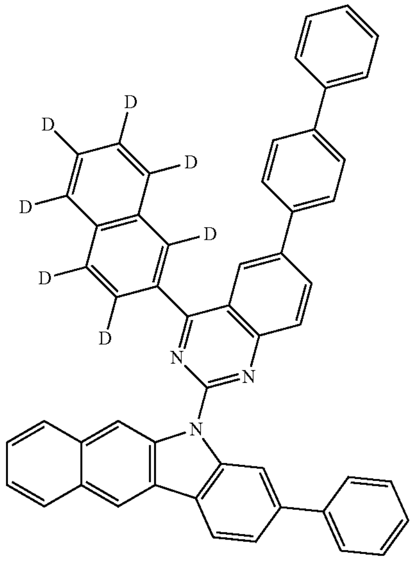
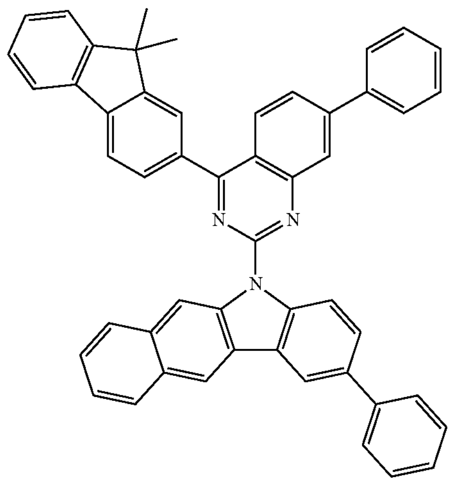
-continued
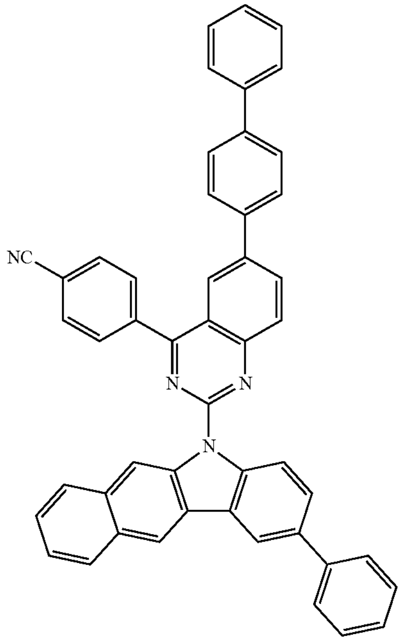
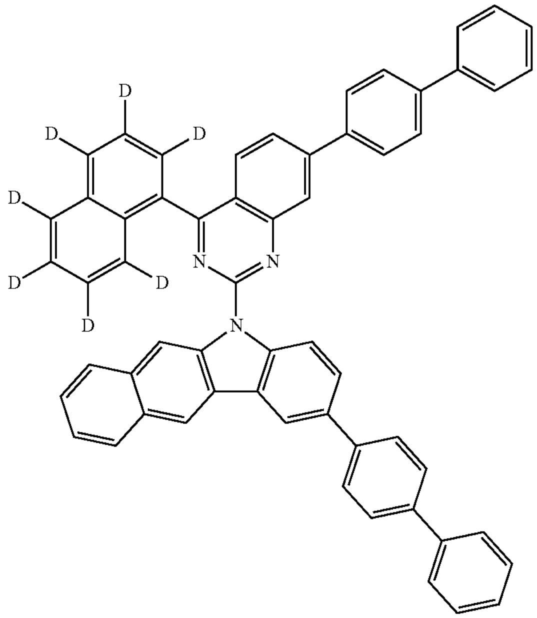

-continued
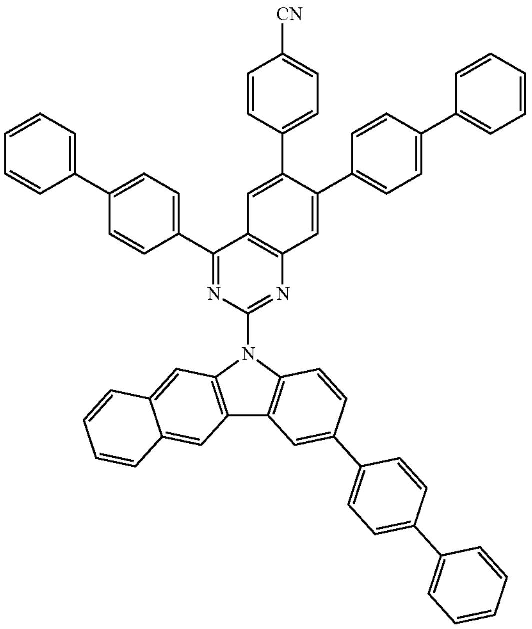
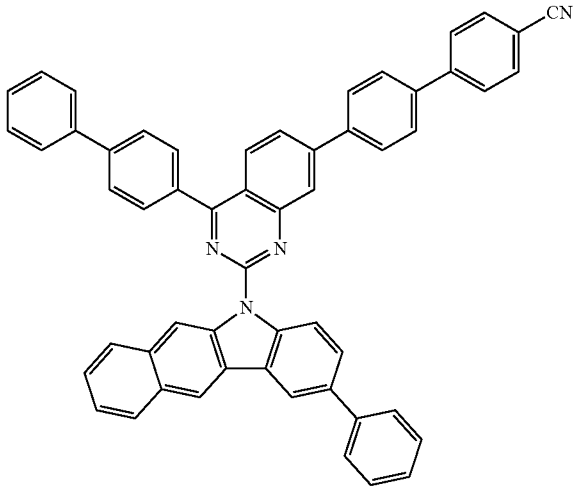
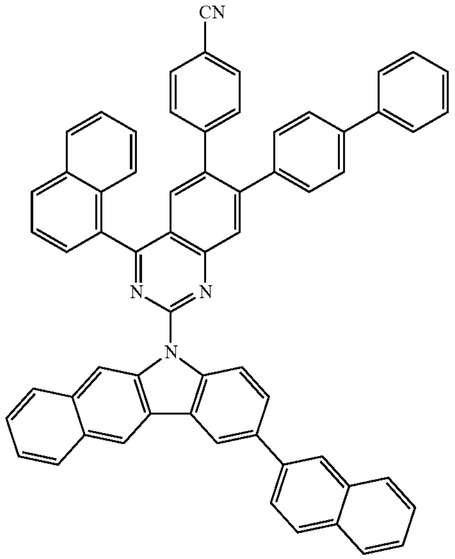
-continued
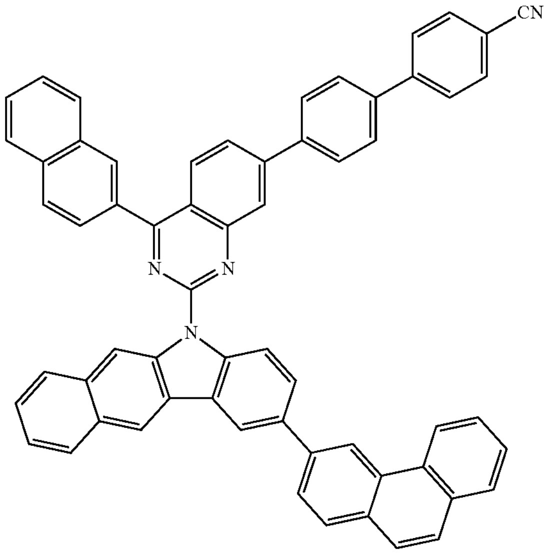
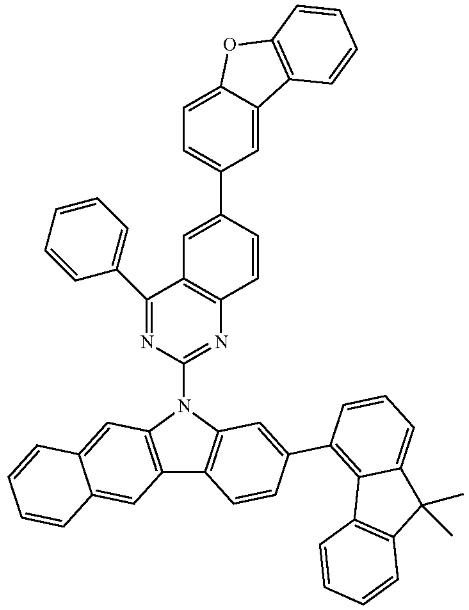
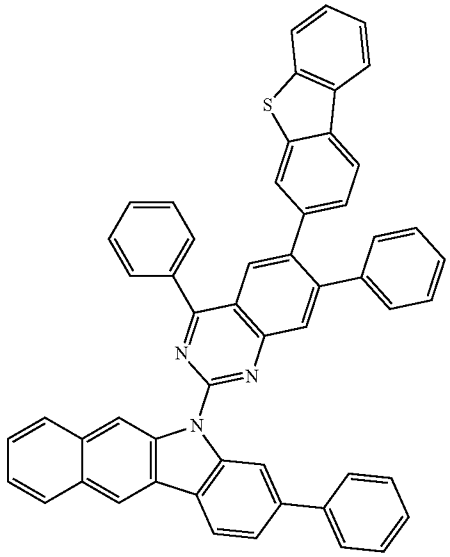

-continued
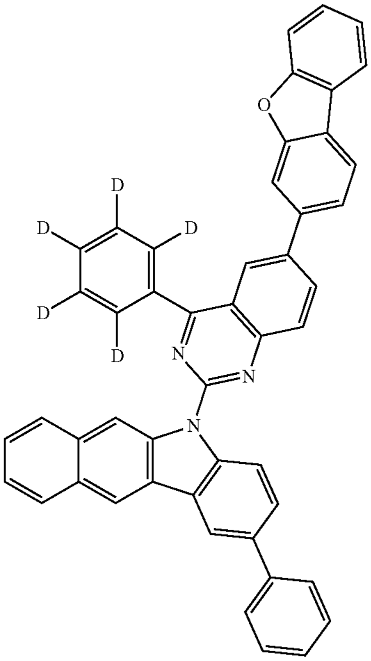
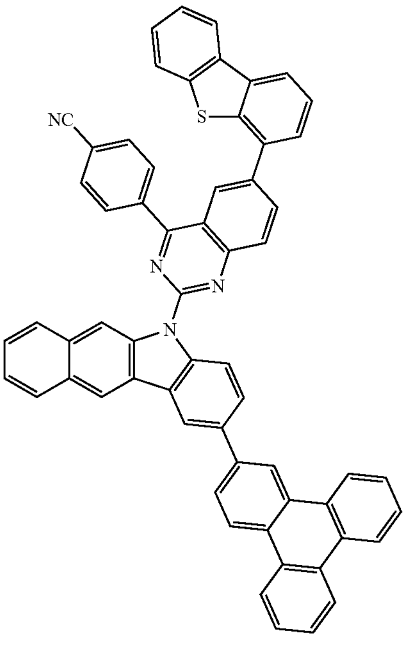
-continued
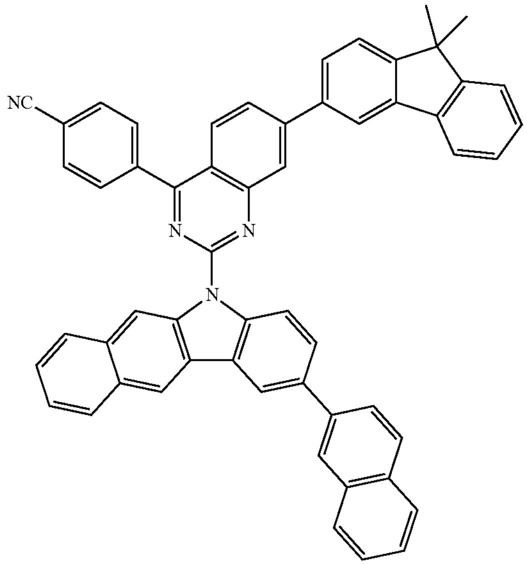
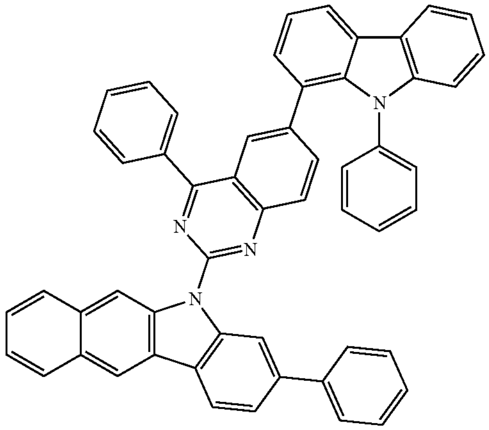
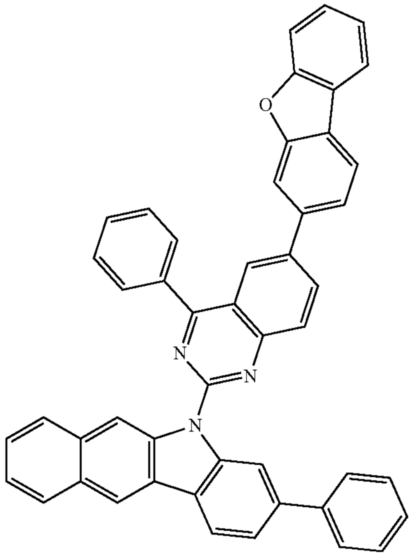

-continued
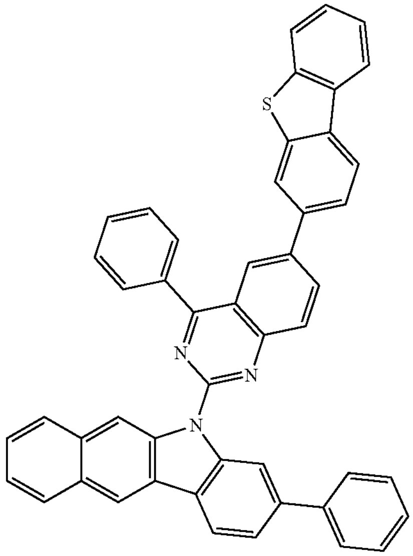
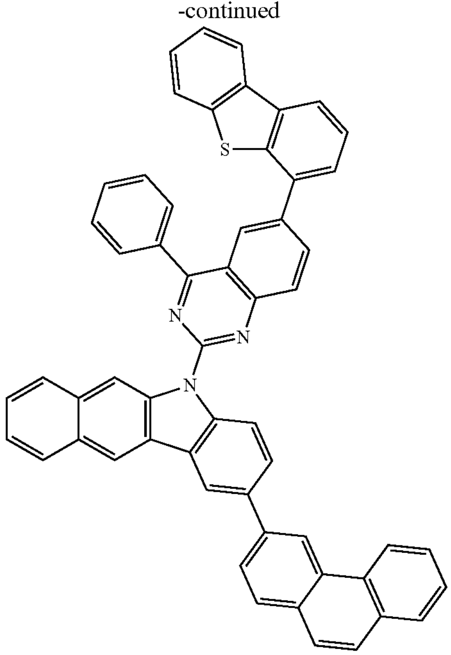
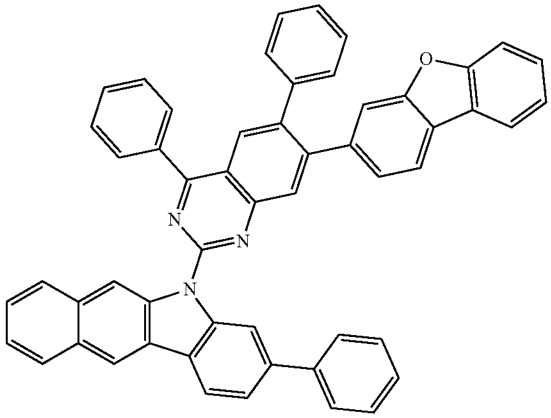
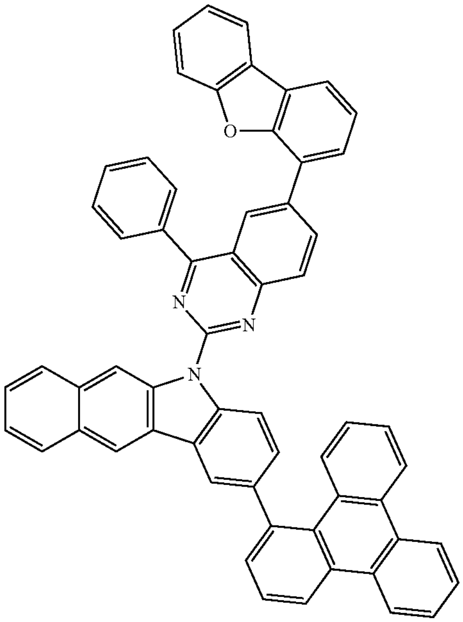
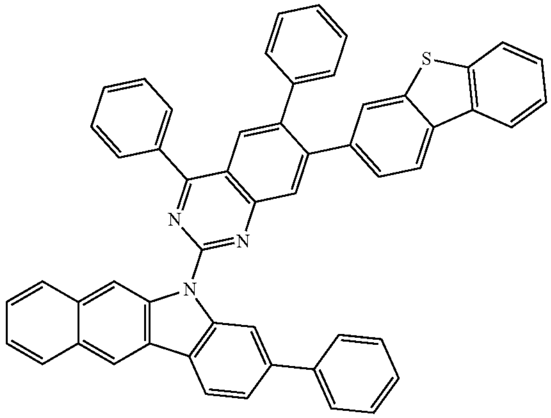
-continued -continued
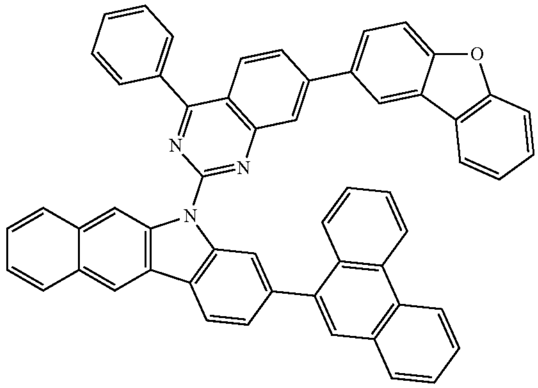
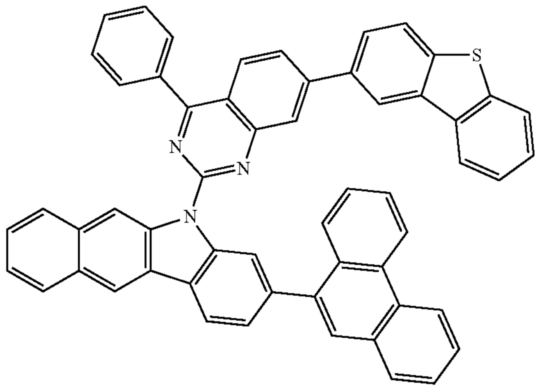
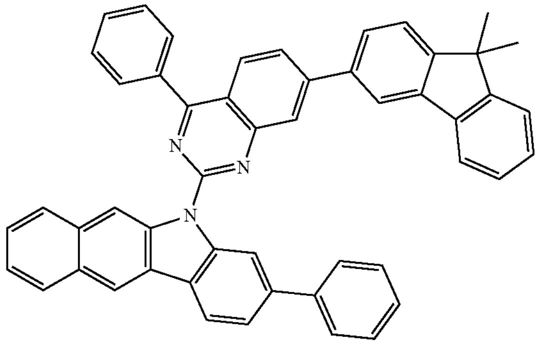
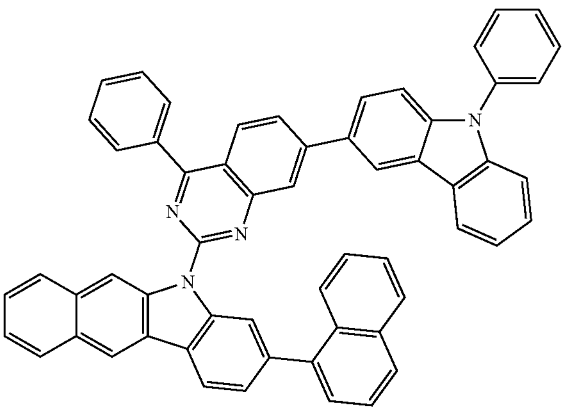
-continued
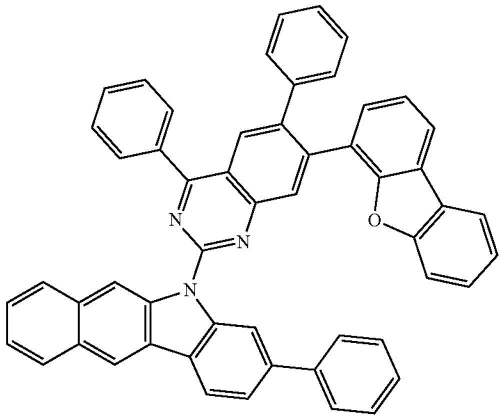
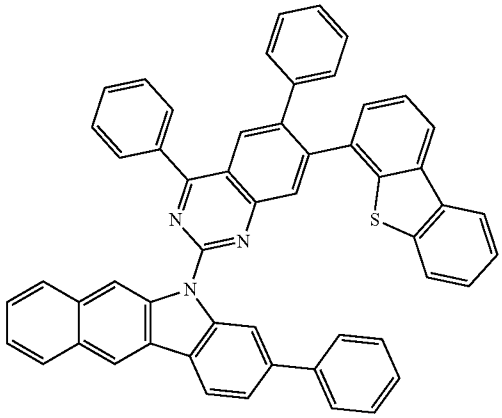
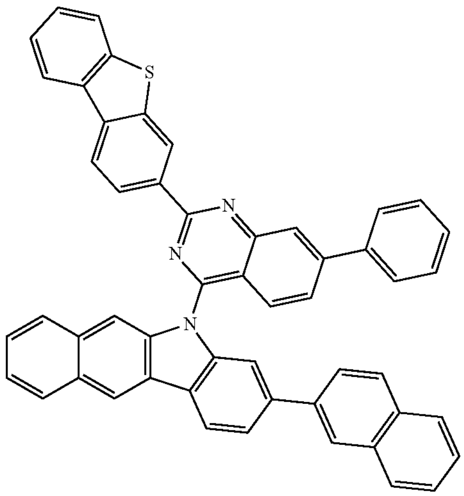

-continued
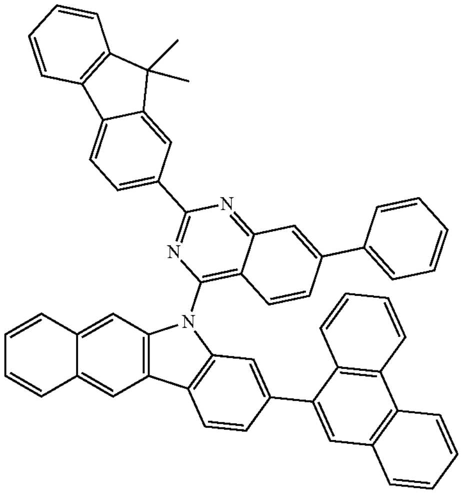
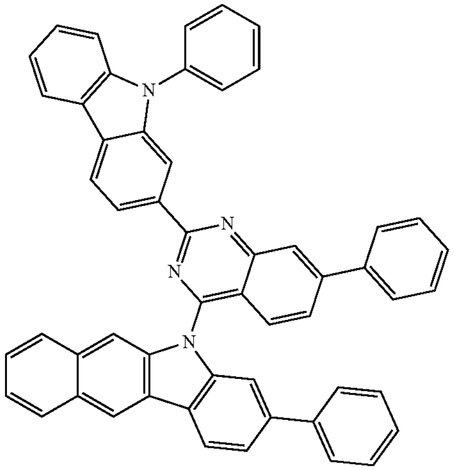
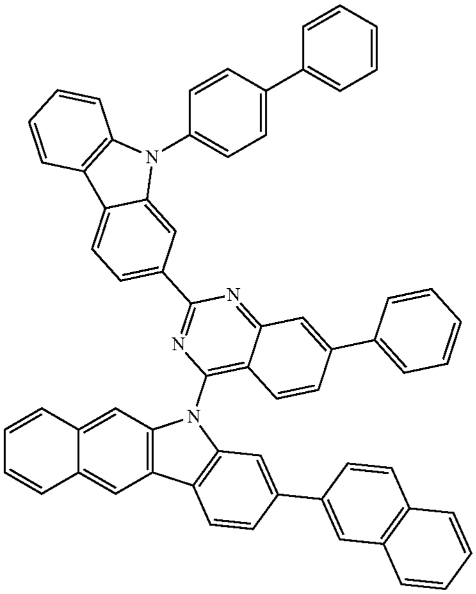
-continued
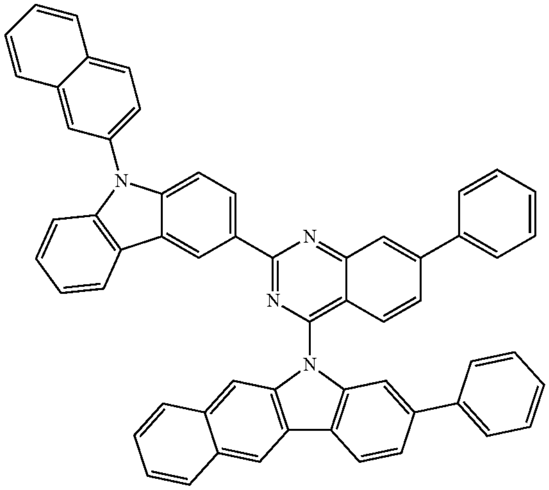
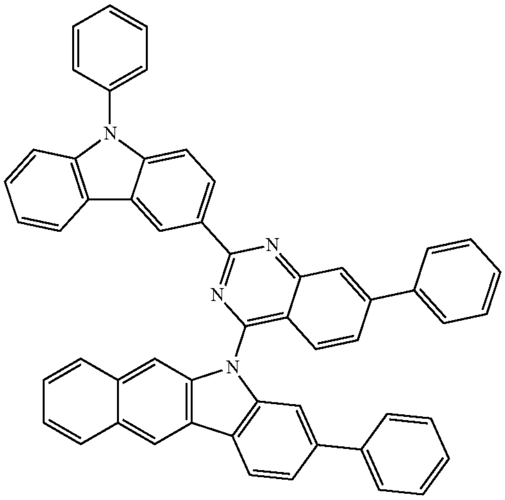
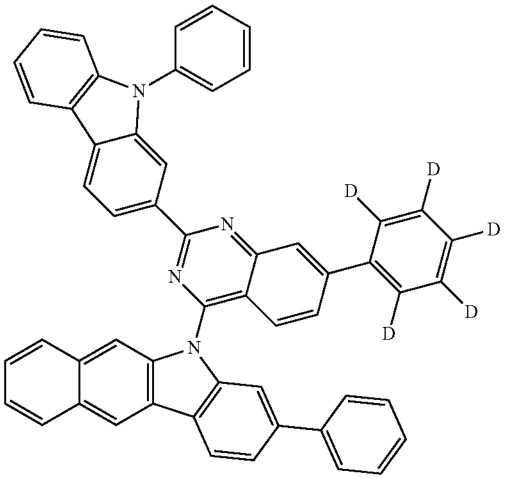

-continued
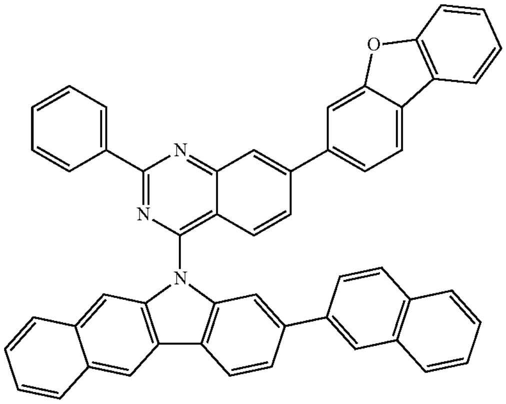
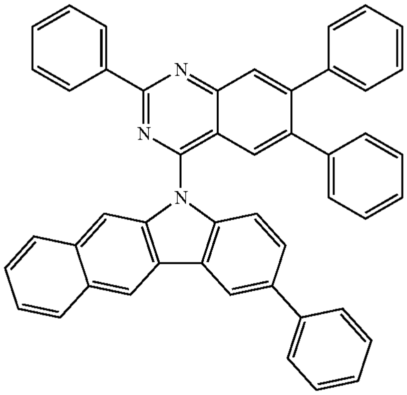
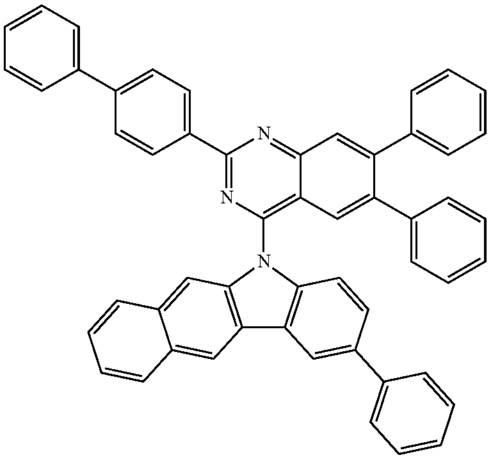
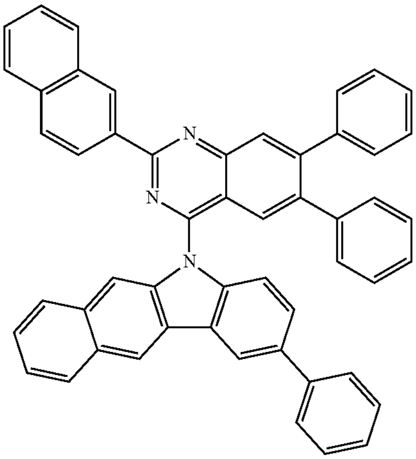
-continued
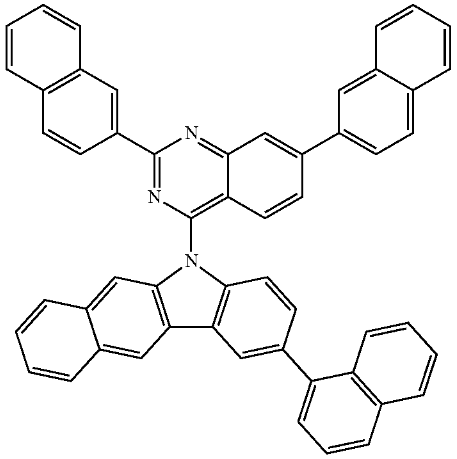
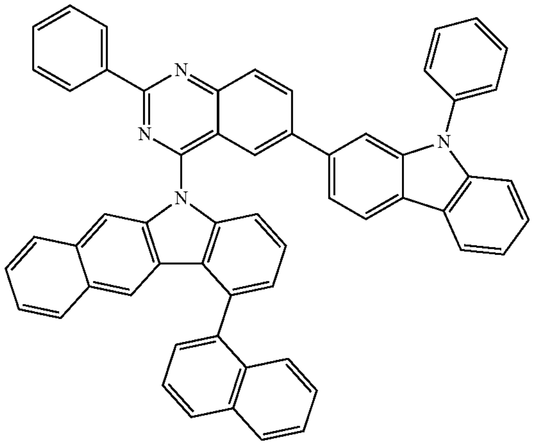
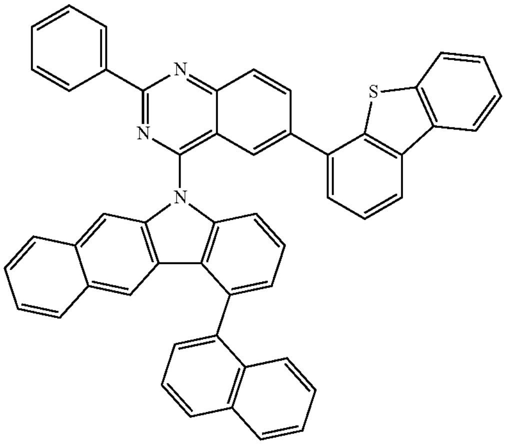

-continued
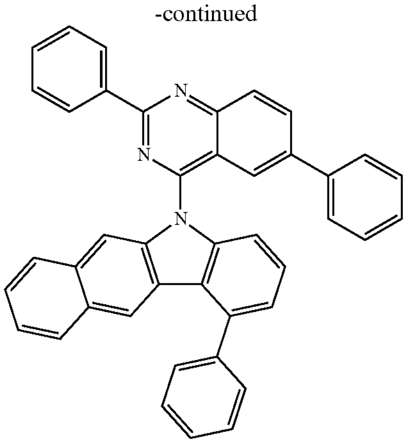
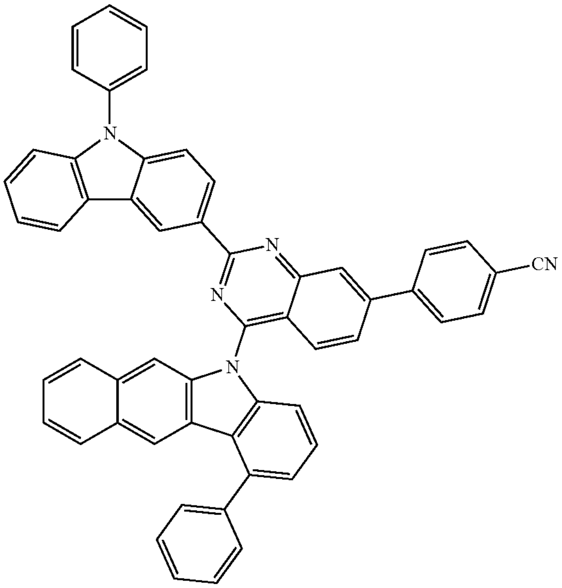
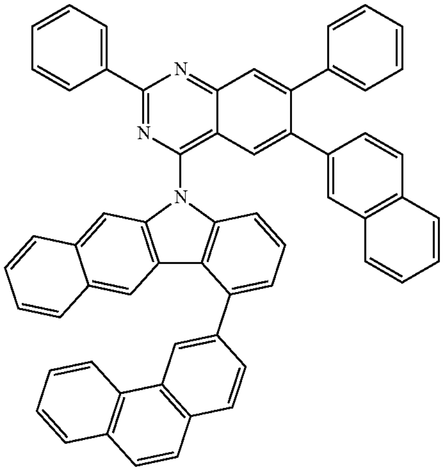
-continued
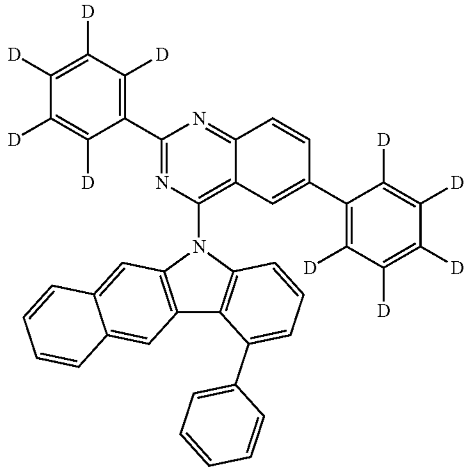
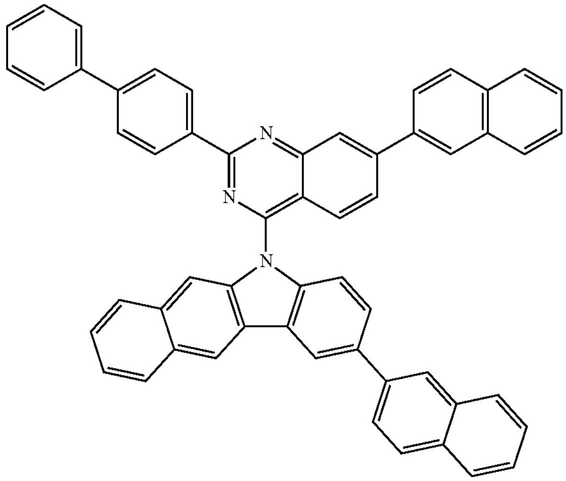
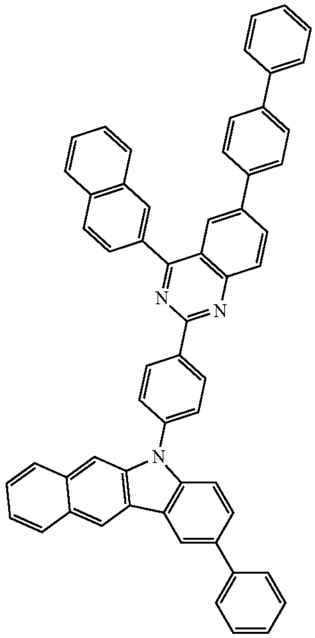

-continued
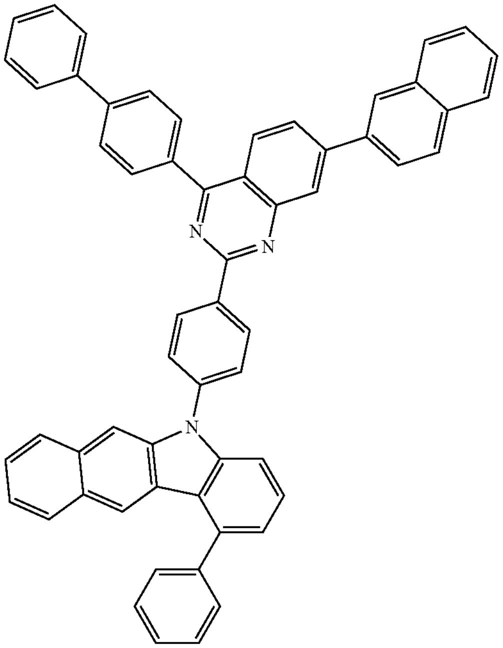
-continued
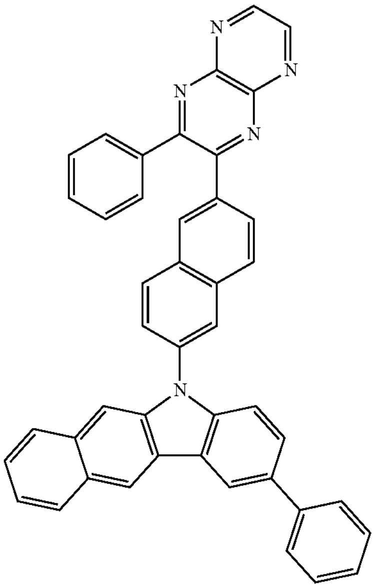
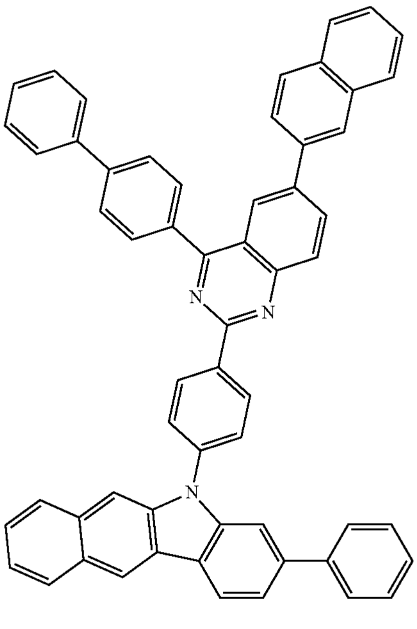
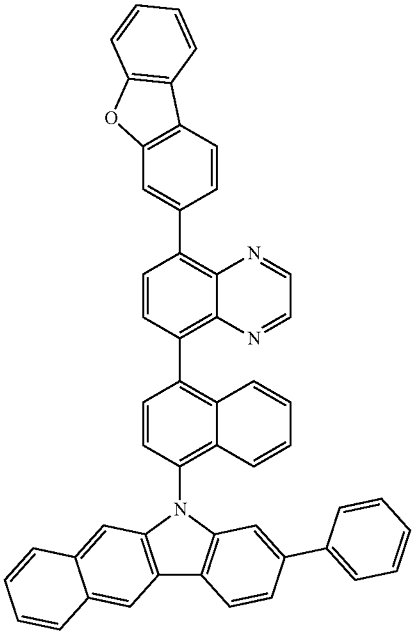

-continued
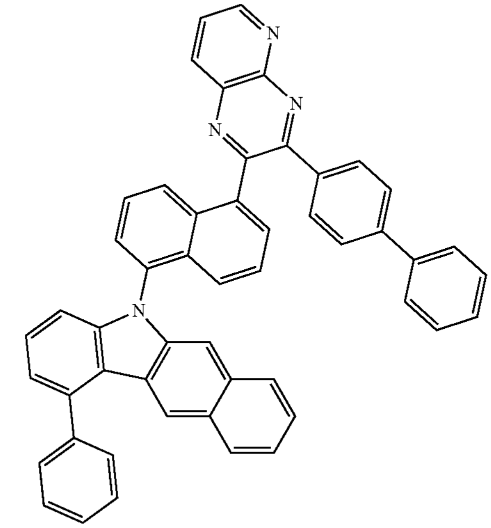
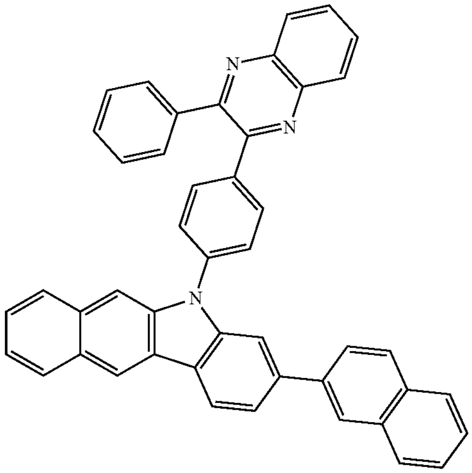
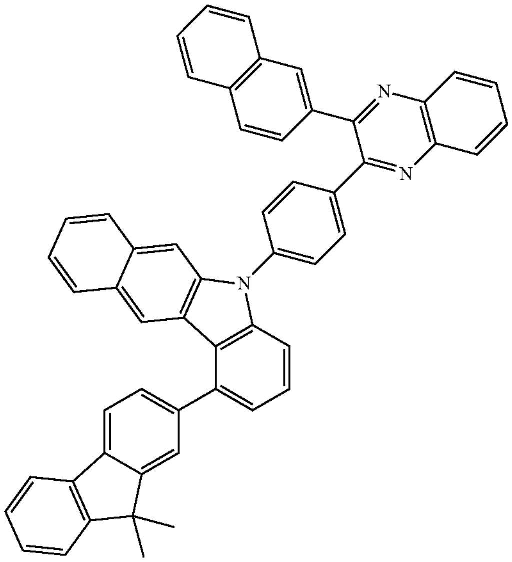
-continued
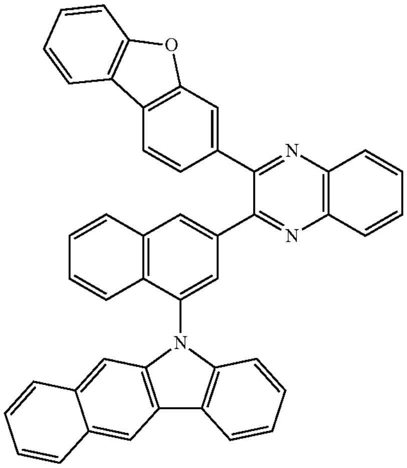
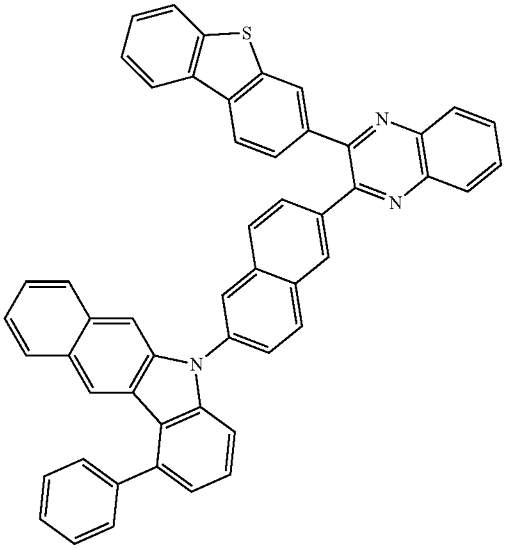
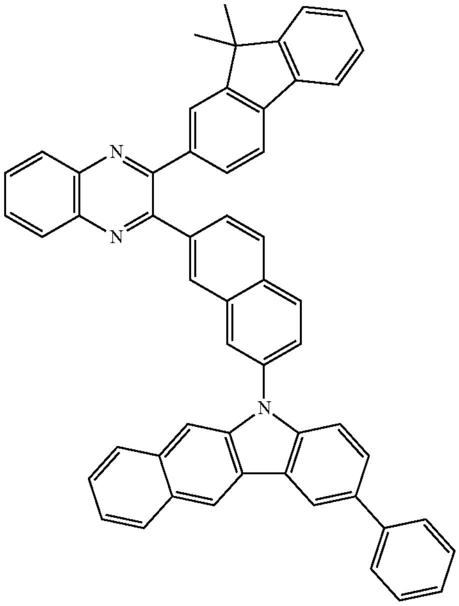

-continued
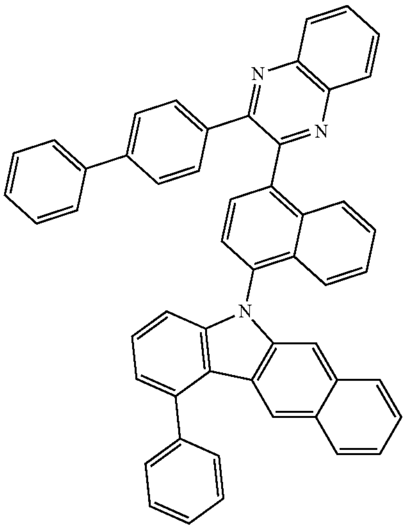
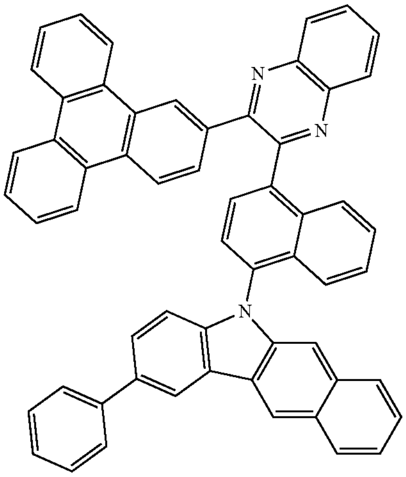
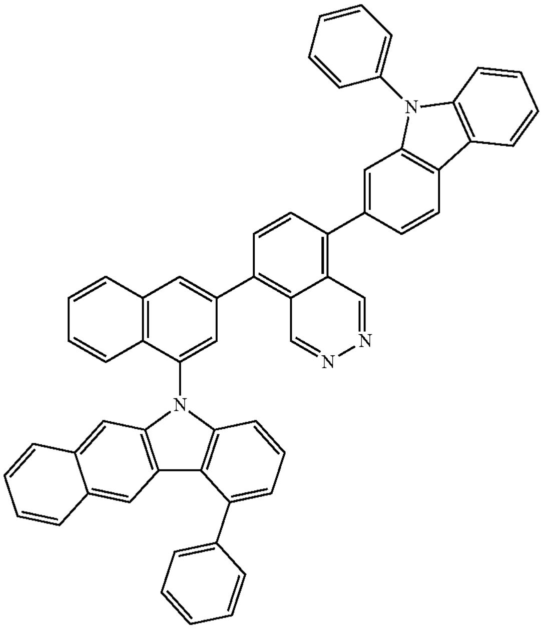
-continued
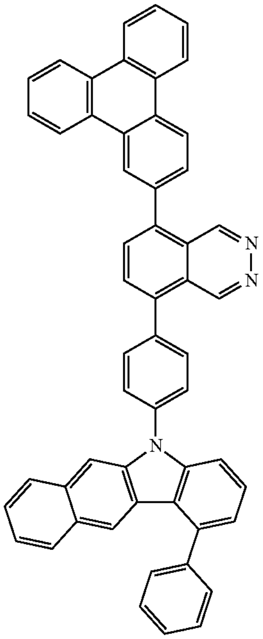
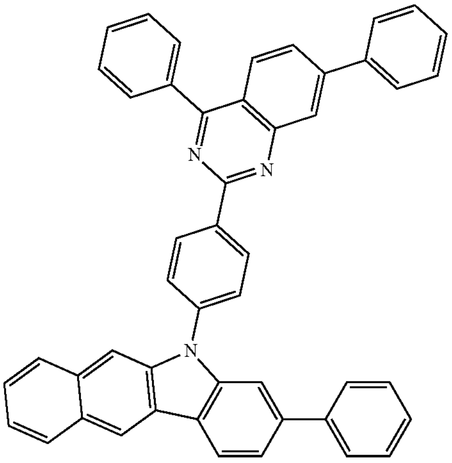

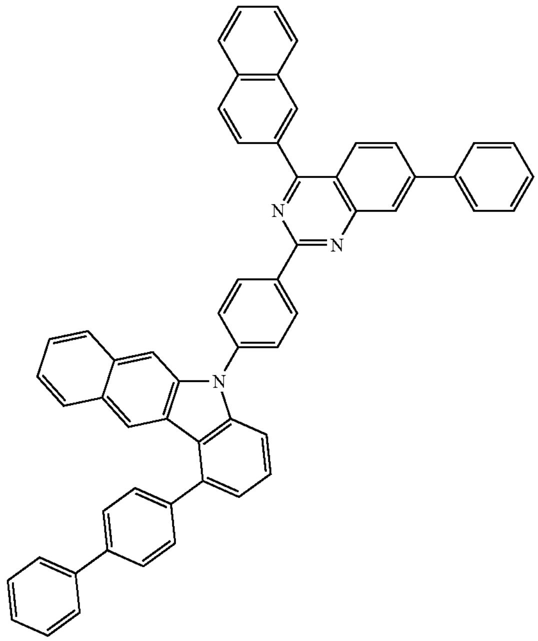
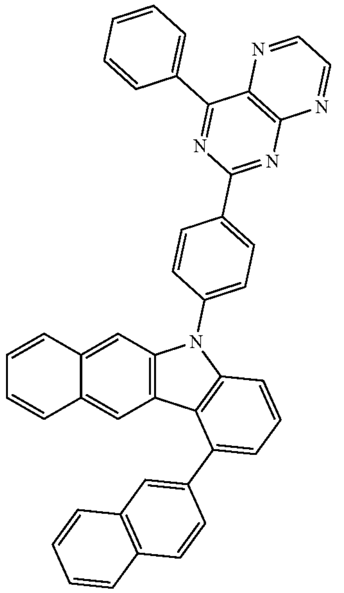
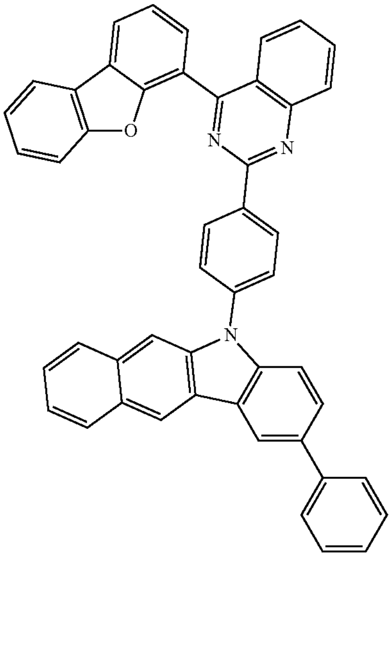
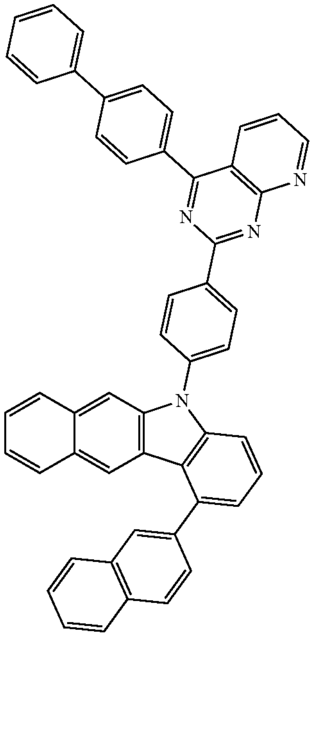

-continued
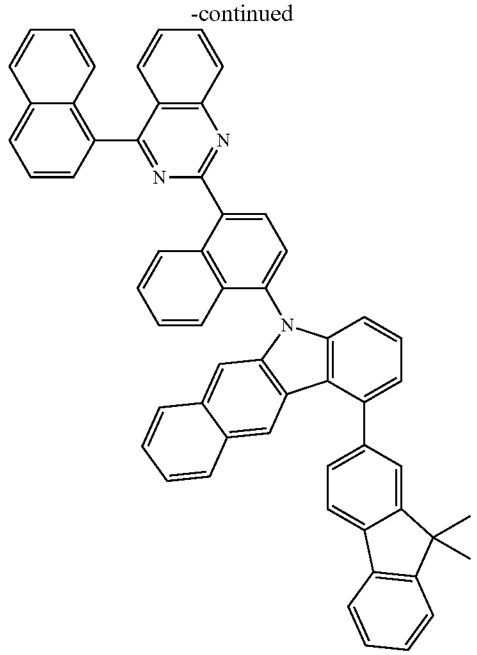
-continued
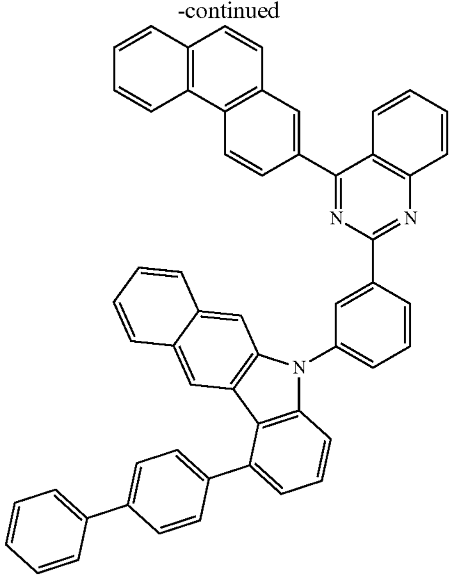
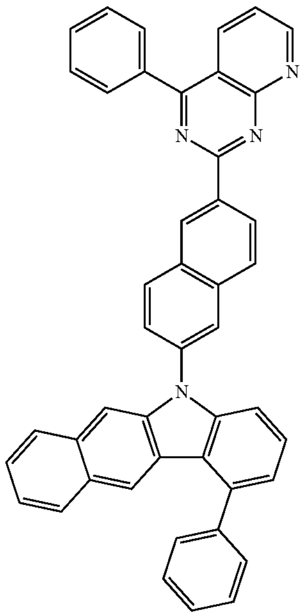
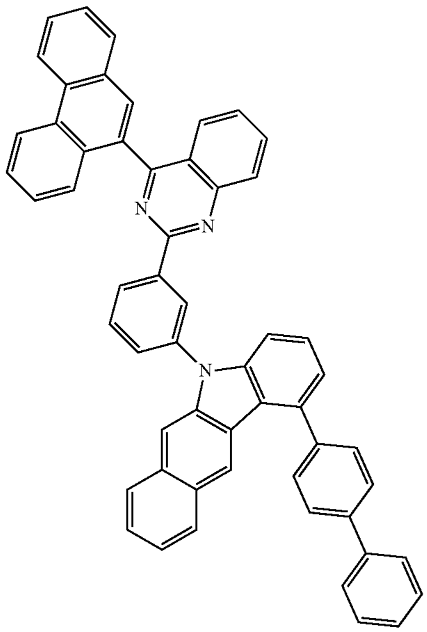

-continued
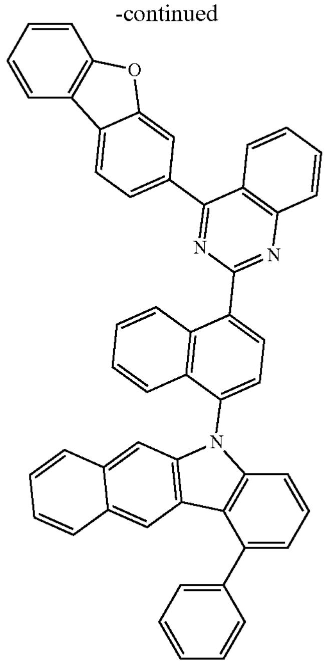
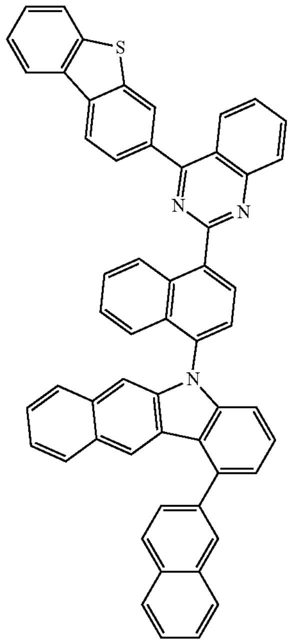
-continued
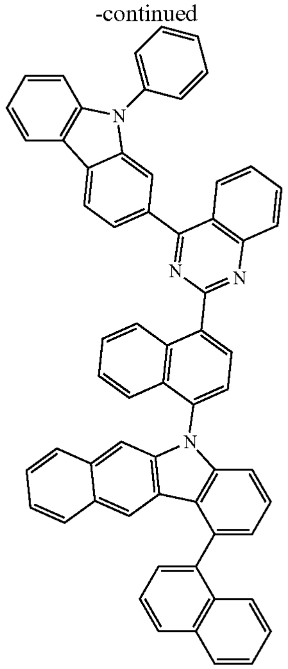
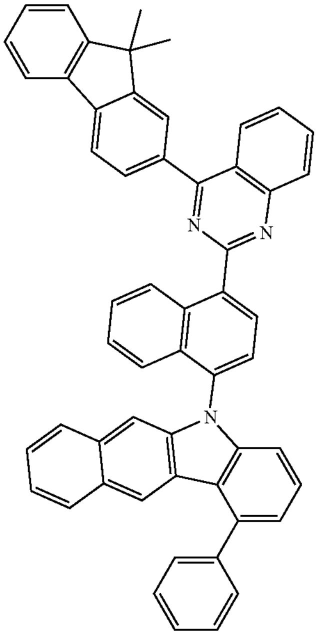

-continued
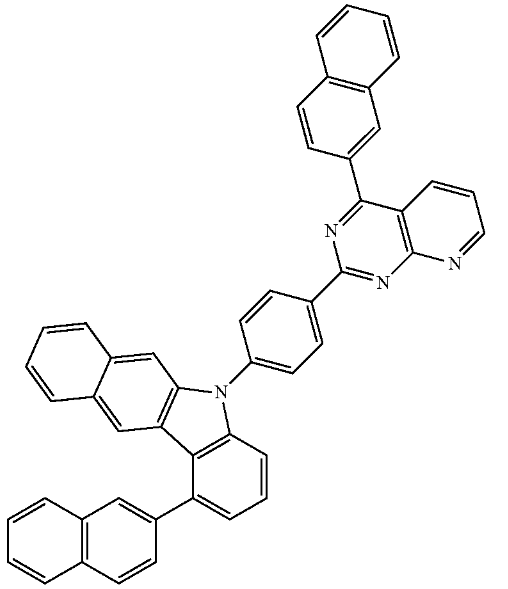
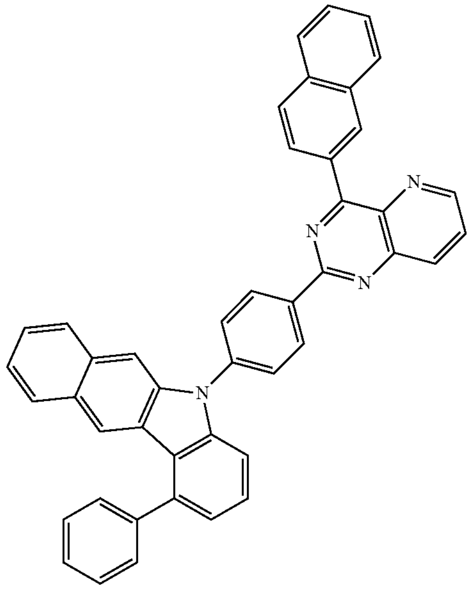
-continued
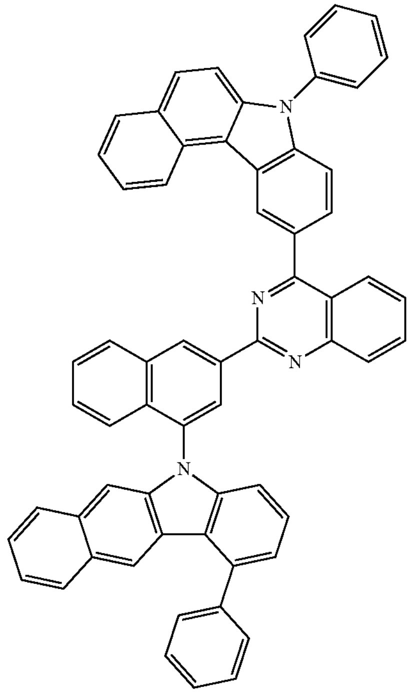
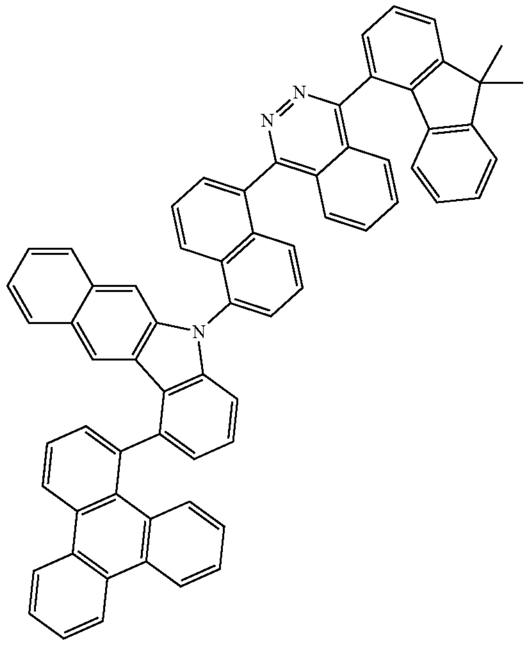

-continued
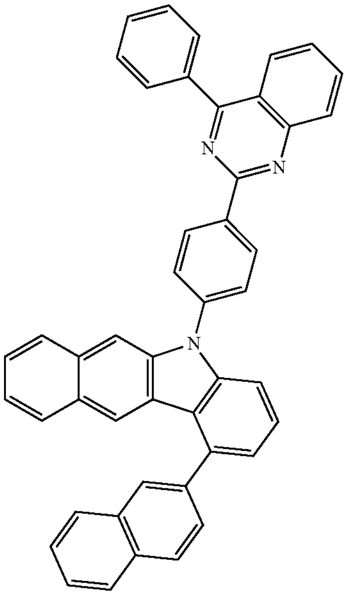
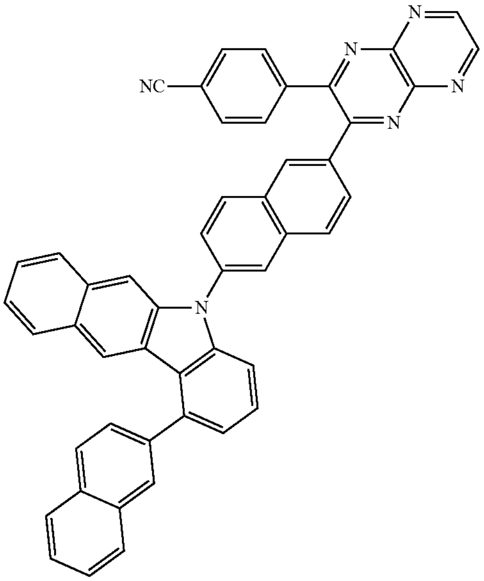
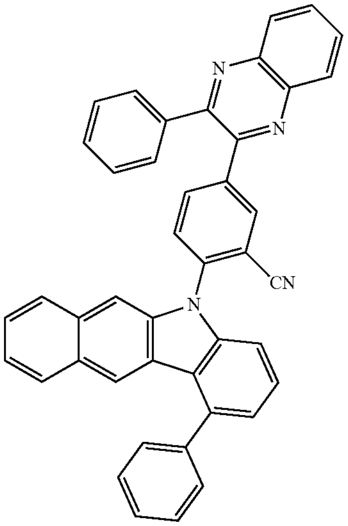
-continued
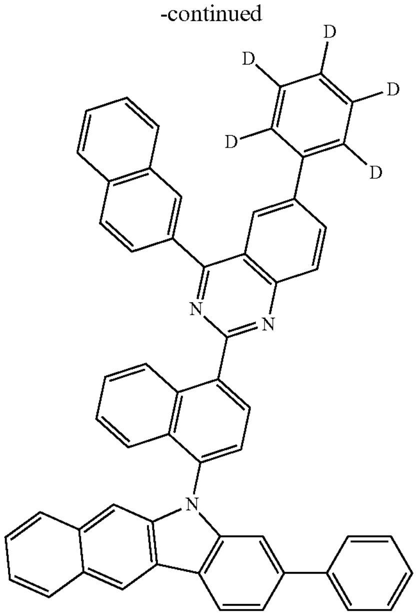
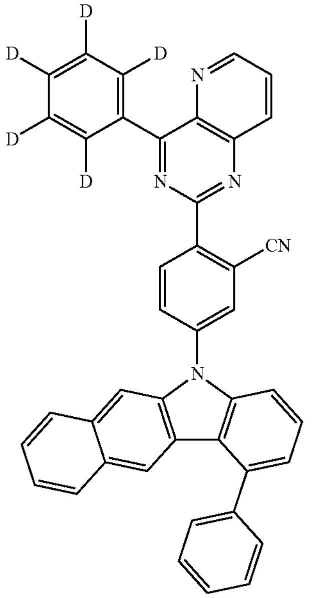

-continued
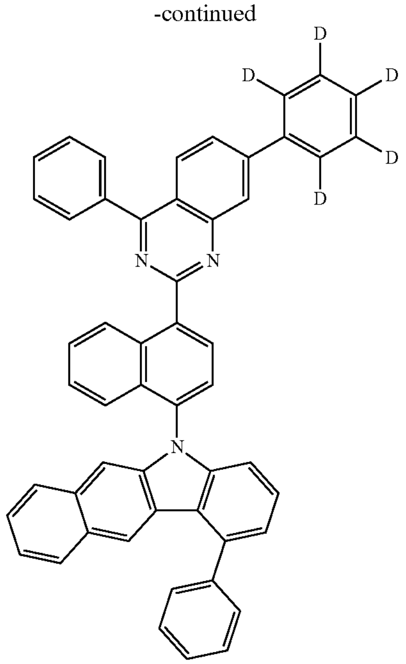
-continued
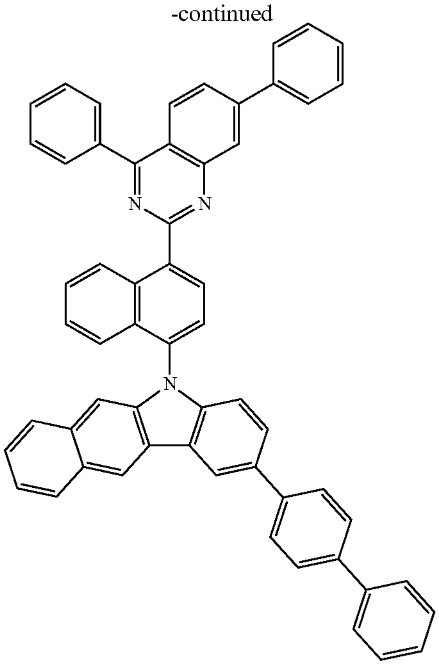
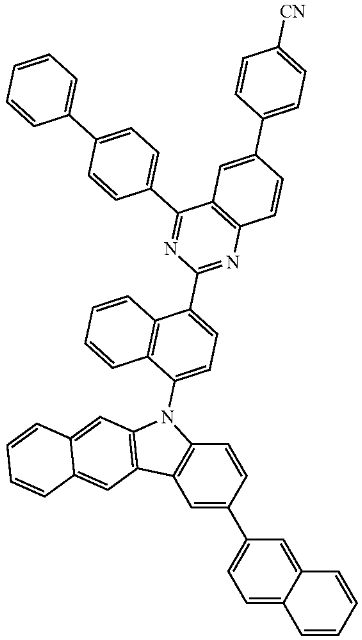
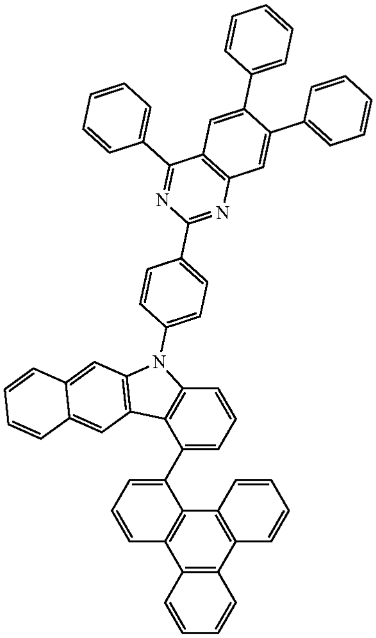

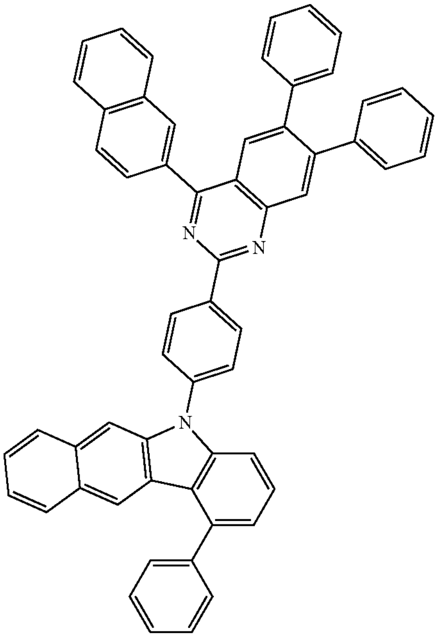
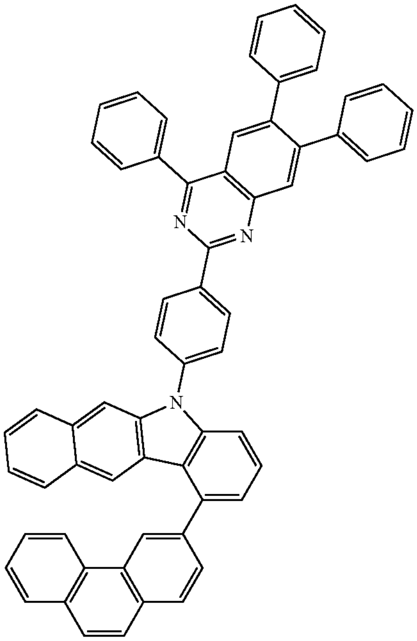
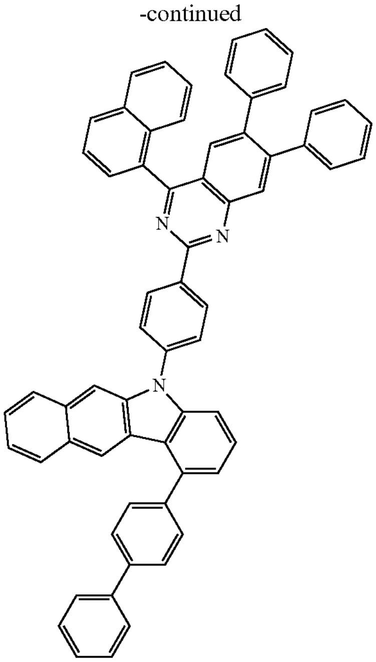
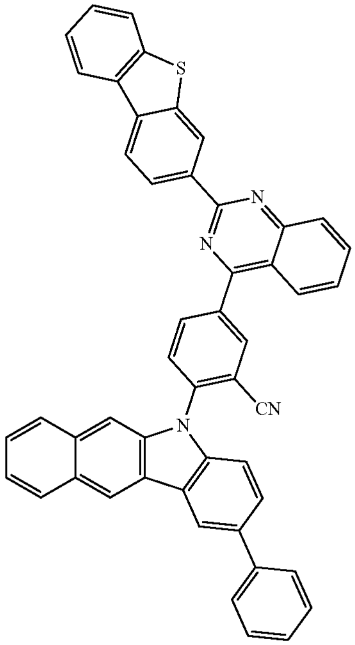

-continued
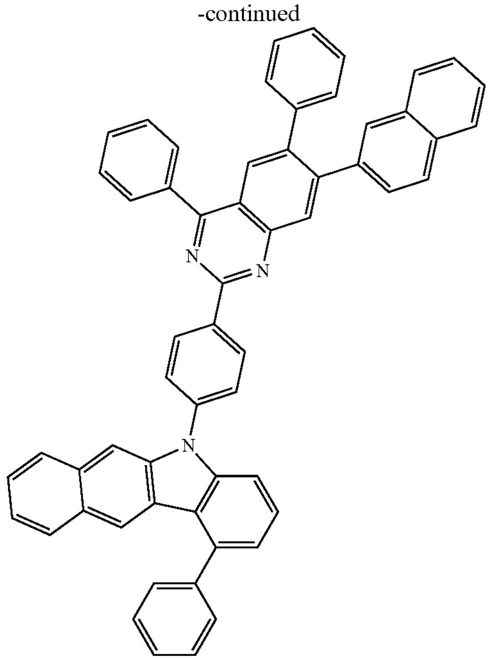
-continued
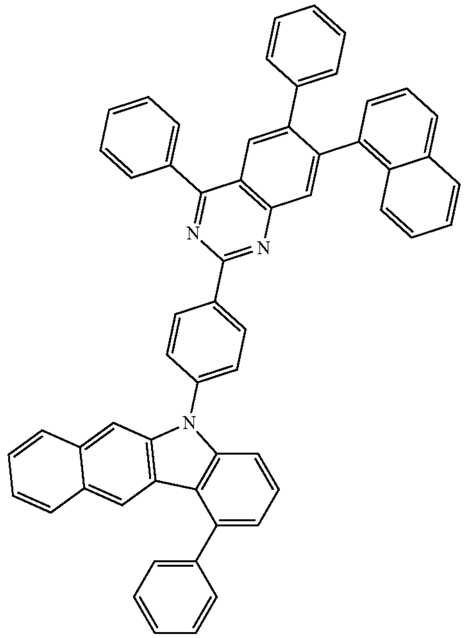
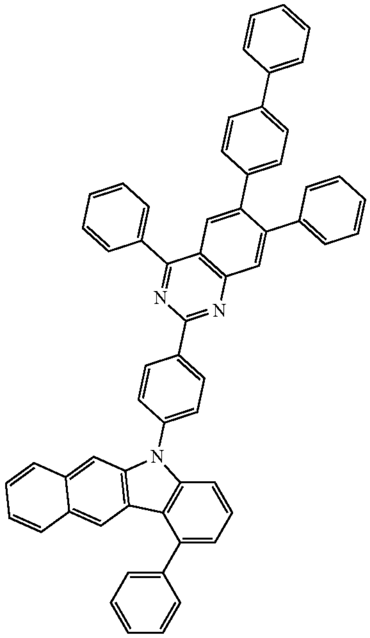
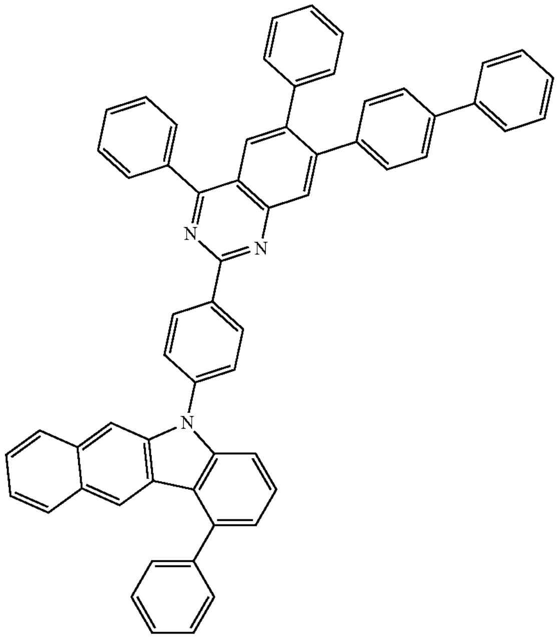

-continued
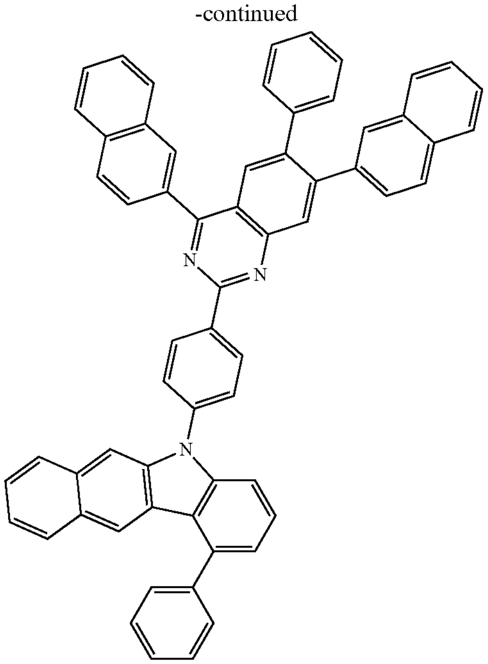
-continued
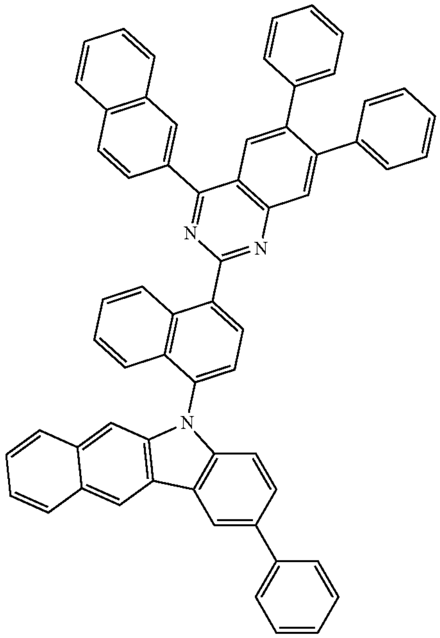
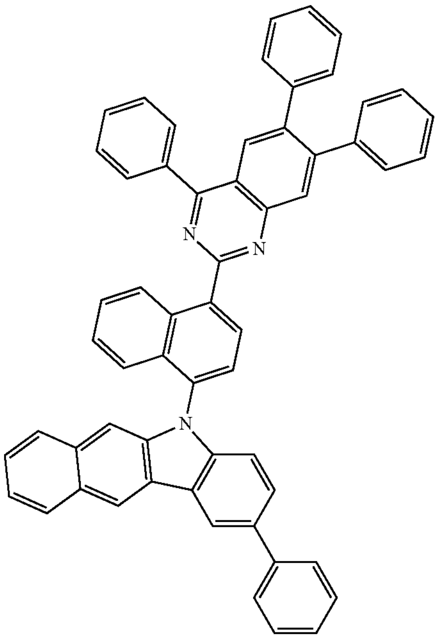
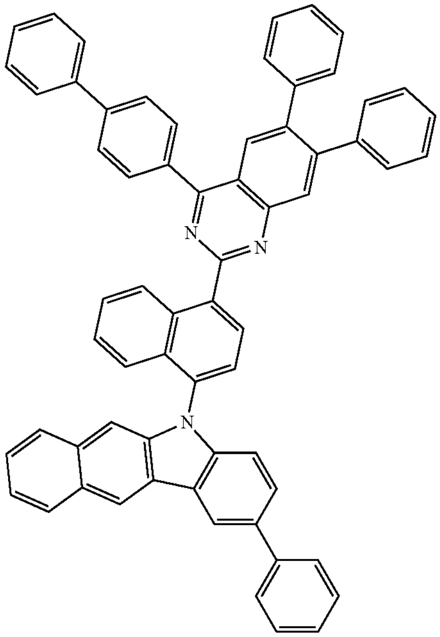

-continued
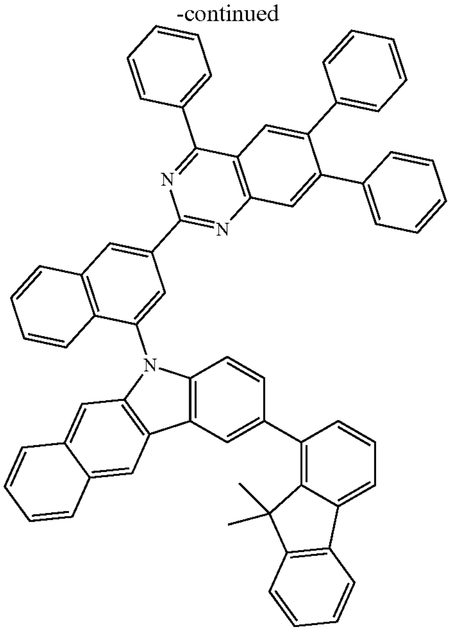
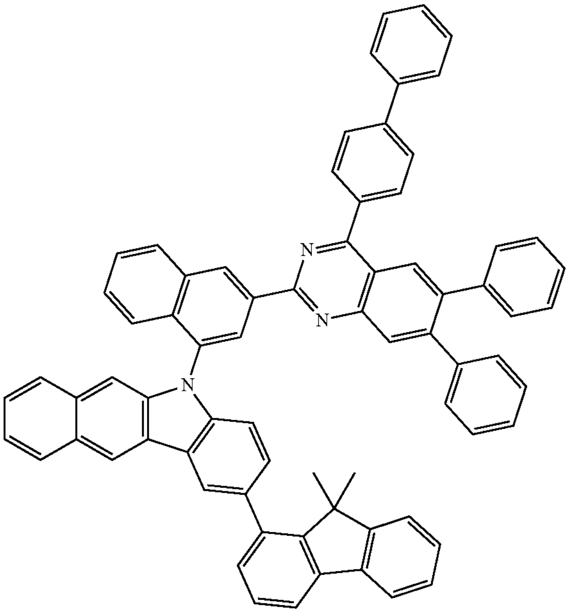
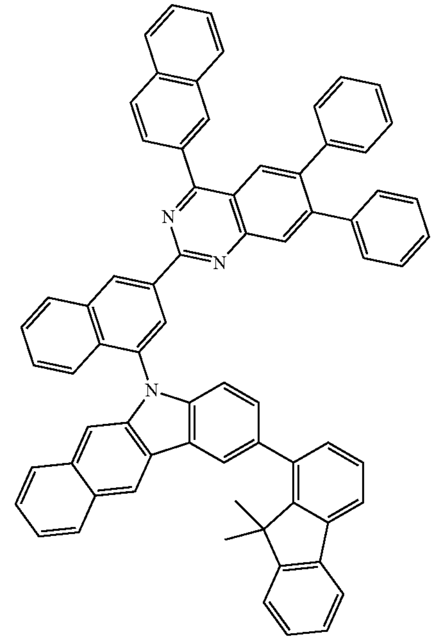
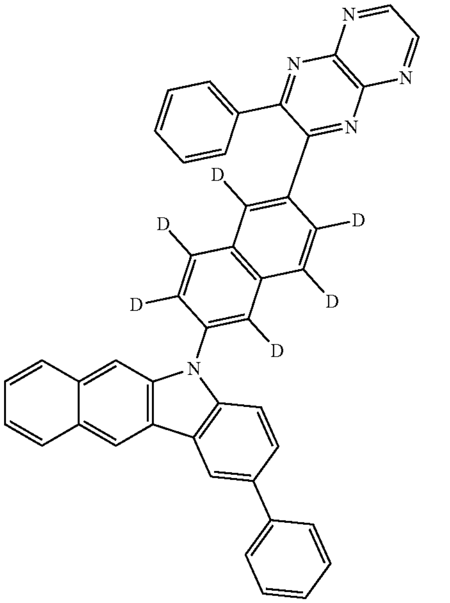

-continued
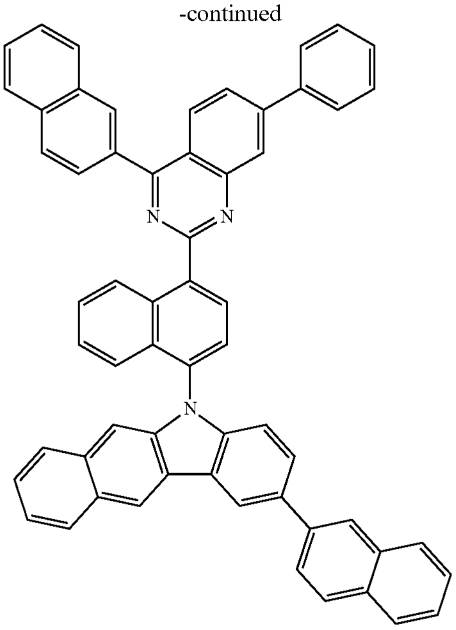
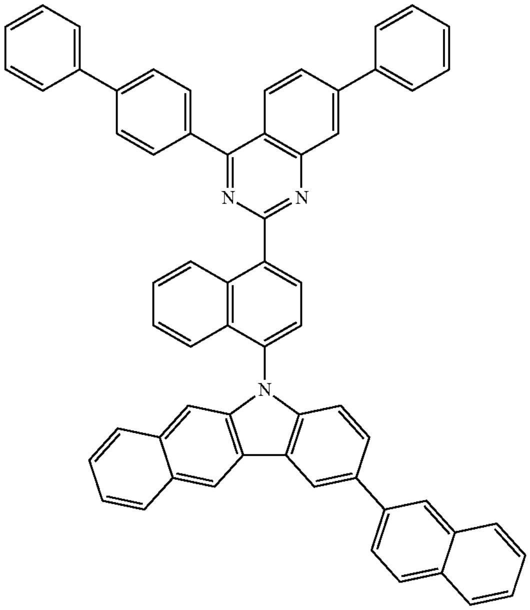
-continued
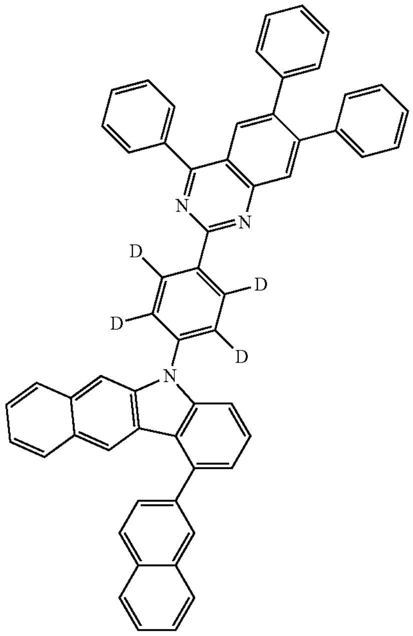
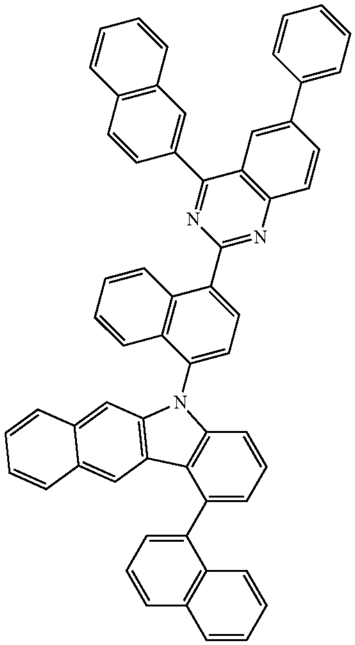

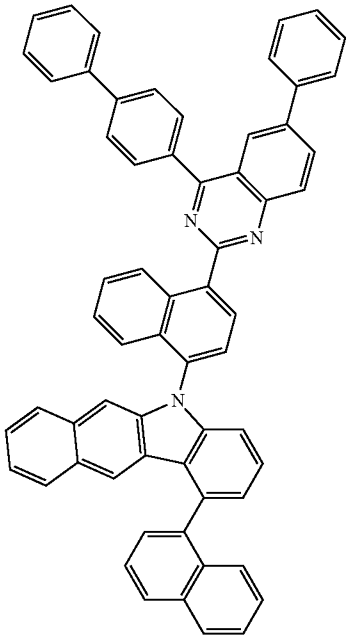
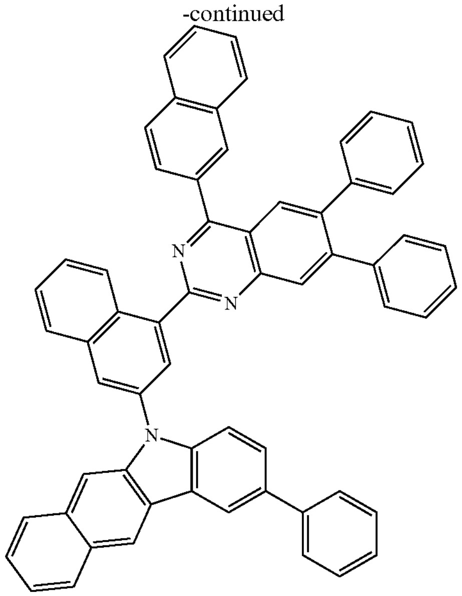
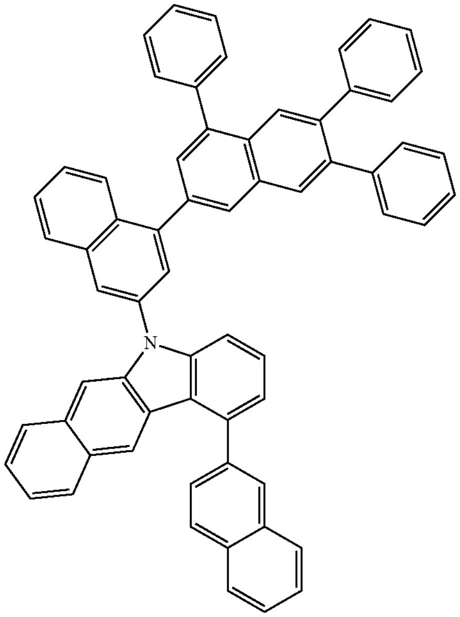
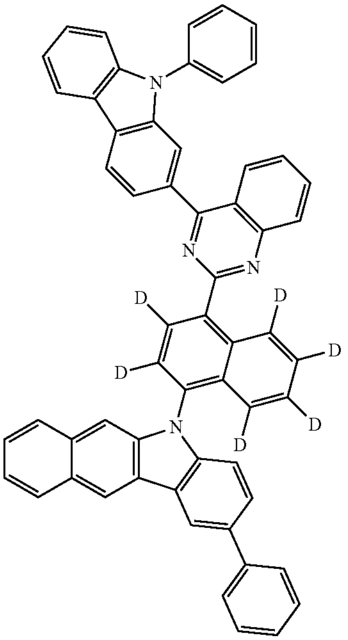

-continued
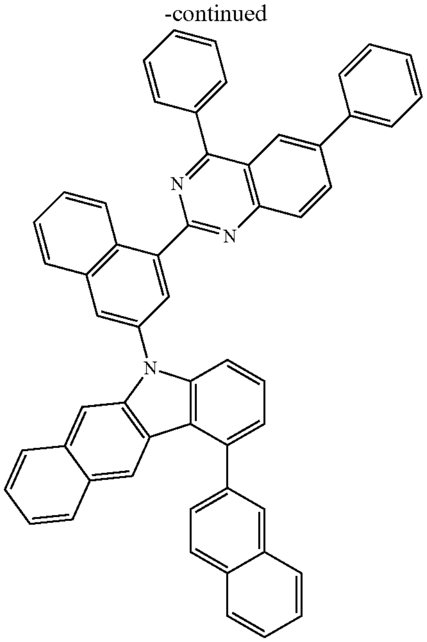
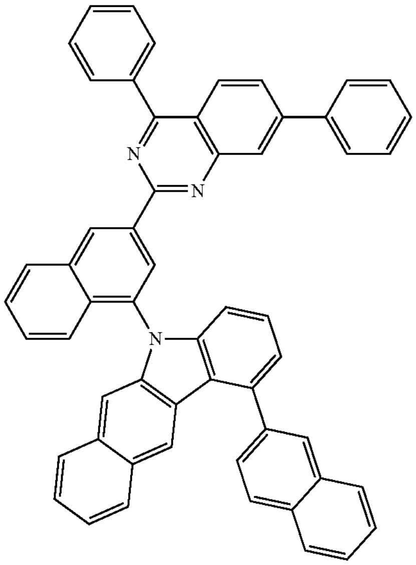
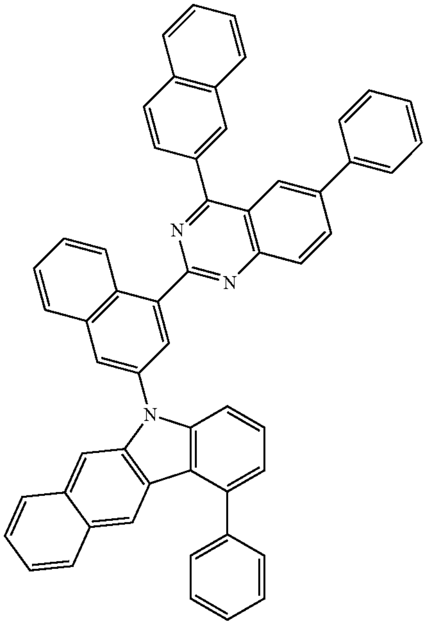
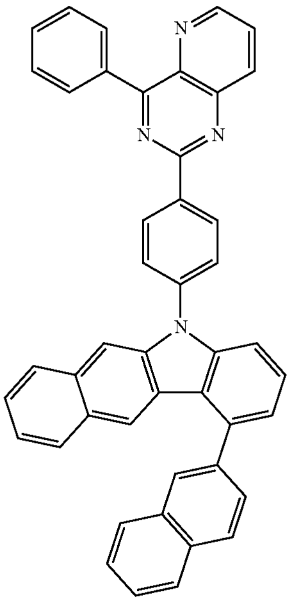
-continued

-continued
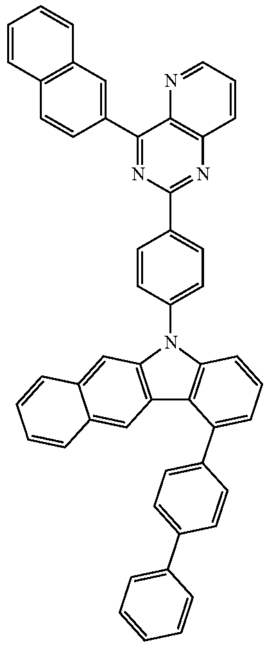
-continued
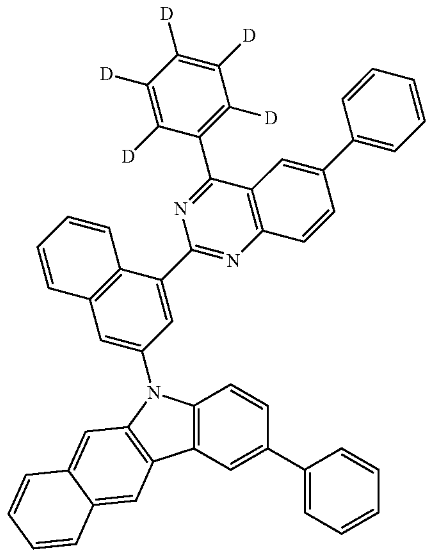
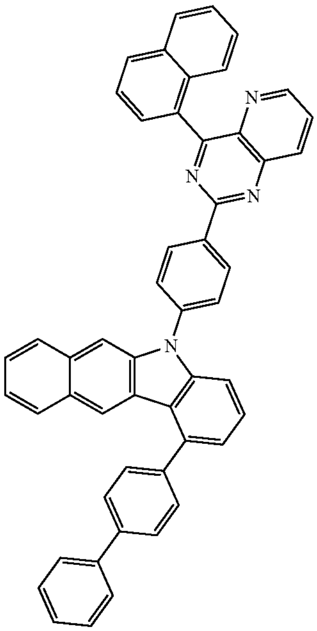
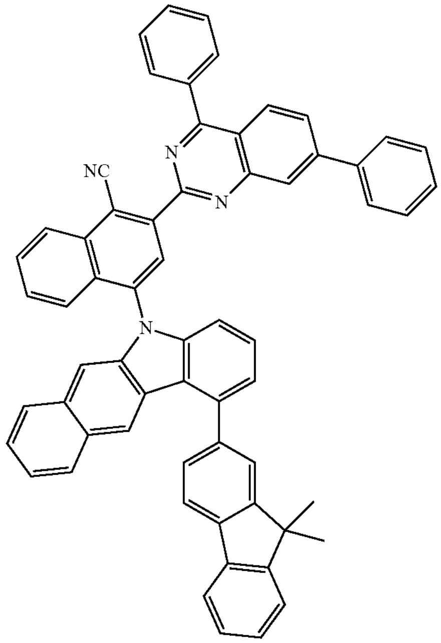

-continued
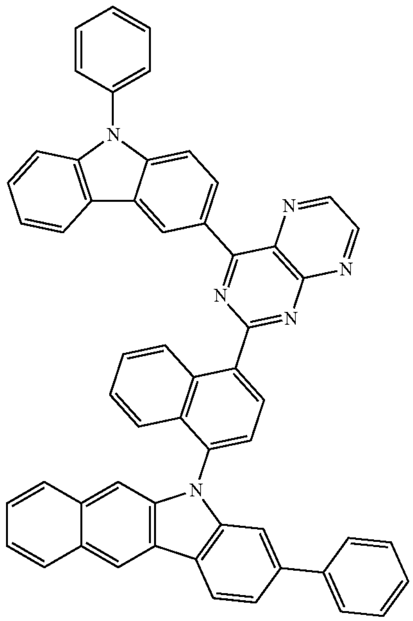
-continued
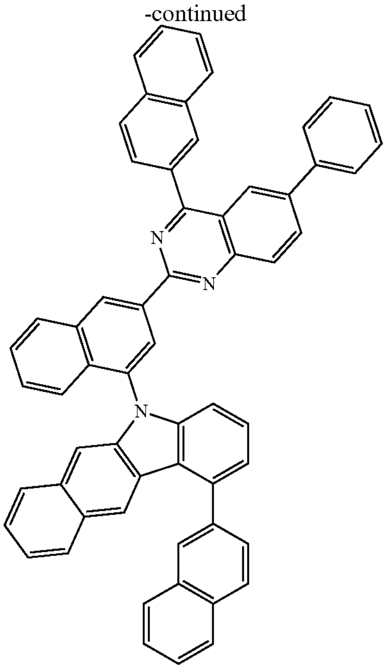
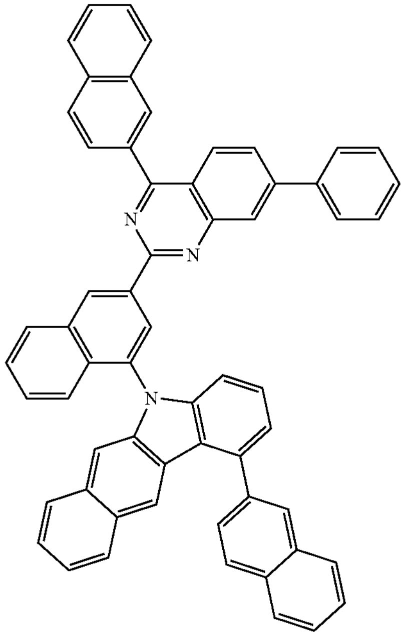
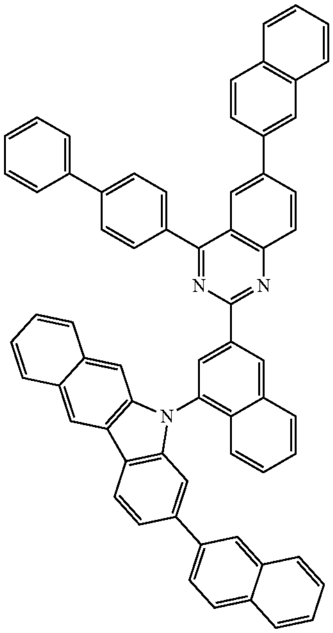

-continued
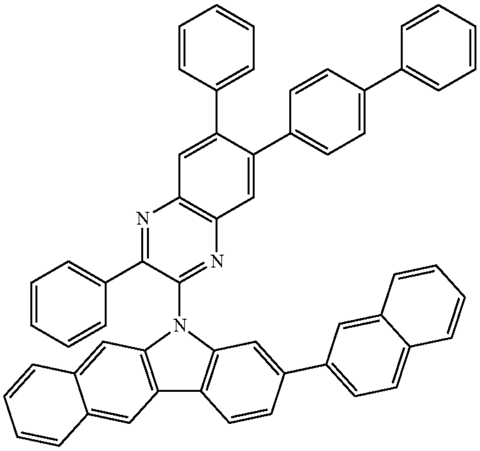
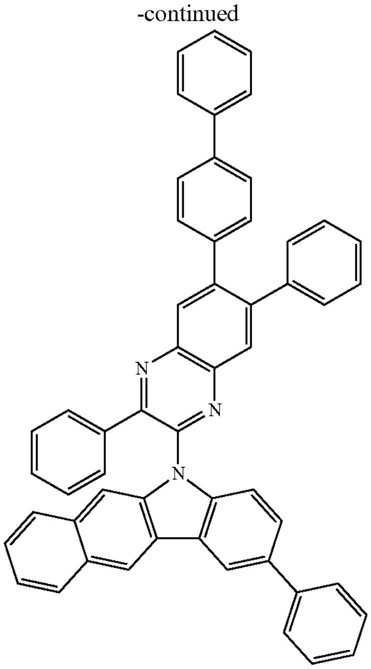
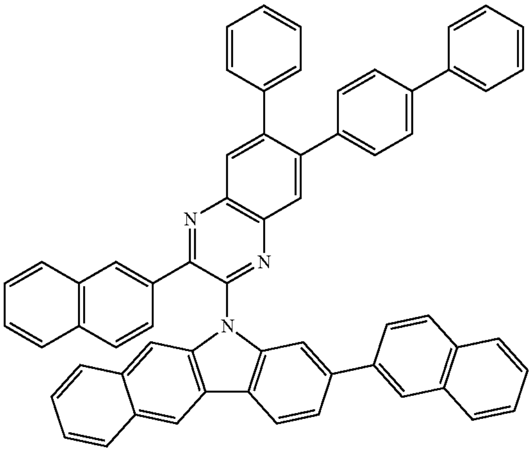
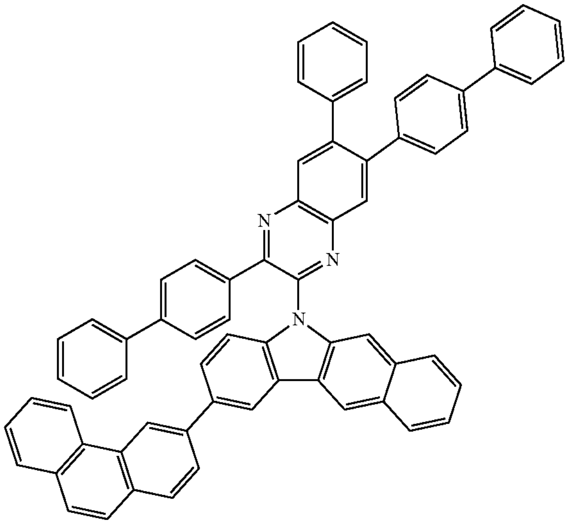
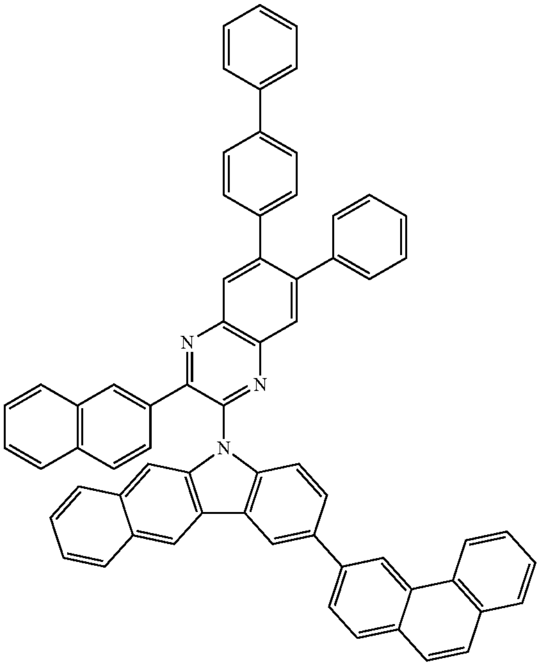

-continued
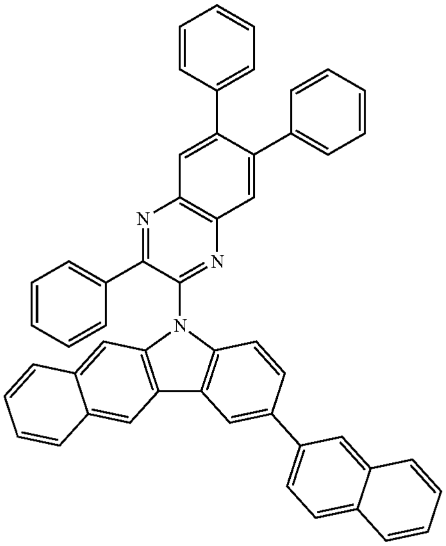
-continued
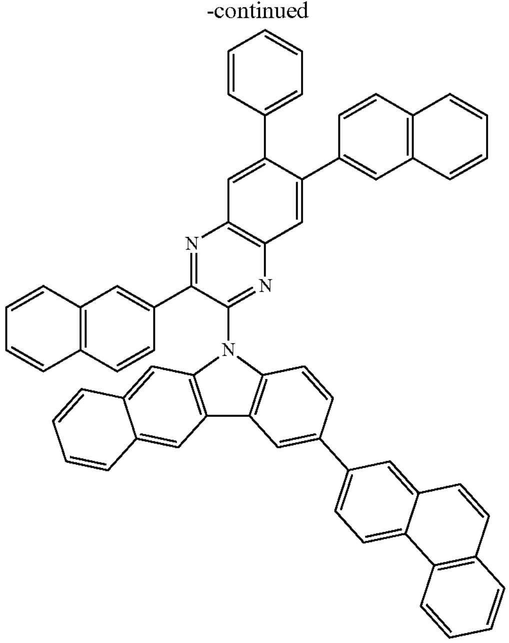
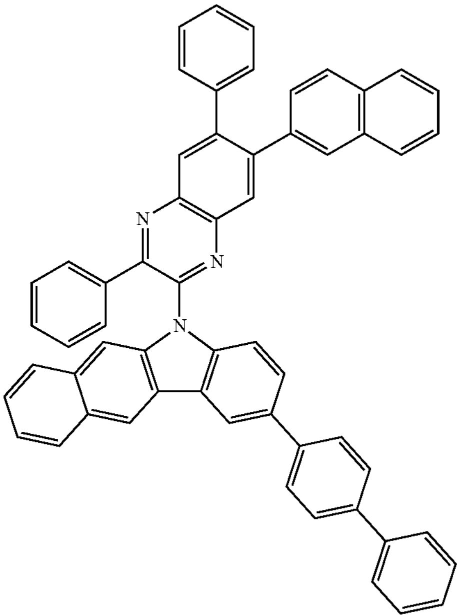
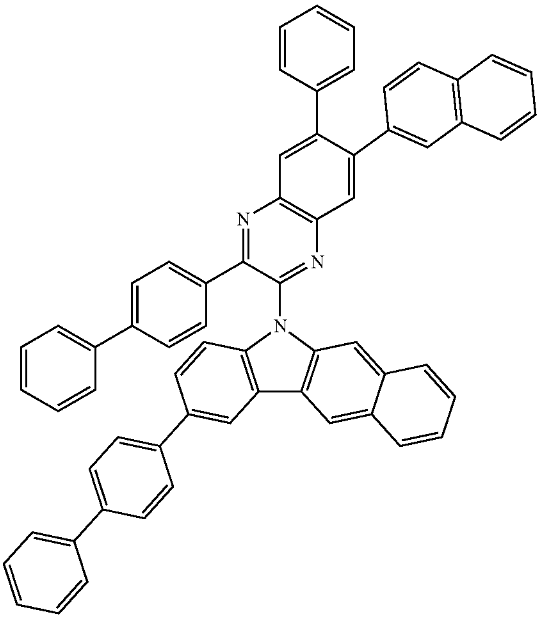

-continued
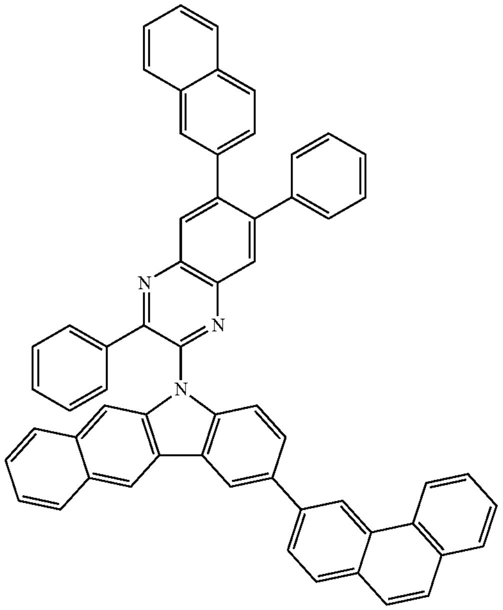
-continued
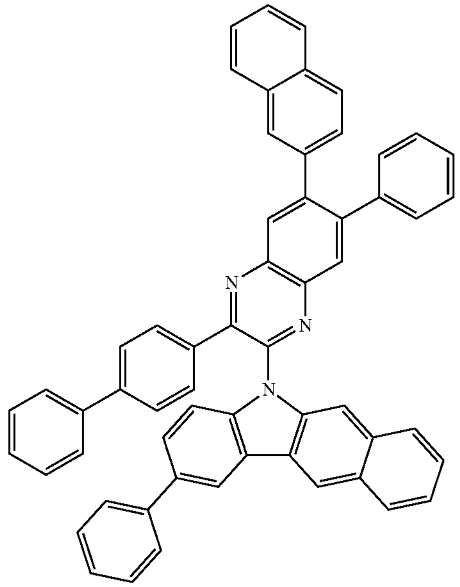
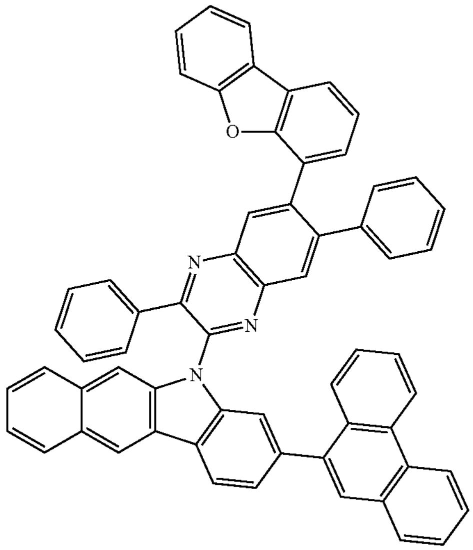
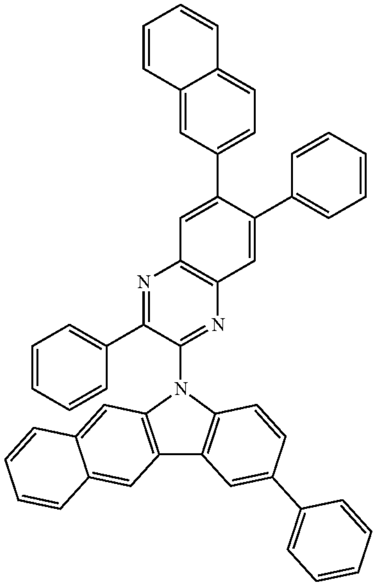
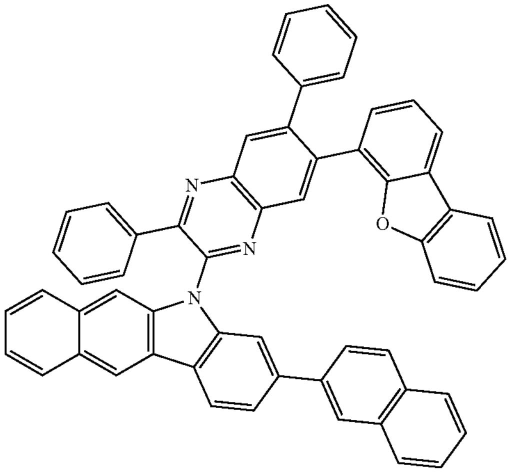

-continued
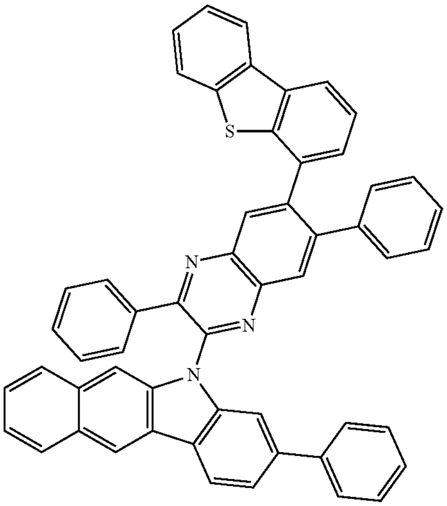
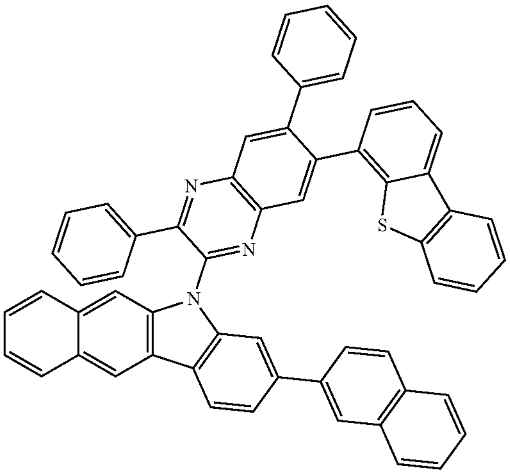
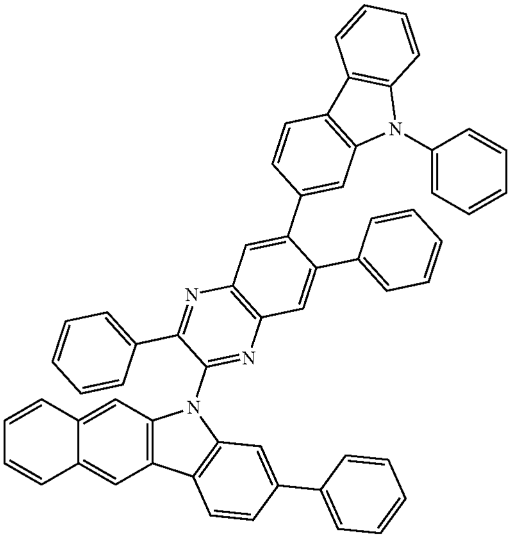
-continued
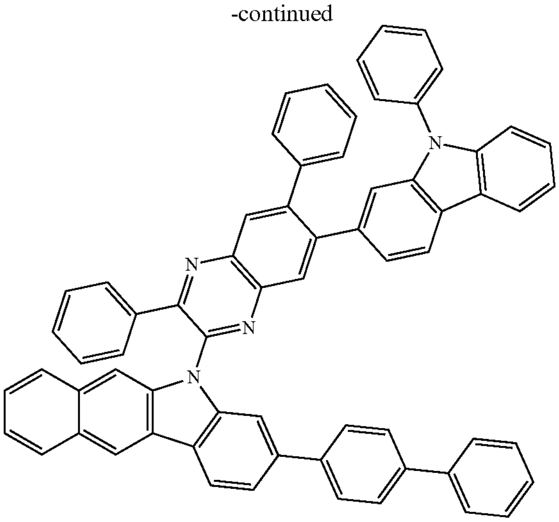
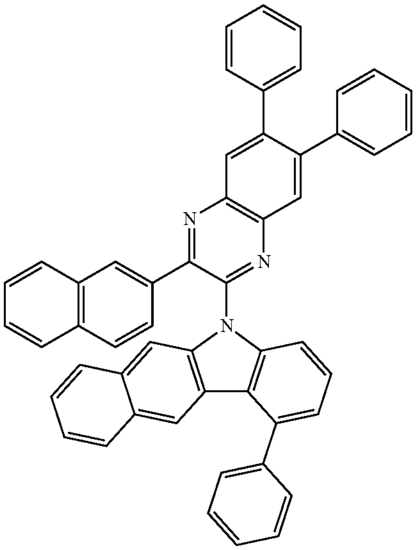 [SMILES: c1ccc(-c2cc3nc(-c4ccc5ccccc5c4)c(-n4c5cc6ccccc6cc5c5c(-c6ccccc6)cccc54)nc3cc2-c2ccccc2)cc1]
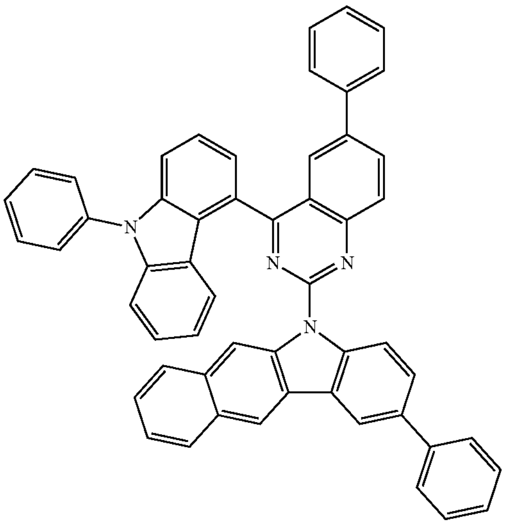

-continued
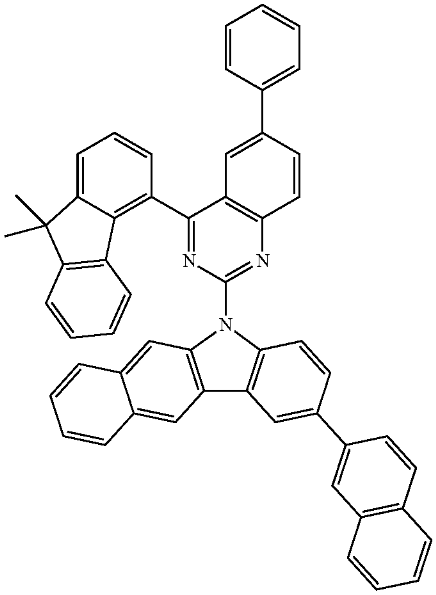
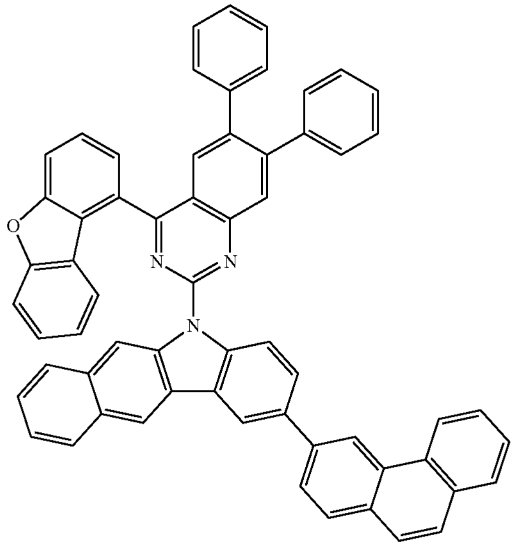
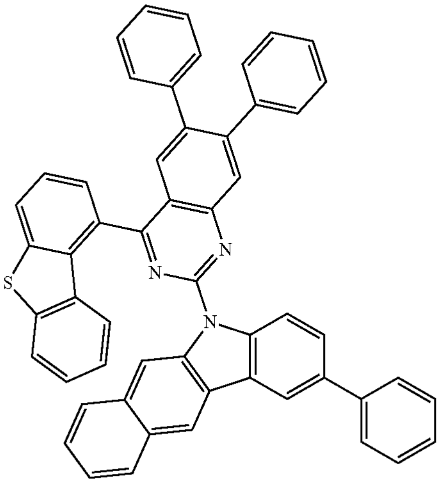
-continued
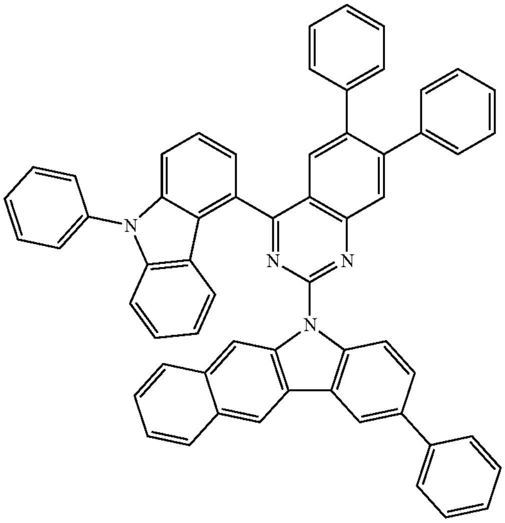
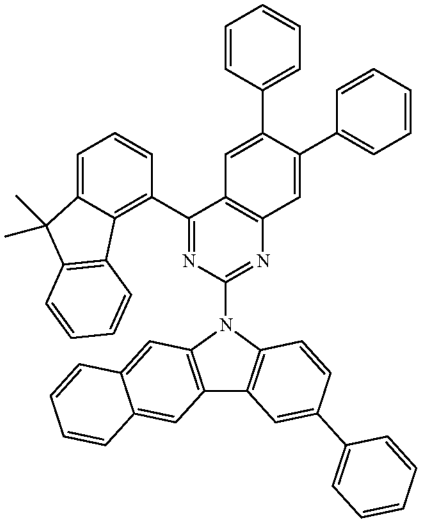
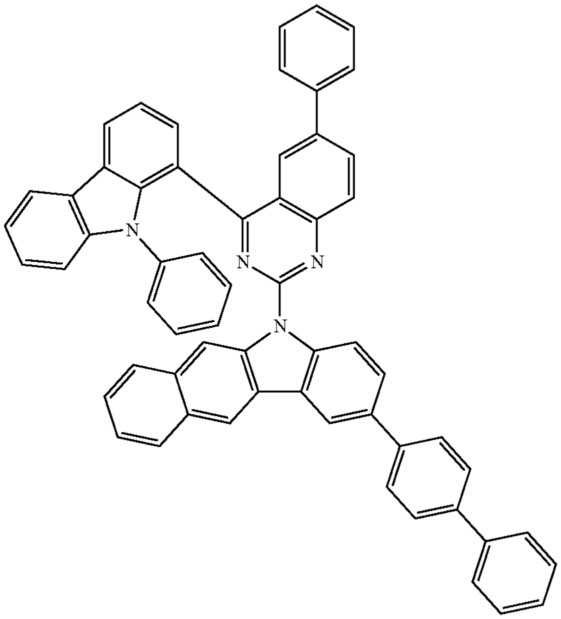

-continued
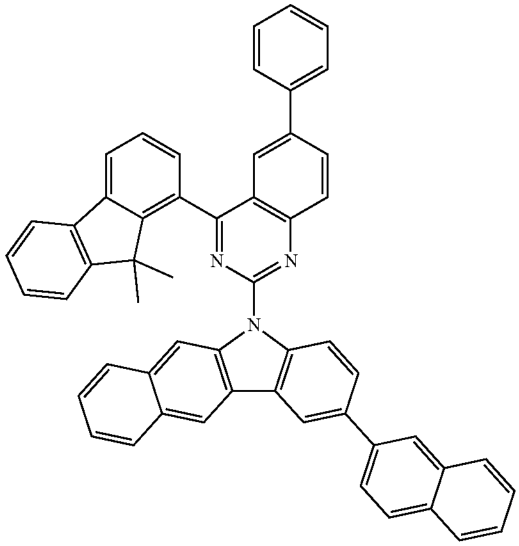
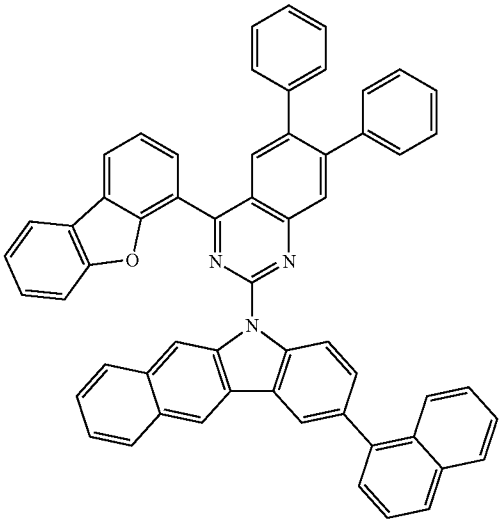
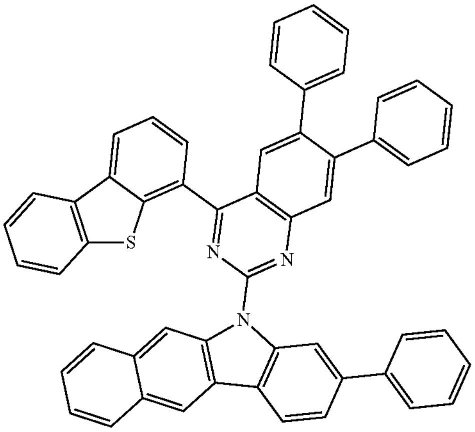
-continued
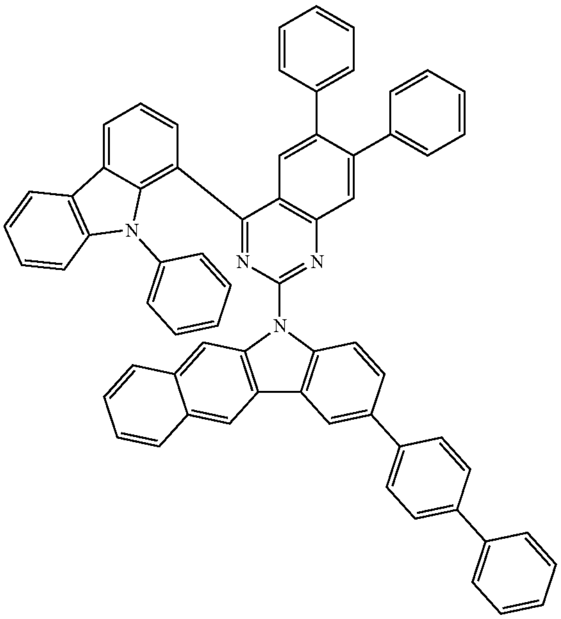
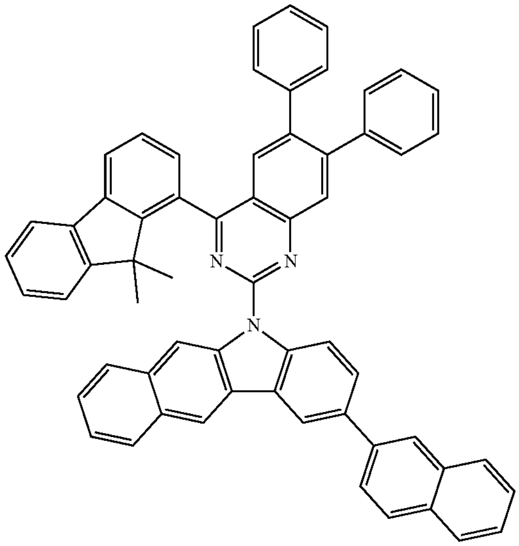
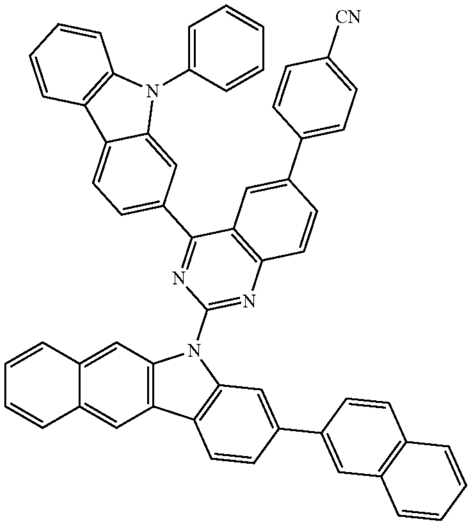

-continued
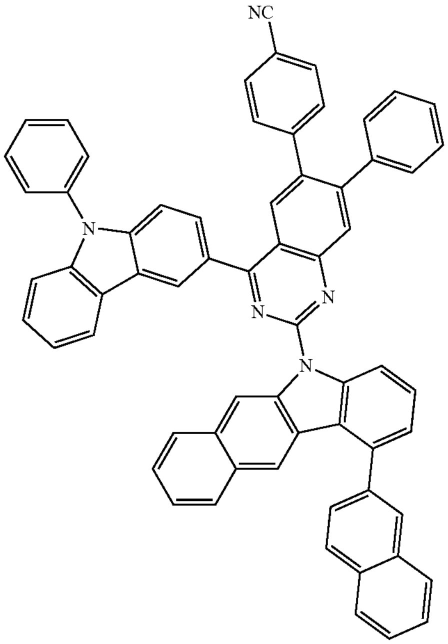
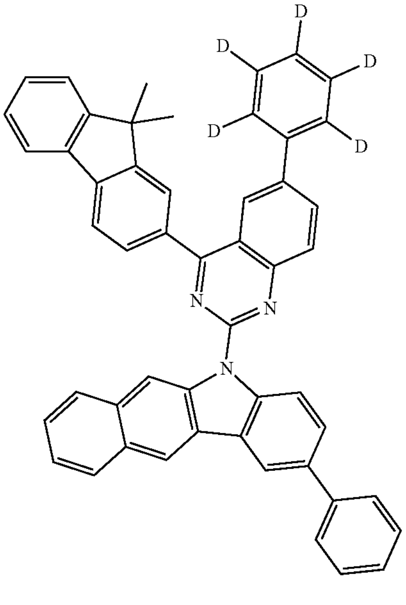
-continued
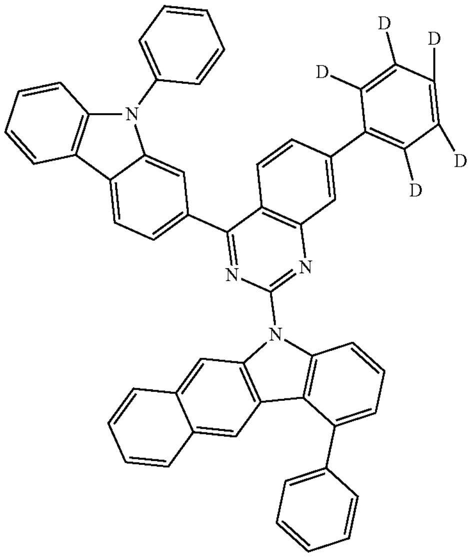
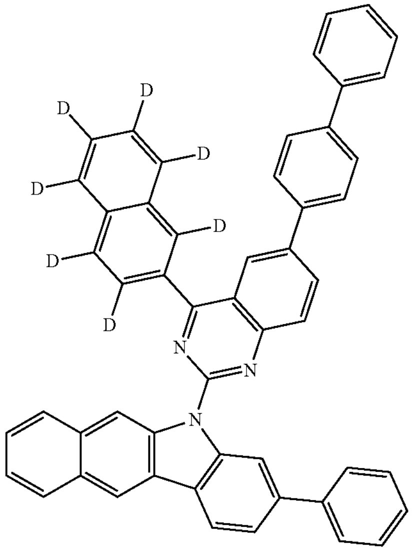
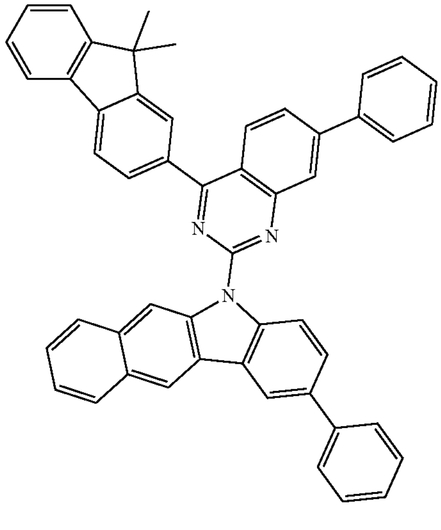

-continued
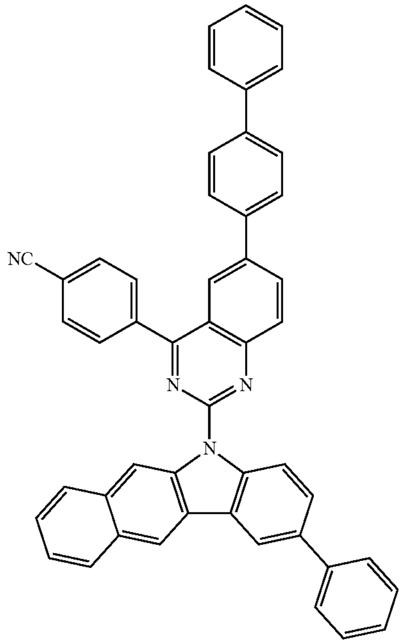
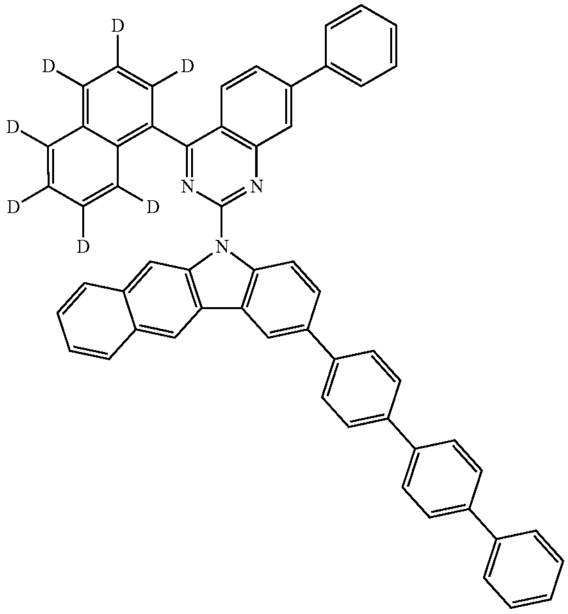
-continued
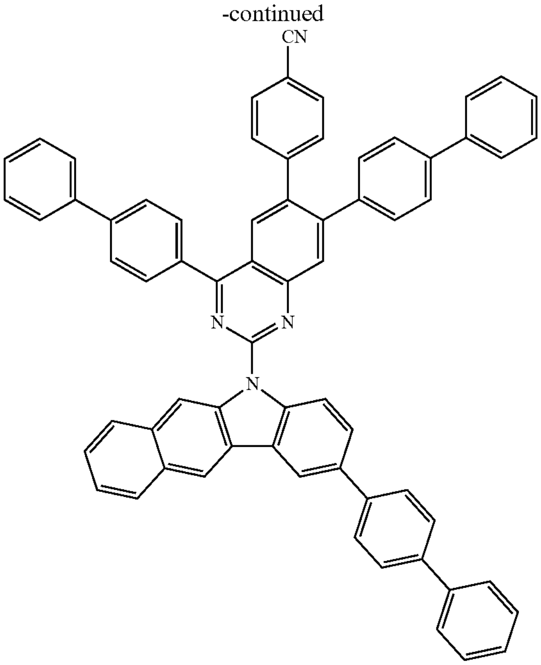
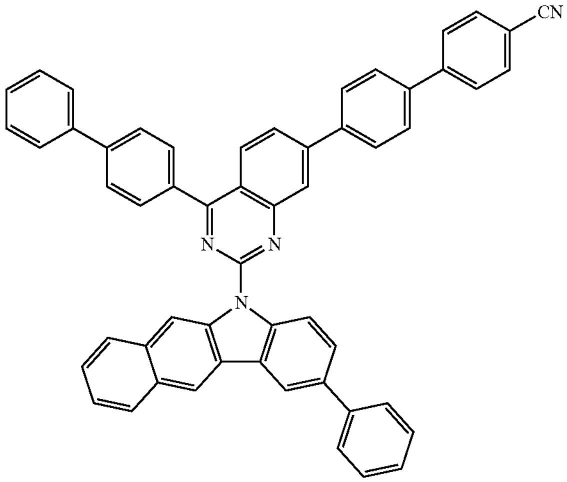
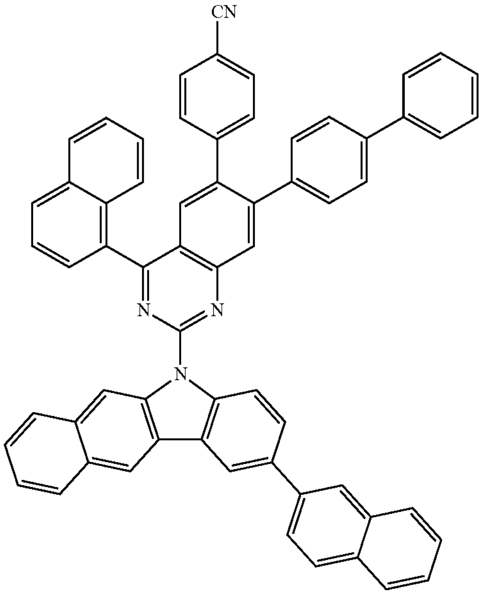

-continued
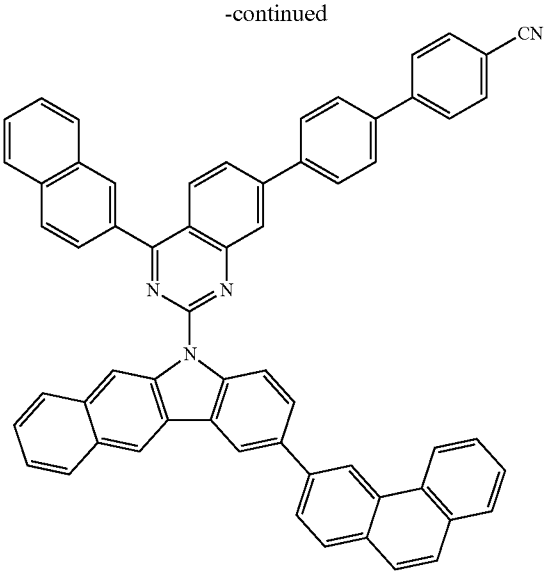
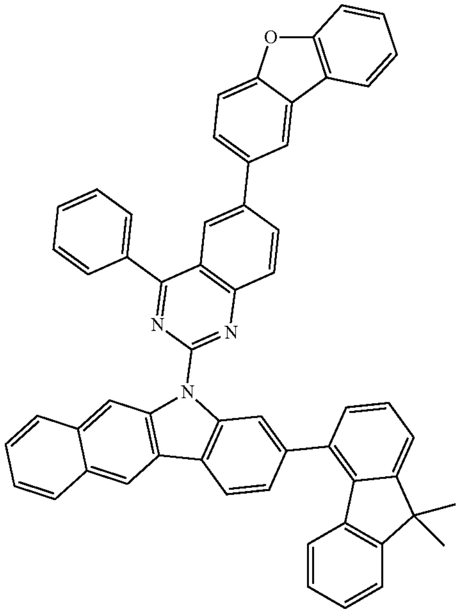
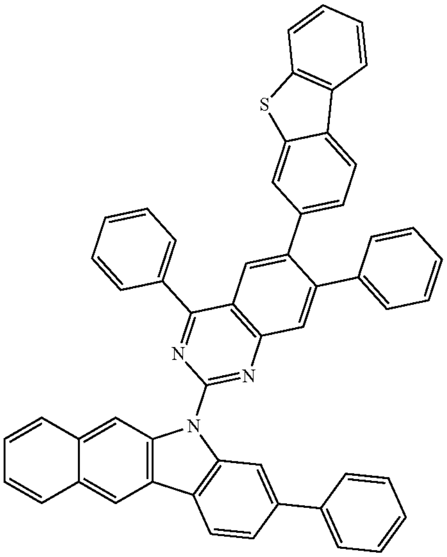
-continued
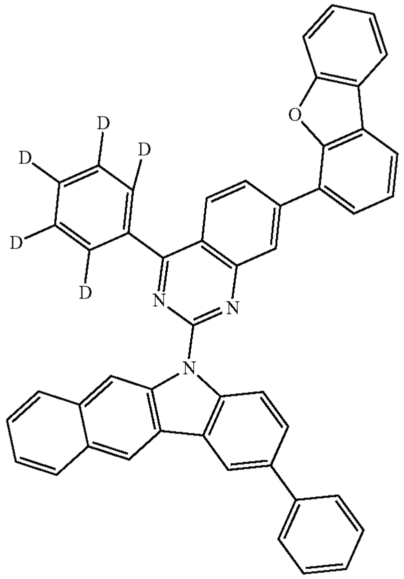
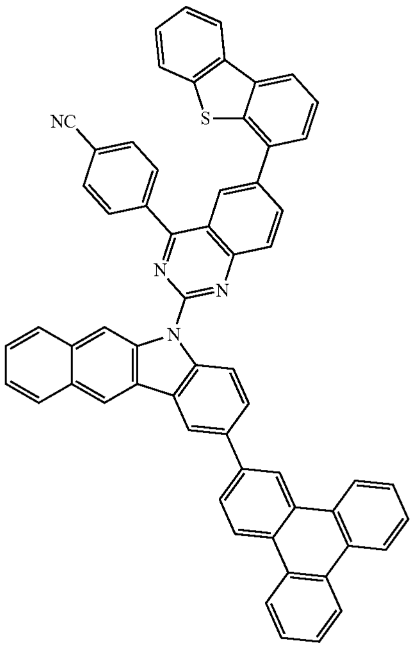

-continued
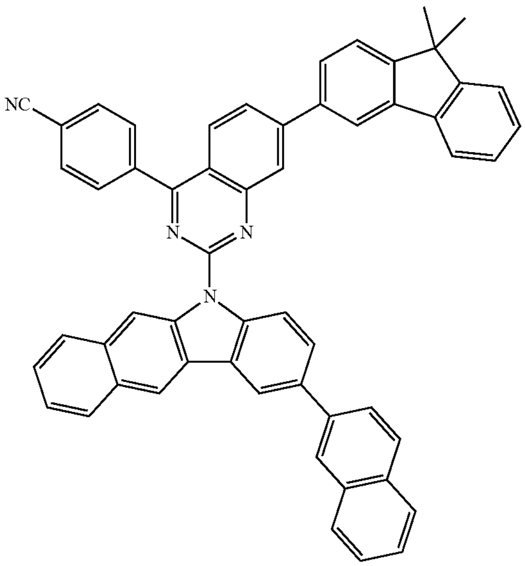
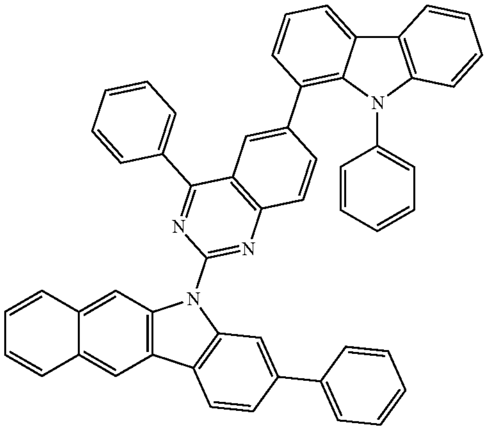
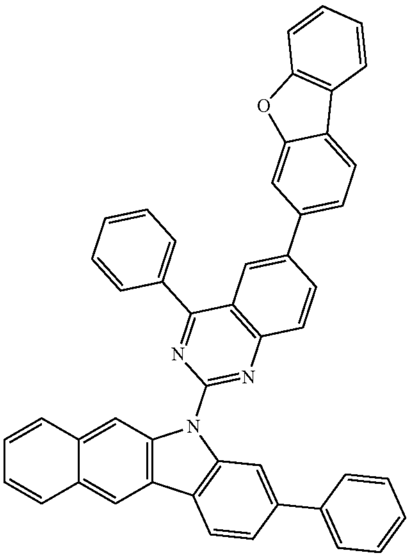
-continued
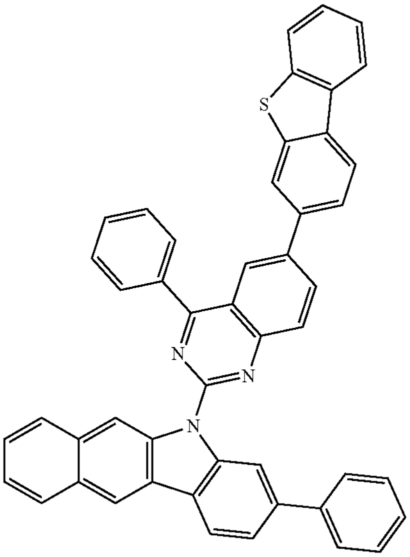
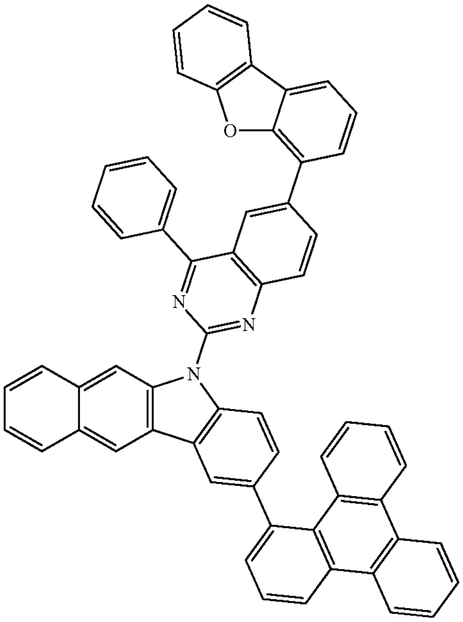

-continued
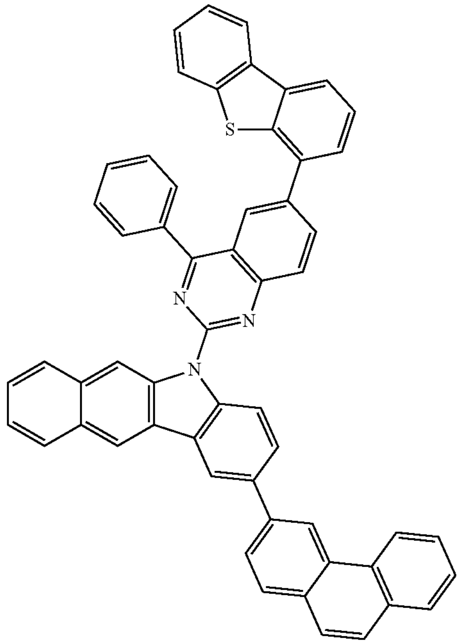
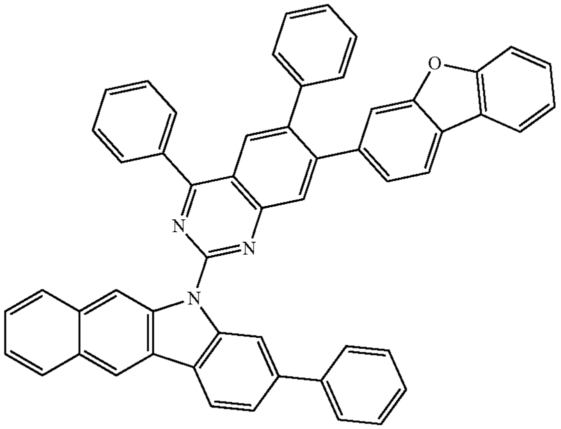
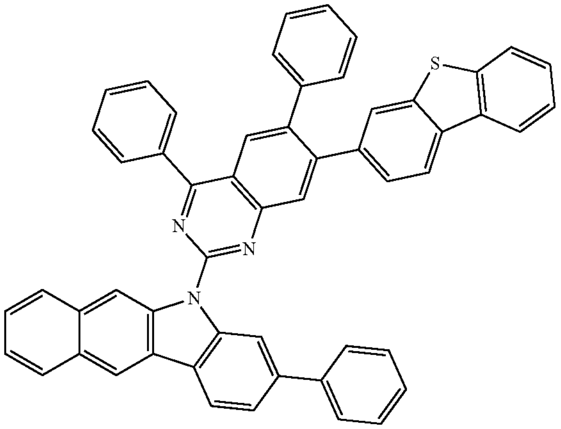
-continued
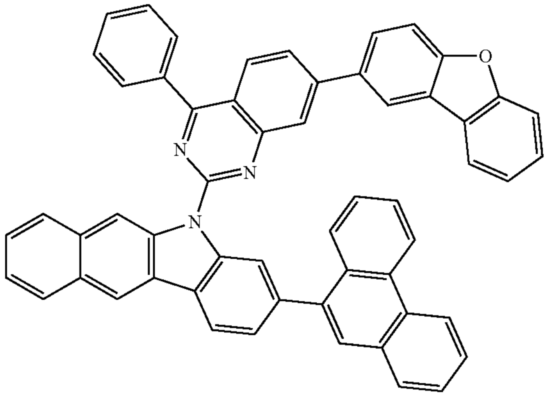
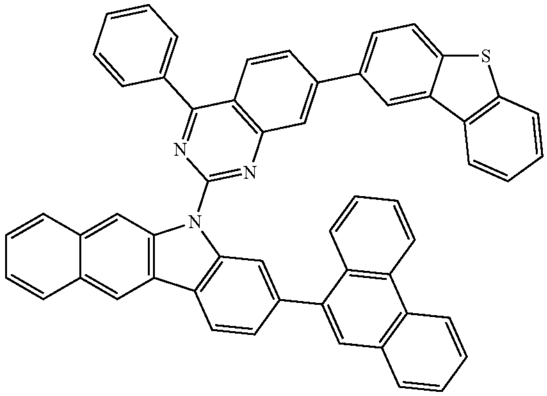
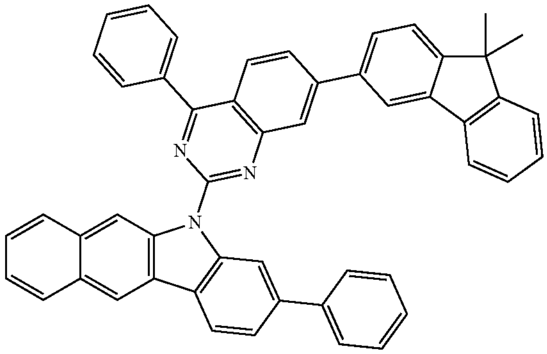
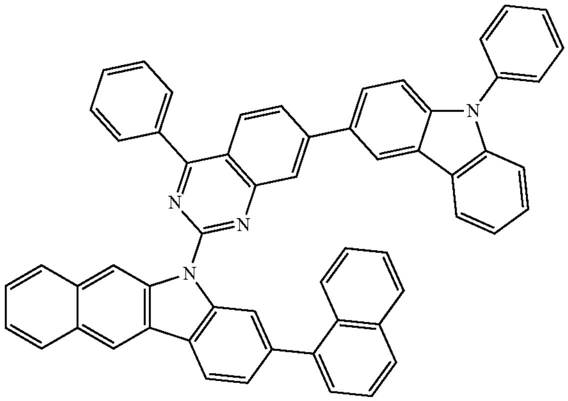

-continued
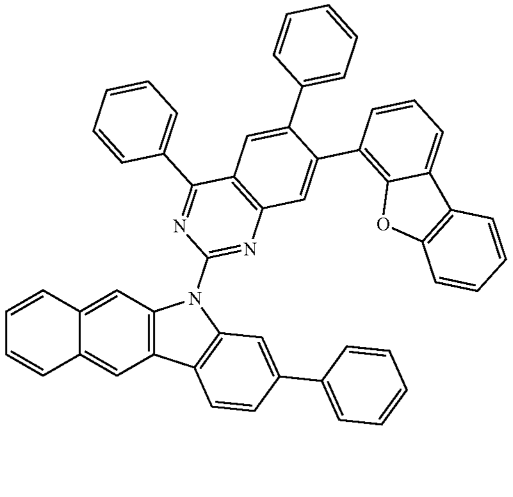
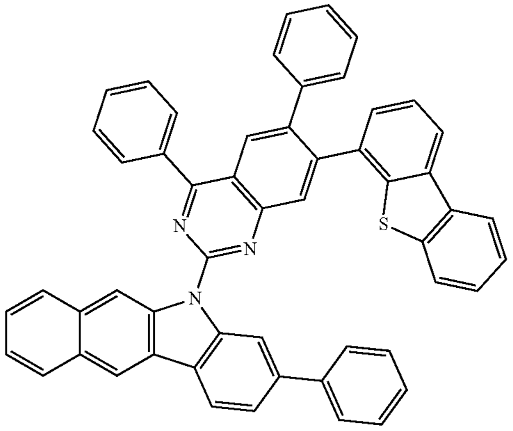
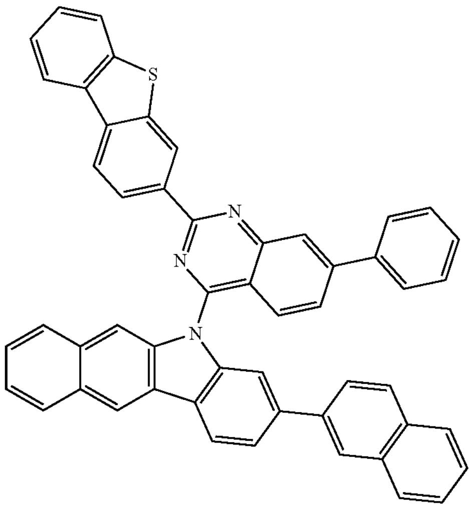
-continued
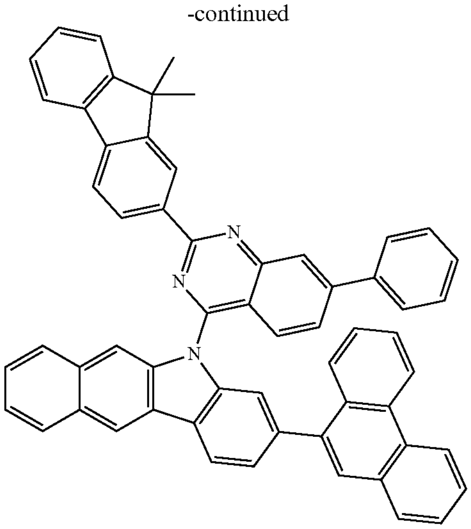
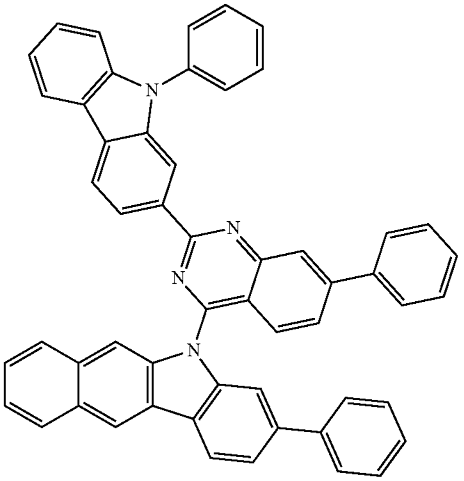
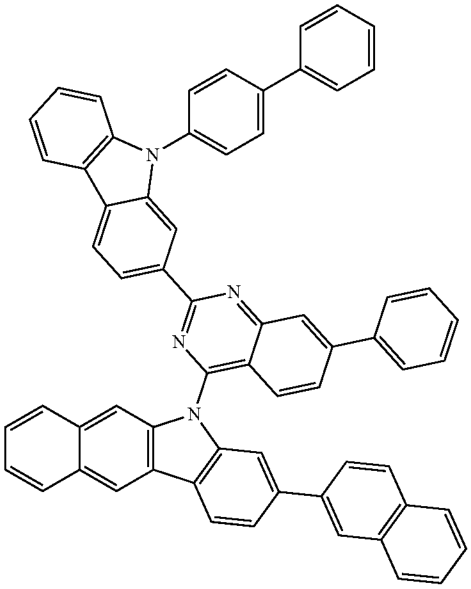

-continued
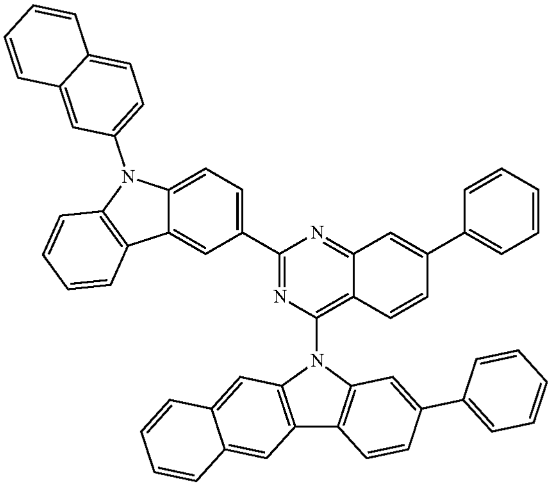
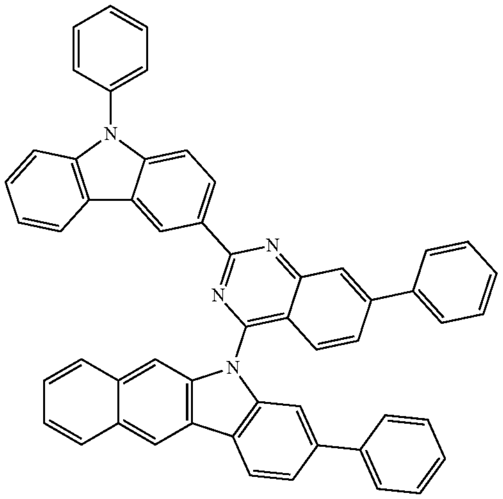
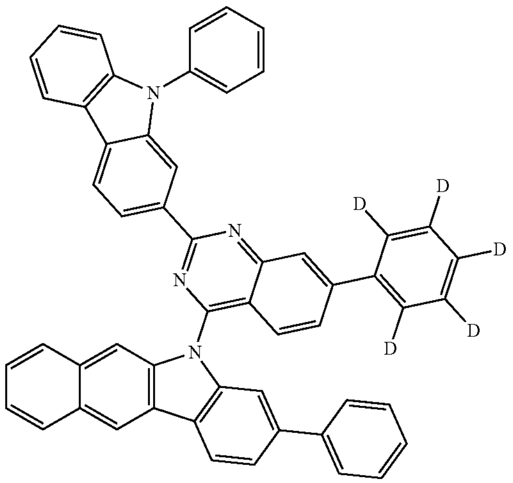
-continued
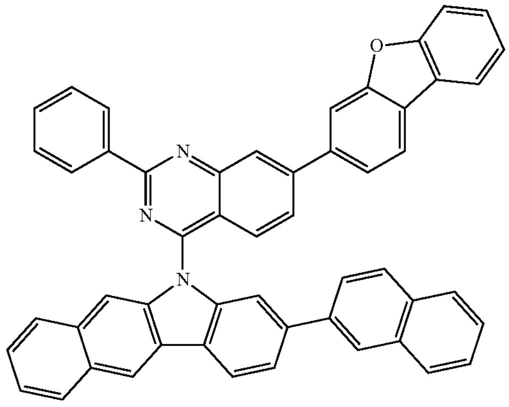
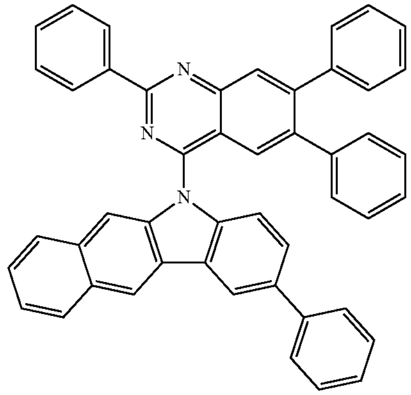
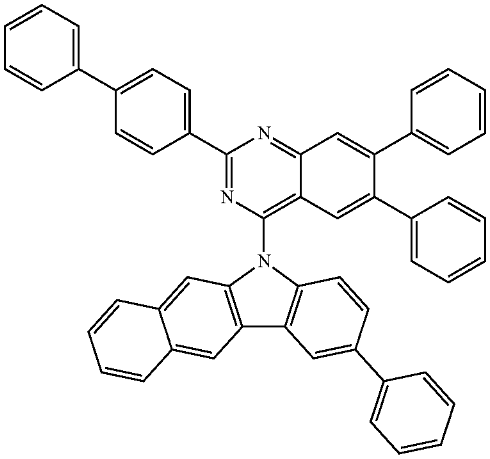
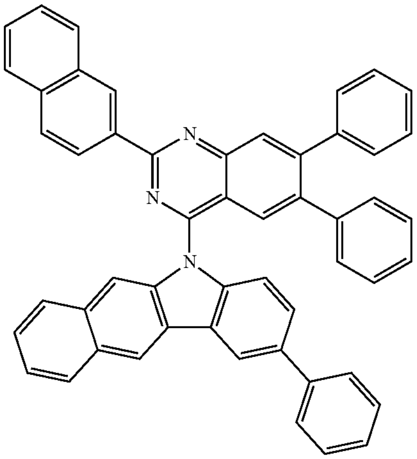

-continued
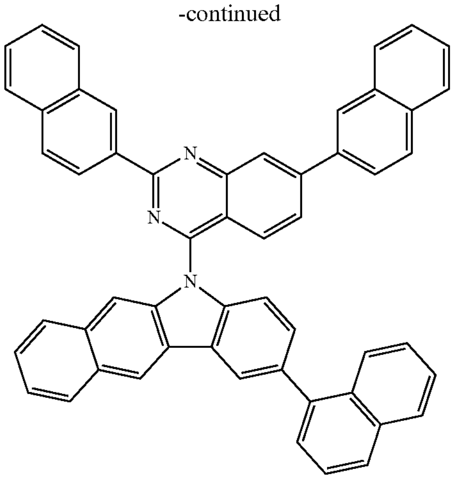
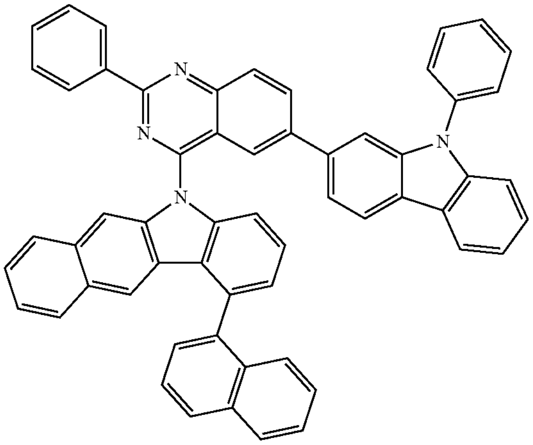
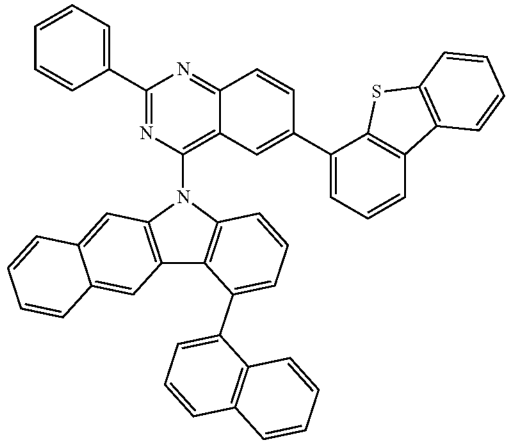
-continued
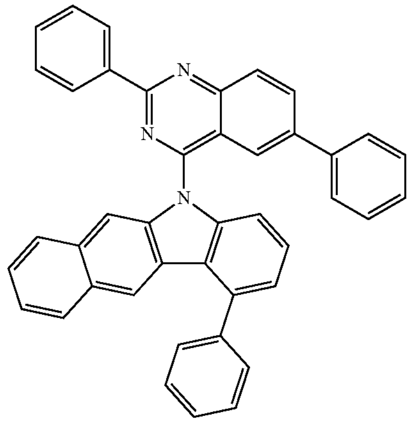
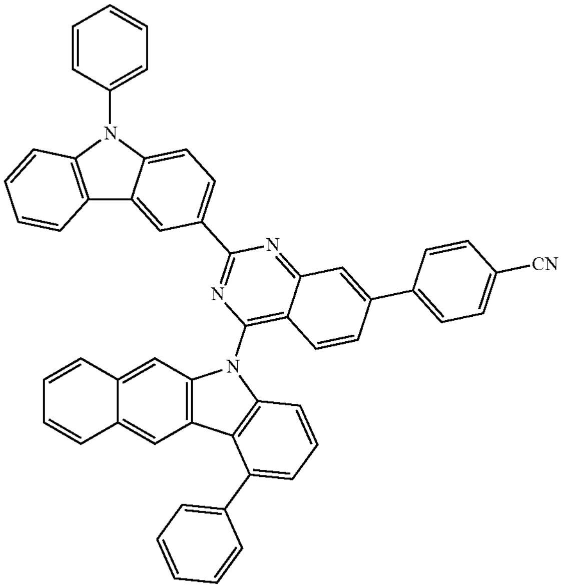
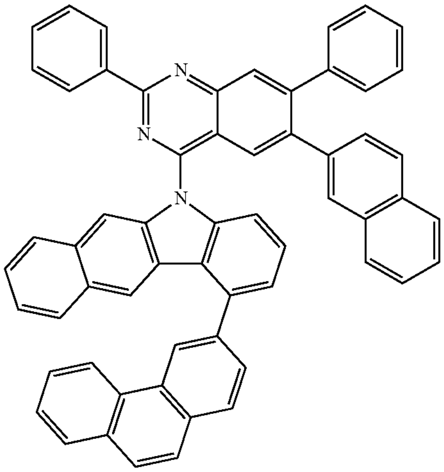

-continued
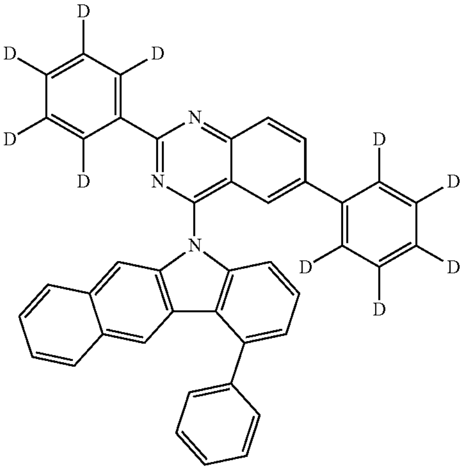
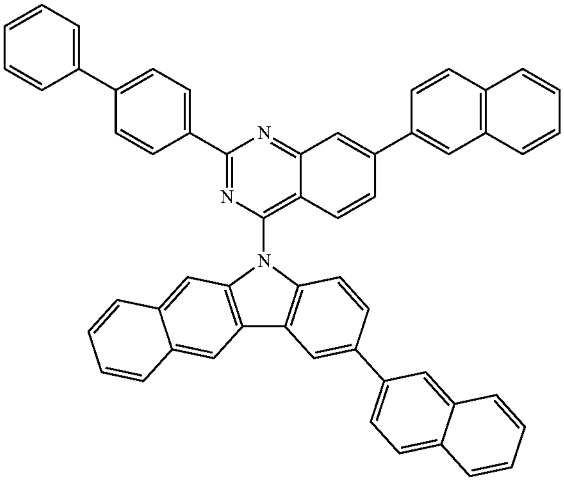
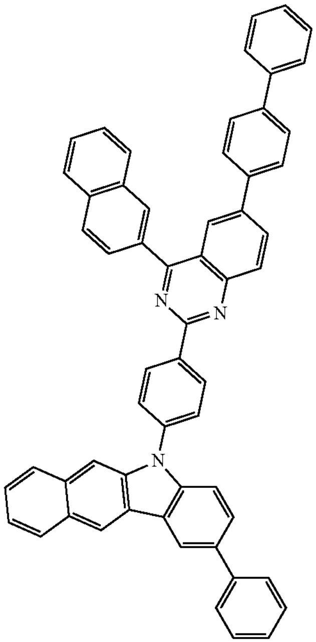
-continued
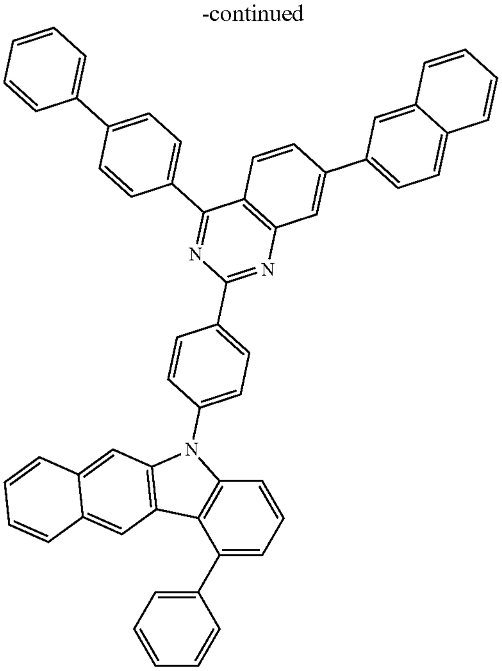
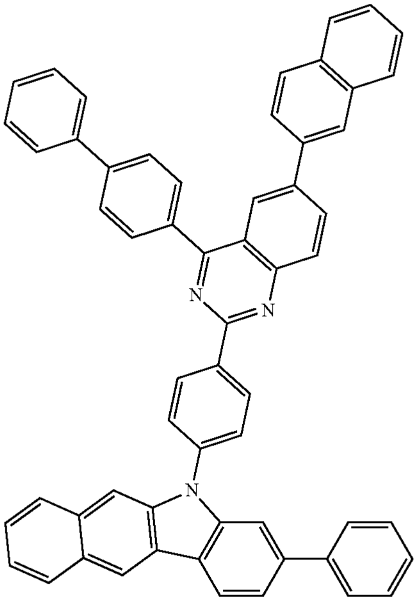

-continued
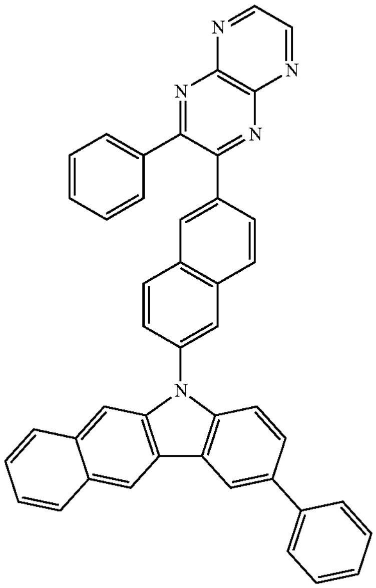
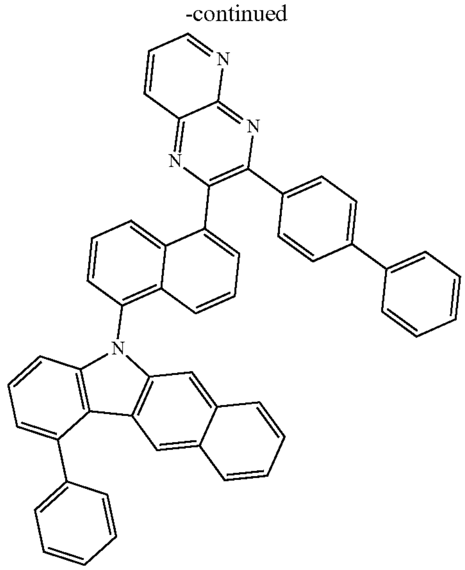
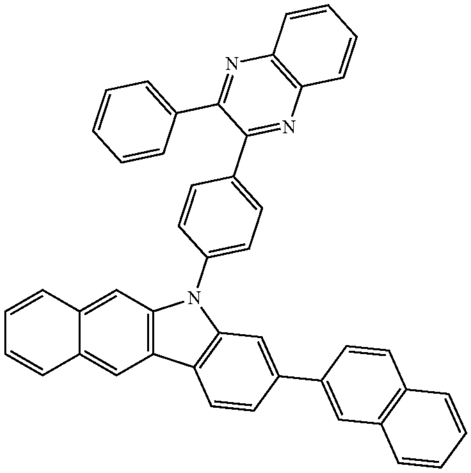
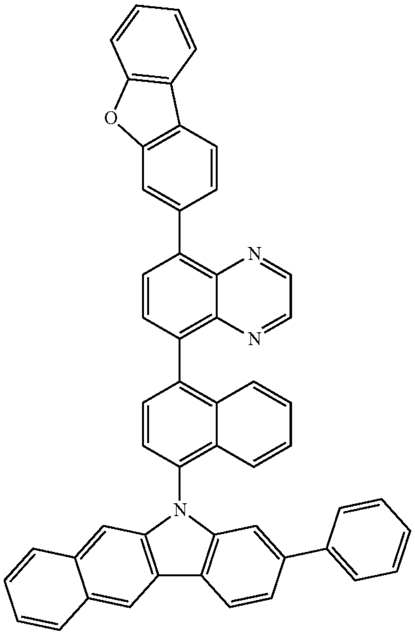
-continued
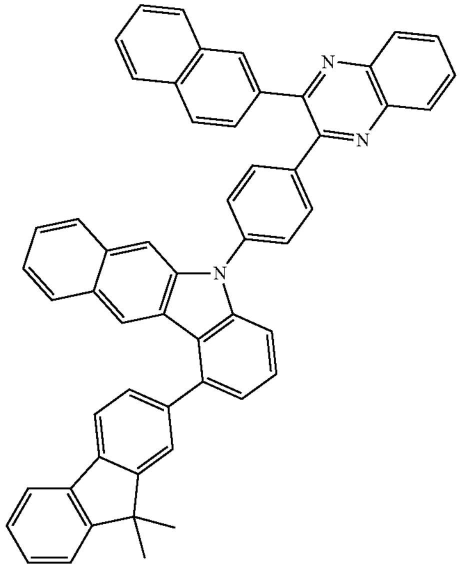

-continued
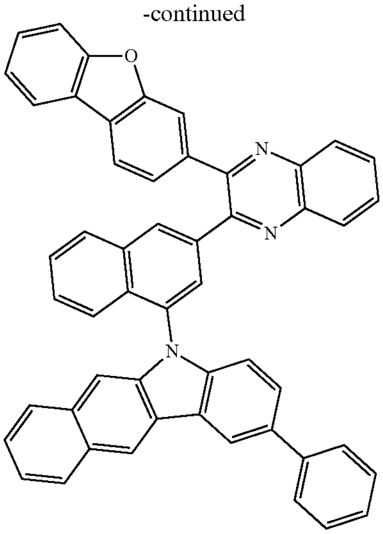
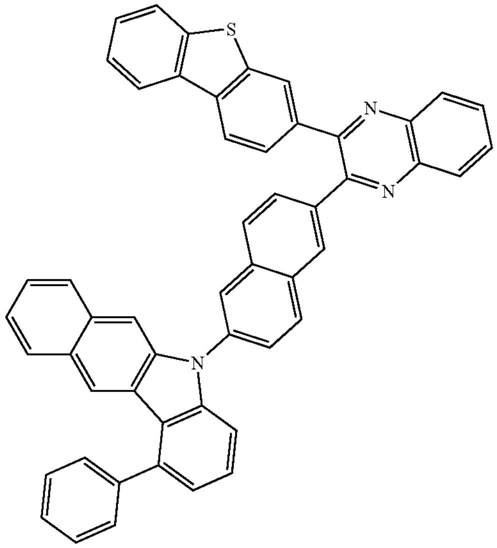
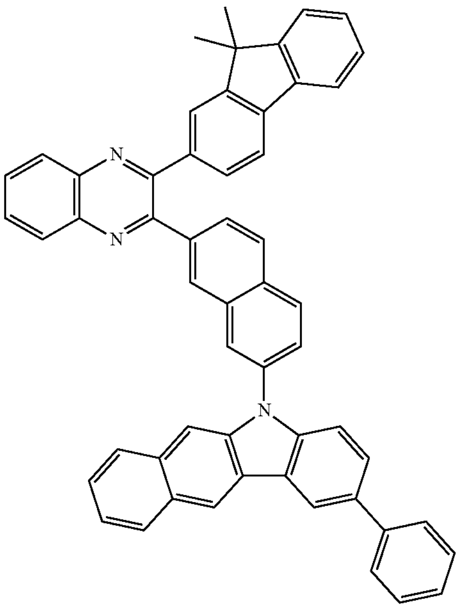
-continued
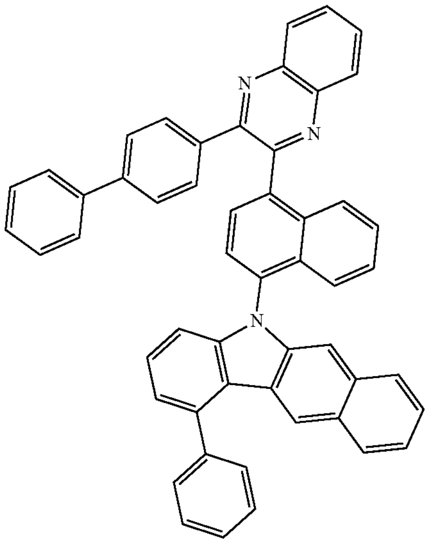
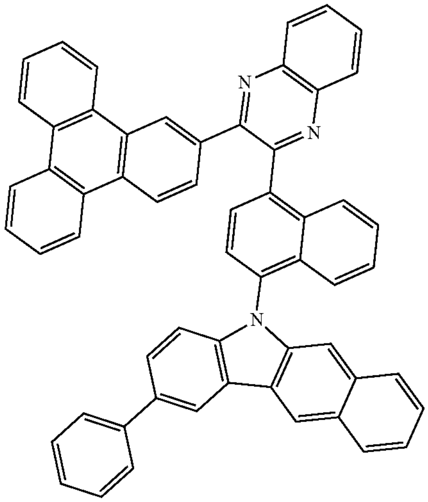
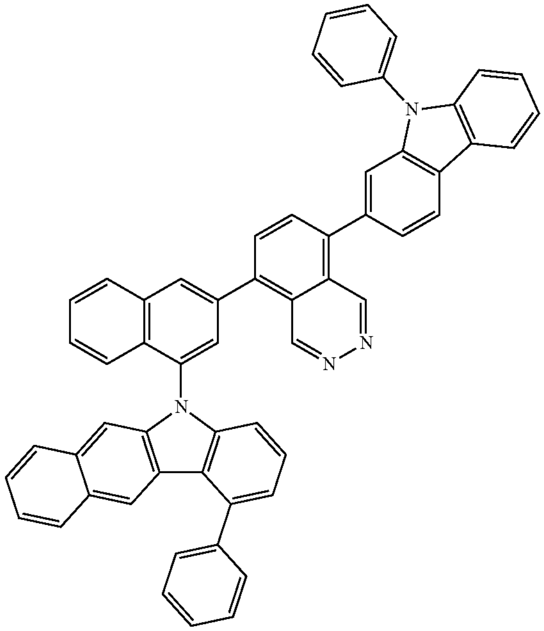

-continued
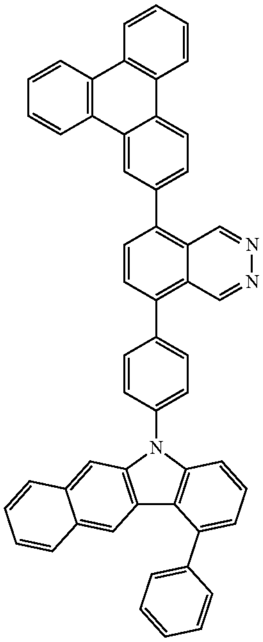
-continued
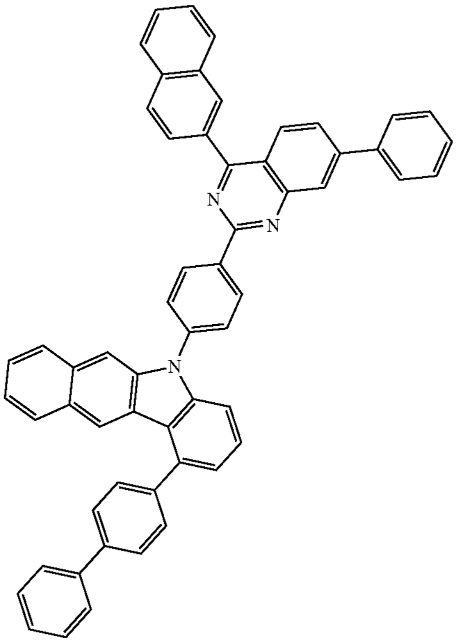
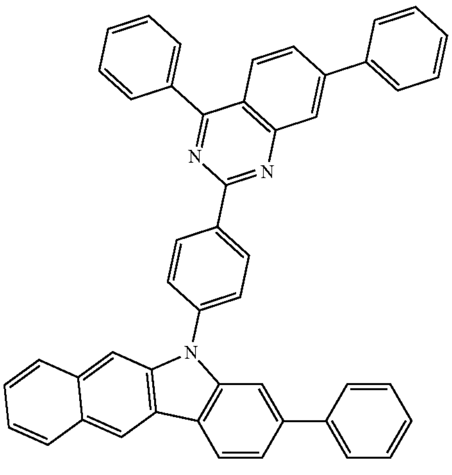
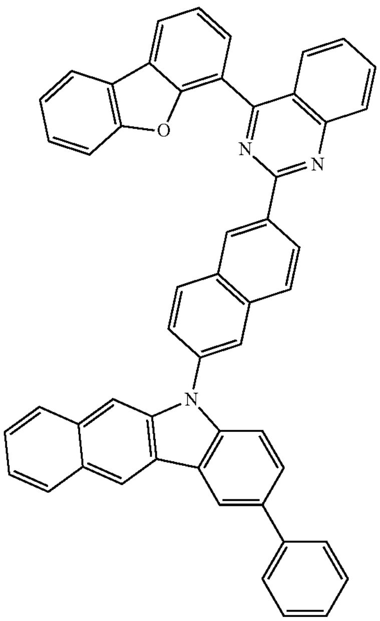

-continued
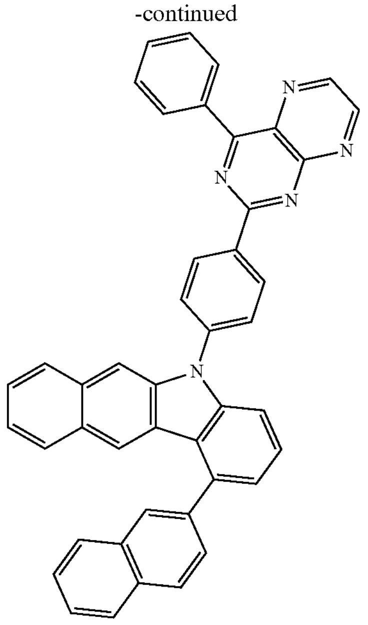
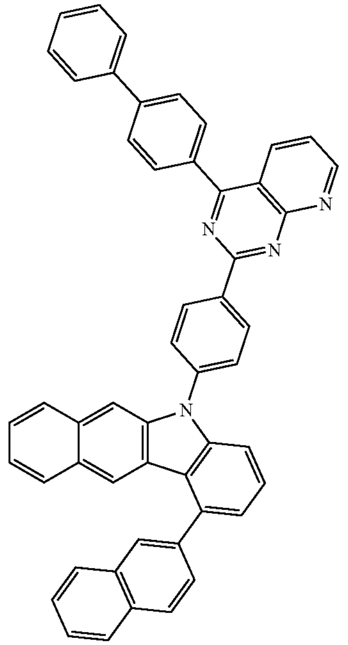
-continued
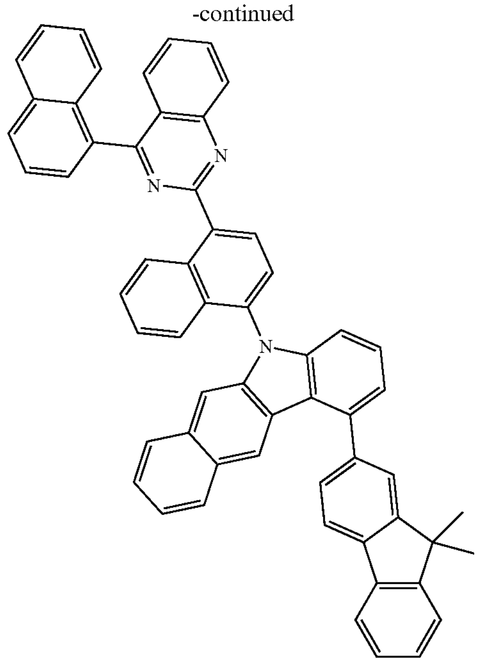
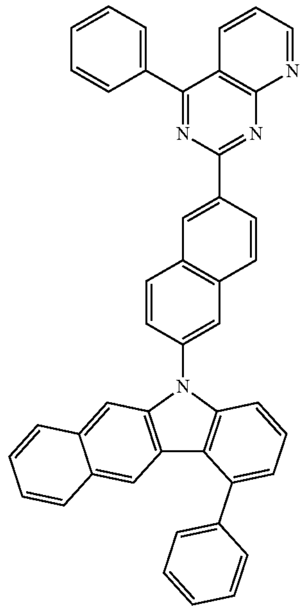

-continued
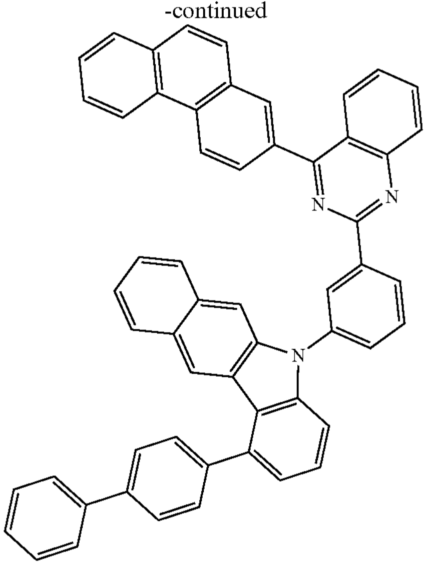
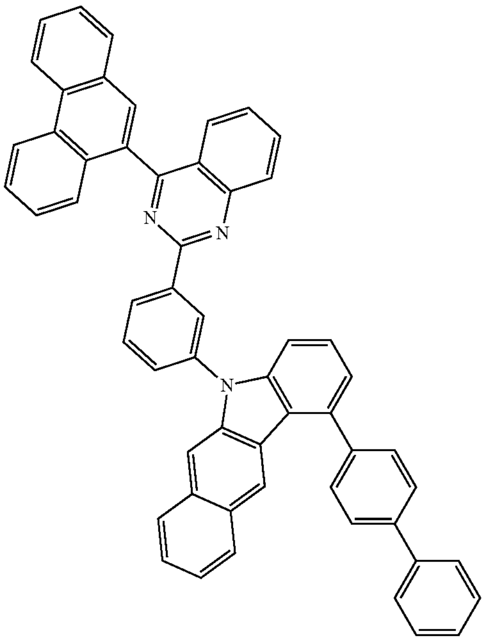
-continued
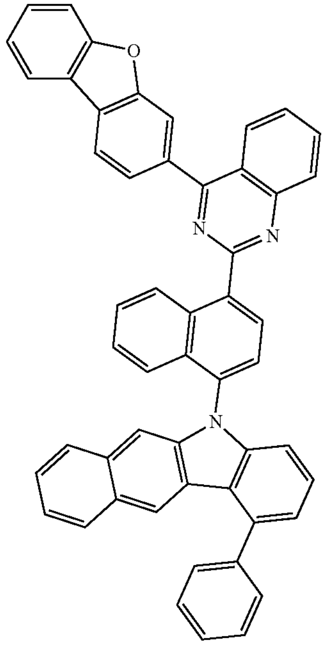
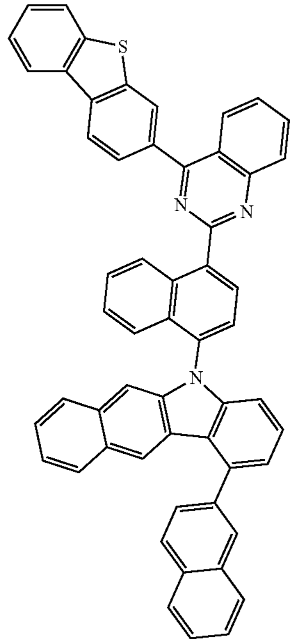

-continued
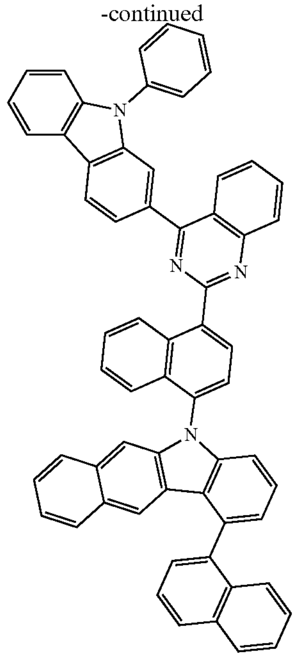
-continued
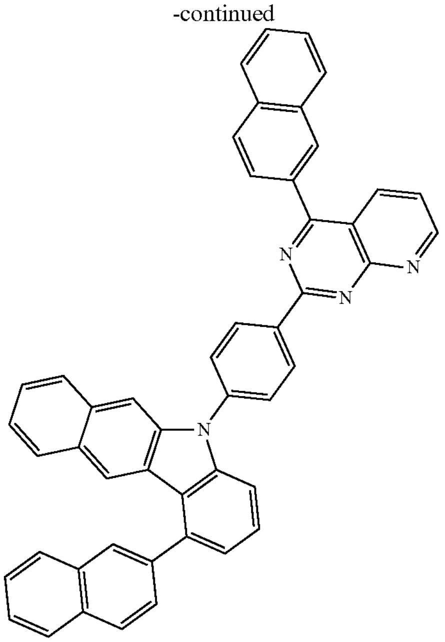
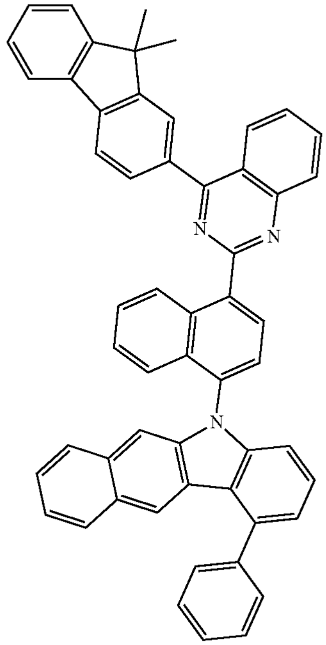
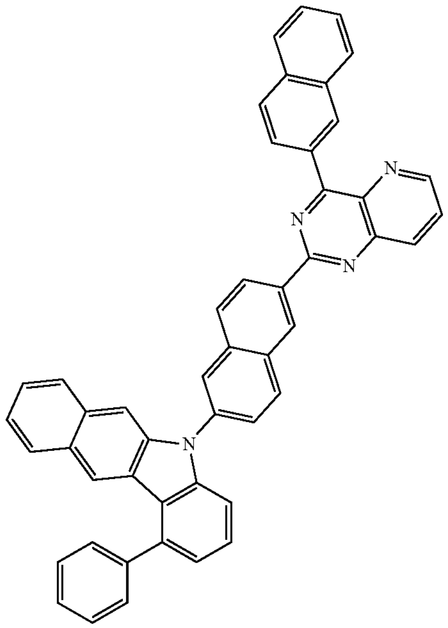

-continued
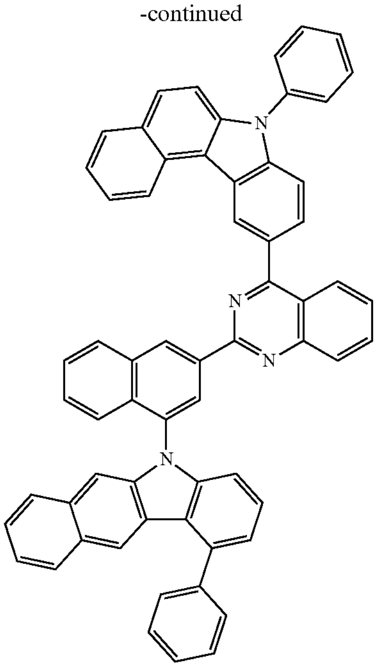
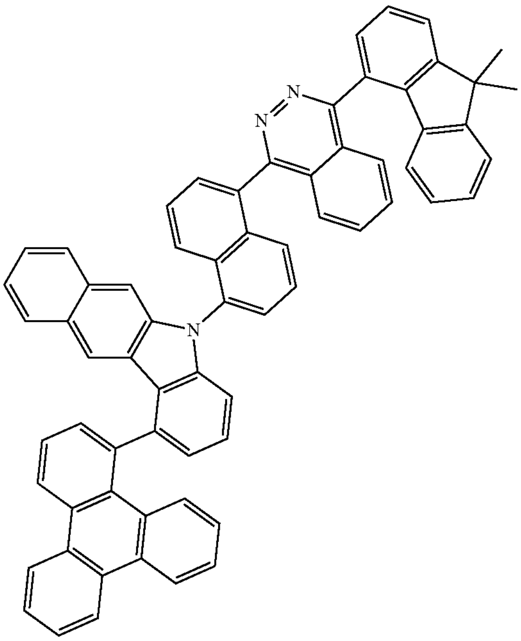
-continued
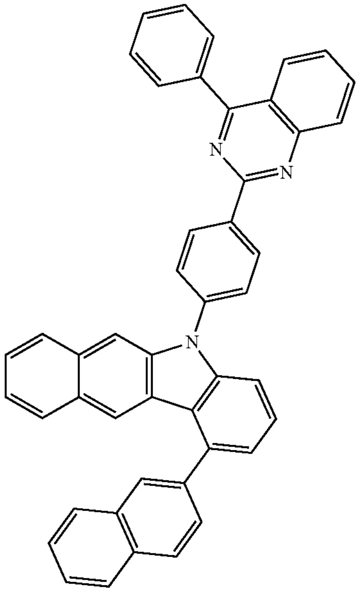
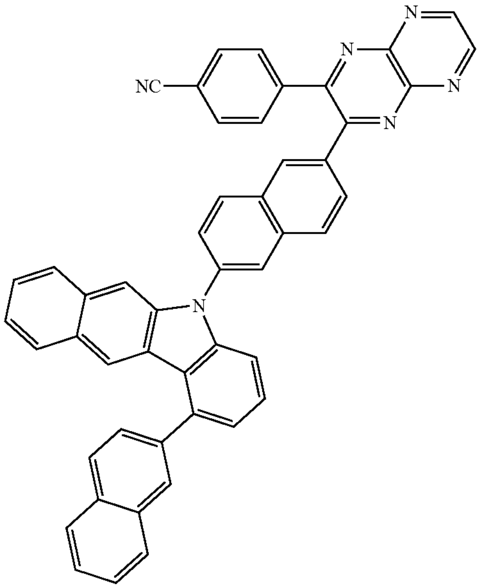
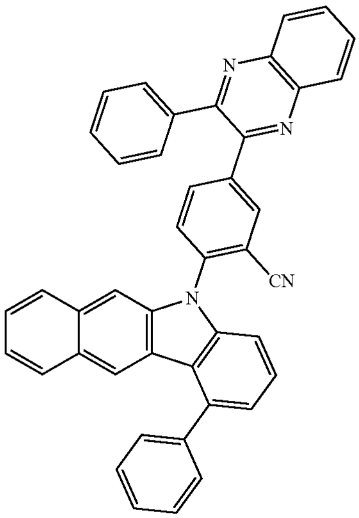

-continued
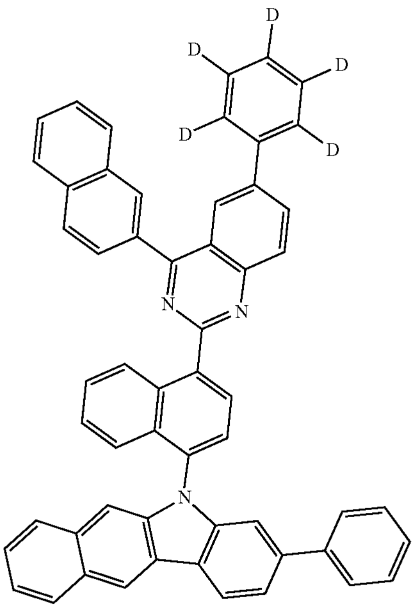
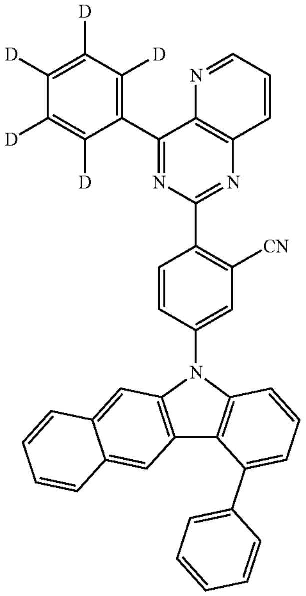
-continued
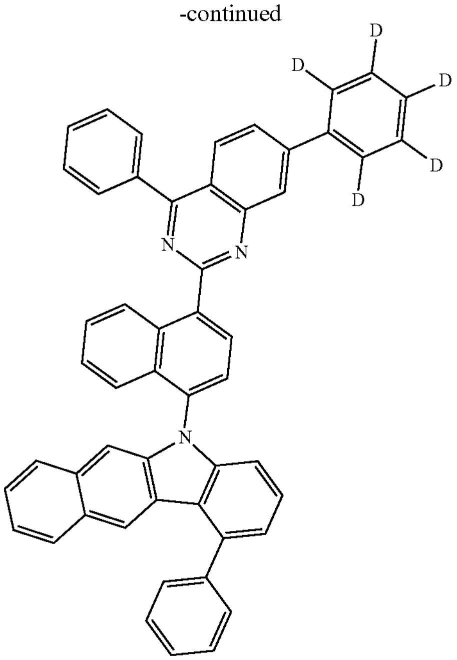
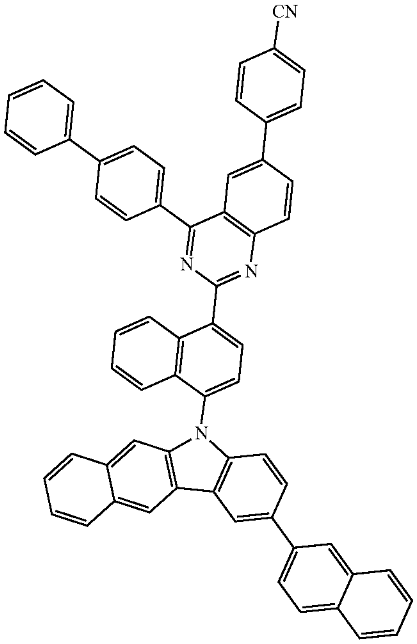

-continued
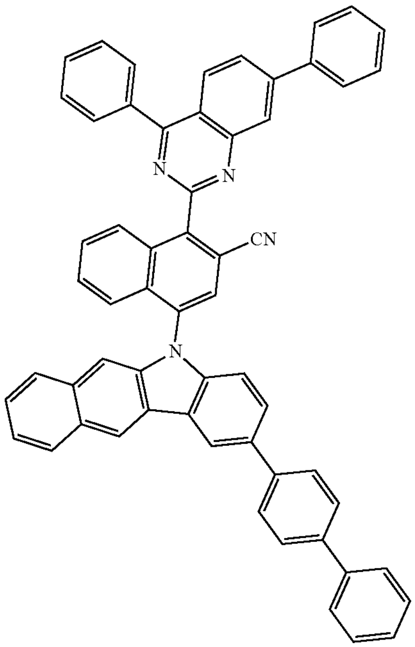
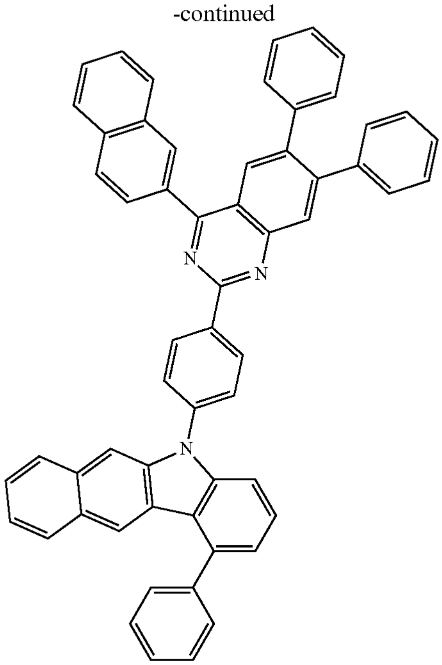
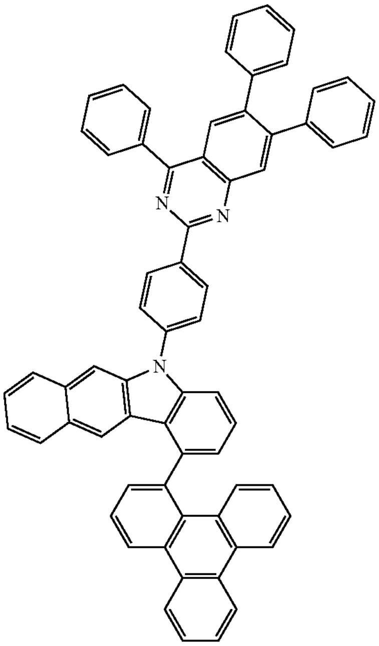
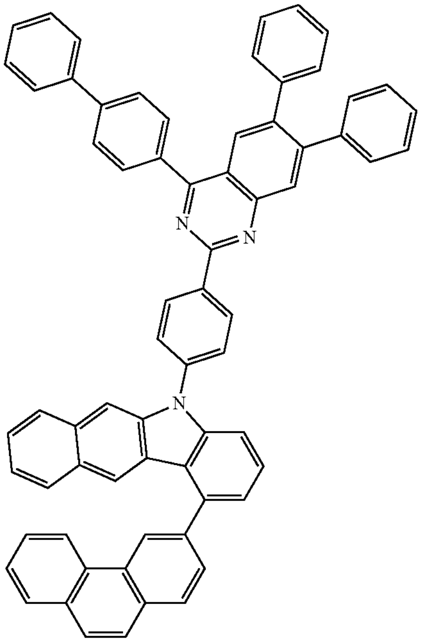

-continued
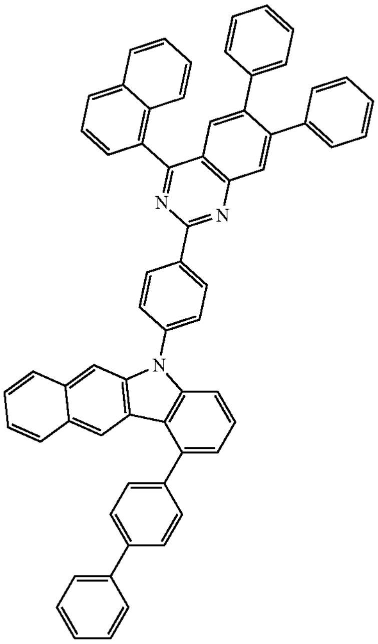
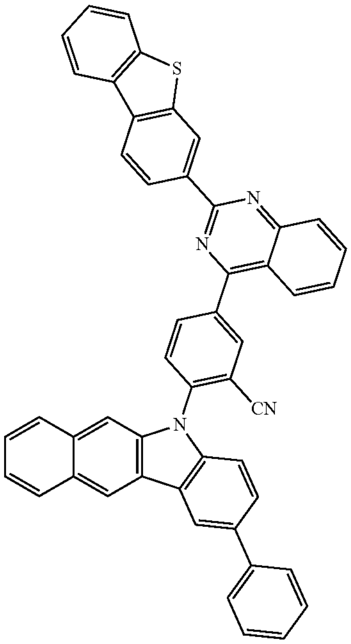
-continued
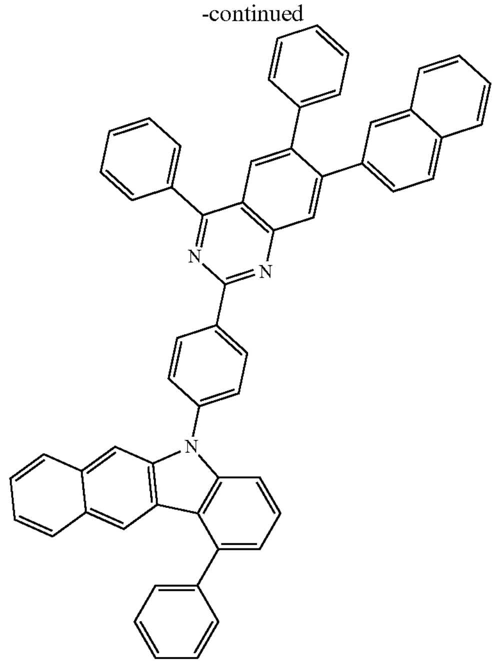
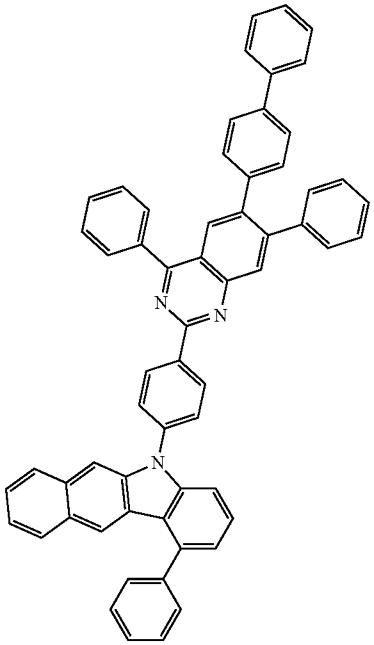

-continued
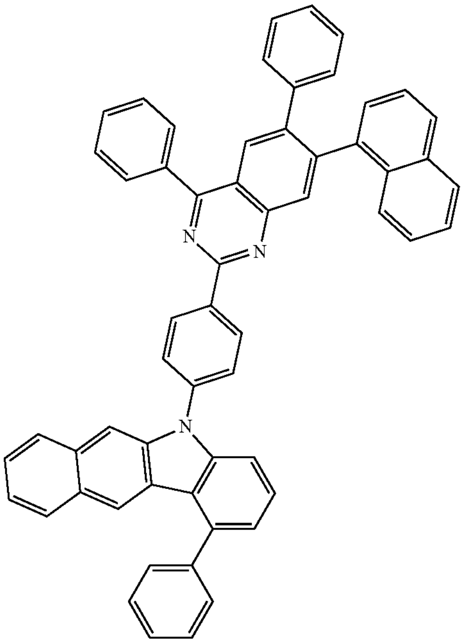
-continued
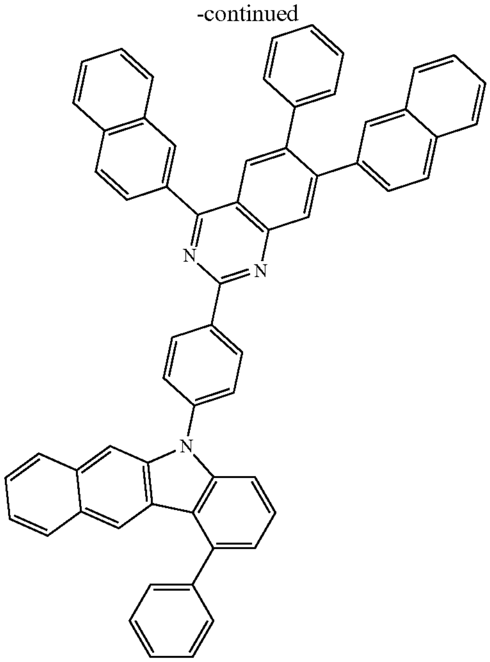
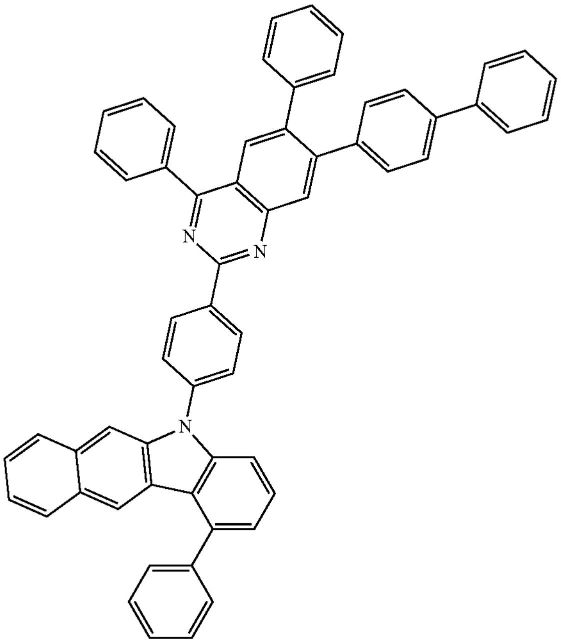
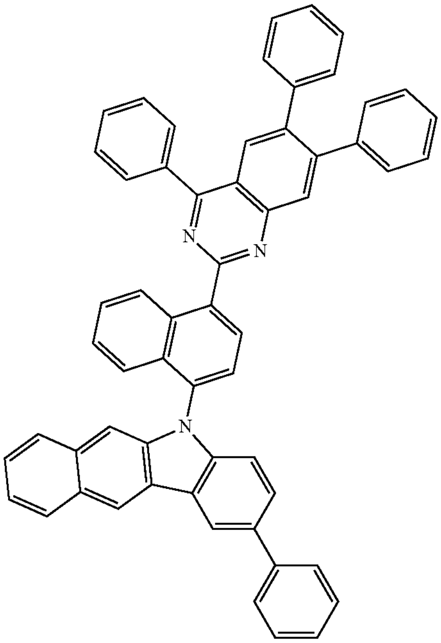

-continued
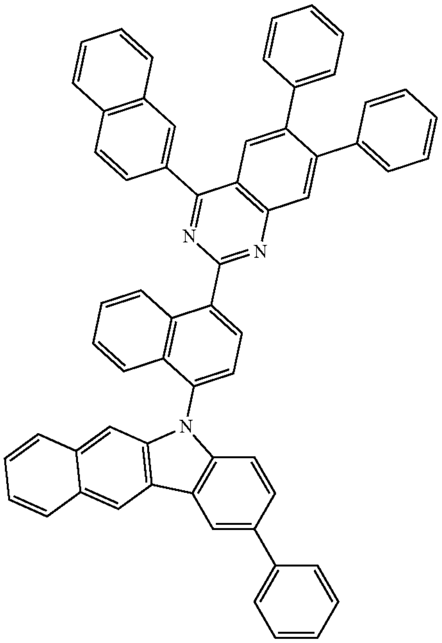
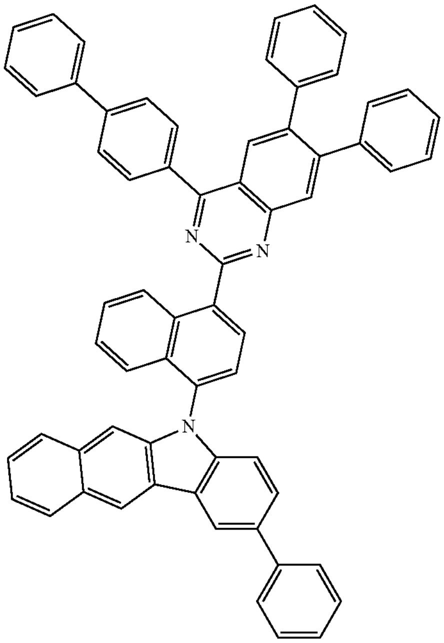
-continued
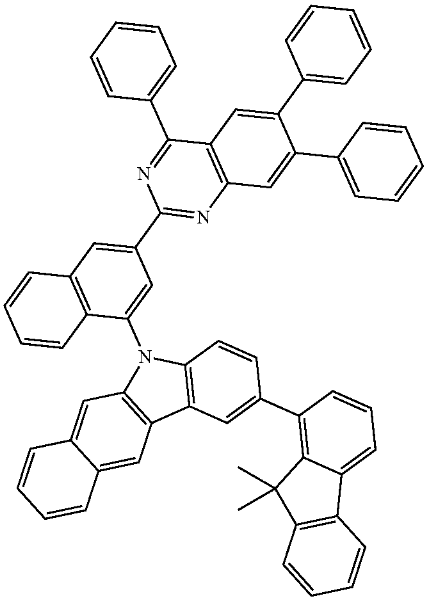
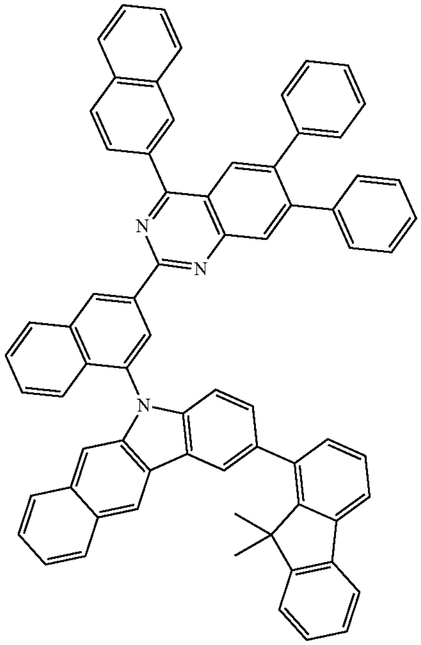

-continued
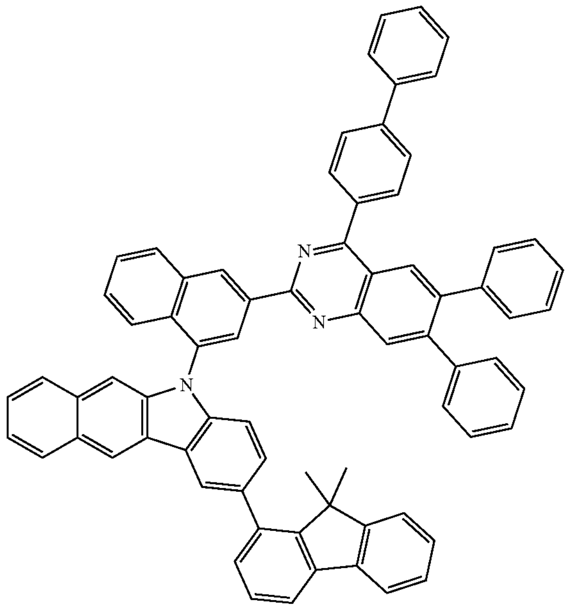
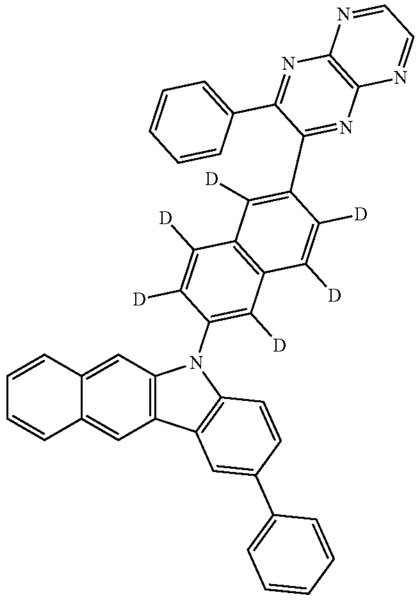
-continued
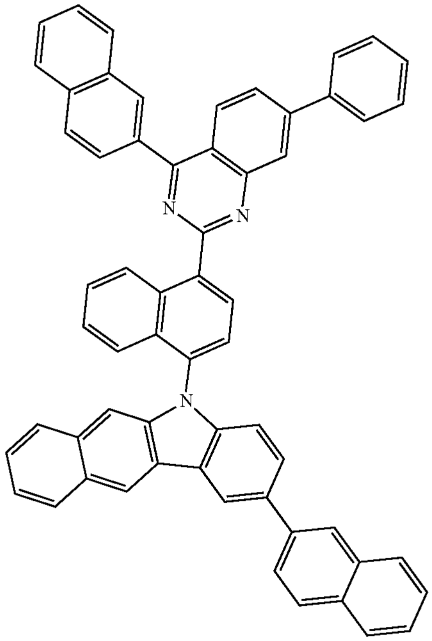
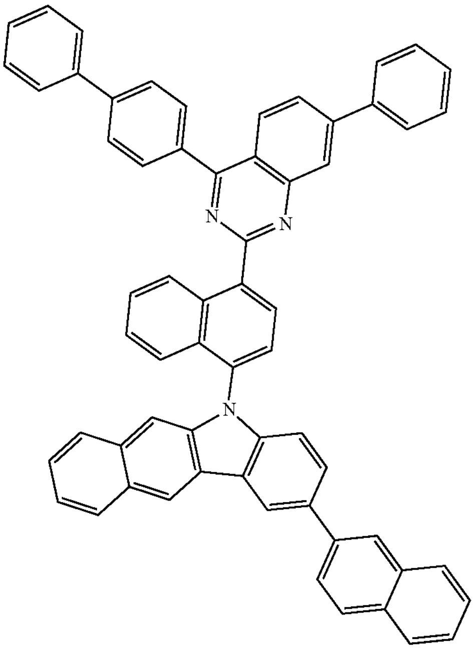

-continued
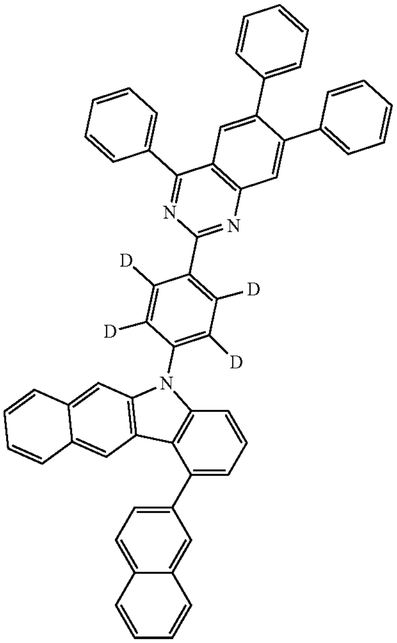
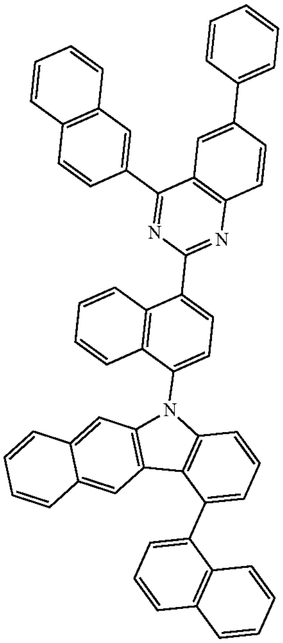
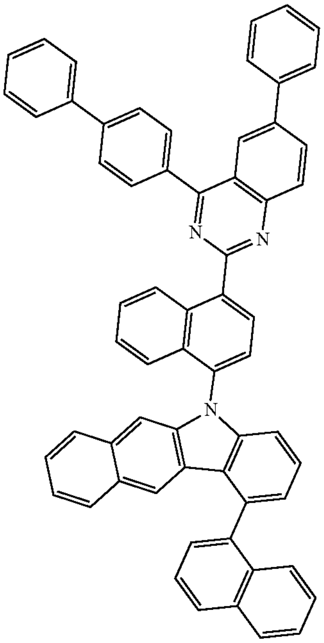
-continued
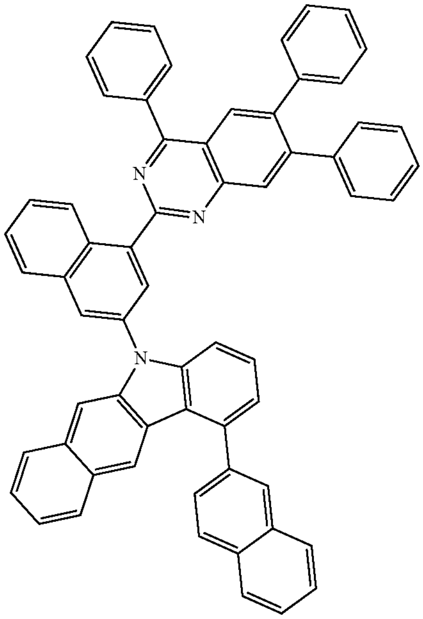

-continued
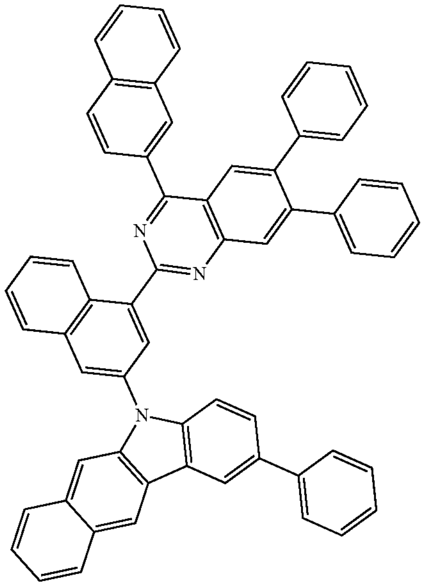
-continued
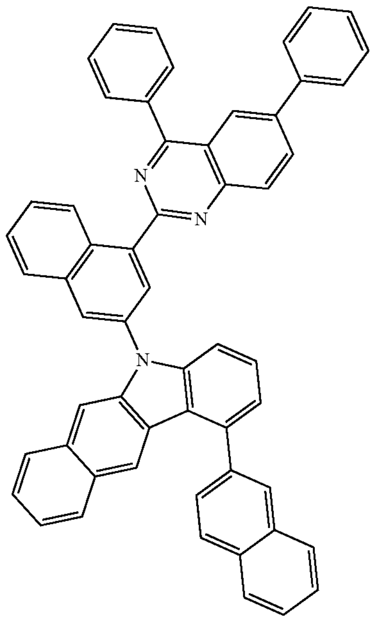
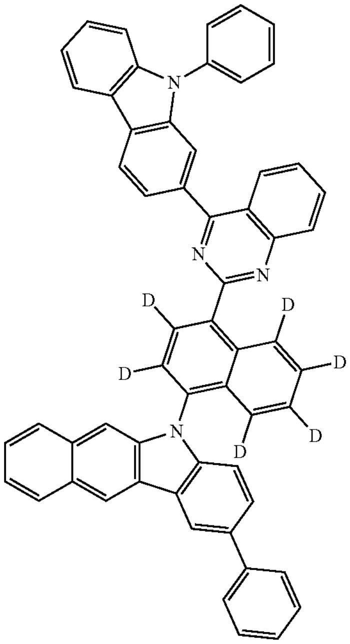
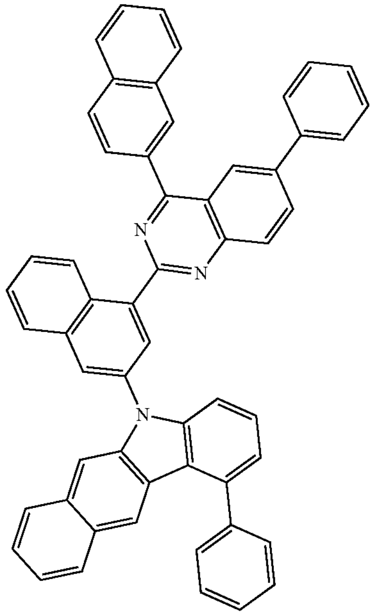

-continued

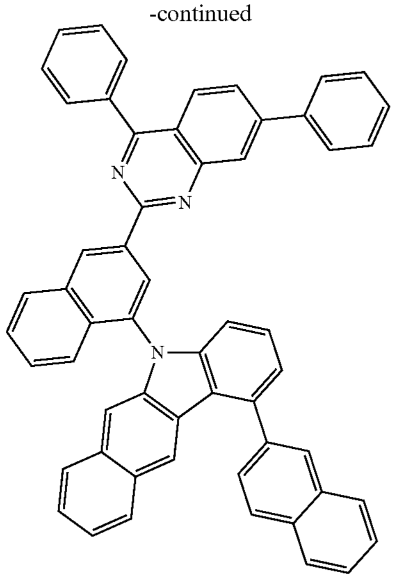

The benzocarbazole-based compound of Chemical Formula 1 according to one embodiment of the present specification may be prepared using a preparation method to describe below.

For example, the benzocarbazole-based compound of Chemical Formula 1 may have its core structure prepared as in the following reaction formula. Substituents may bond using methods known in the art, and types, positions or the number of the substituents may vary depending on technologies known in the art.

<Reaction Formula>

The compound of the present disclosure may be prepared using, as typical reactions, a Buchwald-Hartwig coupling reaction, a Heck coupling reaction, a Suzuki coupling reaction and the like.

Reaction Formula 1.

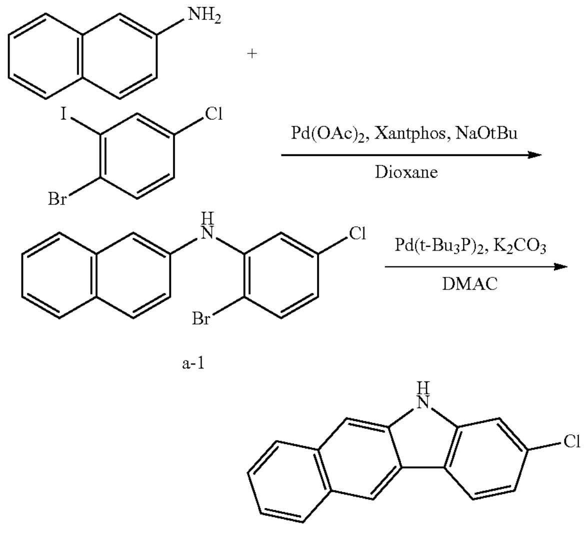

a-1 a

1) Preparation of Chemical Formula a-1

Naphthalene-2-amine (200.0 g, 1.0 eq.), 1-bromo-4-chloro-2-iodobenzene (443.25 g, 1.0 eq.), NaOtBu (201.3 g, 1.5 eq.), Pd(OAc)$_z$ (3.13 g, 0.01 eq.) and Xantphos (8.08 g, 0.01 eq.) are dissolved in 1,4-dioxane (4 L), and the result is stirred under reflux. When the reaction is terminated after 3 hours, the solvent is removed under vacuum. After that, the result is completely dissolved in ethyl acetate, washed with water, and approximately 701 of the solvent is removed under vacuum again. Under reflux again, crystals are dropped while adding hexane thereto, and the result is cooled and then filtered. This goes through column chromatography to obtain Compound a-1 (283.41 g, yield 61%). [M+H]=333

2) Preparation of Chemical Formula a (3-chloro-5H-benzo[b]carbazole)

Pd(t-Bu$_3$P)$_2$ (3.90 g, 0.01 eq.) and $K_2CO_3$ (211.11 g, 2.00 eq.) are added to Chemical Formula a-1 (283.41 g, 1.0 eq.) in dimethylacetamide (2 L), and the result is stirred under reflux. After 3 hours, the reaction material is poured into water to drop crystals, and the result is filtered. The filtered solids are completely dissolved in 1,2-dichlorobenzene, then washed with water, and the solution in which a product is dissolved is vacuum concentrated to drop crystals, and the result is cooled and filtered. This is purified using column chromatography to obtain Chemical Formula a (3-chloro-5H-benzo[b]carbazole) (74.9 g, yield 39%). A graph measuring 1H-NMR of Chemical Formula a is shown in FIG. 3. [M+H]=252

Reaction Formula 2. Preparation of Chemical Formula b (2-chloro-5H-benzo[b]carbazole)

2-Chloro-5H-benzo[b]carbazole is synthesized in the same manner as in the method preparing Chemical Formula a using 2-bromo-4-chloro-1-iodobenzene instead of 1-bromo-4-chloro-2-iodobenzene. A graph measuring 1H-NMR of Chemical Formula b is shown in FIG. 4.

b

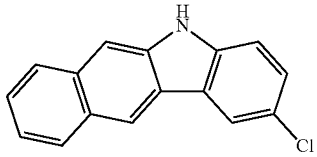

Reaction Formula 3. Preparation of Chemical Formula c (1-chloro-5H-benzo[b]carbazole)

1-Chloro-5H-benzo[b]carbazole is synthesized in the same manner as in the method preparing Chemical Formula a using 2-bromo-1-chloro-3-iodobenzene instead of 1-bromo-4-chloro-2-iodobenzene.

c

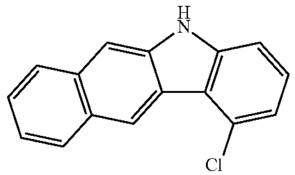

Reaction Formula 4. Synthesis of Chemical Formula d (4-chloro-5H-benzo[b]carbazole)

4-Chloro-5H-benzo[b]carbazole is synthesized in the same manner as in the method preparing Chemical Formula a using 1-bromo-3-chloro-2-iodobenzene instead of 1-bromo-4-chloro-2-iodobenzene.

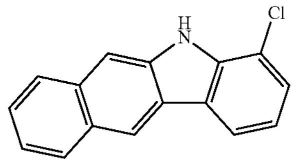

d

A conjugation length of a compound and an energy band gap thereof are closely related. Specifically, as a conjugation length of a compound increases, an energy band gap thereof decreases.

By introducing various substituents to the core structure as above, compounds having various energy band gaps may be synthesized in the present disclosure. In addition, by introducing various substituents to the core structure having structures as above, HOMO and LUMO energy levels of the compound may also be controlled art the present disclosure.

In addition, by introducing various substituents to the core structure having structures as above, compounds having unique properties of the introduced substituents may be synthesized. For example, by introducing substituents normally used as a hole injection layer material, a material for hole transfer, a light emitting layer material and an electron transfer layer material used for manufacturing an organic light emitting device to the core structure, materials satisfying needs required from each organic material layer may be synthesized.

In addition, an organic light emitting device according to the present disclosure comprises a first electrode; a second electrode provided opposite to the first: electrode; and one or more organic material layers provided between the first electrode and the second electrode, wherein one or more layers of the organic material layers comprise the benzocarbazole-based compound of Chemical Formula 1.

The organic light emitting device of the present disclosure may be prepared using common methods and materials for preparing an organic light emitting device except that one or more organic material layers are formed using the benzocarbazole-based compound described above.

The benzocarbazole-based compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present: disclosure may be formed in a single layer structure, but may be formed in a multilayer structure in which two or more organic material layers are laminated. For example, the organic light emitting device of the present disclosure may have a structure comprising a hole injection layer, a hole transfer layer, a hole injection and transfer layer, an electron blocking layer, a light emitting layer, an electron transfer layer, an electron injection layer, a hole blocking layer, an electron injection and transfer layer and the like as the organic material layer. However, the structure of the organic light emitting device is not limited thereto, and may comprise less numbers of organic material layers or more numbers of organic material layers.

In the organic light emitting device of the present disclosure, the organic material layer may comprise an electron transfer layer or an electron injection layer, and the electron transfer layer or the electron injection layer may comprise the benzocarbazole-based compound represented by Chemical Formula 1.

In the organic light emitting device of the present disclosure, the organic material layer may comprise a hole injection layer or a hole transfer layer, and the hole injection layer or the hole transfer layer may comprise the benzocarbazole-based compound represented by Chemical Formula 1.

In another embodiment, the organic material layer comprises a light emitting layer, and the light emitting layer comprises the benzocarbazole based compound represented by Chemical Formula 1. As one example, the compound represented by Chemical Formula 1 may be included as a dopant of the light emitting layer.

In one embodiment of the present specification, the organic light emitting device is a green organic light emitting device in which the light emitting layer comprises the benzocarbazole-based compound represented by Chemical Formula 1.

According to one embodiment, of the present specification, the organic light emitting device is a red organic light emitting device in which the light emitting layer comprises the benzocarbazole-based compound represented by Chemical Formula 1.

In another embodiment, the organic light emitting device is a blue organic light emitting device in which the light emitting layer comprises the benzocarbazole-based compound represented by Chemical Formula 1.

As another example, the organic material layer comprising the benzocarbazole-based compound represented by Chemical Formula 1 comprises the benzocarbazole-based compound represented by Chemical Formula 1 as a dopant, and may comprise a fluorescent host or a phosphorescent host.

In another embodiment, the organic material layer comprising the benzocarbazole-based compound represented by Chemical Formula 2 comprises the benzocarbazole-based compound represented by Chemical Formula 1 as a dopant, comprises a fluorescent host or a phosphorescent host, and may comprise other organic compounds, metals or metal compounds as a dopant.

As another example, the organic material layer comprising the benzocarbazole-based compound represented by Chemical Formula 1 comprises the benzocarbazole-based compound represented by Chemical Formula 1 as a dopant, comprises a fluorescent host or a phosphorescent host, and may be used together with an iridium (Ir)-based dopant.

According to one embodiment of the present disclosure, the organic light emitting device comprises a light emitting layer, and the light emitting layer may comprise the benzocarbazole-based compound represented by Chemical Formula 1 as a host of the light emitting layer.

According to another embodiment, the organic light, emitting device comprises the benzocarbazole-based compound represented by Chemical Formula 1 as a host of the light emitting layer, and may further comprise a dopant.

In another embodiment, the organic light emitting device comprises the benzocarbazole-based compound represented by Chemical Formula 0.1 as a host of the light, emitting layer, and may further comprise an Iridium (Ir)-based dopant. Herein, a weight ratio of the host and the dopant (host:dopant) may be from 90:10 to 99:1, but is not limited thereto.

The structure of the organic light emitting device of the present disclosure may be as illustrated in FIG. 1 and FIG. 2, but is not limited thereto.

FIG. 1 illustrates a structure of the organic light emitting device in which an anode (2), a light emitting layer (3) and a cathode (4) are consecutively laminated on a substrate (1). In such a structure, the compound may be included in the light emitting layer (3).

The organic light emitting device may have, for example, a laminated structure as below, however, the structure is not limited thereto.

(1) Anode/hole transfer layer/light emitting layer/cathode
(2) Anode/hole injection layer/hole transfer layer/light emitting layer/cathode
(3) Anode/hole injection layer/hole buffer layer/hole transfer layer/light emitting layer/cathode
(4) Anode/hole transfer layer/light emitting layer/electron transfer layer/cathode
(5) Anode/hole transfer layer/light emitting layer/electron transfer layer/electron injection layer/cathode
(6) Anode/hole injection layer/hole transfer layer/light, emitting layer/electron transfer layer/cathode
(7) Anode/hole injection layer/hole transfer layer/light emitting layer/electron transfer layer/electron injection layer/cathode
(8) Anode/hole injection layer/hole buffer layer/hole transfer layer/light emitting layer/electron transfer layer/cathode
(9) Anode/hole injection layer/hole buffer layer/hole transfer layer/light emitting layer/electron transfer layer/electron injection layer/cathode
(10) Anode/hole transfer layer/electron blocking layer/light emitting layer/electron transfer layer/cathode
(11) Anode/hole transfer layer/electron blocking layer/light emitting layer/electron transfer layer/electron injection layer/cathode
(12) Anode/hole injection layer/hole transfer layer/electron blocking layer/light emitting layer/electron transfer layer/cathode
(13) Anode/hole injection layer/hole transfer layer/electron blocking layer/light emitting layer/electron transfer layer/electron injection layer/cathode
(14) Anode/hole transfer layer/light emitting layer/hole blocking layer/electron transfer layer/cathode
(15) Anode/hole transfer layer/light emitting layer/hole blocking layer/electron transfer layer/electron injection layer/cathode
(16) Anode/hole injection layer/hole transfer layer/light emitting layer/hole blocking layer/electron transfer layer/cathode
(17) Anode/hole injection layer/hole transfer layer/light emitting layer/hole blocking layer/electron transfer layer/electron injection layer/cathode
(18) Anode/hole injection layer/hole transfer layer/electron blocking layer/light emitting layer/hole blocking layer/electron injection and transfer layer/cathode FIG. 2 illustrates a structure of the organic light emitting device in which an anode (2), a hole injection layer (5), a hole transfer layer (6), an electron blocking layer (7), a light emitting layer (7), a hole blocking layer (9), an electron injection and transfer layer (10) and a cathode (4) are consecutively laminated on a substrate (1). In such a structure, the compound may be included in the hole injection layer (5), the hole transfer layer (6) or the light emitting layer (8).

For example, the organic light emitting device according to the present disclosure may be manufactured by forming an anode on a substrate by depositing a metal, a metal oxide having conductivity, or an alloy thereof using a physical vapor deposition (PVD) method such as sputtering or e-beam evaporation, forming an organic material layer comprising a hole injection layer, a hole transfer layer, an electron blocking layer, a light emitting layer, a hole blocking layer, and an electron injection and transfer layer thereon, and then depositing a material capable of being used as a cathode thereon. In addition to such a method, the organic light emitting device may also be manufactured by consecutively depositing a cathode material, an organic material layer and an anode material on a substrate.

The organic material layer may have a multilayer structure comprising a hole injection layer, a hole transfer layer, a light emitting layer, an electron transfer layer and the like, however, the structure is not limited thereto, and the organic material layer may have a single layer structure. In addition, the organic material layer may be prepared to have less numbers of layers through a solvent process such as spin coating, dip coating, doctor blading, screen printing, inkjet printing or a thermal transfer method instead of a deposition method using various polymer materials.

As the anode material, materials having large work function are normally preferred so that hole injection to an organic material layer is smooth. Specific examples of the anode material capable of being used in the present disclosure comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection material is a material favorably receiving holes from an anode at a low voltage, and the highest occupied molecular orbital (HOMO) of the hole injection material is preferably in between the work function of an anode material and the HOMO of surrounding organic material layers. Specific examples of the hole injection material comprise metal porphyrins oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto, and additional compounds capable of p-doping may be further included.

The hole transfer material is a material capable of receiving holes from an anode or a hole injection layer and transferring the holes to a light emitting layer, and materials having high mobility for the holes are suited. Specific examples thereof comprise arylamine-based organic materials, conductive polymers, block copolymers having conjugated parts and non-conjugated parts together, and the like, but are not limited thereto.

An electron blocking layer may be provided between the hole transfer layer and the light emitting layer. As the electron blocking layer, materials known in the art such as arylamine-based organic materials may be used.

The light emitting layer may emit light of red, green or blue, and may be formed with phosphorescent materials or fluorescent materials. The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof comprise 8-hydroxyquinoline aluminum complexes ($Alq_3$); carbazole-based compounds; dimerized styryl compounds; BAlq; 10-hydroxybenzo quinoline-metal compounds; benzoxazole-, benzothiazole- and benzimidazole-based compounds; poly (p-phenylenevinylene) (PPV) based polymers; spiro compounds; polyfluorene, rubrene, and the like, but are not limited thereto.

The host material of the light emitting layer comprises fused aromatic ring derivatives, heteroring-containing compounds or the like. Specifically, the fused aromatic ring derivative comprises anthracene derivatives, pyreno derivatives, naphthalene derivatives, pentacene derivatives, phenanthrene compounds, fluoranthene compounds and the like, and the heteroring-containing compound comprises carbazole derivatives, dibenzofuran derivatives, ladder-type furan compounds, pyrimidine derivatives and the like, however, the material is not limited thereto.

The iridium-based complex used as a dopant of the light emitting layer is as follows, but is not limited thereto.

Dp-1

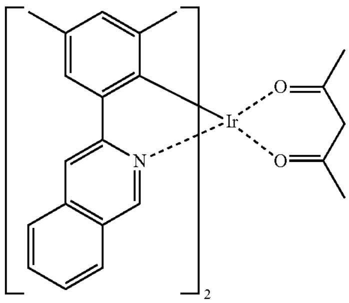

Dp-2

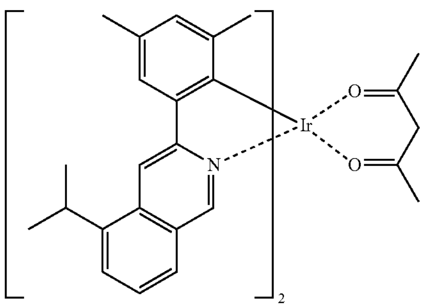

-continued

Dp-3

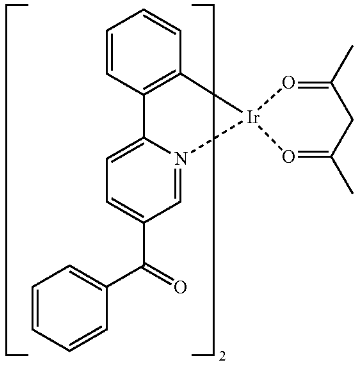

Dp-4

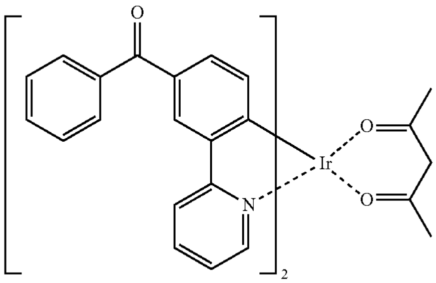

Dp-5

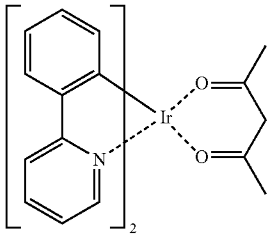

Dp-6

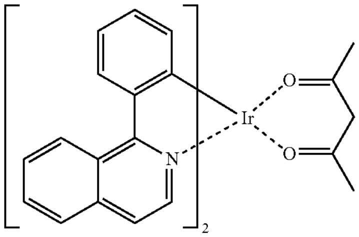

Dp-7

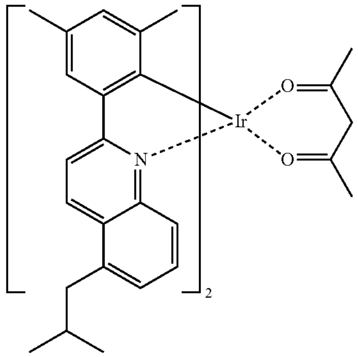

-continued
Dp-8
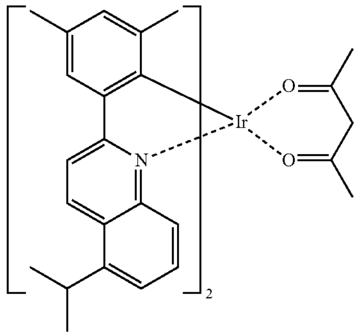
Dp-9
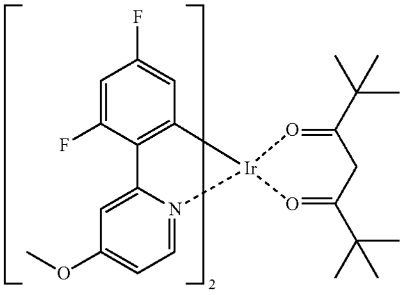
Dp-10
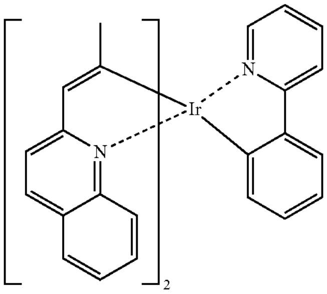
Dp-11
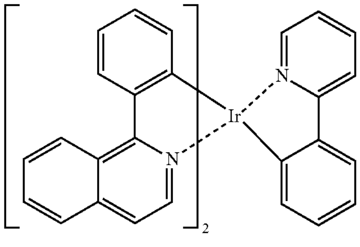
Dp-12
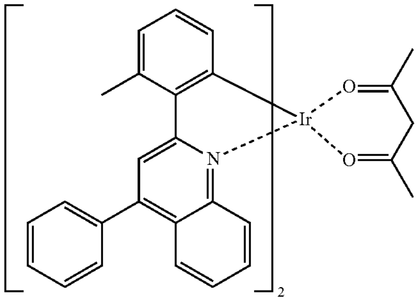
-continued
Dp-13
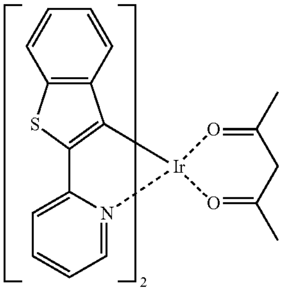
Dp-14
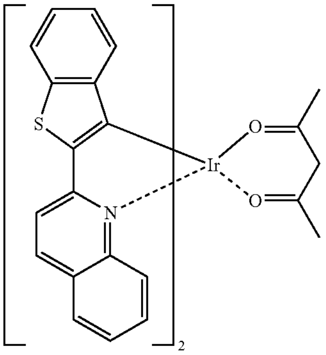
Dp-15
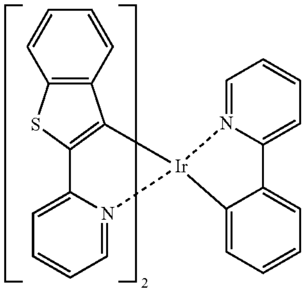
Dp-16
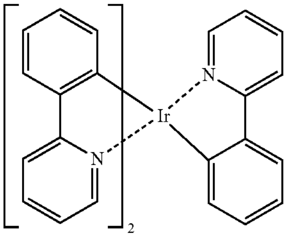
Dp-17
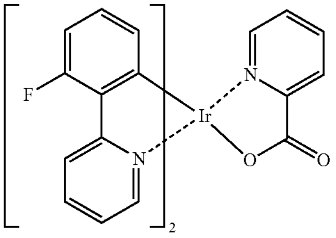

-continued
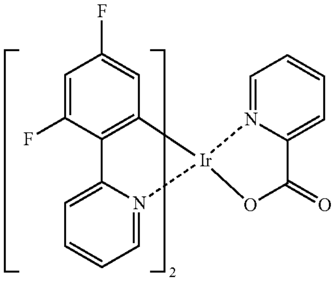
Dp-18
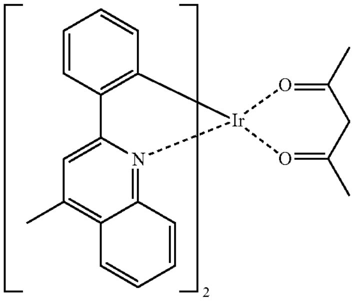
Dp-19
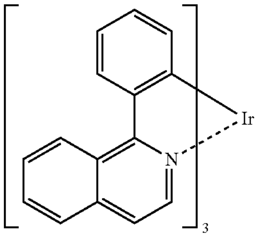
Dp-20
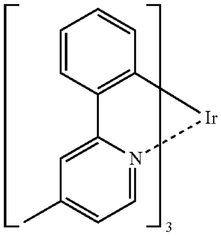
Dp-21
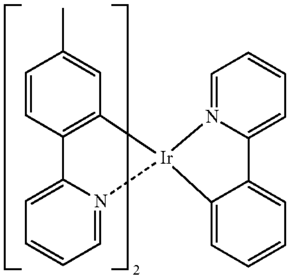
Dp-22
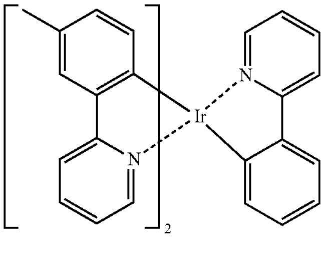
Dp-23
-continued
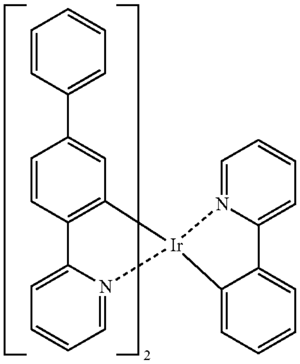
Dp-24
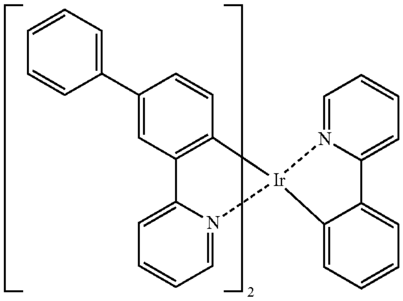
Dp-25
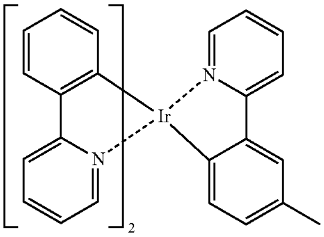
Dp-26
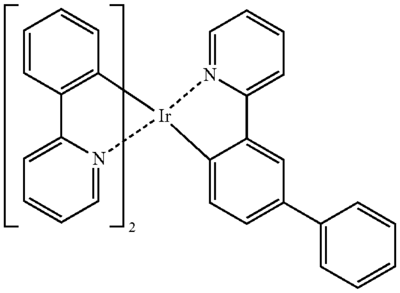
Dp-27
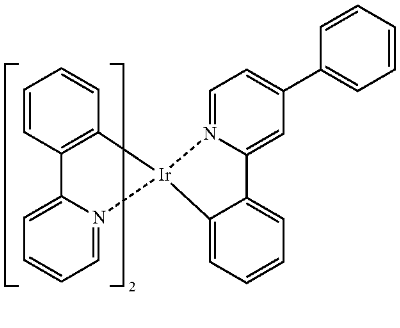
Dp-28

-continued
Dp-29
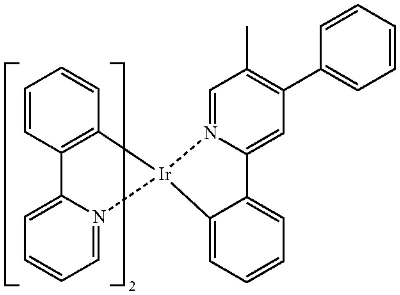
Dp-30
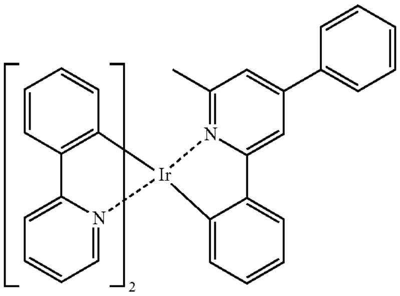
Dp-31
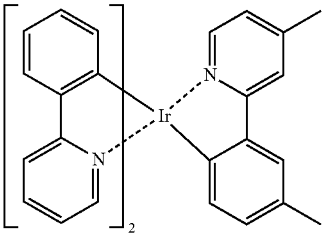
Dp-32
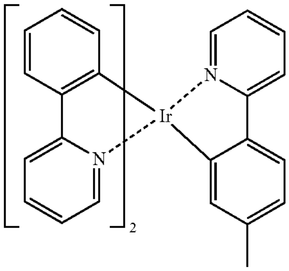
Dp-33
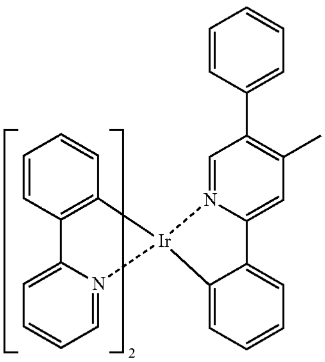
-continued
Dp-34
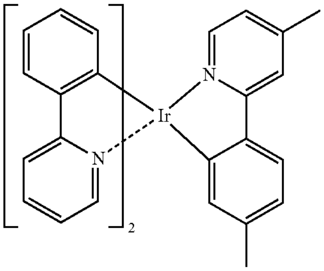
Dp-35
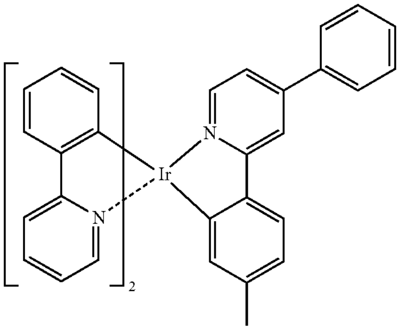
Dp-36
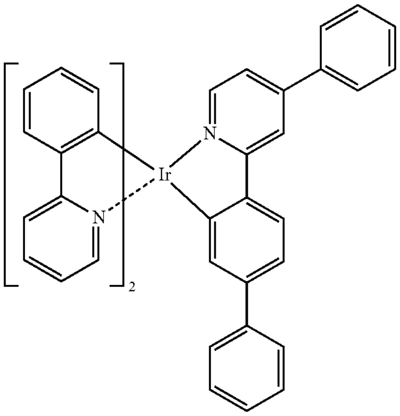
Dp-37
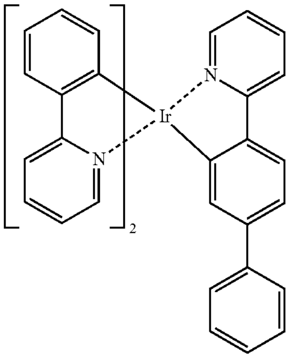

-continued

Dp-38

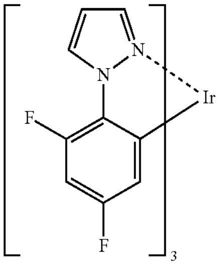

A hole blocking layer may be provided between the electron transfer layer and the light emitting layer, and materials known in the art such as triazine-based compounds may be used.

The electron transfer layer may perform a role of facilitating electron transfer. The electron transfer material is a material favorably receiving electrons from a cathode and transferring the electrons to a light emitting layer, materials having high mobility for the electrons are suited. Specific examples thereof comprise Al complexes of 8-hydroxyquinoline; complexes comprising $Alq_3$; organic radical compounds; hydroxyflavone-metal complexes, and the like, but are not limited thereto. The electron transfer layer may have a thickness of 1 nm to 50 nm. The electron transfer layer having a thickness of 1 nm or greater has an advantage of preventing decline in the electron transfer properties, and the thickness being 50 nm or less has an advantage of preventing an increase in the driving voltage for enhancing electron migration caused by the electron transfer layer being too thick.

The electron inject ion layer may perform a role of facilitating electron injection. The electron injection material is preferably a compound that has an ability to transfer electrons, has an electron injection effect from a cathode, has an excellent electron injection effect for a light emitting layer or a light, emitting material, prevents excitons generated in the light emitting layer from moving to a hole injection layer, and in addition thereto, has an excellent thin film forming ability. Specific examples thereof comprise fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The organic light emitting device according to the present specification may be a top-emission type, a bottom-emission type or a dual-emission type depending on the materials used.

Hereinafter, the present specification will be described in detail with reference to examples in order to specifically describe the present specification. However, examples according to the present specification may be modified to various different forms, and the scope of the present specification is not to be construed as being limited to the examples described below. Examples of the present specification are provided in order to more fully describe the present specification to those having average knowledge in the art.

Synthesis

Synthesis 1

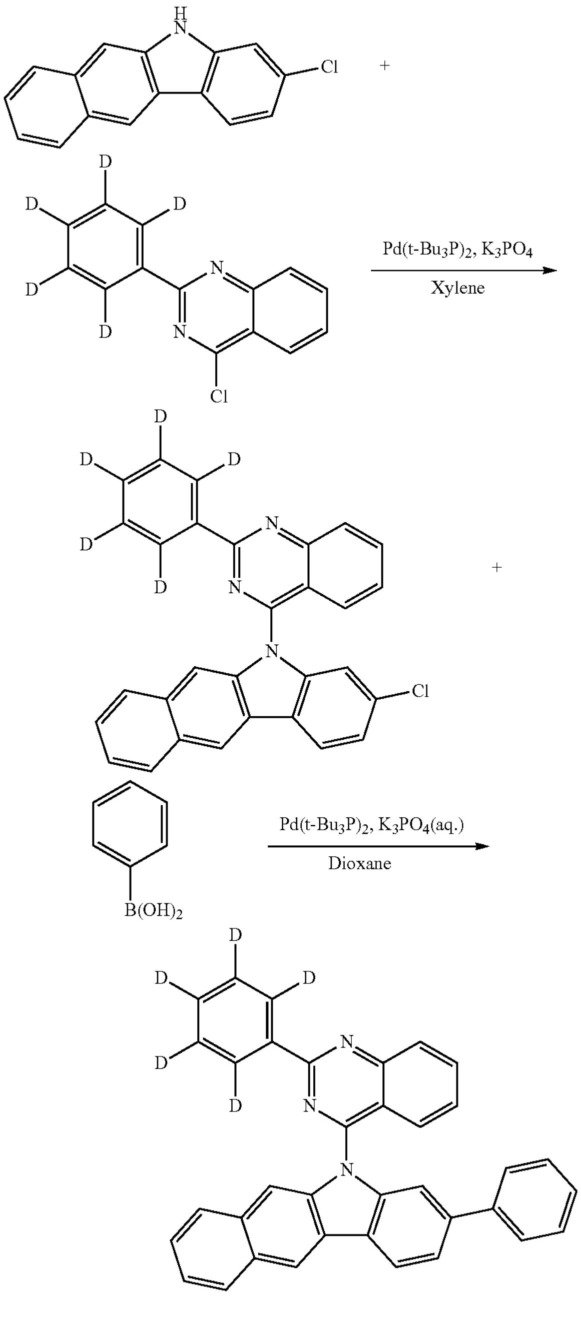

2

Chemical formula a (10.0 g, 1.0 eq.), 4-chloro-2-(phenyl-d5)quinazoline (10.73 g, 1.1 eq.), $K_3PO_4$ (16.86 g, 2.0 eq.) and $Pd(t\text{-}Bu_3P)_2$ (0.10 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 2-1 (13.73 g, yield 75%). [M+H]=461

Chemical Formula 2-1 (13.73 g, 1.0 eq.), phenylboronic acid (3.99 g, 1.1 eq.) and $Pd(t\text{-}Bu_3P)_2$ (0.07 g, 0.005 eq.) were introduced to dioxane (300 ml). $K_3PO_4$ (12.64 g, 2.0 eq.) dissolved an water (100 ml) was introduced thereto, and the result was stirred under reflux. When the reaction was terminated after 2 hours, the salt-dissolved water layer was removed, and the solvent was removed under vacuum. After that, the result was completely dissolved in $CHCl_3$, washed with water, and approximately 50 of the solvent was removed under vacuum again. Under reflux again, crystals were dropped while adding ethyl acetate thereto, and the result was cooled and then filtered. This went through column chromatography to obtain Compound 2 (10.47 g, yield 70%). [M+H]=503

Synthesis 2

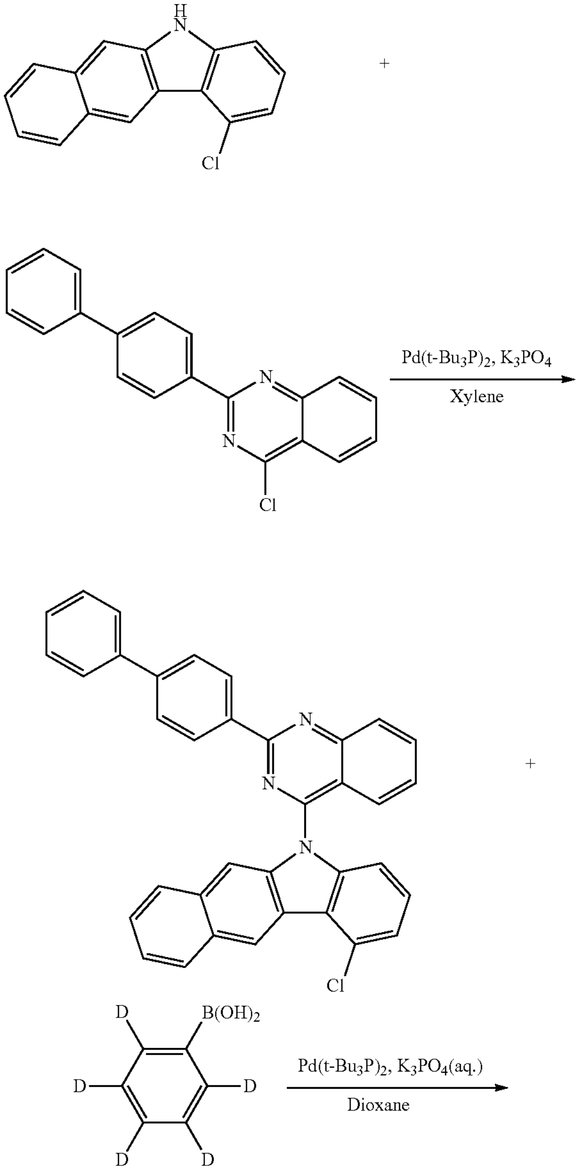

-continued

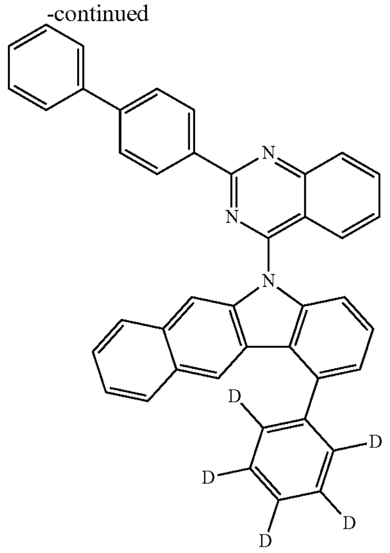

3

Chemical Formula c (10.0 g, 1.0 eq.), 2-([1,1'-biphenyl]-4-yl)-4-chloroquinazoline (13.84 g, 1.1 eq.), $K_3PO_4$ (16.86 g, 2.0 eq.) and $Pd(t\text{-}Bu_3P)_2$ (0.10 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 3-1 (15.43 g, yield 73%). [M+H] =533

Chemical Formula 3-1 (15.43 g, 1.0 eq.), (phenyl-d5) boronic acid (4.05 g, 1.1 eq.) and $Pd(t\text{-}Bu_3P)_2$ (0.07 g, 0.005 eq.) were introduced to dioxane (300 ml), $K_3PO_4$ (12.64 g, 2.0 eq.) dissolved in water (100 ml) was introduced thereto, and the result was stirred under reflux. When the reaction was terminated after 2 hours, the salt-dissolved water layer was removed, and the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went, through column chromatography to obtain Compound 3 (11.91 g, yield 71%). [M+H]=579

Synthesis 3

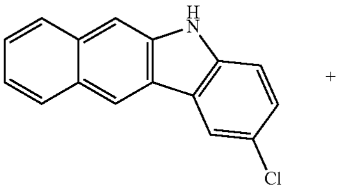

-continued

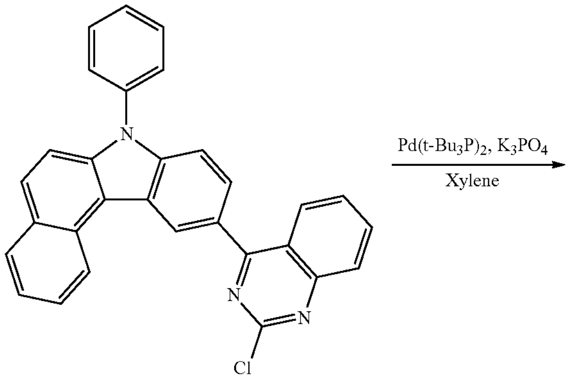

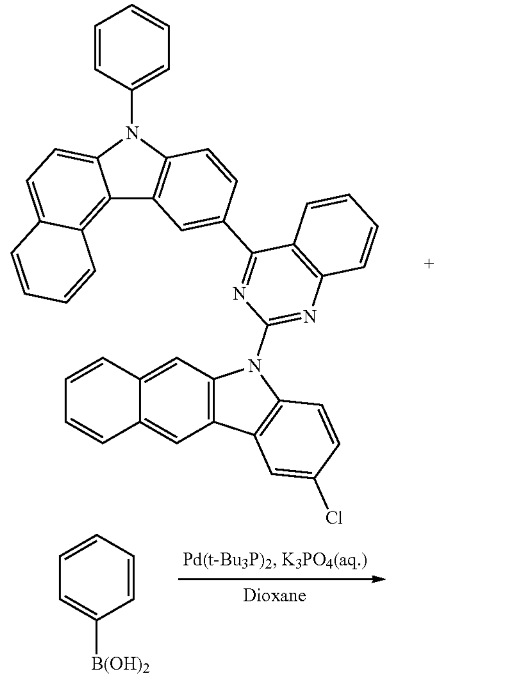

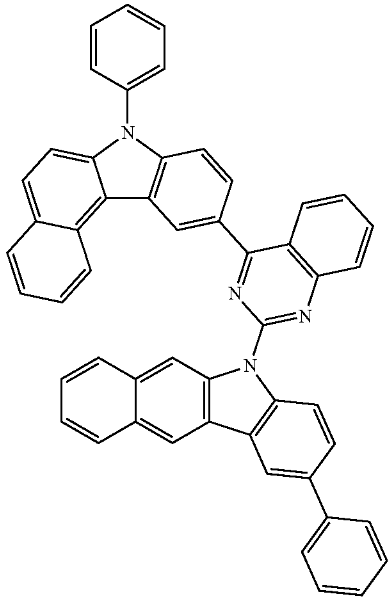

61

Chemical Formula b (10.0 g, 1.0 eq.), 10-(2-chloroquinazolin-4-yl)-7-phenyl-7H-benzo[c]carbazole (19.92 g, 1.1 eq.), $K_3PO_4$ (16.86 g, 2.0 eq.) and $Pd(t\text{-}Bu_3P)_2$ (0.10 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 61-1 (18.93 g, yield 71%). [M+H]=672

Chemical Formula 61-1 (18.93 g, 1.0 eq.), phenylboronic acid (3.78 g, 1.1 eq.) and $Pd(t\text{-}Bu_3P)_2$ (0.07 g, 0.005 eq.) were introduced to dioxane (300 ml), $K_3PO_4$ (12.64 g, 2.0 eq.) dissolved in water (100 ml) was introduced thereto, and the result was stirred under reflux. When the reaction was terminated after 2 hours, the salt-dissolved water layer was removed, and the solvent, was removed under vacuum. After that, the result was completely dissolved in $CHCl_3$, washed wish water, and approximately 50% of the solvent was removed under vacuum again. Under reflux again, crystals were dropped while adding ethyl acetate thereto, and the result was cooled and then filtered. This went, through column chromatography to obtain Compound 61 (14.0 g, yield 70%). [M+H]=713

Synthesis 4

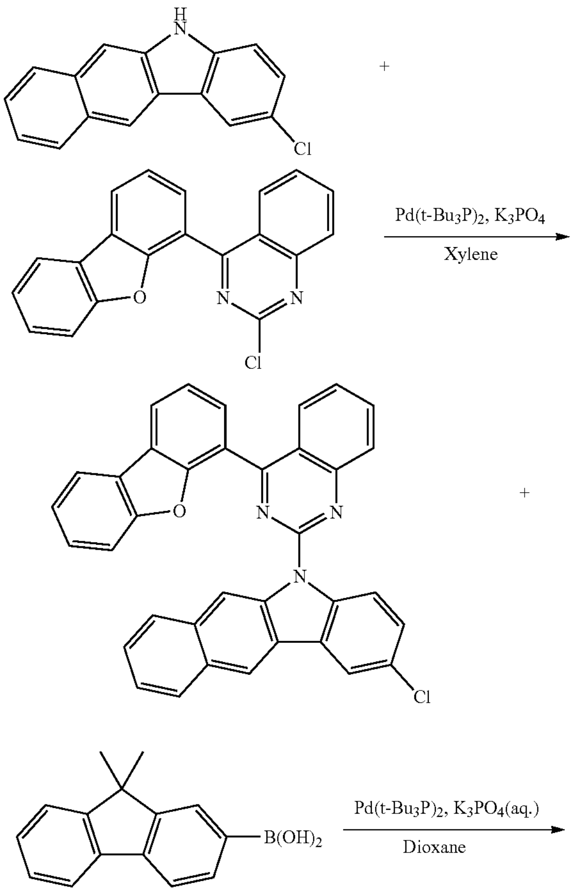

-continued

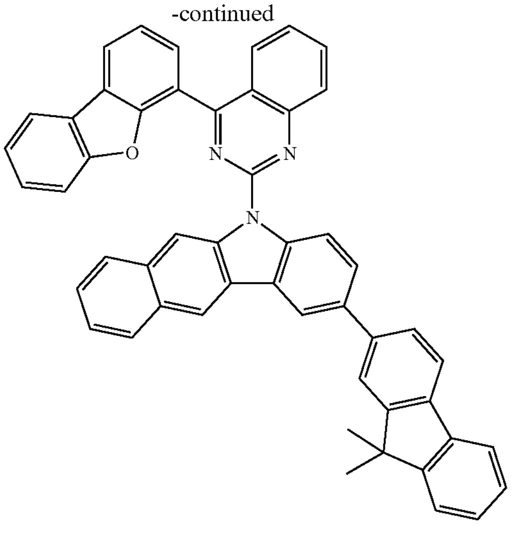

85

Chemical Formula b (10.0 q, 1.0 eq.), 2-chloro-4-(dibenzo[b,d]furan-4-yl)quinazoline (14.45 g, 1.1 eq.), $K_3PO_4$ (16.86 g, 2.0 eq.) and $Pd(t\text{-}Bu_3P)_2$ (0.10 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 85-1 (15.83 g, yield 73%). [M+H]=547

Chemical Formula 85-1 (15.83 g, 1.0 eq.), (9,9-dimethyl-9H-fluoren-2-yl) boronic acid (7.59 g, 1.1 eq.) and $Pd(t\text{-}Bu_3P)_2$ (0.07 g, 0.005 eq.) were introduced to dioxane (300 ml), $K_3PO_4$ (12.64 g, 2.0 eq.) dissolved in water (100 ml) was introduced thereto, and the result was stirred under reflux. When the reaction was terminated alter 2 hours, the salt-dissolved water layer was removed, and the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 85 (16.12 g, yield 79%). [M+H]=704

Synthesis 5

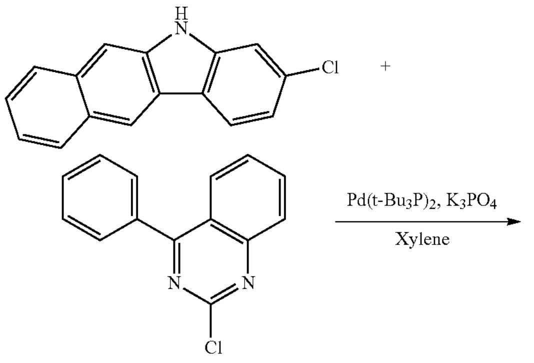

-continued

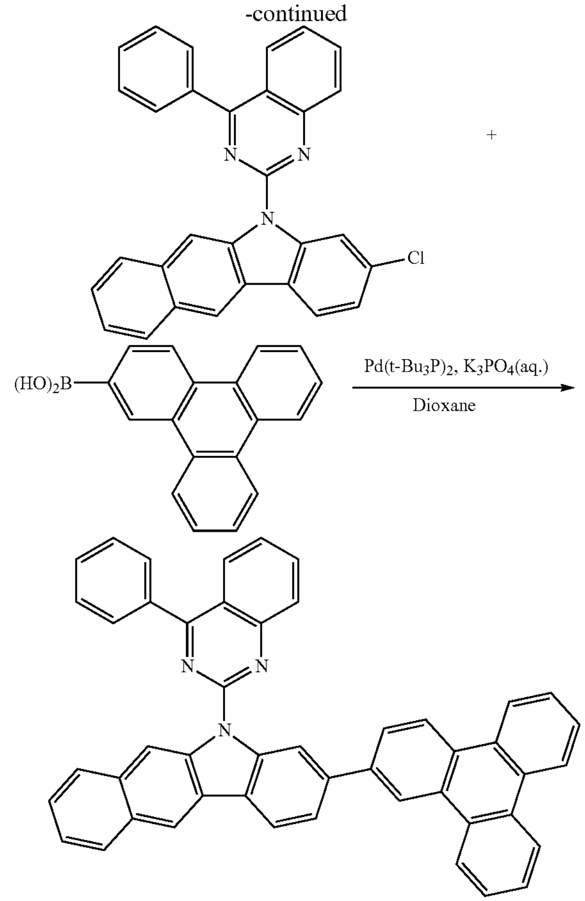

122

Chemical Formula a (10.0 g, 1.0 eq.), 2-chloro-4-phenylquinazoline (10.51 g, 1.1 eq.), $K_3PO_4$ (16.86 g, 2.0 eq.) and $Pd(t\text{-}Bu_3P)_2$ (0.10 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 122-1 (13.40 g, yield 74%). [M+H]=456

Chemical Formula 122-1 (13.40 g, 1.0 eq.), (triphenylen-2-yl)boronic acid (8.79 g, 1.1 eq.) and $Pd(t\text{-}Bu_3P)_2$ (0.07 g, 0.005 eq.) were introduced to dioxane (300 ml), $K_3PO_4$ (12.64 g, 2.0 eq.) dissolved in water (100 ml) was introduced thereto, and the result was stirred under reflux. When the reaction was terminated after 2 hours, the salt-dissolved water layer was removed, and the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 122 (13.13 g, yield 69%). A graph measuring of Compound 122 is shown in FIG. 5, and a graph measuring LC/MS of Compound 122 is shown in FIG. 6. [M+H]=648

Synthesis 6

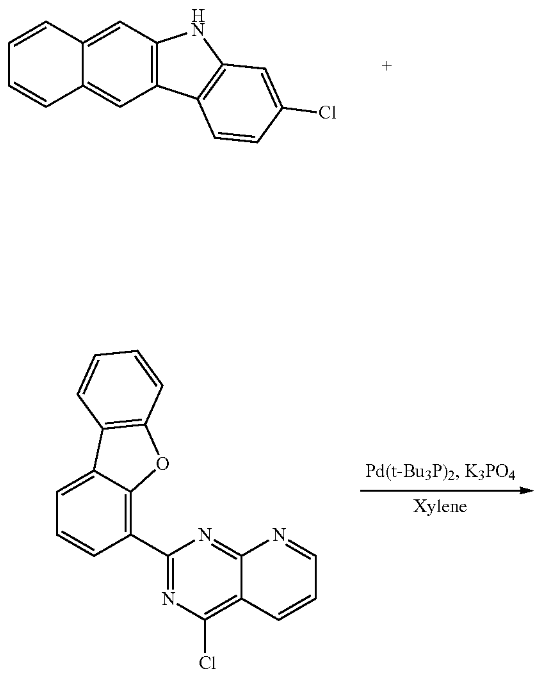

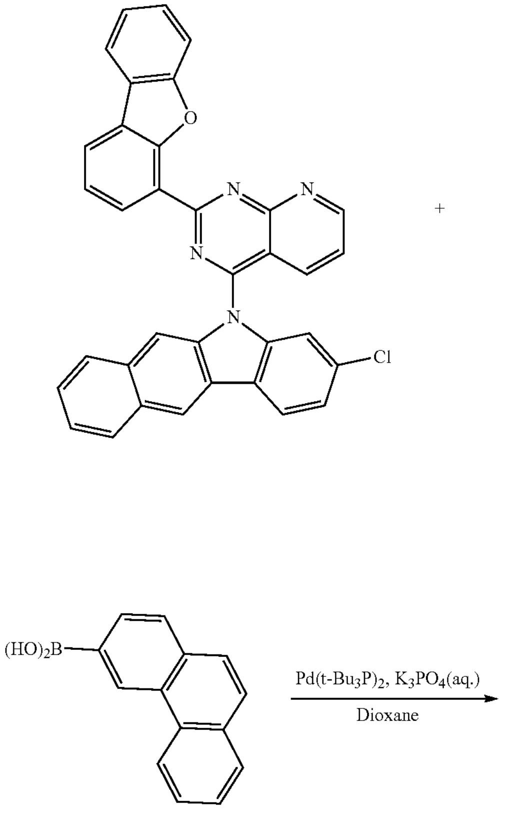

-continued

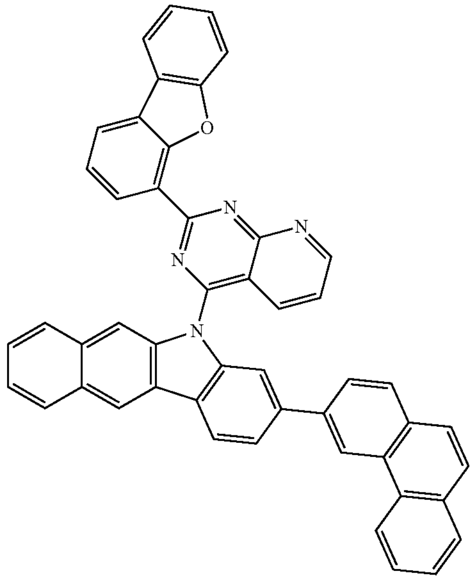

170

Chemical Formula a (10.0 g, 1.0 eq.), 4-chloro-2-(dibenzo[b,d]furan-4-yl)pyrido[2,3-d]pyrimidine (14.49 g, 1.1 eq.), $K_3PO_4$ (16.86 g, 2.0 eq.) and $Pd(t-Bu_3P)_2$ (0.10 g, 0.002 eq.) were dissolved in xylene (250 ml), and the result was stirred under reflux. When the reaction was terminated after 3 hours, the solvent, was removed under vacuum. After that, the result was completely dissolved in $CHCl_3$, washed with water, and approximately 50% of the solvent was removed under vacuum again. Cinder reflux again, crystals were dropped while adding ethyl acetate thereto, and the result was cooled and then filtered. This went through column chromatography to obtain Compound 170-1 (14.77 g, yield 68%). [M+H]=548

Chemical Formula 170-1 (14.77 g, 1.0 eq.), (phenanthren-3-yl)boronic acid (6.59 g, 1.1 eq.) and $Pd(t-Bu_3P)_2$ (0.07 g, 0.005 eq.) were introduced to dioxane (300 ml), $K_3PO_4$ (12.64 g, 2.0 eq.) dissolved in water (100 ml) was introduced thereto, and the result was stirred under reflux. When the reaction was terminated after 2 hours, the salt-dissolved water layer was removed, and the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 170 (13.20 g, yield 71%). [M+H]=689

Synthesis 7

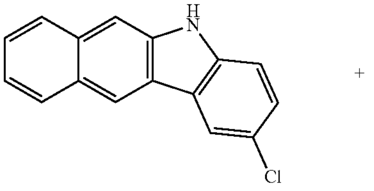

-continued

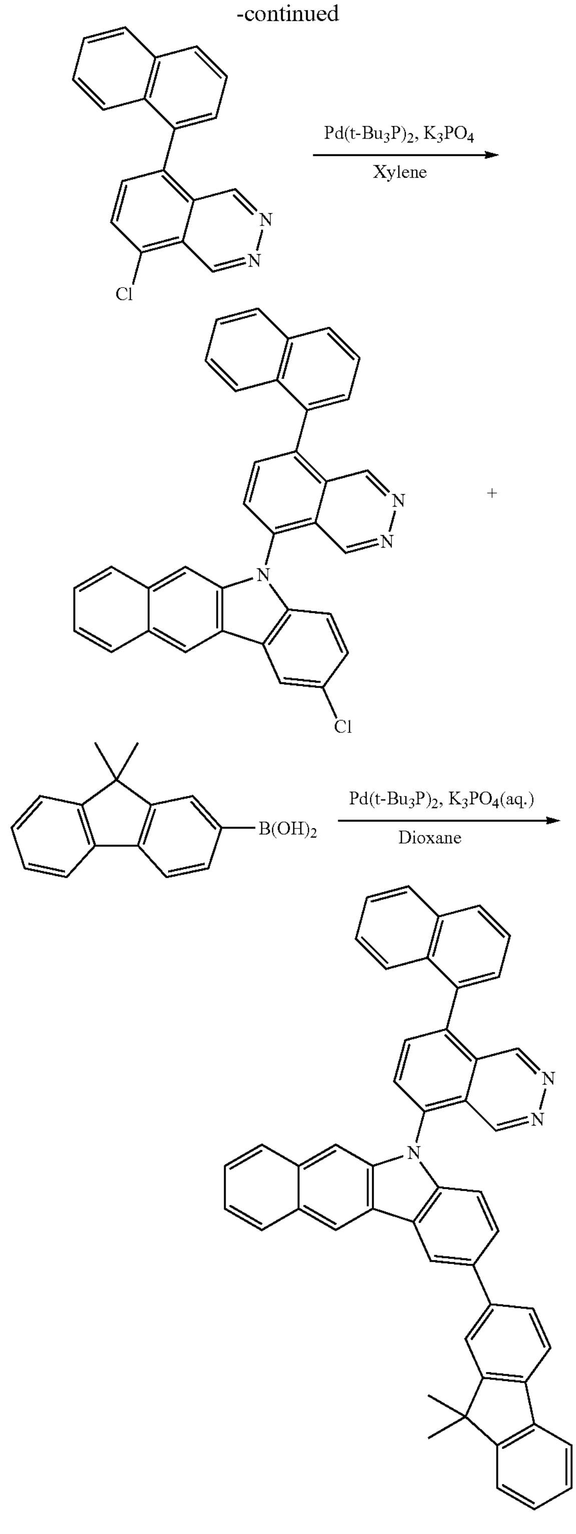

328

Chemical Formula b (10.0 g, 1.0 eq.), 5-chloro-8-(naphthalen-1-yl)phthalazine (12.70 g, 1.1 eq.), $K_3PO_4$ (16.86 g, 2.0 eq.) and $Pd(t\text{-}Bu_3P)_2$ (0.10 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 328-1 (14.27 g, yield 71%). [M+H]=507

Chemical formula 328-1 (14.27 g, 1.0 eq.), (9,9-dimethyl-9H-fluoren-2-yl)boronic acid (7.38 g, 1.1 eq.) and $Pd(t\text{-}Bu_3P)_2$ (0.07 g, 0.005 eq.) were introduced to dioxane (300 ml), $K_3PO_4$ (12.64 g, 2.0 eq.) dissolved in water (100 ml) was introduced thereto, and thus result was stirred under reflux. When the reaction was terminated after 2 hours, the salt-dissolved water layer was removed, and the solvent, was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 328 (13.10 g, yield 70%). [M+H]=664

Synthesis 8

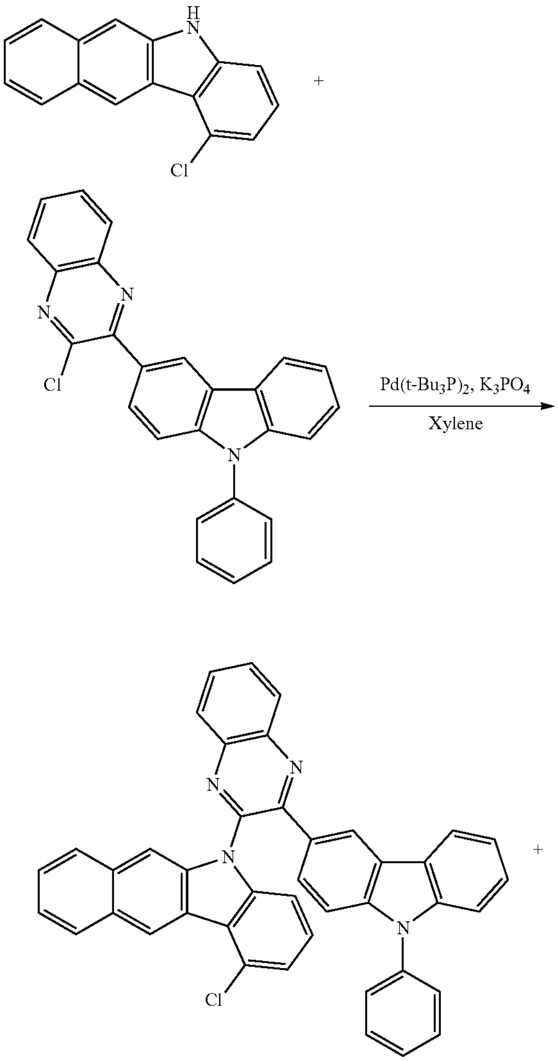

-continued

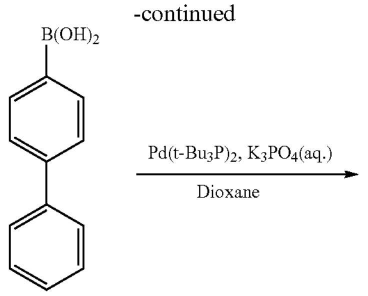

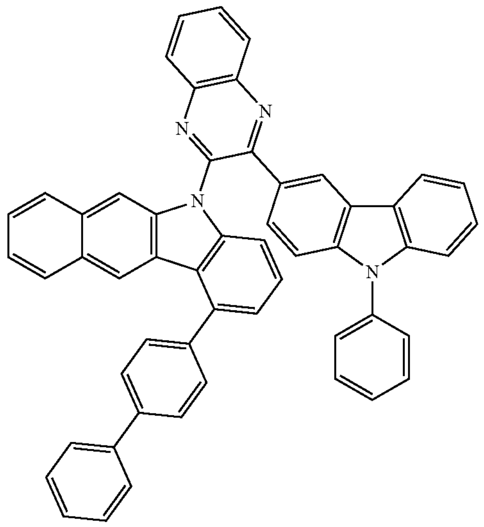

382

Chemical Formula c (10.0 g, 1.0 eq.), 3-(3-chloroquinazolin-2-yl)-9-phenyl-9H-carbazole (17.73 g, 1.1 eq.), $K_3PO_4$ (16.86 g, 2.0 eq.) and $Pd(t\text{-}Bu_3P)_2$ (0.10 q, 0.002 eq.) were dissolved in xylene (250 ml), and the result was stirred under reflux. When the reaction was terminated after 3 hours, the solvent, was relieved under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 382-1 (16.53 g, yield 67%). [M+H]=622

Chemical Formula 382-1 (16.53 g, 1.0 eq.), ([1,1'-biphenyl]-4-yl)boronic acid (7.38 g, 1.1 eq.) and $Pd(t\text{-}Bu_3P)_2$ (0.07 g, 0.005 eq.) were introduced to dioxane (300 ml), $K_3PO_4$ (12.64 g, 2.0 eq.) dissolved in water (100 ml) was introduced thereto, and the result, was stirred under reflux. When the reaction was terminated after 2 hours, the salt-dissolved water layer was removed, and the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 382 (14.15 g, yield 72%). [M+M]=739

Synthesis 9

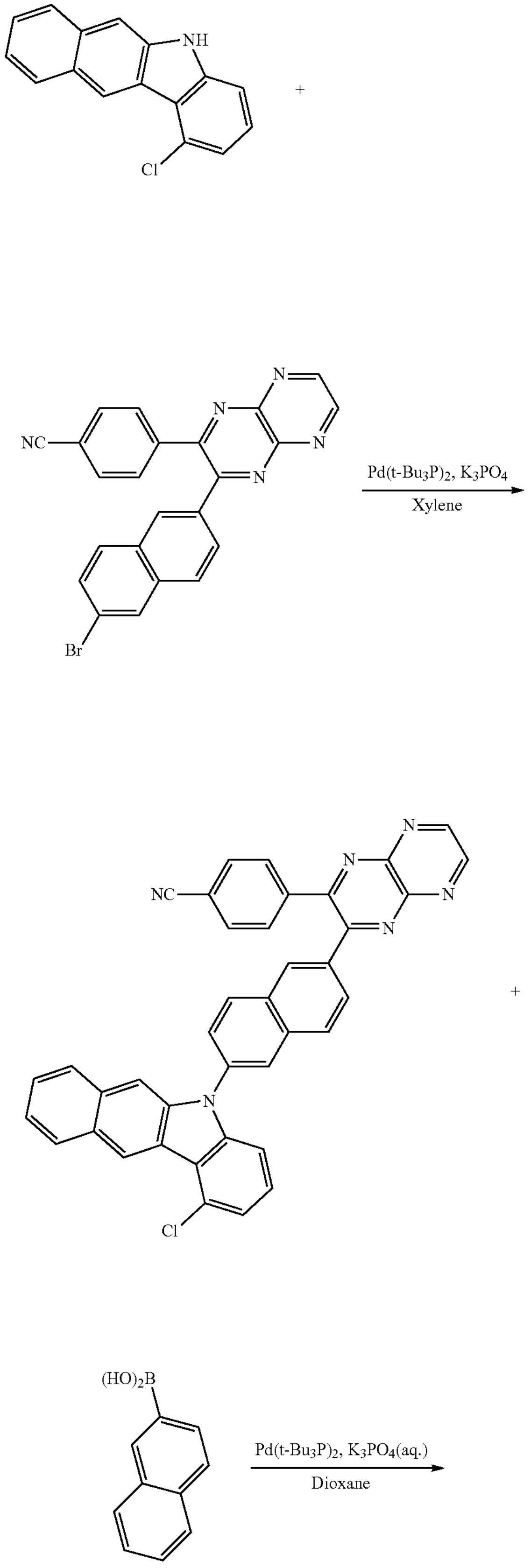

-continued

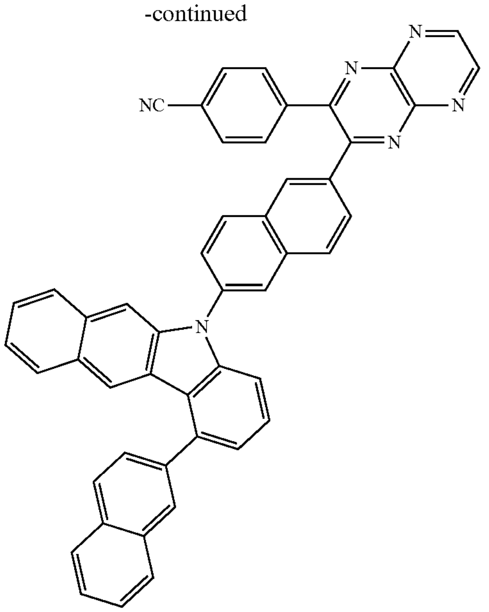

781

Chemical Formula c (10.0 g, 1.0 eq.), 4-(3-(6-bromonaphthalen-2-yl) pyrazino[2,3-b]pyrazin-2-yl)benzonitrile (19.15 g, 1.1 eq.), $K_3PO_4$ (16.86 g, 2.0 eq.) and $Pd(t\text{-}Bu_3P)_2$ (0.10 g, 0.002 eq.) were dissolved in xylene (250 ml), and the result was stirred under reflux. When the reaction was terminated after 3 hours, the solvent was removed under vacuum. After that, the result was completely dissolved an $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 781-1 (17.18 g, yield 74%). [M+H]=610

Chemical Formula 781-1 (17.18 g, 1.0 eq.), (naphthalen-2-yl)boronic acid (5.33 g, 1.1 eq.) and $Pd(t\text{-}Bu_3P)_2$ (0.07 q, 0.005 eq.) were introduced to dioxane (300 ml), $K_3PO_4$ (12.64 g, 2.0 eq.) dissolved in water (100 ml) was introduced thereto, and the result was stirred under reflux. When the reaction was terminated after 2 hours, the salt-dissolved water layer was removed, and the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 781 (14.62 g, yield 74%). [M+H]=701

Synthesis 10

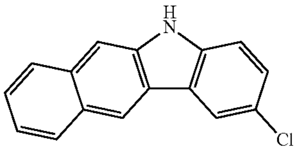

+

-continued

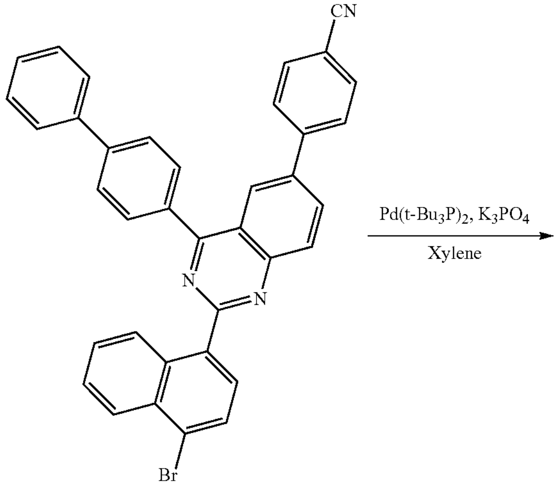

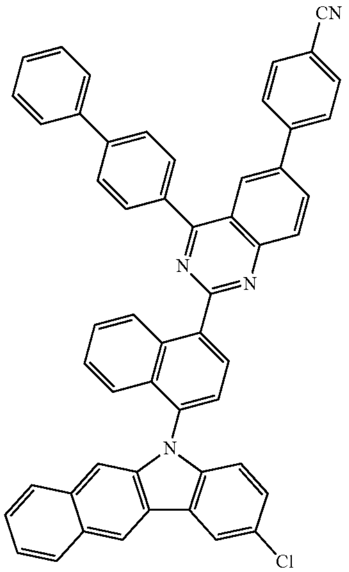

+

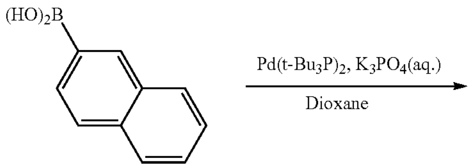

-continued

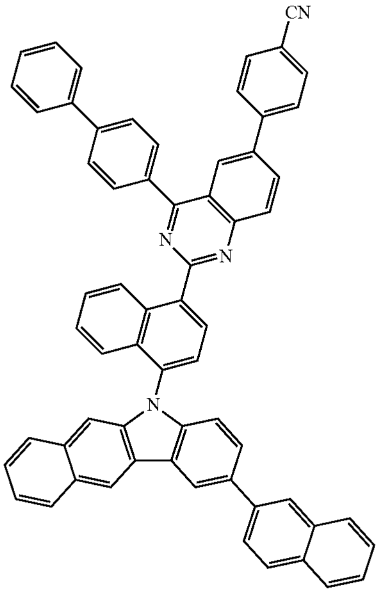

789

Chemical Formula b (10.0 g, 1.0 eq.), 4-(4-([1,1'-biphenyl]-4-yl)-2-(4-bromonaphthalen-1-yl)quinazolin-6-yl)benzonitrile (25.71 g, 1.1 eq.), $K_3PO_4$ (16.86 g, 2.0 eq.) and $Pd(t\text{-}Bu_3P)_2$ (0.10 g, 0.002 eq.) were dissolved in xylene (250 ml), and the result was stirred under reflux. When the reaction was terminated after 3 hours, the solvent, was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 789-1 (21.11 g, yield 70%). [M+H]=760

Chemical Formula 789-1 (21.11 g, 1.0 eq.), (naphthalen-2-yl)boronic acid (5.29 g, 1.1 eq.) and $Pd(t\text{-}Bu_3P)_2$ (0.07 g, 0.005 eq.) were introduced to dioxane (300 ml), $K_3PO_4$ (12.64 g, 2.0 eq.) dissolved in water (100 ml) was introduced thereto, and the result was stirred under reflux. When the reaction was terminated after 2 hours, the salt-dissolved water layer was removed, and the solvent was removed under vacuum. After that, the result was completely dissolved in $CHCl_3$, washed with water, and approximately 50% of the solvent was removed under vacuum again, Under reflux again, crystals were dropped while adding ethyl acetate thereto, and the result was cooled and then filtered. This went through column chromatography to obtain Compound 789 (17.74 g, yield 75%). [M+H]=852

Synthesis 11

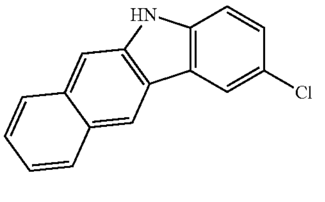

+

-continued

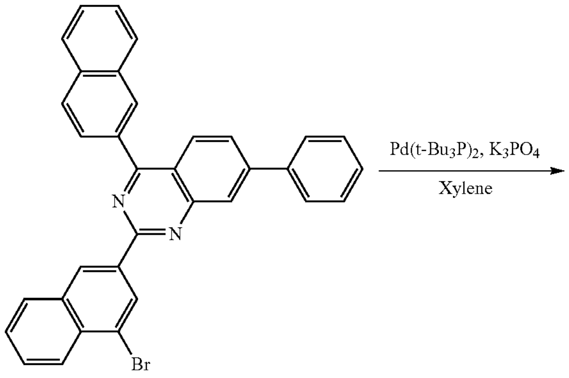

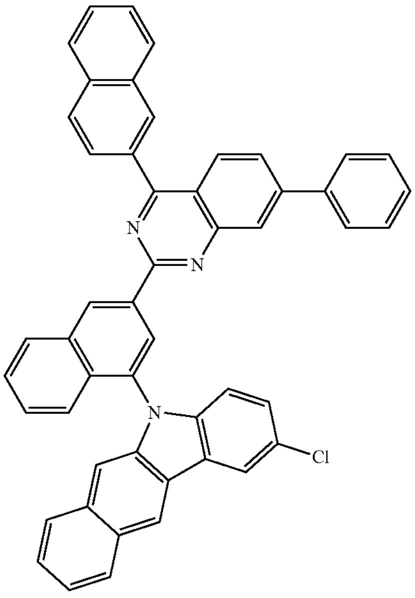

+

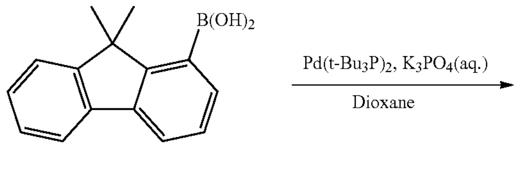

-continued

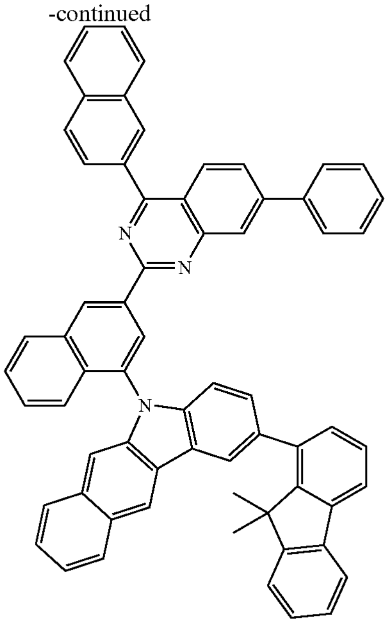

818

Chemical Formula c (10.0 g, 1.0 eq.), 2-(4-bromonaphthalen-2-yl)-4-(naphthalen-2-yl)-7-phenyl)quinazoline (23.48 g, 1.1 eq.), $K_3PO_4$ (16.86 g, 2-0 eq.) and Pd(t-$Bu_3P)_2$ (0.10 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 815-1 (18.85 g, yield 67%). [M+H]=709

Chemical Formula 815-1 (18.85 g, 1.0 eq.), (9,9-dimethyl-9H-fluoren-1-yl) boronic acid (5.03 g, 1.1 eq.) and Pd(t-$Bu_3P)_2$ 0.07 g, 0.005 eq.) were introduced to dioxane (300 ml), $K_3PO_4$ (12.64 g, 2.0 eq.) dissolved in water (100 ml) was introduced thereto, and the result was stirred under reflux. When the reaction was terminated alter 2 hours, the salt-dissolved water layer was removed, and the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 815 (17.28 g, yield 75%). [M+H]=867

Synthesis 12

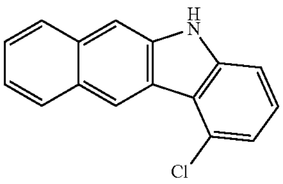

+

-continued

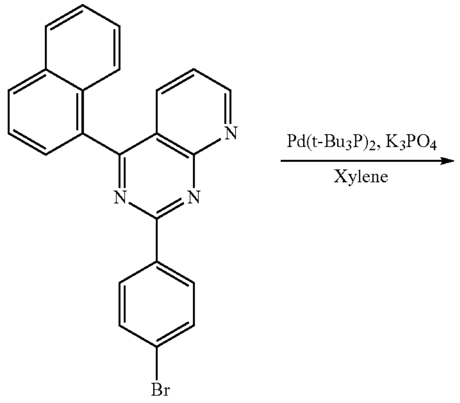

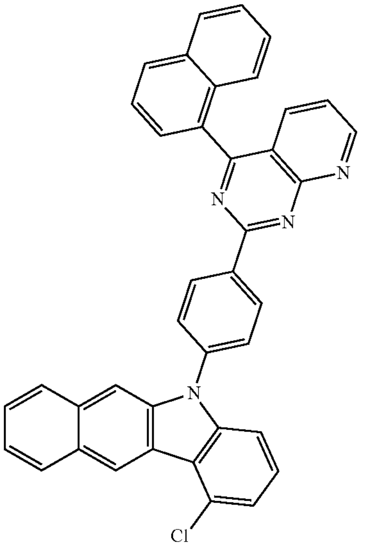

+

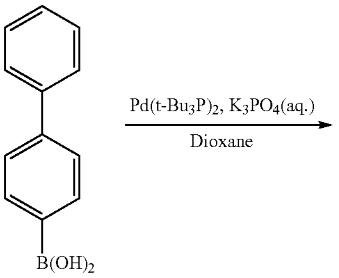

-continued

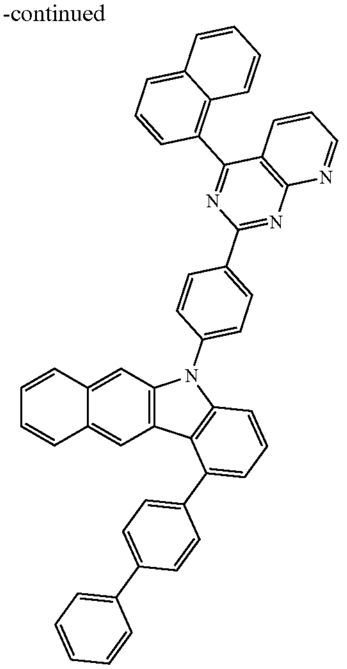

849

Chemical Formula c (10.0 g, 1.0 eq.), 2-(4-bromophenyl)-4-(naphthalen-1-yl)pyrido[2,3-d]pyrimidine (18.01 q, 1.1 eq.), $K_3PO_4$ (16.86 g, 2.0 eq.) and Pd(t-$Bu_3P)_2$ (0.10 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 849-1 (17.14 g, yield 74%). [M+H]=584

Chemical Formula 849-1 (17.14 g, 1.0 eq.), ([1,1'-biphenyl]-4-yl)boronic acid (6.40 g, 1.1 eq.) and Pd(t-$Bu_3P)_2$ (0.07 g, 0.005 eq.) were introduced to dioxane (300 ml), $K_3PO_4$ (12.64 g, 2.0 eq.) dissolved in water (100 ml) was introduced thereto, and the result was stirred under reflux. When the reaction was terminated after 2 hours, the salt-dissolved water layer was removed, and the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 849 (14.62 g, yield 71%). [M+H]=701

-continued

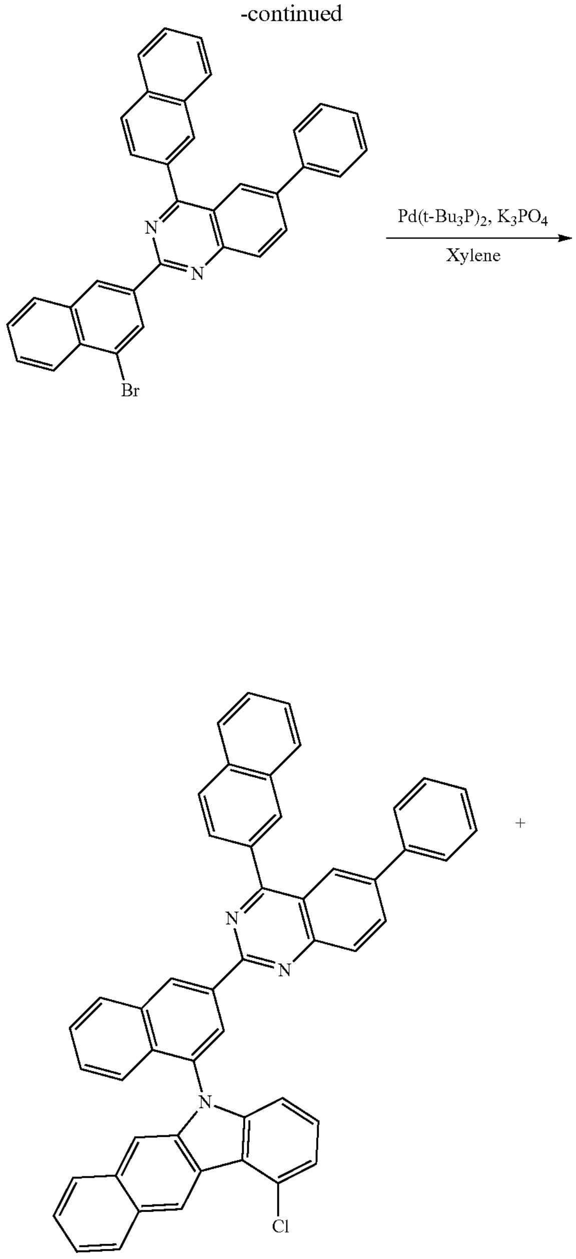

Synthesis 13

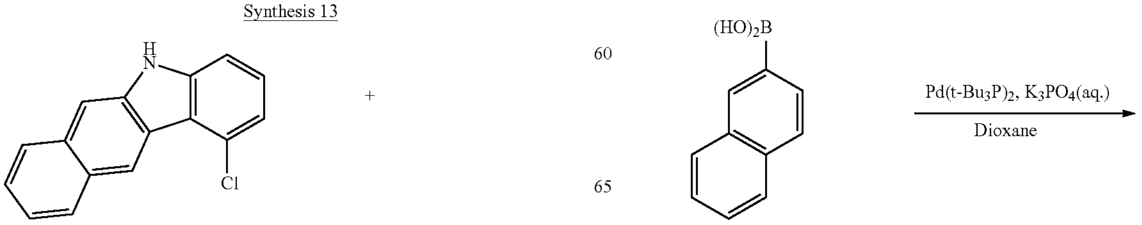

-continued

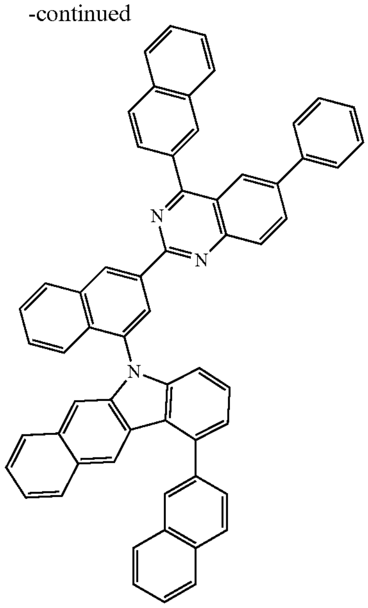

875

Chemical Formula c (10.0 g, 1.0 eq.), 2-(4-bromonaphthalen-2-yl)-4-(naphthalen-2-yl)-6-phenylquinazoline (23.48 g, 1.1 eq.), $K_3PO_4$ (16.86 g, 2.0 eq.) and $Pd(t-Bu_3P)_2$ (0.10 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 875-1 (38.85 g, yield 67%). [M+H]=709

Chemical Formula 875-1 (18.85 g, 1.0 eq.), (naphthalen-2-yl)boronic acid (5.03 g, 1.1 eq.) and $Pd(t-Bu_3P)_2$ (0.07 g, 0.005 eq.) were introduced to dioxane (300 ml), $K_3PO_4$ (12.64 g, 2.0 eq.) dissolved in water (100 ml) was introduced thereto, and the result was stirred under reflux. When the reaction was terminated after 2 hours, the salt-dissolved water layer was removed, and the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 875 (14.90 g, yield 70%). [M+H]=800

Experimental Example

Comparative Example 1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, the following HI-1 Compound was formed to a thickness of 1150 Å as a hole injection layer with the following A-1 Compound being p-doped in a concentration of 1.5%. A hole transfer layer having a film thickness of 800 Å wan formed by vacuum depositing the following HT-1 Compound on the hole injection layer. Subsequently, an electron blocking layer was formed by vacuum depositing the following EB-1 Compound on the hole transfer layer to a film thickness of 150 Å. Then, on the EB-1 deposited film, a red light emitting layer having a thickness of 400 Å was formed by vacuum depositing the following RH-1 Compound and the following Dp-7 Compound in a weight ratio of 98:2. On the light emitting layer, a hole blocking layer was formed by vacuum depositing the following HB-1 Compound to a film thickness of 30 Å. Then, on the hole blocking layer, an electron injection and transfer layer was formed to a thickness of 300 Å by vacuum depositing the following ET-1 Compound and the following LiQ Compound in a weight ratio of 2:1. A cathode was formed on the electron injection and transfer layer by depositing lithium fluoride (LiF) to a thickness of 12 Å and aluminum to a thickness of 1,000 Å in consecutive order.

HI-1
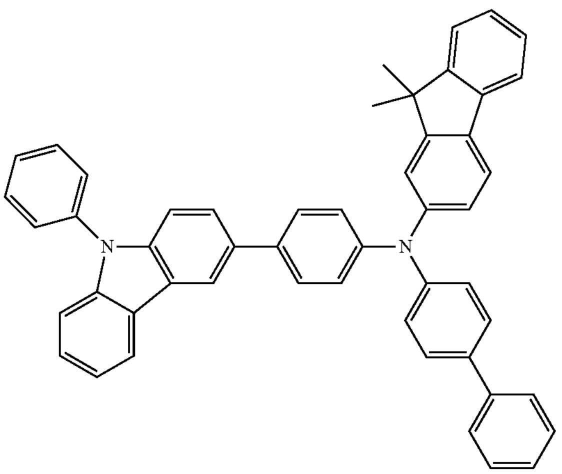
A-1
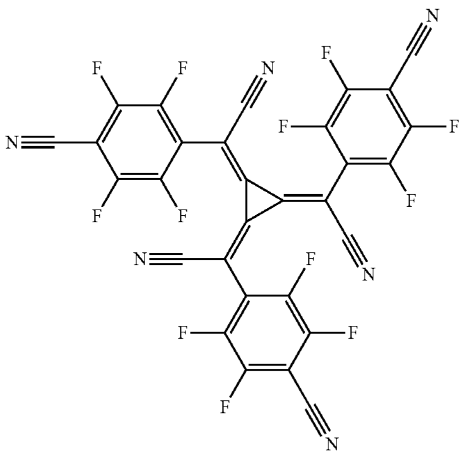
HT-1
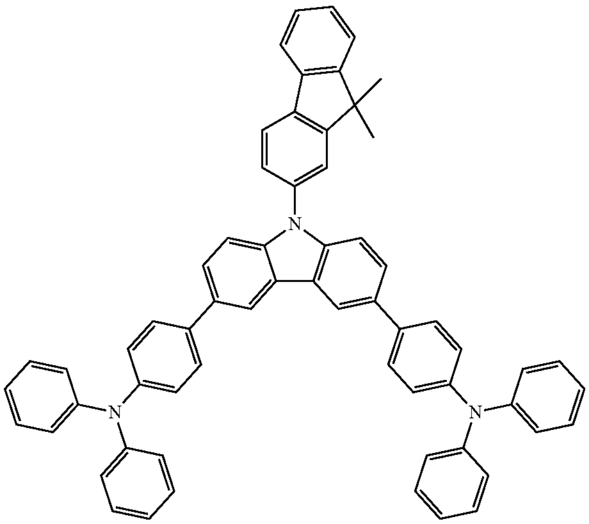
EB-1
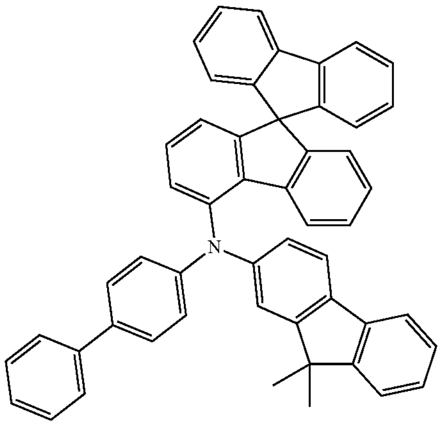
RH-1
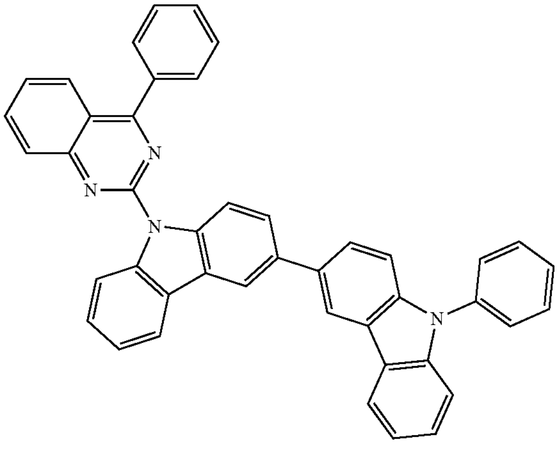
Dp-7
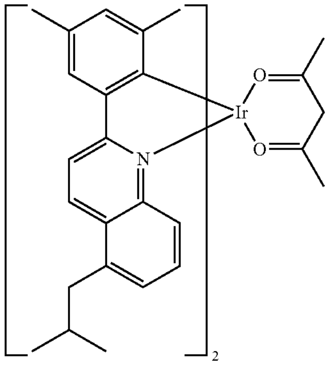

-continued
HB-1
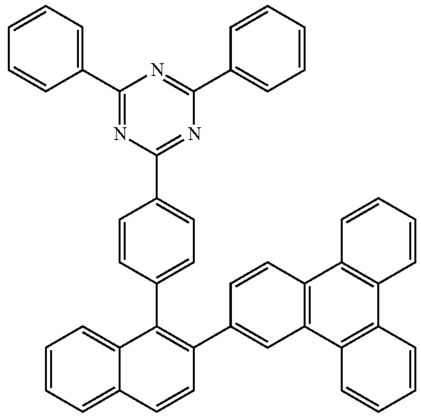
ET-1
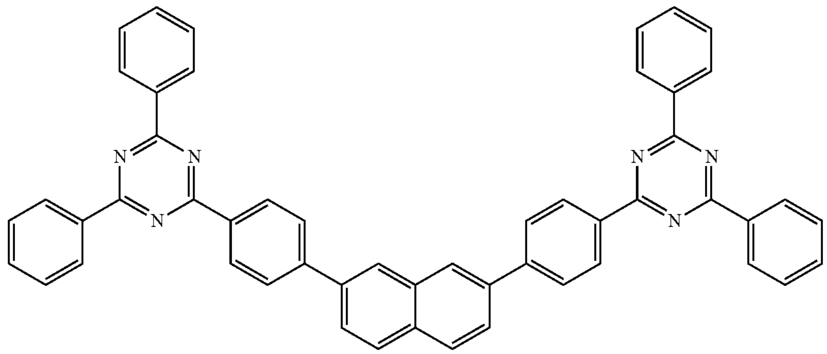
LiQ
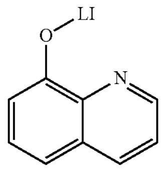
RH-2
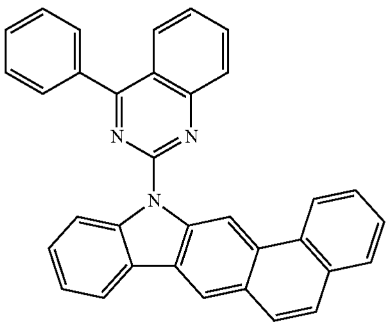
RH-3
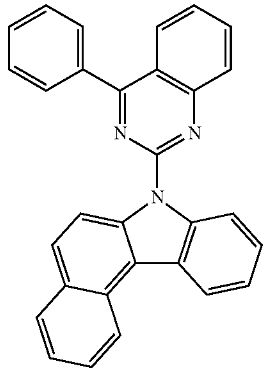
RH-4
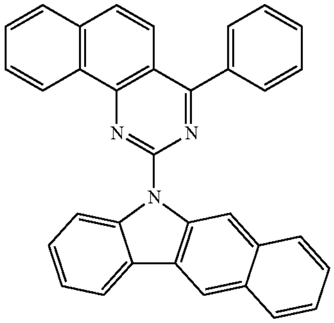

-continued
RH-5
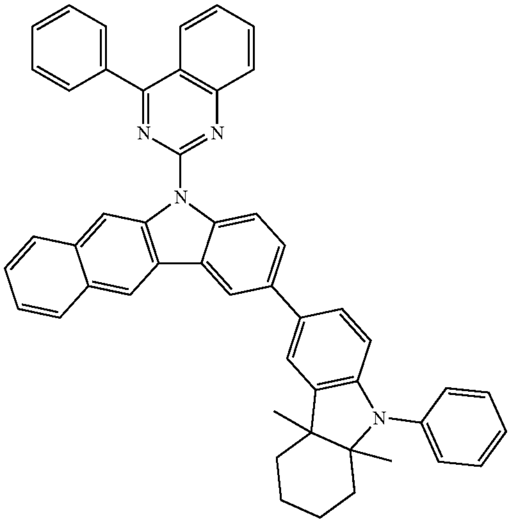
RH-6
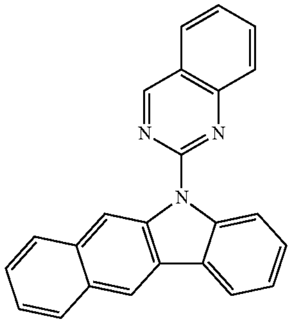
RH-7
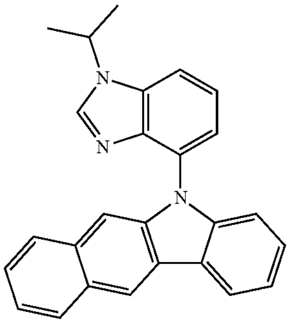
RH-8
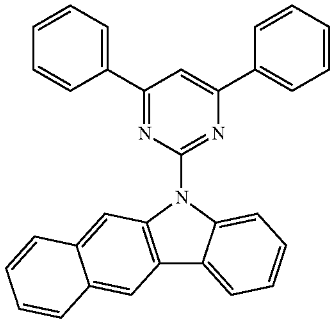
RH-9
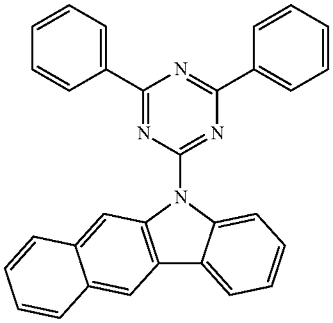
RH-10
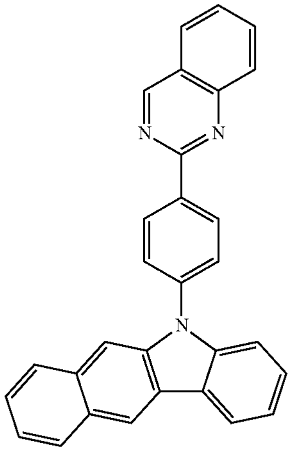

-continued
RH-11
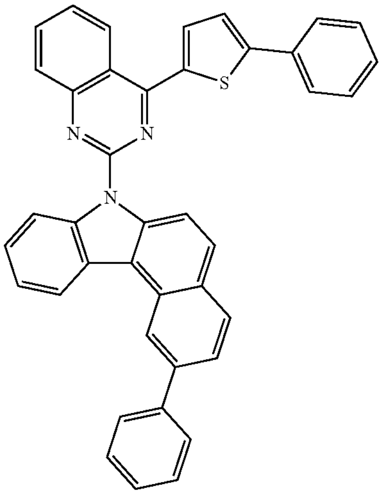
RH-12
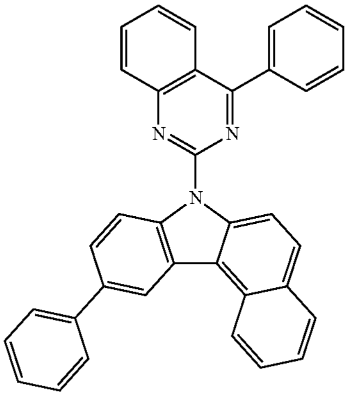
RH-13
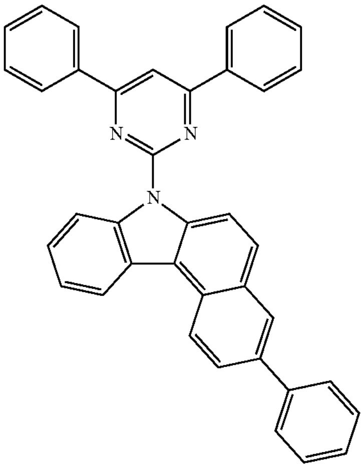
RH-14
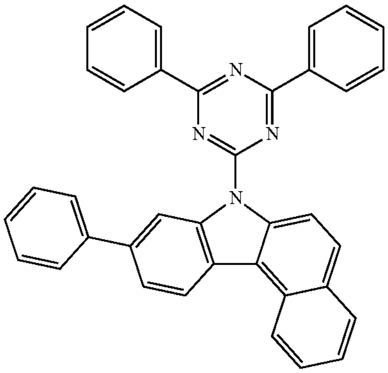
RH-15
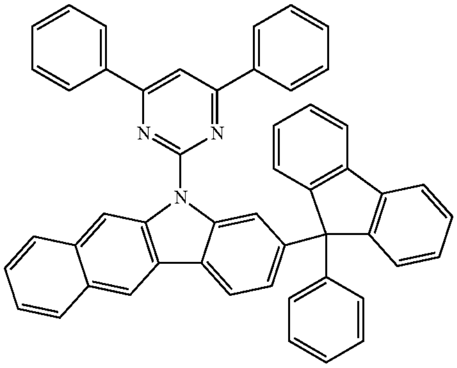
RH-16
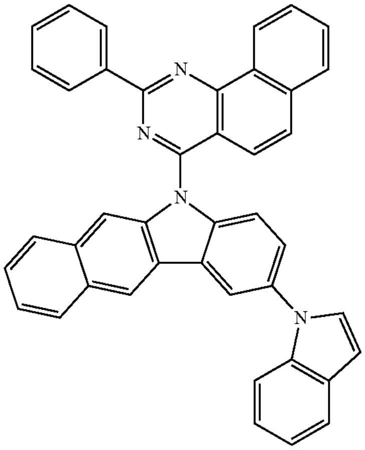

-continued
RH-17
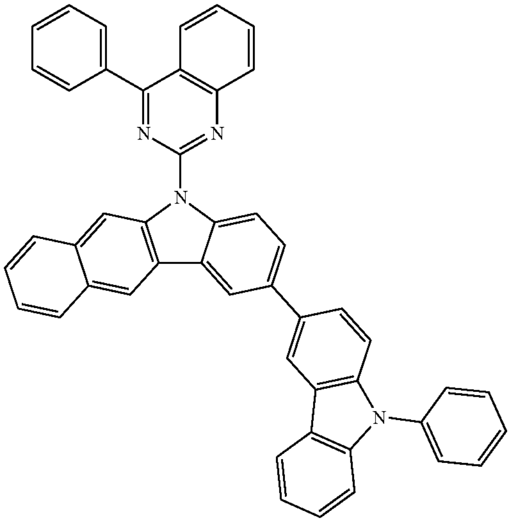
RH-18
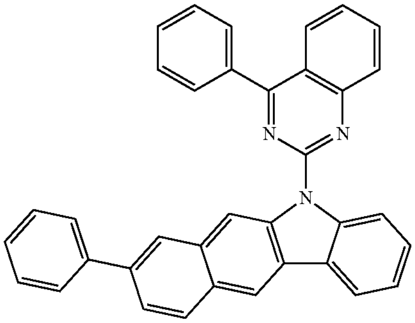
RH-19
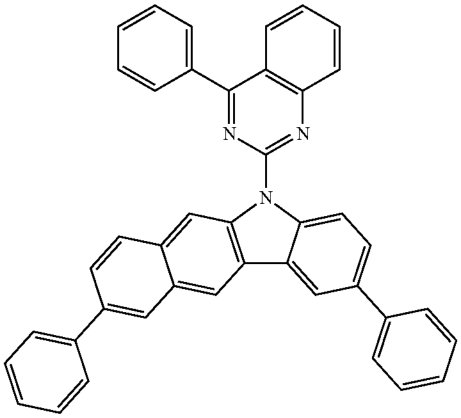
RH-20
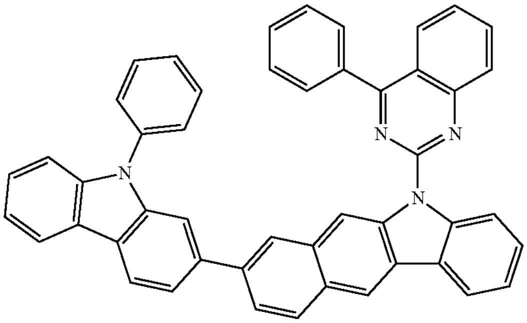
RH-21
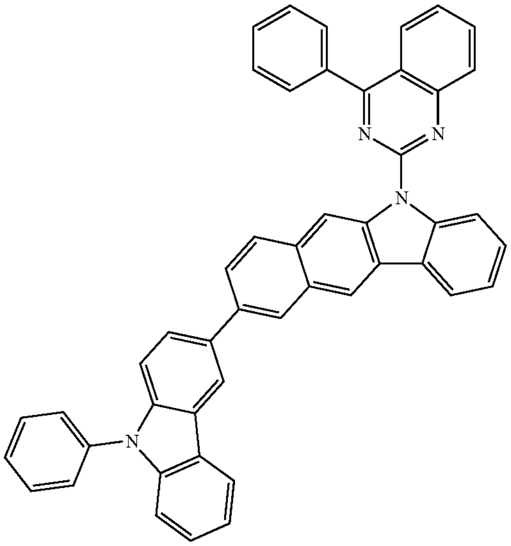

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2\times10^{-7}$ torr to $5\times10^{-6}$ torr.

Example 1 to Example 13

Organic light emitting devices were manufactured in the same manner as in Comparative Example 1 except that, in the organic light emitting device of Comparative Example 1, compounds described in the following Table 3 were used instead of RH-1.

Comparative Example 2 to Comparative Example 21

Organic light emitting devices were manufactured in the same manner as in Comparative Example 1 except that, in the organic light emitting device of Comparative Example 1, compounds described in the following Table 1 were used instead of RH-1.

When a current was applied to the organic light emitting devices manufactured in Example 1 to Example 13, and Comparative Example 3 to Comparative Example 21, a voltage, efficiency and a lifetime were measured, and the results are shown in the following Table 1. T95 means time taken for the luminance decreasing to 95% from its initial luminance (5000 nit).

TABLE 1

| Category | Material | Driving Voltage (V) | Efficiency (cd/A) | Lifetime T95 (hr) | Light Emitting Color |
|---|---|---|---|---|---|
| Comparative Example 1 | RH-1 | 4.52 | 33.5 | 192 | Red |
| Example 1 | Compound 2 | 4.20 | 35.1 | 240 | Red |
| Example 2 | Compound 3 | 4.27 | 34.6 | 281 | Red |
| Example 3 | Compound 61 | 3.98 | 37.5 | 330 | Red |
| Example 4 | Compound 85 | 3.92 | 38.7 | 327 | Red |
| Example 5 | Compound 122 | 3.99 | 38.1 | 335 | Red |
| Example 6 | Compound 170 | 4.30 | 35.7 | 263 | Red |
| Example 7 | Compound 328 | 4.29 | 35.2 | 238 | Red |
| Example 8 | Compound 382 | 3.88 | 40.2 | 267 | Red |
| Example 9 | Compound 781 | 3.95 | 39.1 | 279 | Red |
| Example 10 | Compound 789 | 3.81 | 37.5 | 288 | Red |
| Example 11 | Compound 815 | 3.97 | 39.3 | 293 | Red |
| Example 12 | Compound 849 | 3.99 | 38.8 | 258 | Red |
| Example 13 | Compound 875 | 4.21 | 37.7 | 248 | Red |
| Comparative Example 2 | RH-2 | 4.23 | 36.2 | 151 | Red |
| Comparative Example 3 | RH-3 | 4.92 | 33.4 | 159 | Red |
| Comparative Example 4 | RH-4 | 4.35 | 35.7 | 187 | Red |
| Comparative Example 5 | RH-5 | 4.77 | 34.3 | 95 | Red |
| Comparative Example 6 | RH-6 | 4.38 | 31.5 | 106 | Red |
| Comparative Example 7 | RH-7 | 4.70 | 29.1 | 82 | Red |
| Comparative Example 8 | RH-8 | 4.25 | 33.9 | 105 | Red |
| Comparative Example 9 | RH-9 | 4.21 | 36.7 | 114 | Red |
| Comparative Example 10 | RH-10 | 4.37 | 31.3 | 127 | Red |
| Comparative Example 11 | RH-11 | 4.07 | 35.2 | 130 | Red |

TABLE 1-continued

| Category | Material | Driving Voltage (V) | Efficiency (cd/A) | Lifetime T95 (hr) | Light Emitting Color |
|---|---|---|---|---|---|
| Comparative Example 12 | RH-12 | 4.42 | 33.4 | 170 | Red |
| Comparative Example 13 | RH-13 | 4.25 | 33.7 | 150 | Red |
| Comparative Example 14 | RH-14 | 4.07 | 35.3 | 173 | Red |
| Comparative Example 15 | RH-15 | 4.32 | 33.4 | 159 | Red |
| Comparative Example 16 | RH-16 | 4.05 | 34.7 | 187 | Red |
| Comparative Example 17 | RH-17 | 4.37 | 36.3 | 203 | Red |
| Comparative Example 18 | RH-18 | 4.57 | 32.2 | 137 | Red |
| Comparative Example 19 | RH-19 | 4.50 | 32.4 | 178 | Red |
| Comparative Example 20 | RH-20 | 4.38 | 35.9 | 193 | Red |
| Comparative Example 21 | RH-21 | 4.39 | 35.3 | 190 | Red |

When Applying a current to the organic light emitting devices manufactured in Examples 1 to 13 and Comparative Examples 1 to 21, results of Table 1 were obtained. The red organic light emitting device of Comparative Example 1 used materials that have been widely used in the art, and had a structure using Compound [EB-1] as an electron blocking layer and using RH-1/Dp-7 as a red light emitting layer. Comparative Examples 2 to 21 manufactured organic light emitting devices using RH-2 to RH-21 instead of RH-1. When examining the results of Table 1, it was seen that, when using the compound of the present disclosure as a host of a red light emitting layer, energy transfer from a host to a red dopant was well achieved from the fact that a driving voltage decreased closer to as much as 30% and efficiency increased by 25% or greater compared to the materials in the comparative examples. In addition, it was seen that lifetime properties were greatly improved by a factor of two or more while maintaining high efficiency. This may ultimately be due to the fact that the compounds of the present disclosure have higher stability for electrons and holes compared to the compounds of the comparative examples. As a result, it can be identified that, when using the compound of the present disclosure as a host of d red light emitting layer, a driving voltage, light emission efficiency and lifetime properties of an organic light emitting device are improved.

The invention claimed is:

1. A benzocarbazole-based compound represented by the following Chemical Formula 1:

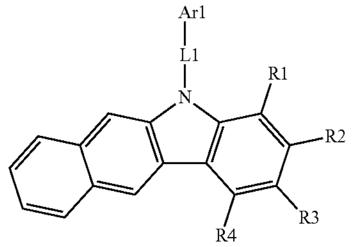

wherein, in Chemical Formula 1,

R1 to R4 are the same as or different from each other, and each independently hydrogen; a phenyl group unsubstituted or substituted with deuterium, an alkyl group or an aryl group; a biphenyl group unsubstituted or substituted with deuterium, an alkyl group or an aryl group; a naphthyl group unsubstituted or substituted with deuterium, an alkyl group or an aryl group; a fluorenyl group unsubstituted or substituted with deuterium, an alkyl group or an aryl group; a fluoranthene group unsubstituted or substituted with deuterium, an alkyl group or an aryl group; a phenanthrene group unsubstituted or substituted with deuterium, an alkyl group or an aryl group; a triphenylene group unsubstituted or substituted with deuterium, an alkyl group or an aryl group; or a spirobifluorenyl group unsubstituted or substituted with deuterium, an alkyl group or an aryl group, and at least one of R1, R2 and R4 is the biphenyl group unsubstituted or substituted with deuterium, an alkyl group or an aryl group; the naphthyl group unsubstituted or substituted with deuterium, an alkyl group or an aryl group; the fluorenyl group unsubstituted or substituted with deuterium, an alkyl group or an aryl group; the fluoranthene group unsubstituted or substituted with deuterium, an alkyl group or an aryl group; the phenanthrene group unsubstituted or substituted with deuterium, an alkyl group or an aryl group; the triphenylene group unsubstituted or substituted with deuterium, an alkyl group or an aryl group; or the spirobifluorenyl group unsubstituted or substituted with deuterium, an alkyl group or an aryl group, L1 is a direct bond; a phenylene group unsubstituted or substituted with deuterium, a nitrile group, an alkyl group or an aryl group; a biphenylene group unsubstituted or substituted with deuterium, a nitrile group, an alkyl group or an aryl group; a naphthylene group unsubstituted or substituted with deuterium, a nitrile group, an alkyl group or an aryl group; a fluorenylene group unsubstituted or substituted with deuterium, a nitrile group, an alkyl group or an aryl group; or a spirobifluorenyl group unsubstituted or substituted with deuterium, a nitrile group, an alkyl group or an aryl group, Ar1 is represented by the following Chemical Formula 2:

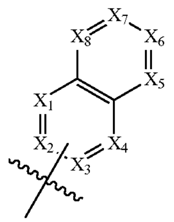

in Chemical Formula 2, one of $X_1$ to $X_4$ is C bonded to L1 and the others of $X_1$ to $X_4$ are N, CH or CR, $X_5$ to $X_8$ are N, CH or CR, two or more of $X_1$ to $X_8$ are N, and two or more of $X_1$ to $X_8$ are CR, R is a phenyl group unsubstituted or substituted with deuterium, a nitrile group, an aryl group unsubstituted or substituted with deuterium, a heteroaryl group, or an alkyl group; a naphthyl group unsubstituted or substituted with deuterium, a nitrile group, an aryl group unsubstituted or substituted with deuterium, a heteroaryl group, or an alkyl group; a biphenyl group unsubstituted or substituted with deuterium, a nitrile group, an aryl group unsubstituted or substituted with deuterium, a heteroaryl group, or an alkyl group; a phenanthrenyl group unsubstituted or substituted with deuterium, a nitrile group, an aryl group unsubstituted or substituted with deuterium, a heteroaryl group, or an alkyl group; a triphenylene group unsubstituted or substituted with deuterium, a nitrile group, an aryl group unsubstituted or substituted with deuterium, a heteroaryl group, or an alkyl group; a fluorenyl group unsubstituted or substituted with deuterium, a nitrile group, an aryl group unsubstituted or substituted with deuterium, a heteroaryl group, or an alkyl group; a benzofluorenyl group unsubstituted or substituted with deuterium, a nitrile group, an aryl group unsubstituted or substituted with deuterium, a heteroaryl group, or an alkyl group; a carbazole group unsubstituted or substituted with deuterium, a nitrile group, an aryl group unsubstituted or substituted with deuterium, a heteroaryl group, or an alkyl group; a dibenzofuranyl group unsubstituted or substituted with deuterium, a nitrile group, an aryl group unsubstituted or substituted with deuterium, a heteroaryl group, or an alkyl group; a dibenzothiophenyl group unsubstituted or substituted with deuterium, a nitrile group, an aryl group unsubstituted or substituted with deuterium, a heteroaryl group, or an alkyl group; a benzocarbazole group unsubstituted or substituted with deuterium, a nitrile group, an aryl group unsubstituted or substituted with deuterium, a heteroaryl group, or an alkyl group; a pyridyl group unsubstituted or substituted with deuterium, a nitrile group, an aryl group unsubstituted or substituted with deuterium, a heteroaryl group, or an alkyl group; a quinoline group unsubstituted or substituted with deuterium, a nitrile group, an aryl group unsubstituted or substituted with deuterium, a heteroaryl group, or an alkyl group; a naphthobenzofuranyl group unsubstituted or substituted with deuterium, a nitrile group, an aryl group unsubstituted or substituted with deuterium, a heteroaryl group, or an alkyl group; or a naphthobenzothiophenyl group unsubstituted or substituted with deuterium, a nitrile group, an aryl group unsubstituted or substituted with deuterium, a heteroaryl group, or an alkyl group, wherein when two of $X_1$ to $X_8$ are N, $X_2$ and $X_3$ are not simultaneously N, or $X_6$ and $X_7$ are not simultaneously N, or $X_1$ and $X_4$ are not simultaneously N, or $X_5$ and $X_8$ are not simultaneously N, wherein the aryl group is a phenyl group, a biphenyl group, a terphenyl group, a naphthyl group, an anthracenyl group, a pyrenyl group, a perylenyl group, a triphenyl group, a chrysenyl group, a fluorenyl group, a fluoranthene group, a phenanthrene group, a triphenylene group, or a spirobifluorenyl group, and wherein the heteroaryl group is a carbazole group, a dibenzofuranyl group, a dibenzothiophenyl group, a benzocarbazole group, a pyridyl group, a quinoline group, a naphthobenzofuranyl group, or a naphthobenzothiophenyl group.

2. An organic light emitting device comprising:

a first electrode;

a second electrode provided opposite to the first electrode; and one or more organic material layers provided between the first electrode and the second electrode, wherein one or more layers of the one or more organic material layers comprise the benzocarbazole-based compound of claim 1.

3. The organic light emitting device of claim 2, wherein the one or more organic material layers comprise a hole injection layer or a hole transfer layer, and the hole injection layer or the hole transfer layer comprises the benzocarbazole-based compound.

4. The organic light emitting device of claim 2, wherein the one or more organic material layers comprise an electron transfer layer or an electron injection layer, and the electron transfer layer or the electron injection layer comprises the benzocarbazole-based compound.

5. The organic light emitting device of claim 2, wherein the one or more organic material layers comprise a light emitting layer, and the light emitting layer comprises the benzocarbazole-based compound.

6. A benzocarbazole-based compound represented by any one of the following compounds:

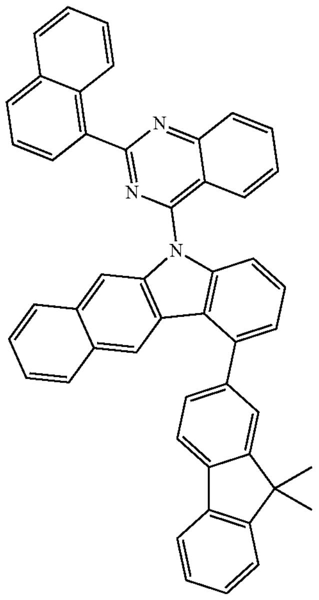 [SMILES: CC1(C)c2ccccc2-c2ccc(-c3cccc4c3c3cc5ccccc5cc3n4-c3nc(-c4cccc5ccccc45)nc4ccccc34)cc21]

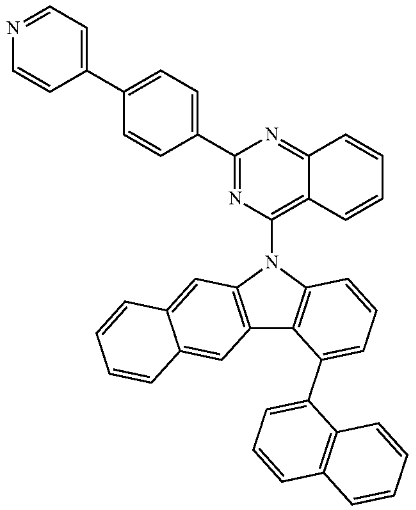 [SMILES: c1ccc2cc3c(cc2c1)c1c(-c2cccc4ccccc24)cccc1n3-c1nc(-c2ccc(-c3ccncc3)cc2)nc2ccccc12]

-continued

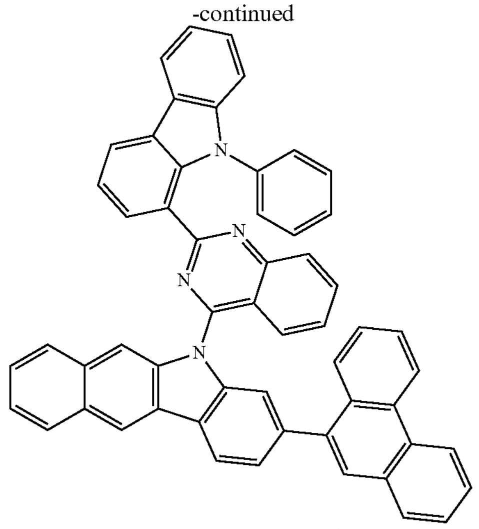

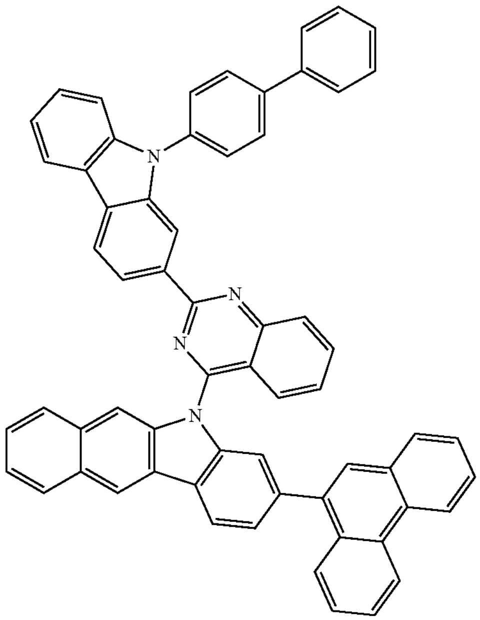 [SMILES: c1ccc(-c2ccc(-n3c4ccccc4c4ccc(-c5nc(-n6c7cc(-c8cc9ccccc9c9ccccc89)ccc7c7cc8ccccc8cc76)c6ccccc6n5)cc43)cc2)cc1]

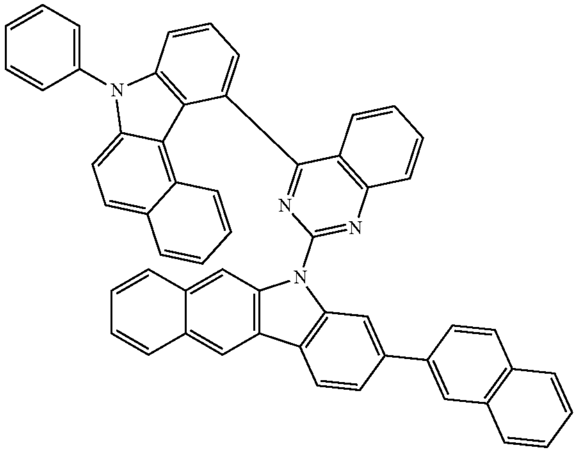 [SMILES: c1ccc(-n2c3cccc(-c4nc(-n5c6cc(-c7ccc8ccccc8c7)ccc6c6cc7ccccc7cc65)nc5ccccc45)c3c3c4ccccc4ccc32)cc1]

-continued
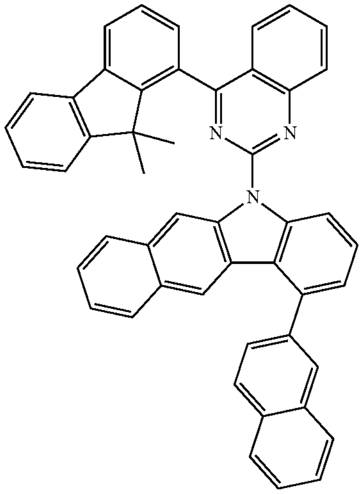
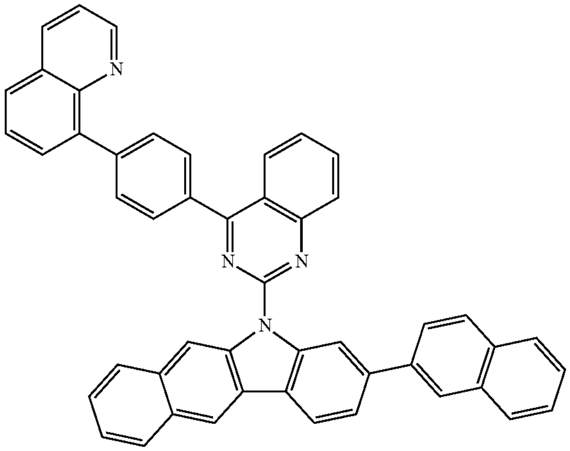
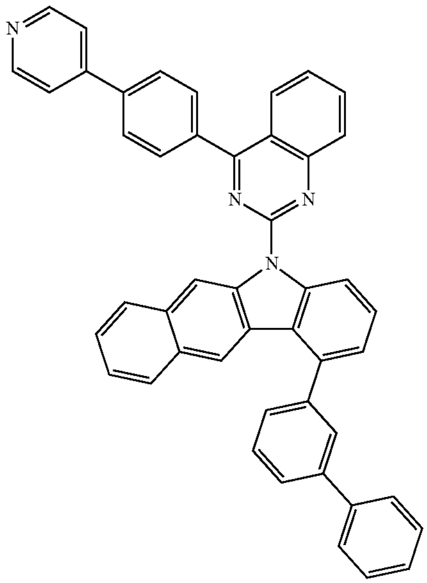 [SMILES: c1ccc(-c2cccc(-c3cccc4c3c3cc5ccccc5cc3n4-c3nc(-c4ccc(-c5ccncc5)cc4)c4ccccc4n3)c2)cc1]
-continued
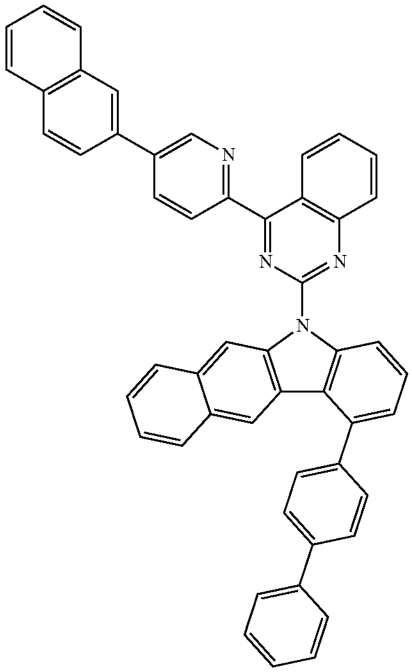 [SMILES: c1ccc(-c2ccc(-c3cccc4c3c3cc5ccccc5cc3n4-c3nc(-c4ccc(-c5ccc6ccccc6c5)cn4)c4ccccc4n3)cc2)cc1]
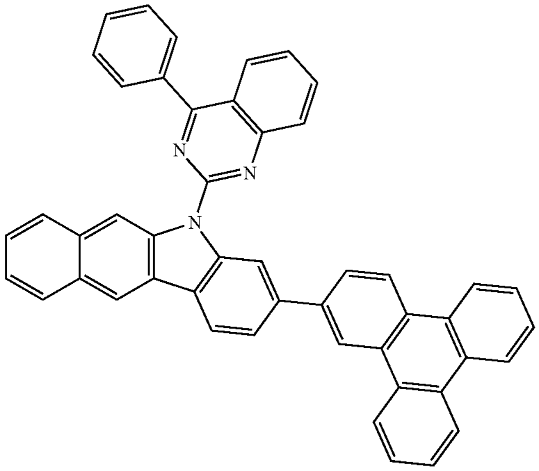 [SMILES: c1ccc(-c2nc(-n3c4cc(-c5ccc6c7ccccc7c7ccccc7c6c5)ccc4c4cc5ccccc5cc43)nc3ccccc23)cc1]
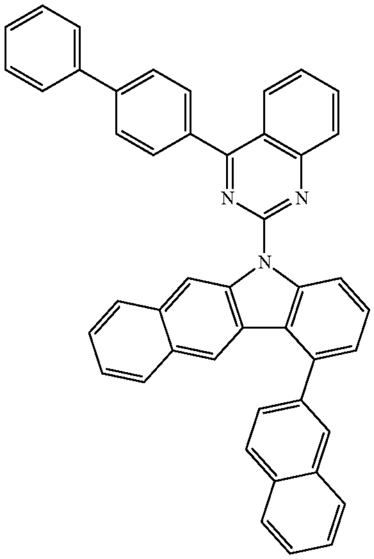 [SMILES: c1ccc(-c2ccc(-c3nc(-n4c5cc6ccccc6cc5c5c(-c6ccc7ccccc7c6)cccc54)nc4ccccc34)cc2)cc1]

-continued
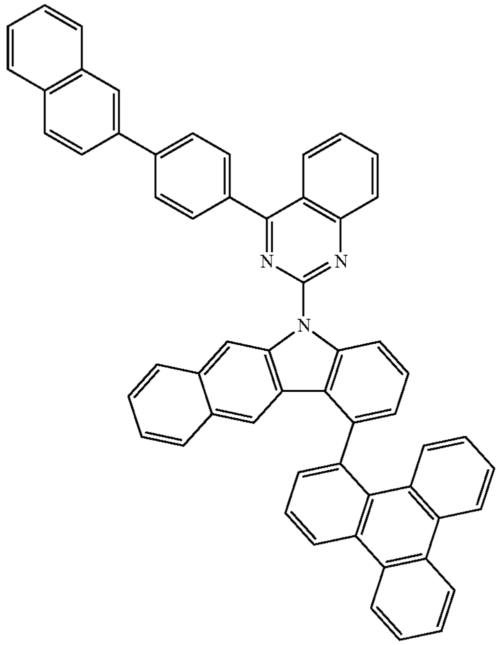 [SMILES: c1ccc2cc(-c3ccc(-c4nc(-n5c6cc7ccccc7cc6c6c(-c7cccc8c9ccccc9c9ccccc9c78)cccc65)nc5ccccc45)cc3)ccc2c1]
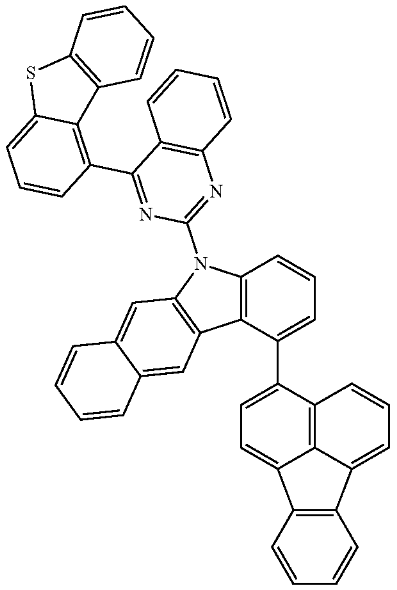 [SMILES: c1ccc2c(c1)-c1cccc3c(-c4cccc5c4c4cc6ccccc6cc4n5-c4nc(-c5cccc6sc7ccccc7c56)c5ccccc5n4)ccc-2c13]
-continued
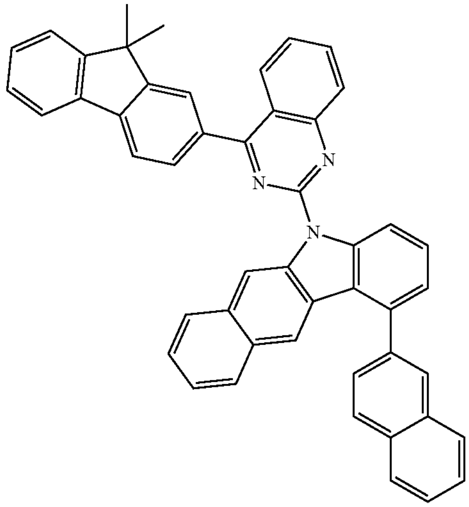 [SMILES: CC1(C)c2ccccc2-c2ccc(-c3nc(-n4c5cc6ccccc6cc5c5c(-c6ccc7ccccc7c6)cccc54)nc4ccccc34)cc21]
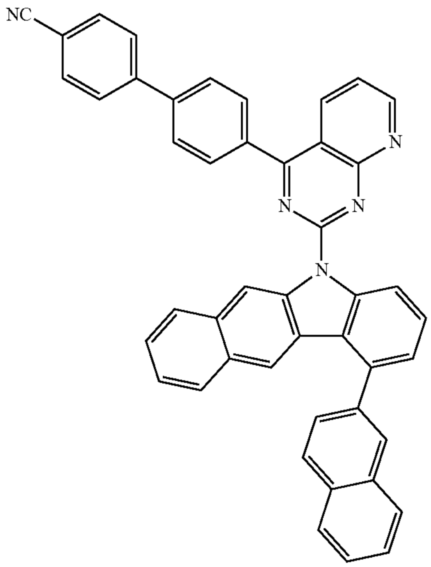
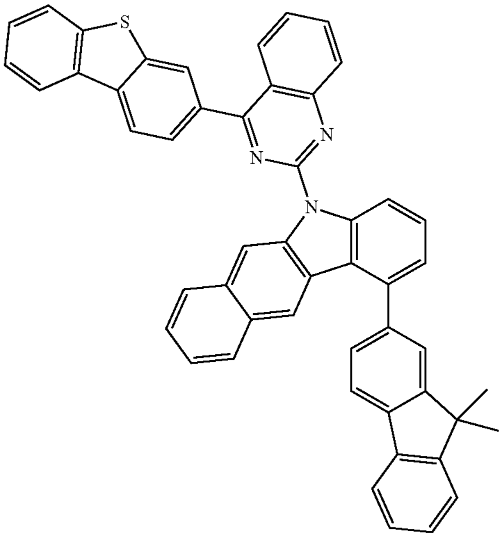

-continued
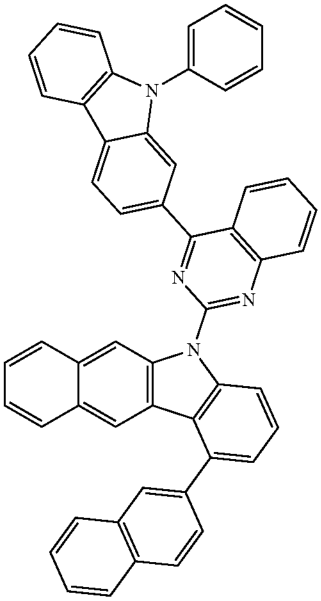 [SMILES: c1ccc(-n2c3ccccc3c3ccc(-c4nc(-n5c6cc7ccccc7cc6c6c(-c7ccc8ccccc8c7)cccc65)nc5ccccc45)cc32)cc1]
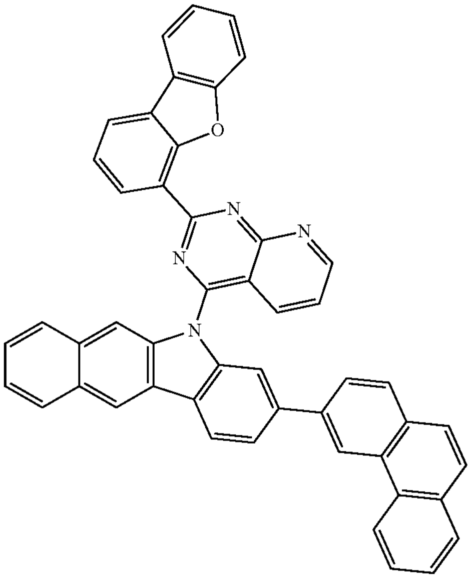 [SMILES: c1ccc2cc3c(cc2c1)c1ccc(-c2ccc4ccc5ccccc5c4c2)cc1n3-c1nc(-c2cccc3c2oc2ccccc23)nc2ncccc12]
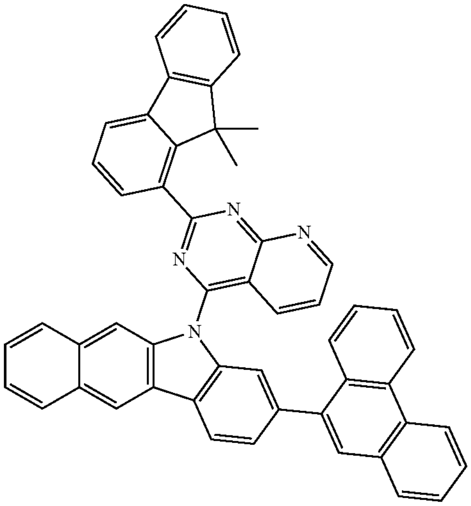
-continued
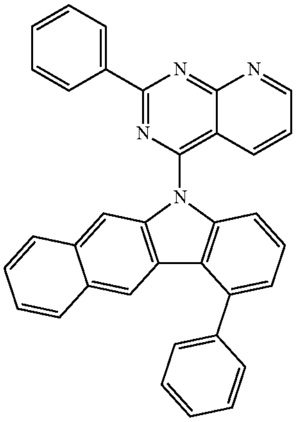
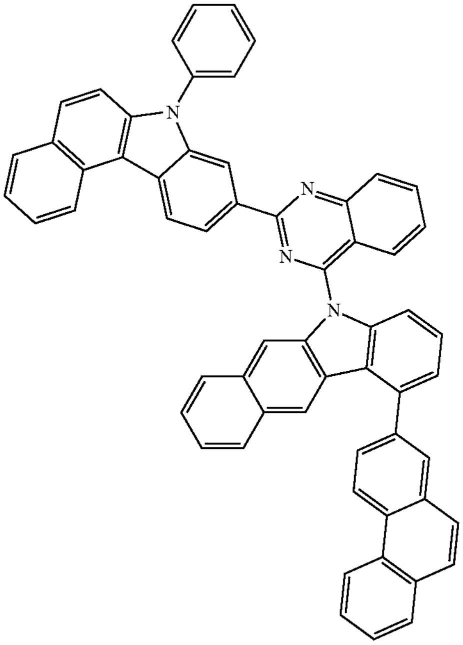 [SMILES: c1ccc(-n2c3cc(-c4nc(-n5c6cc7ccccc7cc6c6c(-c7ccc8c(ccc9ccccc98)c7)cccc65)c5ccccc5n4)ccc3c3c4ccccc4ccc32)cc1]
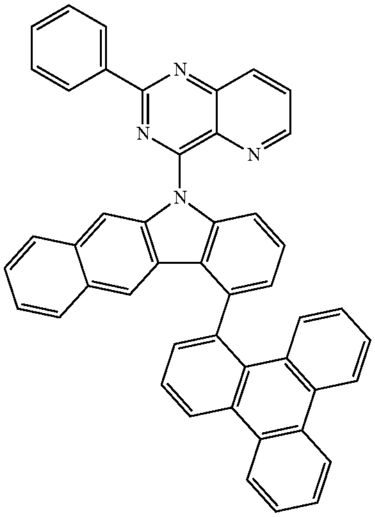 [SMILES: c1ccc(-c2nc(-n3c4cc5ccccc5cc4c4c(-c5cccc6c7ccccc7c7ccccc7c56)cccc43)c3ncccc3n2)cc1]

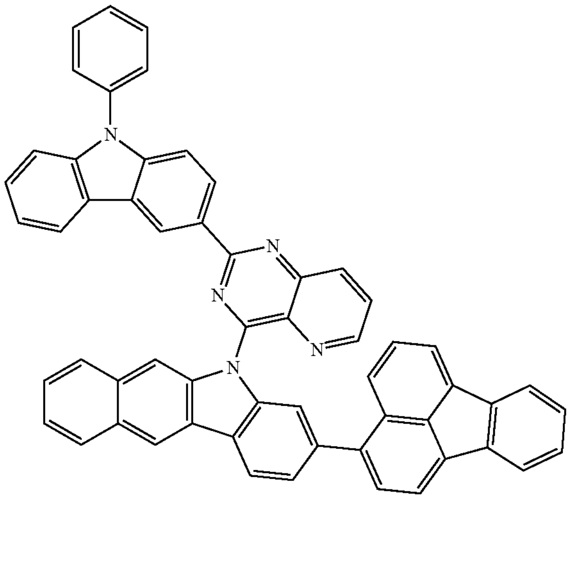 [SMILES: c1ccc(-n2c3ccccc3c3cc(-c4nc(-n5c6cc(-c7ccc8c9c(cccc79)-c7ccccc7-8)ccc6c6cc7ccccc7cc65)c5ncccc5n4)ccc32)cc1]
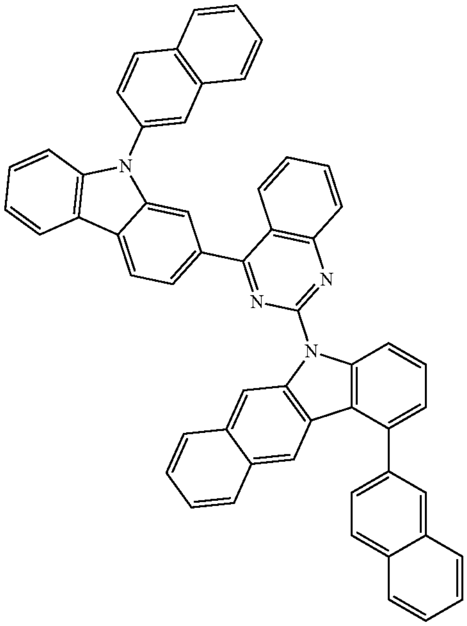
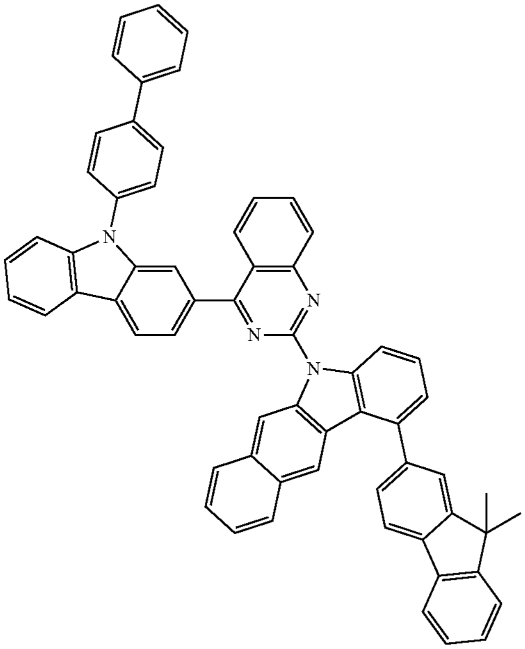 [SMILES: CC1(C)c2ccccc2-c2ccc(-c3cccc4c3c3cc5ccccc5cc3n4-c3nc(-c4ccc5c6ccccc6n(-c6ccc(-c7ccccc7)cc6)c5c4)c4ccccc4n3)cc21]
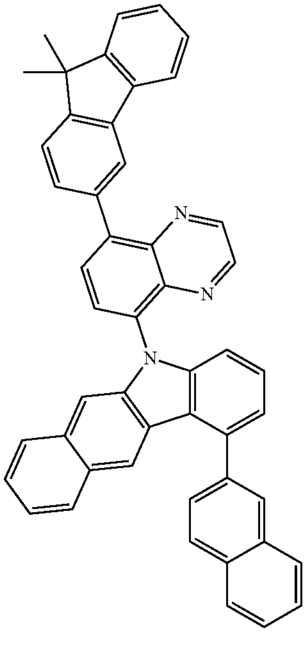 [SMILES: CC1(C)c2ccccc2-c2cc(-c3ccc(-n4c5cc6ccccc6cc5c5c(-c6ccc7ccccc7c6)cccc54)c4nccnc34)ccc21]

-continued
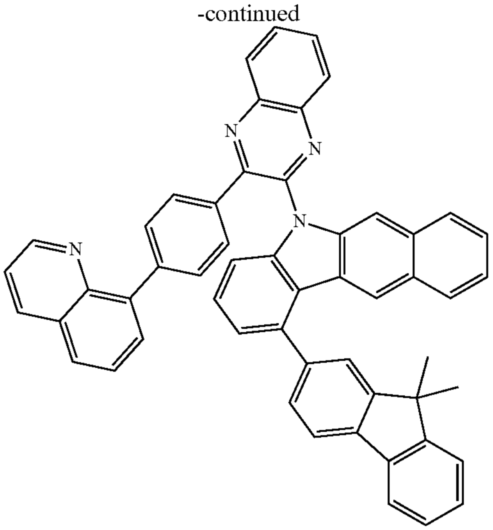
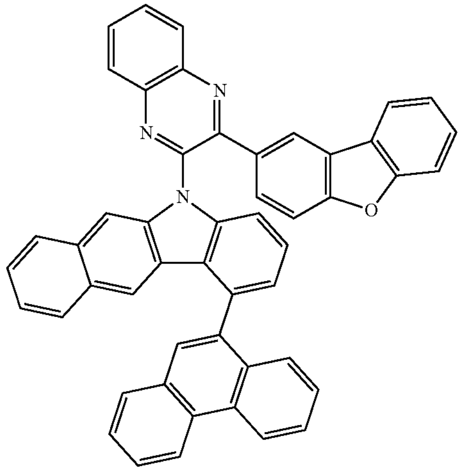 [SMILES: c1ccc2cc3c(cc2c1)c1c(-c2cc4ccccc4c4ccccc24)cccc1n3-c1nc2ccccc2nc1-c1ccc2oc3ccccc3c2c1]
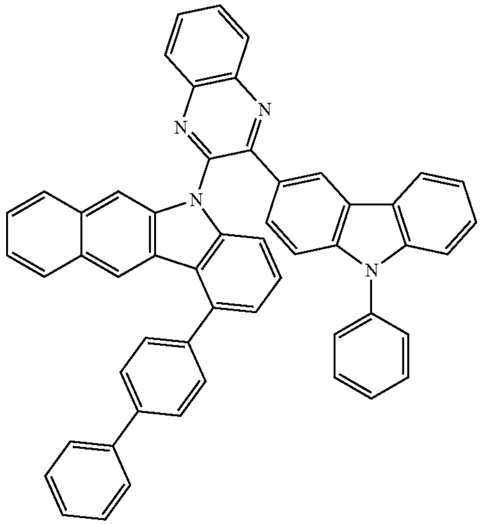 [SMILES: c1ccc(-c2ccc(-c3cccc4c3c3cc5ccccc5cc3n4-c3nc4ccccc4nc3-c3ccc4c(c3)c3ccccc3n4-c3ccccc3)cc2)cc1]
-continued
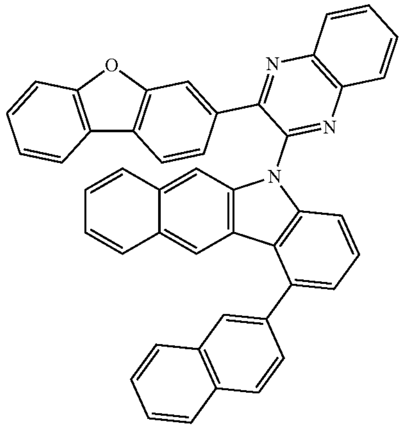 [SMILES: c1ccc2cc(-c3cccc4c3c3cc5ccccc5cc3n4-c3nc4ccccc4nc3-c3ccc4c(c3)oc3ccccc34)ccc2c1]
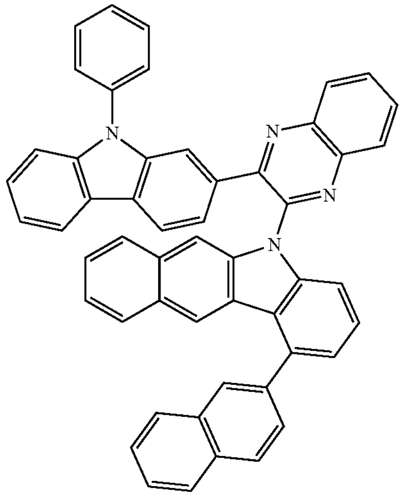
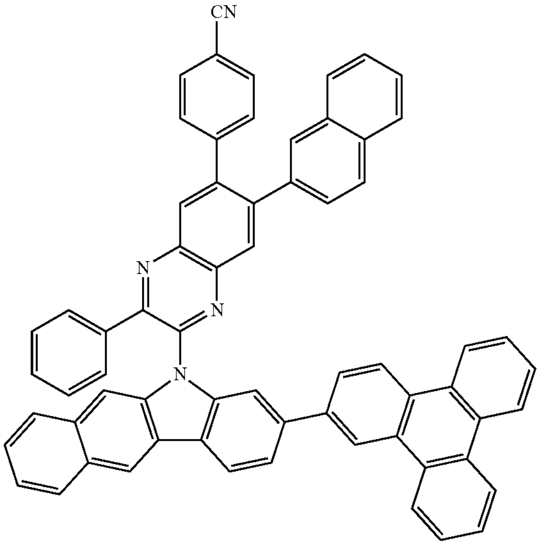

-continued
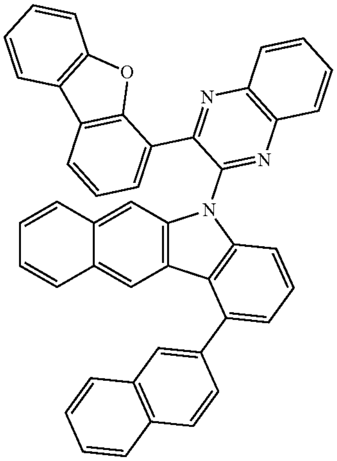
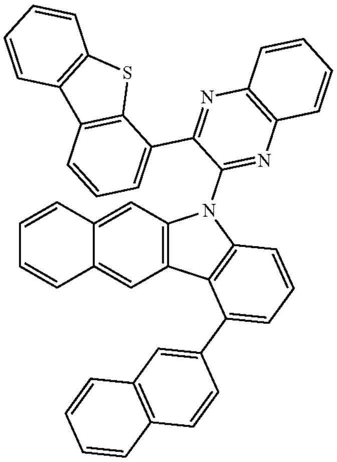
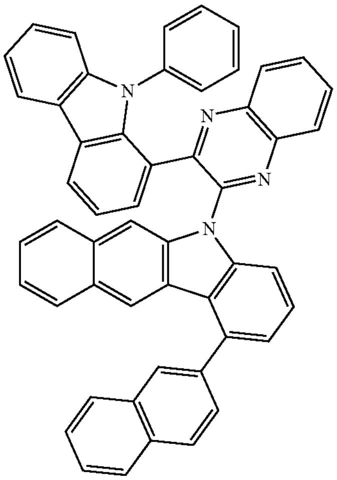 [SMILES: c1ccc(-n2c3ccccc3c3cccc(-c4nc5ccccc5nc4-n4c5cc6ccccc6cc5c5c(-c6ccc7ccccc7c6)cccc54)c32)cc1]
-continued
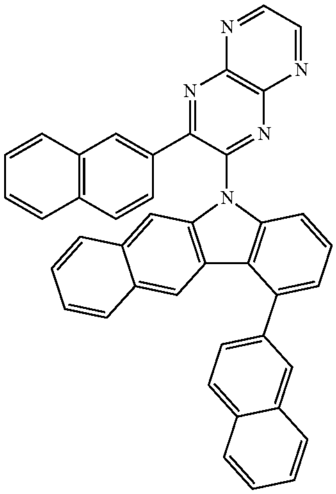 [SMILES: c1ccc2cc(-c3nc4nccnc4nc3-n3c4cc5ccccc5cc4c4c(-c5ccc6ccccc6c5)cccc43)ccc2c1]
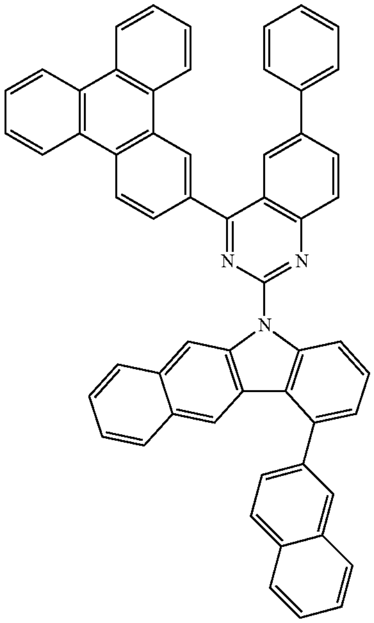 [SMILES: c1ccc(-c2ccc3nc(-n4c5cc6ccccc6cc5c5c(-c6ccc7ccccc7c6)cccc54)nc(-c4ccc5c6ccccc6c6ccccc6c5c4)c3c2)cc1]

-continued
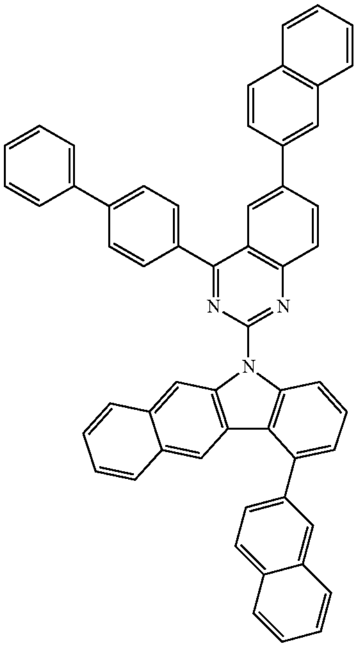 [SMILES: c1ccc(-c2ccc(-c3nc(-n4c5cc6ccccc6cc5c5c(-c6ccc7ccccc7c6)cccc54)nc4ccc(-c5ccc6ccccc6c5)cc34)cc2)cc1]
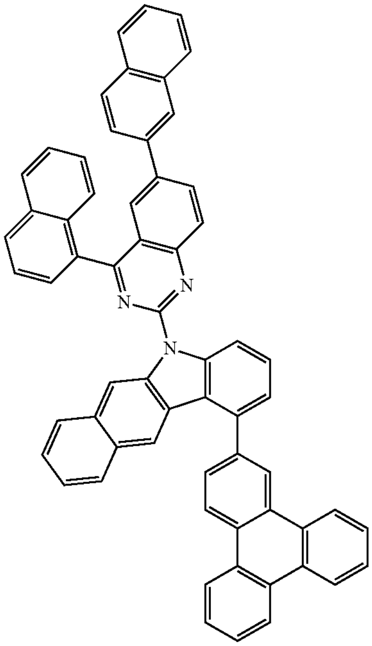 [SMILES: c1ccc2cc(-c3ccc4nc(-n5c6cc7ccccc7cc6c6c(-c7ccc8c9ccccc9c9ccccc9c8c7)cccc65)nc(-c5cccc6ccccc56)c4c3)ccc2c1]
-continued
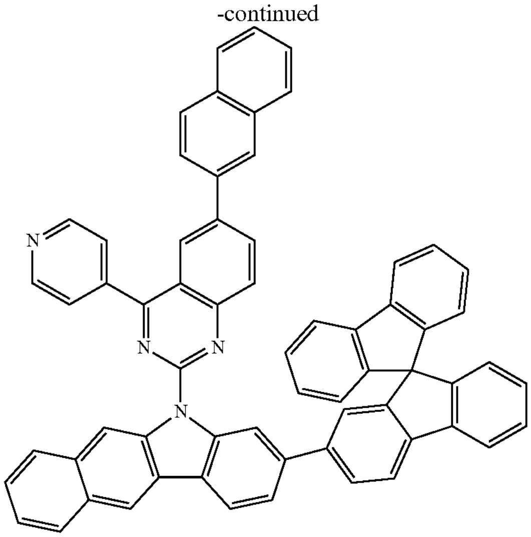
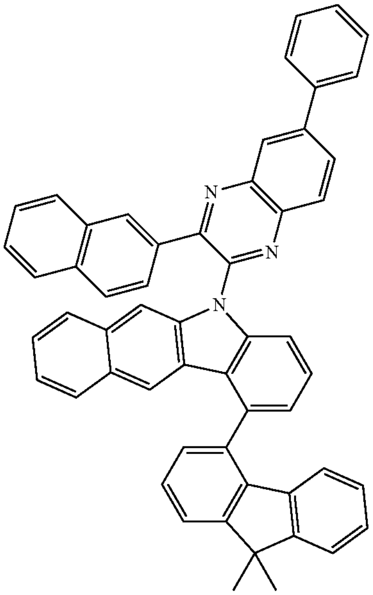
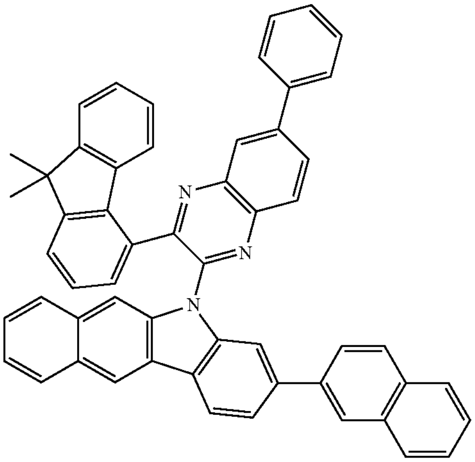

-continued
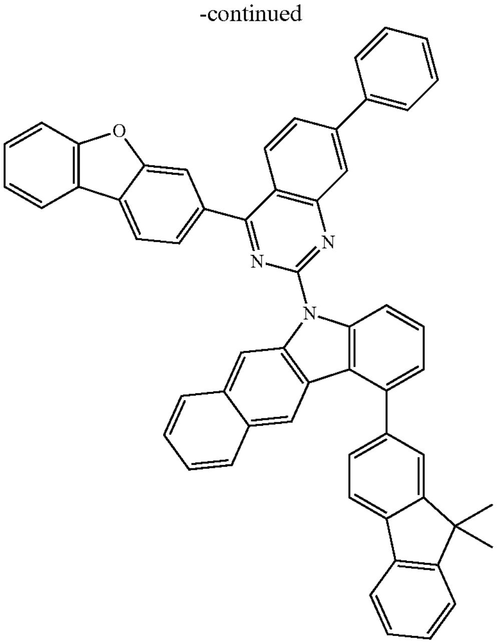
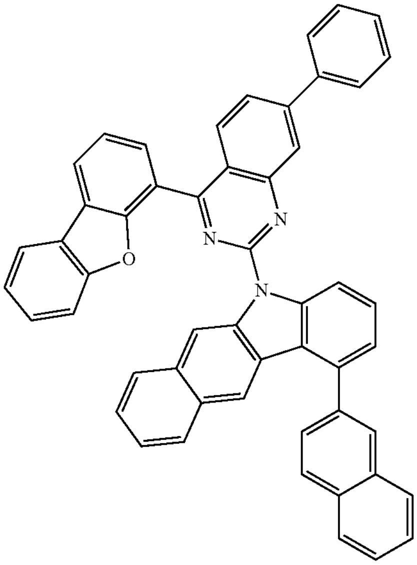
-continued
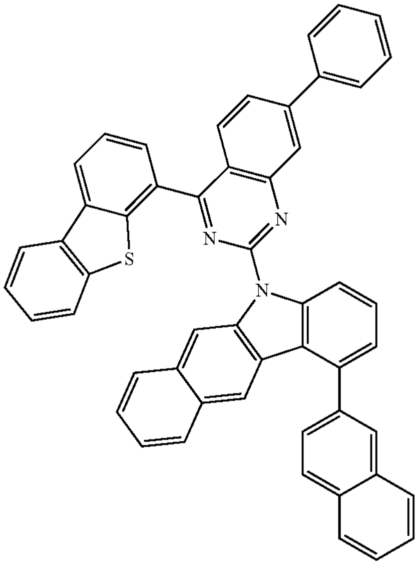
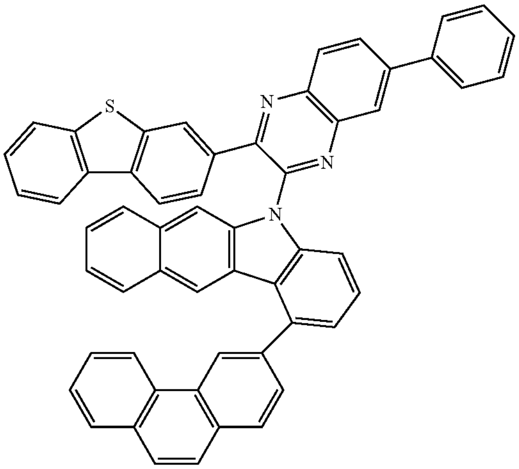
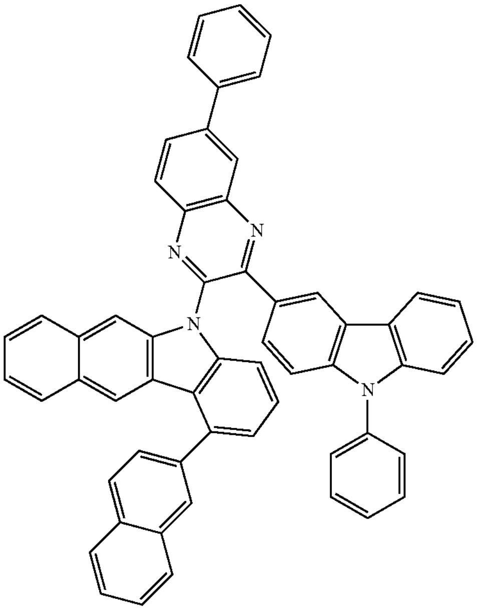

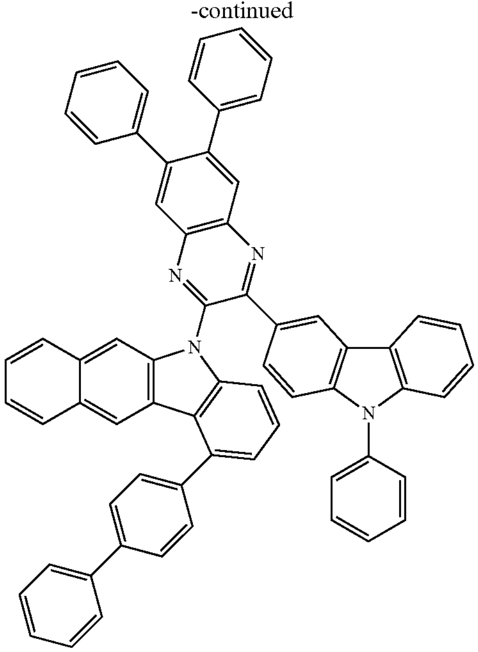
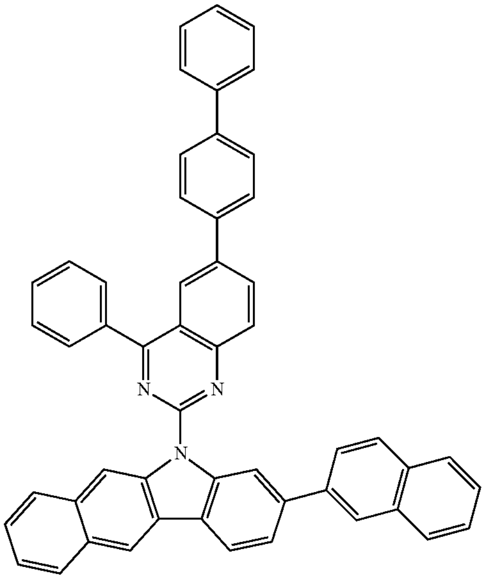
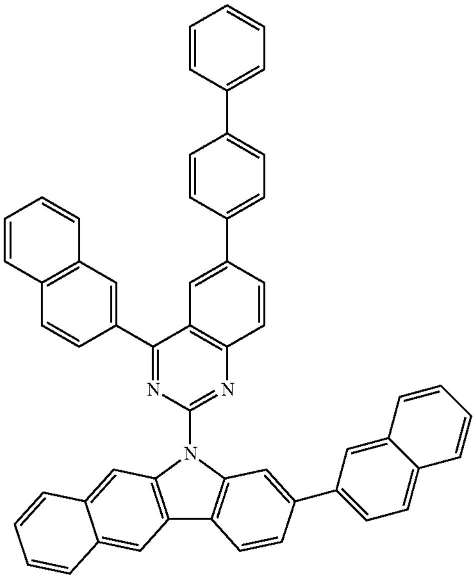
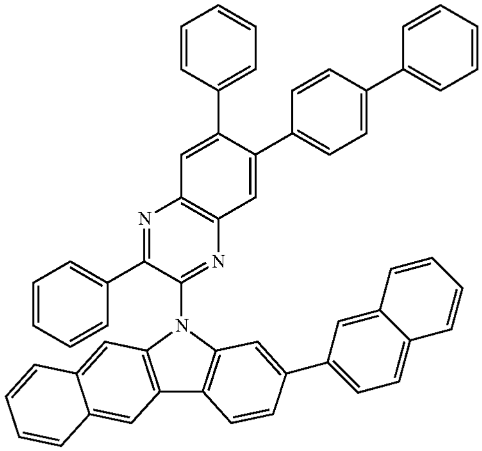 [SMILES: c1ccc(-c2ccc(-c3cc4nc(-n5c6cc(-c7ccc8ccccc8c7)ccc6c6cc7ccccc7cc65)c(-c5ccccc5)nc4cc3-c3ccccc3)cc2)cc1]
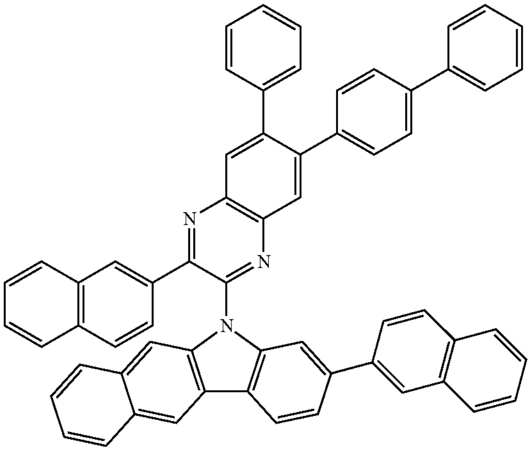 [SMILES: c1ccc(-c2ccc(-c3cc4nc(-n5c6cc(-c7ccc8ccccc8c7)ccc6c6cc7ccccc7cc65)c(-c5ccc6ccccc6c5)nc4cc3-c3ccccc3)cc2)cc1]

-continued
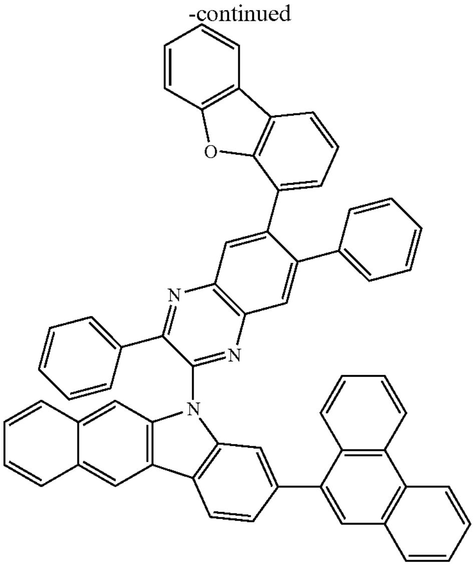
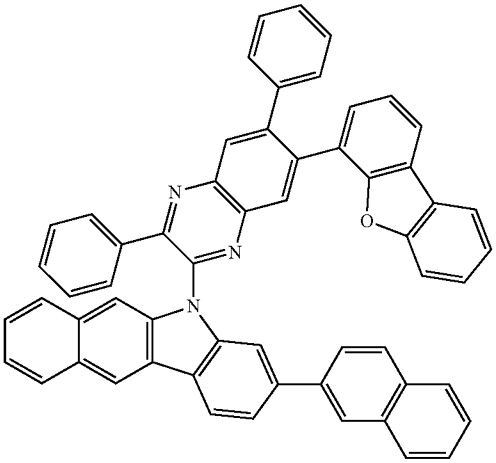
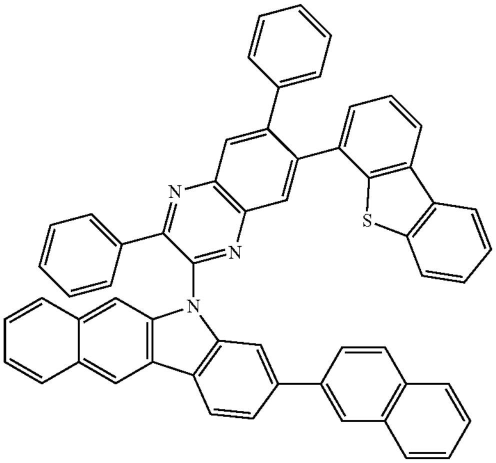
-continued
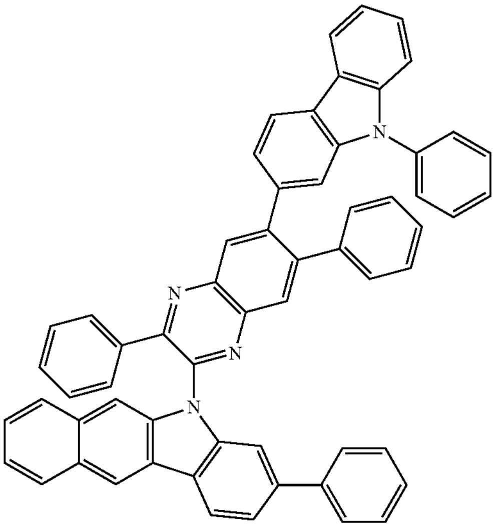
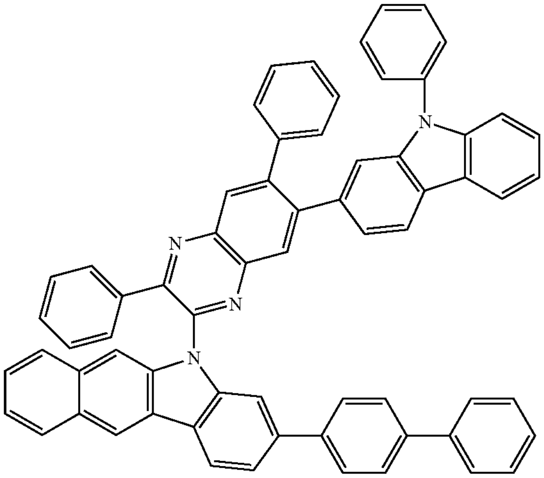
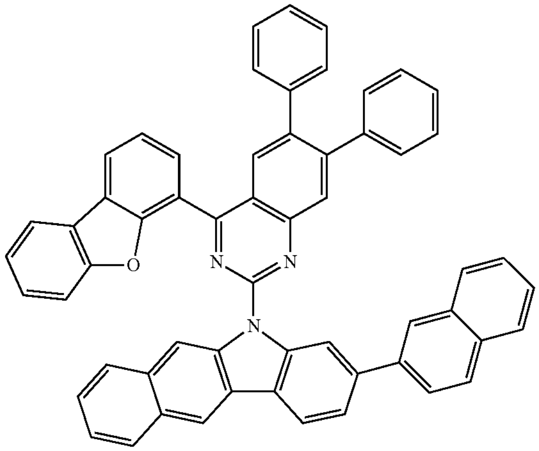 [SMILES: c1ccc(-c2cc3nc(-n4c5cc(-c6ccc7ccccc7c6)ccc5c5cc6ccccc6cc54)nc(-c4cccc5c4oc4ccccc45)c3cc2-c2ccccc2)cc1]

-continued
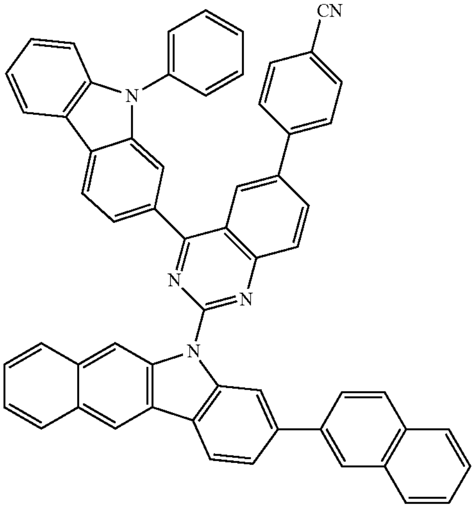
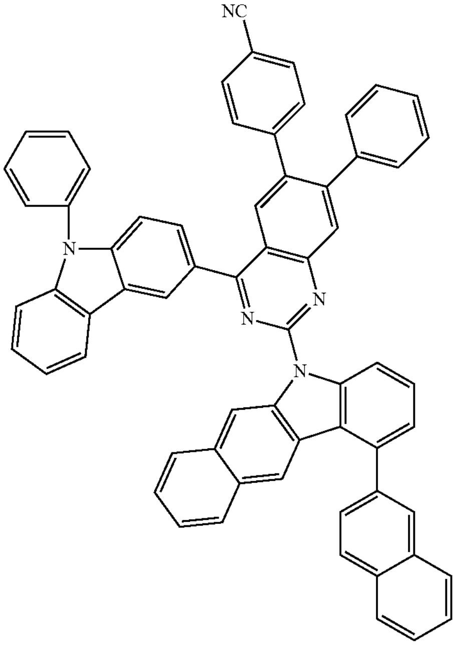
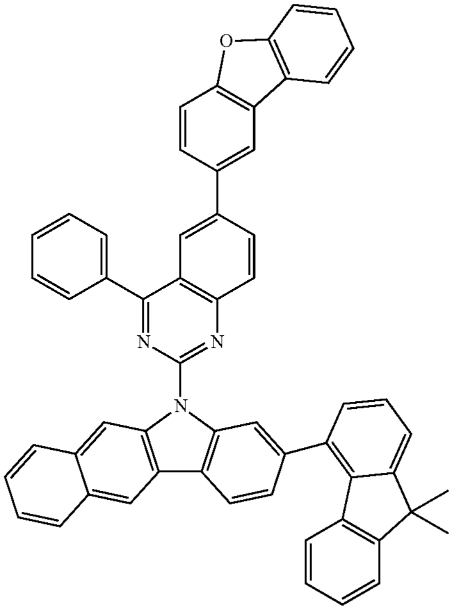 [SMILES: CC1(C)c2ccccc2-c2c(-c3ccc4c5cc6ccccc6cc5n(-c5nc(-c6ccccc6)c6cc(-c7ccc8oc9ccccc9c8c7)ccc6n5)c4c3)cccc21]
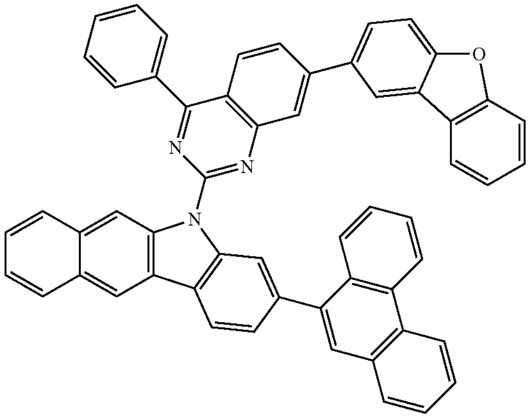
-continued
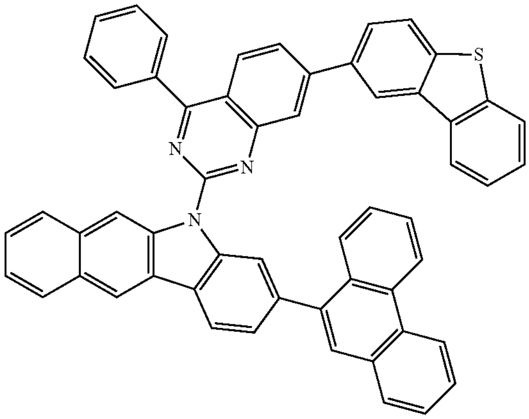

-continued
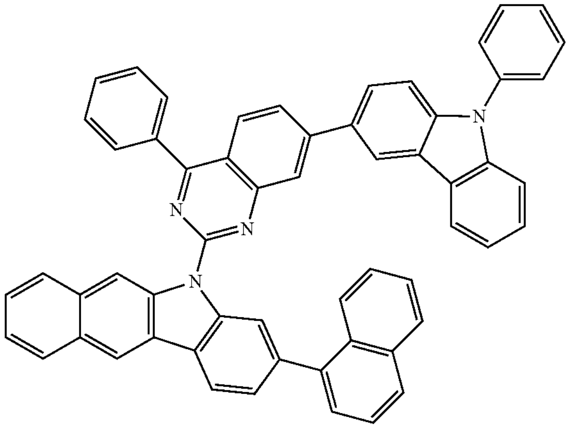 [SMILES: c1ccc(-c2nc(-n3c4cc(-c5cccc6ccccc56)ccc4c4cc5ccccc5cc43)nc3cc(-c4ccc5c(c4)c4ccccc4n5-c4ccccc4)ccc23)cc1]
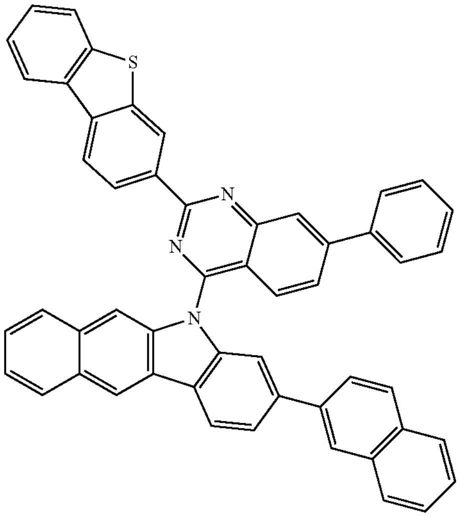
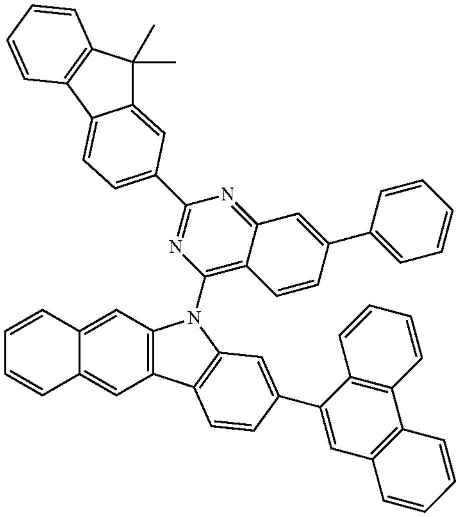
-continued
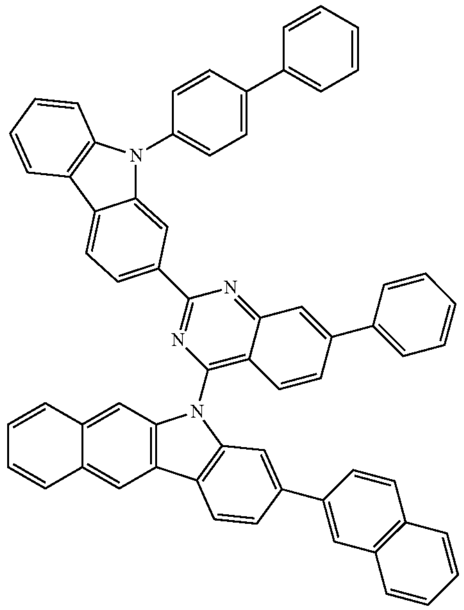 [SMILES: c1ccc(-c2ccc(-n3c4ccccc4c4ccc(-c5nc(-n6c7cc(-c8ccc9ccccc9c8)ccc7c7cc8ccccc8cc76)c6ccc(-c7ccccc7)cc6n5)cc43)cc2)cc1]
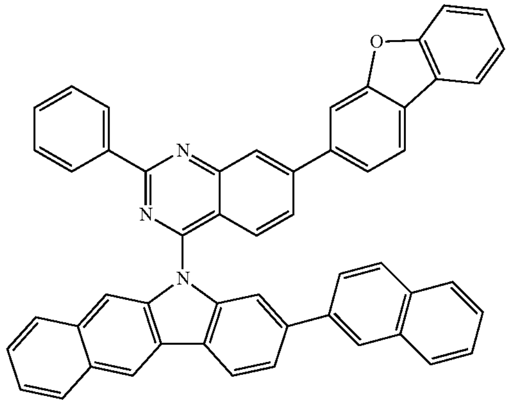 [SMILES: c1ccc(-c2nc(-n3c4cc(-c5ccc6ccccc6c5)ccc4c4cc5ccccc5cc43)c3ccc(-c4ccc5c(c4)oc4ccccc45)cc3n2)cc1]
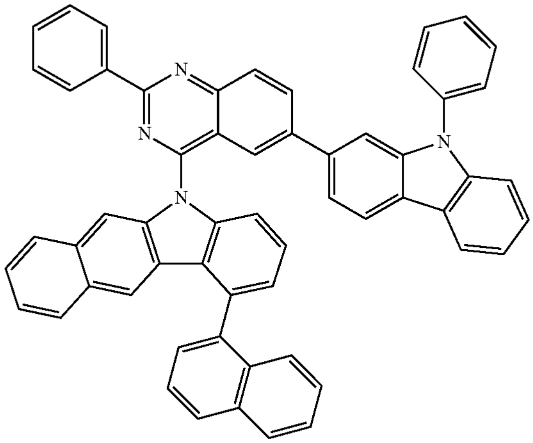 [SMILES: c1ccc(-c2nc(-n3c4cc5ccccc5cc4c4c(-c5cccc6ccccc56)cccc43)c3cc(-c4ccc5c6ccccc6n(-c6ccccc6)c5c4)ccc3n2)cc1]

-continued
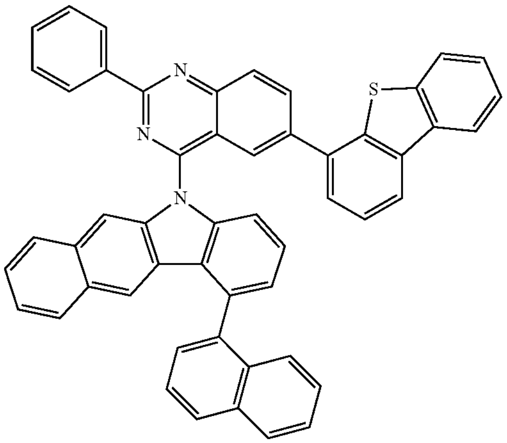 [SMILES: c1ccc(-c2nc(-n3c4cc5ccccc5cc4c4c(-c5cccc6ccccc56)cccc43)c3cc(-c4cccc5c4sc4ccccc45)ccc3n2)cc1]
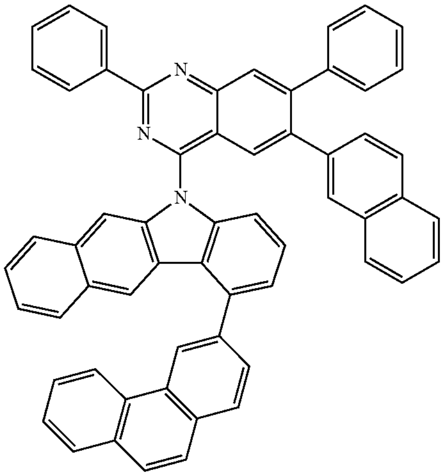 [SMILES: c1ccc(-c2nc(-n3c4cc5ccccc5cc4c4c(-c5ccc6ccc7ccccc7c6c5)cccc43)c3cc(-c4ccc5ccccc5c4)c(-c4ccccc4)cc3n2)cc1]
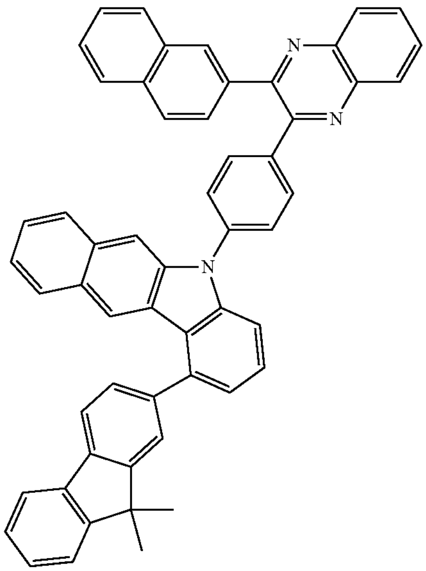 [SMILES: CC1(C)c2ccccc2-c2ccc(-c3cccc4c3c3cc5ccccc5cc3n4-c3ccc(-c4nc5ccccc5nc4-c4ccc5ccccc5c4)cc3)cc21]
-continued
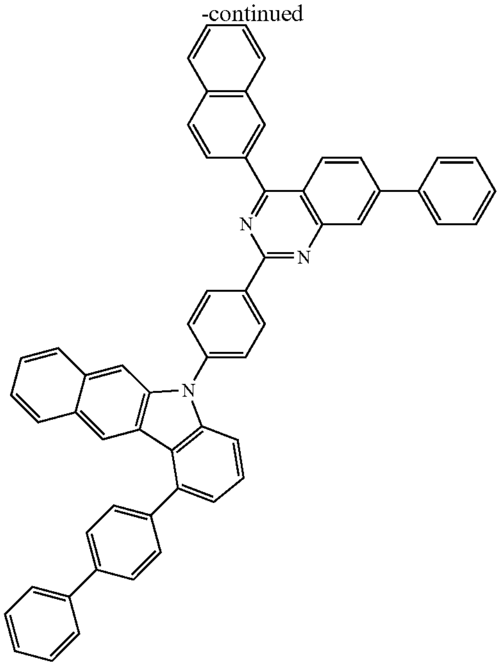
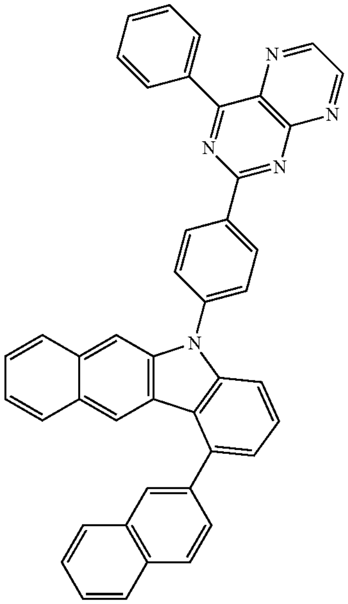 [SMILES: c1ccc(-c2nc(-c3ccc(-n4c5cc6ccccc6cc5c5c(-c6ccc7ccccc7c6)cccc54)cc3)nc3nccnc23)cc1]

-continued
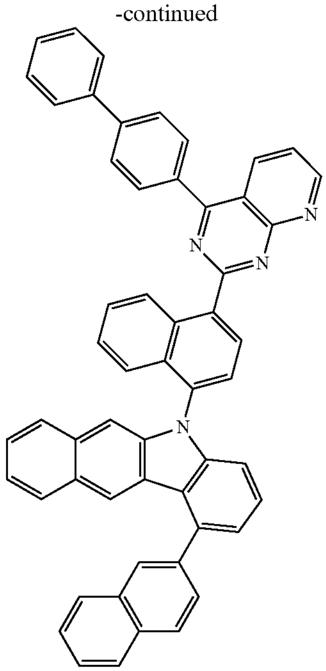
-continued
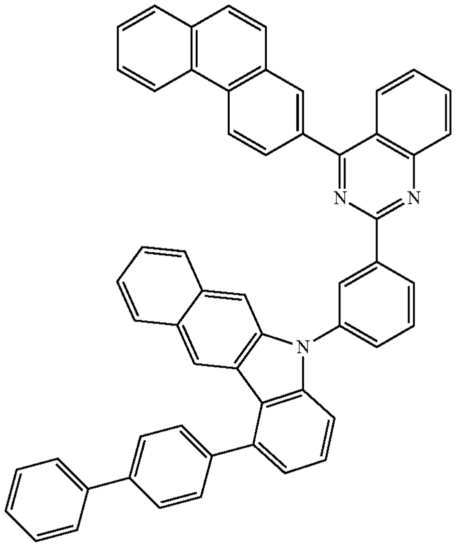
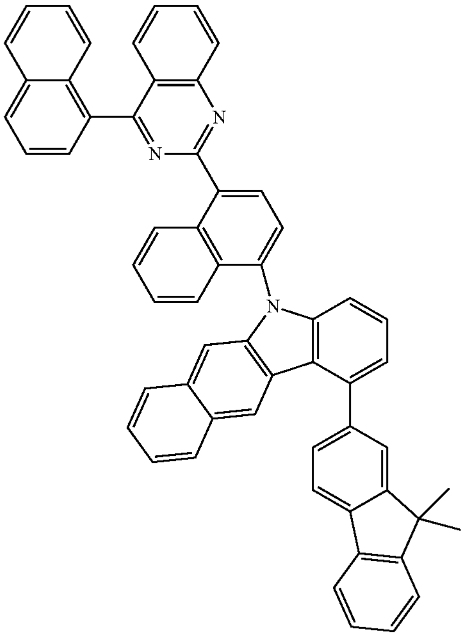
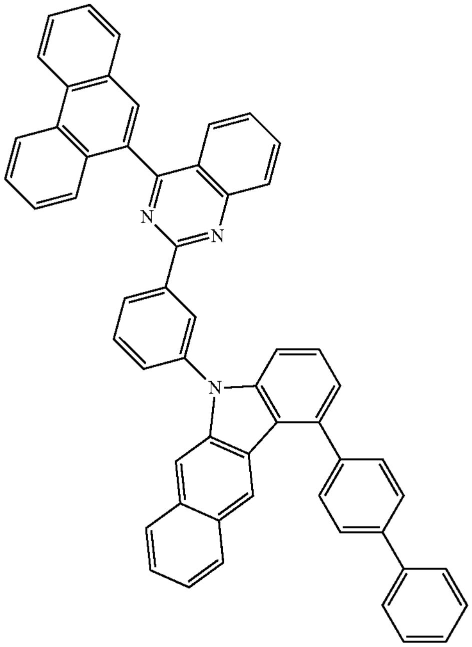

-continued
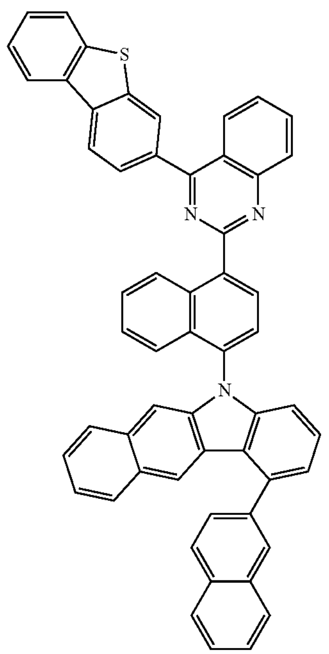 [SMILES: c1ccc2cc(-c3cccc4c3c3cc5ccccc5cc3n4-c3ccc(-c4nc(-c5ccc6c(c5)sc5ccccc56)c5ccccc5n4)c4ccccc34)ccc2c1]
-continued
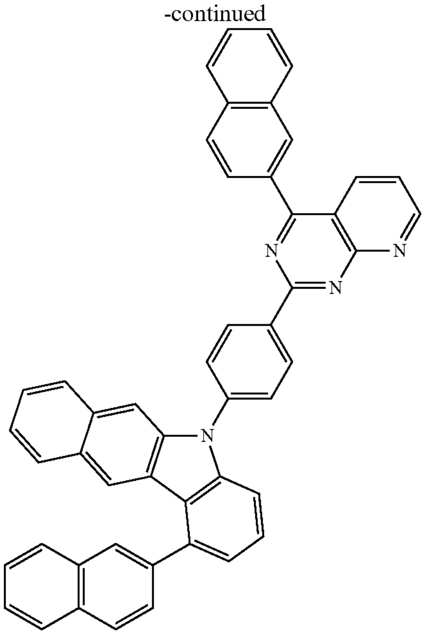
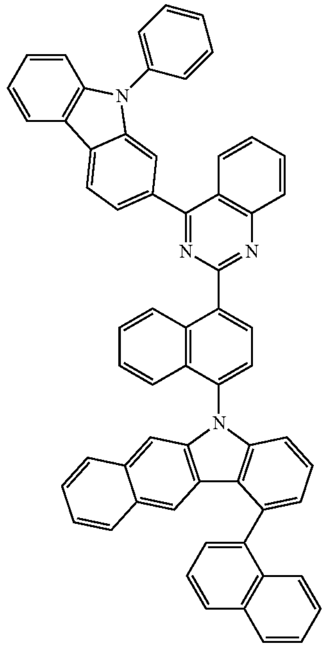 [SMILES: c1ccc(-n2c3ccccc3c3ccc(-c4nc(-c5ccc(-n6c7cc8ccccc8cc7c7c(-c8cccc9ccccc89)cccc76)c6ccccc56)nc5ccccc45)cc32)cc1]
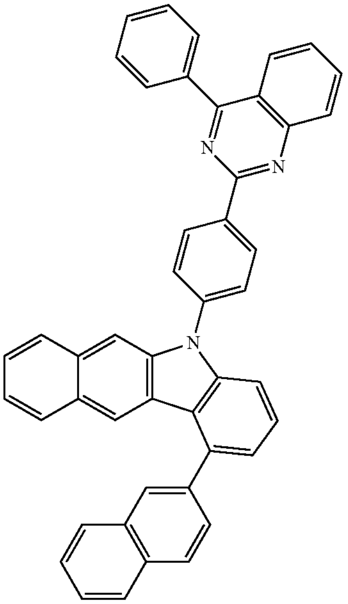

-continued
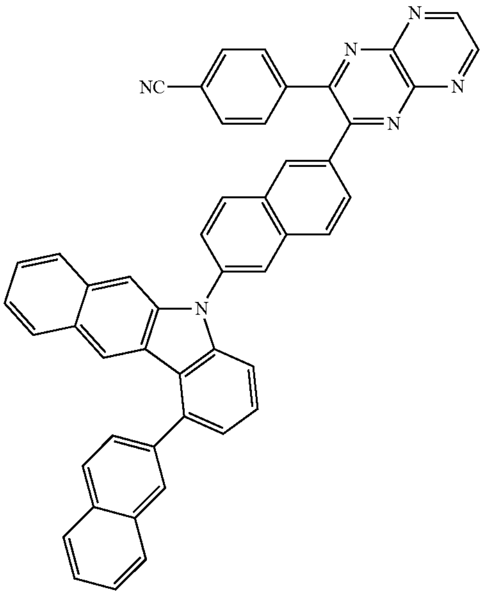
-continued
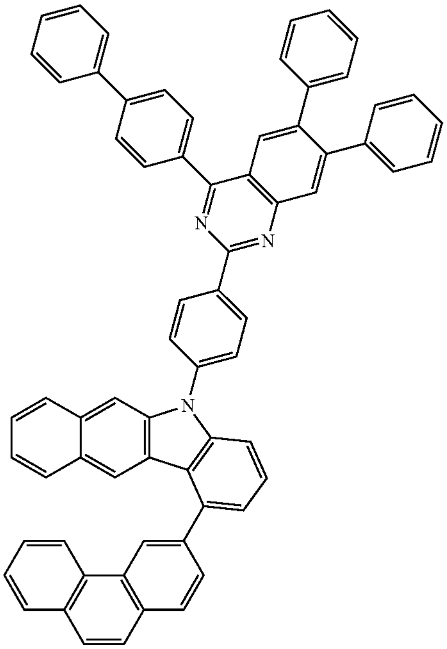
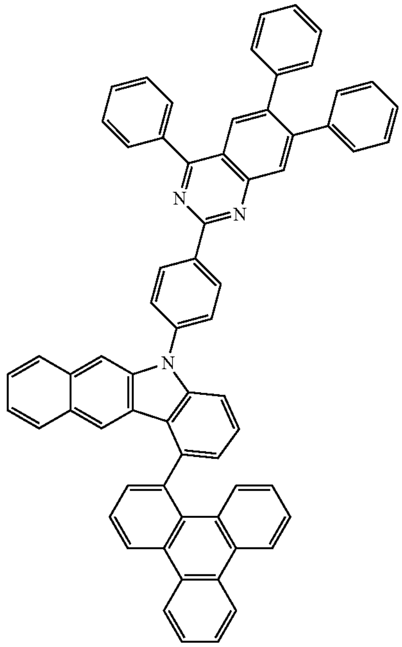 [SMILES: c1ccc(-c2cc3nc(-c4ccc(-n5c6cc7ccccc7cc6c6c(-c7cccc8c9ccccc9c9ccccc9c78)cccc65)cc4)nc(-c4ccccc4)c3cc2-c2ccccc2)cc1]
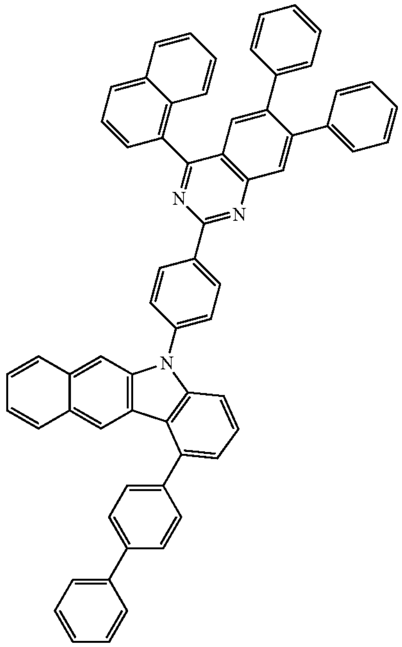 [SMILES: c1ccc(-c2ccc(-c3cccc4c3c3cc5ccccc5cc3n4-c3ccc(-c4nc(-c5cccc6ccccc56)c5cc(-c6ccccc6)c(-c6ccccc6)cc5n4)cc3)cc2)cc1]

-continued
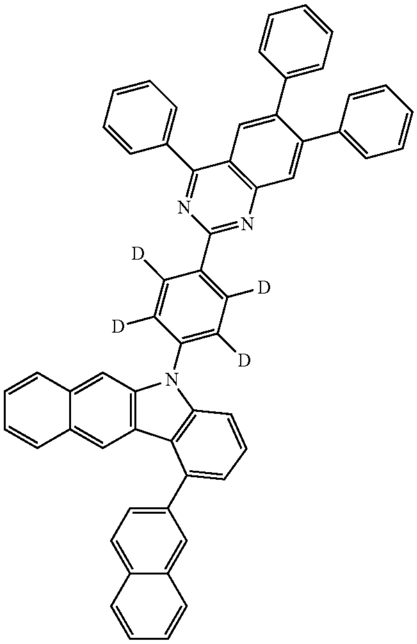
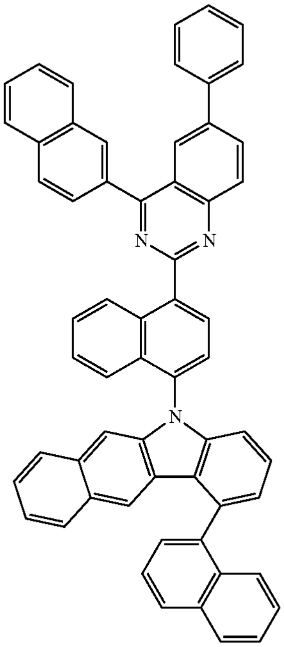
-continued
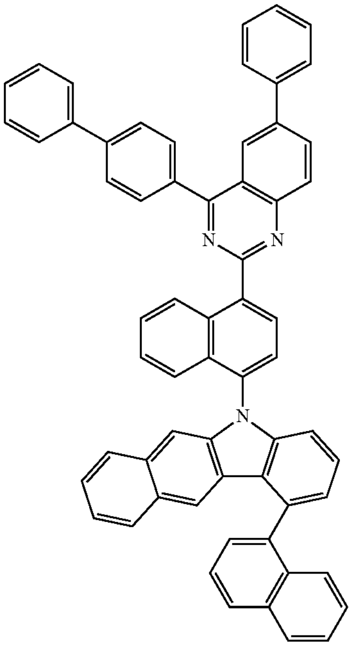
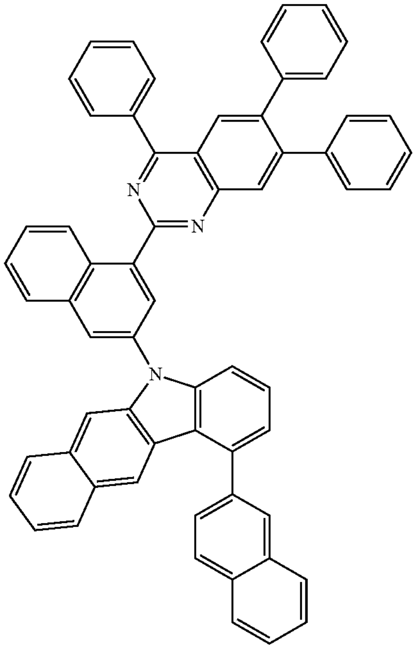

-continued
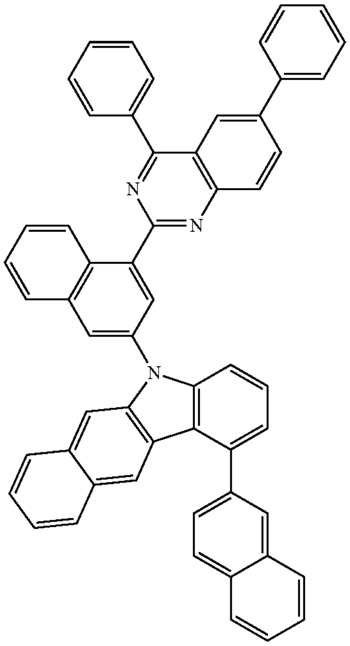
-continued
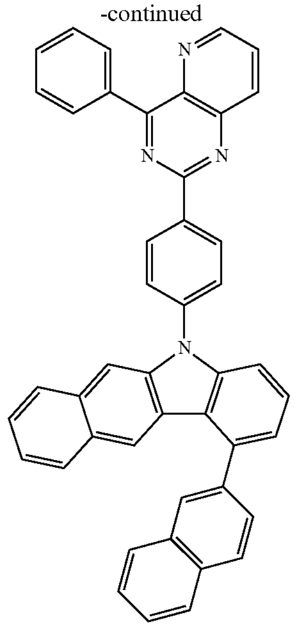
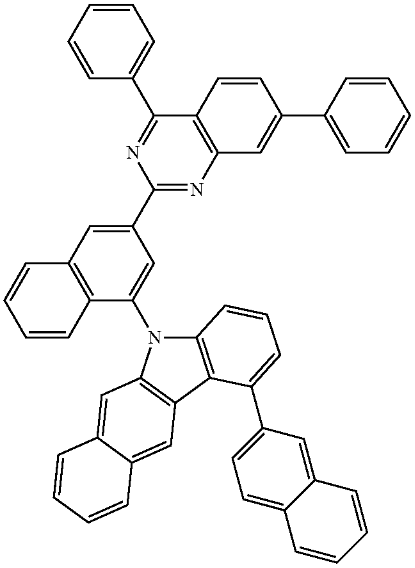
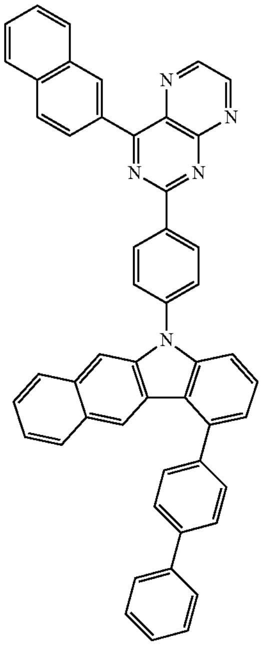

-continued
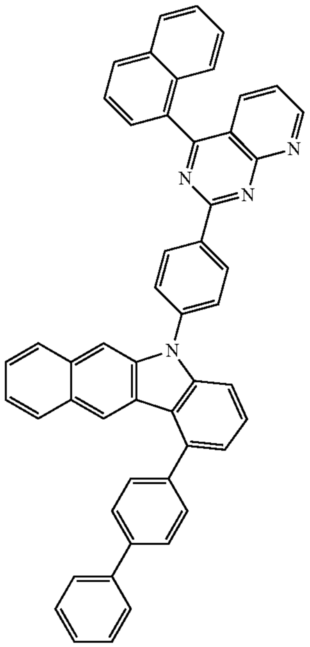
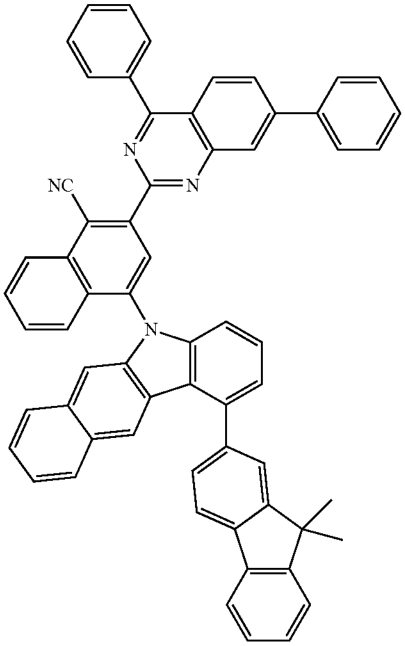
-continued
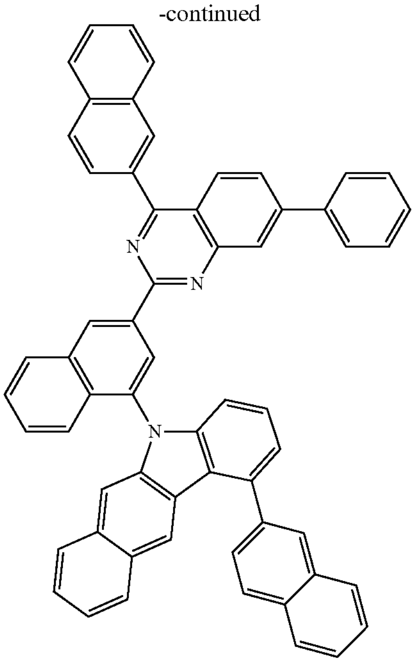
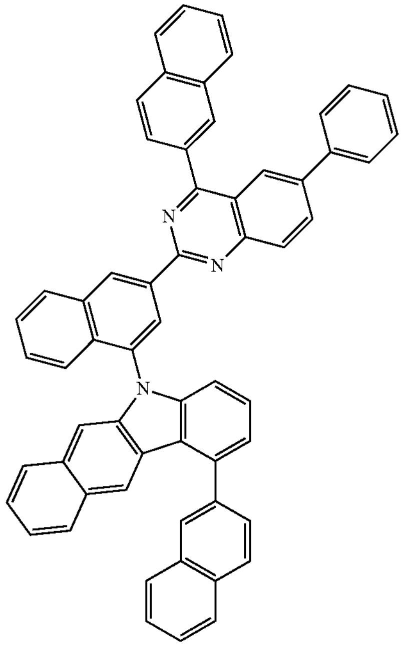

-continued
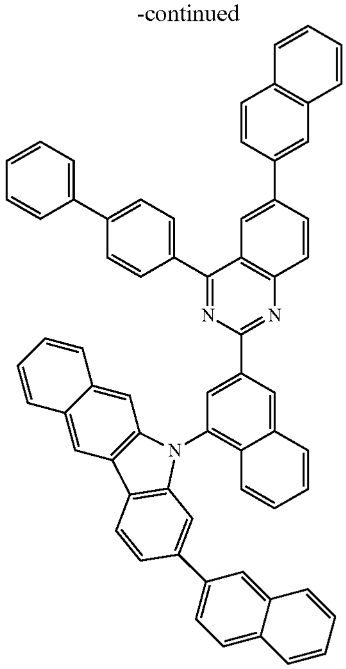
.
* * * * *